US011453726B2

(12) United States Patent
Ali et al.

(10) Patent No.: US 11,453,726 B2
(45) Date of Patent: Sep. 27, 2022

(54) MULTIMERS, TETRAMERS AND OCTAMERS

(71) Applicant: Quadrucept Bio Limited, London (GB)

(72) Inventors: Hanif Ali, London (GB); Terence Rabbitts, London (GB); Christian Grøndahl, London (GB); Jasper Clube, London (GB)

(73) Assignee: QUADRUCEPT BIO LIMITED, London (GB)

( * ) Notice: Subject to any disclaimer, the term of this patent is extended or adjusted under 35 U.S.C. 154(b) by 454 days.

(21) Appl. No.: 16/333,583

(22) PCT Filed: Sep. 18, 2017

(86) PCT No.: PCT/EP2017/073527
§ 371 (c)(1),
(2) Date: Mar. 14, 2019

(87) PCT Pub. No.: WO2018/050902
PCT Pub. Date: Mar. 22, 2018

(65) Prior Publication Data
US 2019/0225710 A1 Jul. 25, 2019

(30) Foreign Application Priority Data

Sep. 15, 2016 (GB) .................................. 1615768
Aug. 20, 2017 (GB) .................................. 1713342
Aug. 21, 2017 (GB) .................................. 1713351

(51) Int. Cl.
| | |
|---|---|
| C07K 16/46 | (2006.01) |
| C07K 14/55 | (2006.01) |
| C07K 14/725 | (2006.01) |
| C07K 14/47 | (2006.01) |
| C07K 16/28 | (2006.01) |
| C07K 16/24 | (2006.01) |
| C07K 16/22 | (2006.01) |

(52) U.S. Cl.
CPC .......... *C07K 16/46* (2013.01); *C07K 14/4702* (2013.01); *C07K 14/55* (2013.01); *C07K 14/7051* (2013.01); *C07K 16/22* (2013.01); *C07K 16/241* (2013.01); *C07K 16/2863* (2013.01); *C07K 16/2896* (2013.01); *C07K 2317/55* (2013.01); *C07K 2317/569* (2013.01); *C07K 2317/622* (2013.01); *C07K 2319/00* (2013.01); *C07K 2319/02* (2013.01); *C07K 2319/21* (2013.01); *C07K 2319/30* (2013.01); *C07K 2319/31* (2013.01); *C07K 2319/35* (2013.01); *C07K 2319/43* (2013.01); *C07K 2319/735* (2013.01)

(58) Field of Classification Search
None
See application file for complete search history.

(56) References Cited

U.S. PATENT DOCUMENTS

| | | | |
|---|---|---|---|
| 6,258,562 B1 * | 7/2001 | Salfeld | A61P 25/00 435/69.6 |
| 6,818,418 B1 | 11/2004 | Lipovsek et al. | |
| 7,250,297 B1 | 7/2007 | Beste et al. | |
| 2004/0132028 A1 | 7/2004 | Stumpp et al. | |
| 2005/0043519 A1 | 2/2005 | Dooley et al. | |
| 2007/0224633 A1 | 9/2007 | Skerra et al. | |
| 2008/0139791 A1 | 6/2008 | Lipovsek et al. | |
| 2011/0071919 A1 | 3/2011 | Spry | |
| 2015/0139991 A1 * | 5/2015 | Ivarez | C12N 15/62 424/134.1 |
| 2022/0162285 A1 | 5/2022 | Ali et al. | |

FOREIGN PATENT DOCUMENTS

| | | |
|---|---|---|
| EP | 1641818 A1 | 4/2006 |
| WO | 199201047 A1 | 1/1992 |
| WO | 199606213 A1 | 2/1996 |
| WO | 199708320 A1 | 3/1997 |
| WO | 200029004 A1 | 5/2000 |
| WO | 2005003156 A1 | 1/2005 |
| WO | 2005056764 A2 | 6/2005 |
| WO | 2005113595 A2 | 12/2005 |
| WO | 2005056764 A3 | 5/2006 |
| WO | 2005113595 A3 | 6/2006 |
| WO | 2007024715 A2 | 3/2007 |
| WO | 2008098796 A1 | 8/2008 |
| WO | 2007024715 A3 | 10/2008 |
| WO | 2010142551 A2 | 12/2010 |
| WO | 2010142551 A3 | 6/2011 |
| WO | 2015136541 A2 | 9/2015 |
| WO | 2015136541 A3 | 11/2015 |
| WO | 2017123650 A2 | 7/2017 |
| WO | 2017123650 A3 | 9/2017 |
| WO | 2018050902 A2 | 3/2018 |

(Continued)

OTHER PUBLICATIONS

Liu et al. (Biochem. J. (2007) 406, 237-246). (Year: 2007).*
Zamora-Atenza et al. (Arthritis Research & Therapy 2014, 16:R153). (Year: 2014).*
Abbott Laboratories Receives FDA Approval Earlier Than Anticipated for Humira™ (Adalimumab) for the Treatment of Rheumatoid Arthritis (Ra), Jan. 6, 2003, pp. 1-4. (Year: 2003).*
Adams, G.P. et al. (Mar. 1, 2006). Avidity-Mediated Enhancement of In vivo Tumor Targeting by Single-Chain Fv Dimers, Clin Cancer Res. 12(5):1599-1605.

(Continued)

*Primary Examiner* — Zachary S Skelding
(74) *Attorney, Agent, or Firm* — Morrison & Foerster LLP

(57) ABSTRACT

The invention relates to multimers such as tetramers of polypeptides and tetramers and octamers of effector domains, such as antigen binding sites (eg, antibody or TCR binding sites that specifically bind to antigen or pMHC, or variable domains thereof) or peptides such as incretin, insulin or hormone peptides.

25 Claims, 30 Drawing Sheets

Specification includes a Sequence Listing.

(56) References Cited

FOREIGN PATENT DOCUMENTS

| | | |
|---|---|---|
| WO | 2018050902 A3 | 4/2018 |
| WO | 2020187711 A1 | 9/2020 |

OTHER PUBLICATIONS

Alam, K. et al. (2018). "A Novel Synthetic Trivalent Single Chain Variable Fragment (tri-scFv) Construction Platform Based on the SpyTag/SpyCatcher Protein Ligase System," 18:55, 8 pages.
Ali, S.A. (Aug. 20, 1999). "Transferrin Trojan Horses as a Rational Approach for the Biological Delivery of Therapeutic Peptide Domains," J. Biol. Chem 274(34):24066-24073.
Barbas, C.F. et al. (May 1992). "Semisynthetic Combinatorial Antibody Libraries: A Chemical Solution to the Diversity Problem," Proc. Natl. Acad. Sci. USA, 89: 4457-4461.
Bentley, G.A. et al. (1996). "The Structure of the T Cell Antigen Receptor," Annual Review of Immunology 14(1):563-590. Abstract Only.
Binz, H.K. et al. (Sep. 12, 2003). "Designing Repeat Proteins: Well-Expressed, Soluble and Stable Proteins From Combinatorial Libraries of Consensus Ankyrin Repeat Proteins," J. Mol. Biol. 332(2):489-503.
Bixby, K.A. et al. (Jan. 1999). "Zn2+-Binding and Molecular Determinants of Tetramerization in Voltage-Gated K+ Channels," Nature Structural Biology 6(1):38-43.
Borghouts, C. et al. (Jun. 2005). "Peptide Aptamers: Recent Developments for Cancer Therapy," Expert Opinion on Biological Therapy 5(6):783-797.
Boruah, B.M. et al. (Aug. 20, 2013). "Single Domain Antibody Multimers Confer Protection against Rabies Infection," PLoS One 8(8): e71383, 10 pages.
Braddock, M. et al. (2009). "11th Annual Inflammatory and Immune Diseases Drug Discovery and Development Summit Mar. 12-13, 2007, San Francisco, USA," Expert Opinion on Investigational Drugs 16(6):909-917.
Brünker, P. et al. (May 2016). "RG7386, a Novel tetravalent FAP-DR5 Antibody, Effectively Triggers FAP-Dependent, Avidity-Driven DR5 Hyperclustering and Tumor Cell Apoptosis," Mol. Cancer Ther. 15(5):946-957.
Hausammann, G.J. et al. (Dec. 10, 2013). "Chimeric hERG Channels Containing a Tetramerization Domain Are Functional and Stable," Biochemistry 52(51):9237-9245. Abstract Only.
International Preliminary Report on Patentability, dated Mar. 19, 2019, for PCT Application No. PCT/EP2017/073527, filed Sep. 2017, 10 pages.
International Search Report and Written Opinion, dated Jul. 15, 2020, on Patentability, for PCT Application No. PCT/EP2020/056737, filed Mar. 12, 2020, 10 pages.
International Search Report and Written Opinion, dated Mar. 16, 2018 on Patentability, for PCT Application No. PCT/EP2017/073527, filed Sep. 18, 2017, 10 pages.
Li, L. et al. (Apr. 24, 2018). "Amplification of CD20 Cross-Linking in Rituximab-Resistant B-Lymphoma Cells Enhances Apoptosis Induction by Drug-Free Macromolecular Therapeutics," ACS Nano 12(4):3658-3670, 25 pages.
Mayes, P.A. (Jul. 2018, e-pub. Jun. 15, 2018). "The Promise and Challenges of Immune Agonist Antibody Development in Cancer," Nature Reviews Drug Discovery, 17(7):509-527. Abstract Only.
Miller, A. et al. (Jan. 1, 2020, e-pub. Apr. 22, 2020). "Multimeric Antibodies With Increased Valency Surpassing Functional Affinity and Potency Thresholds Using Novel Formats," Mabs 12(1):1752529, 11 pages.
Rheinnecker, M. et al. (1996). "Multivalent Antibody Fragments with High Functional Affinity for a Tumor-Associated Carbohydrate Antigen," The Journal of Immunology 157:2989-2997.
Richard, G. et al. (Jul. 22, 2013) "In vivo Neutralization of α-cobratoxin With High-Affinity Llama Single-Domain Antibodies (VHHs) and a VHH-Fc Antibody," PLoS One. 8(7):e69495.
Rudnick, S.I. et al. (2009). "Affinity and Avidity in Antibody-Based Tumor Targeting," Cancer Biotherapy and Radiopharmaceuticals 24(2):155-161.
Slaga, D. et al. (Oct. 17, 2018). "Avidity-Based Binding to HER2 Results in Selective Killing of HER2-Overexpressing Cells by Anti-HER2/CD3," Science Translational Medicine, 10:eaat5775, 11 pages.
Wu, A.M. et al. (2001). "Multimerization of a Chimeric Anti-CD20 Single-Chain Fv-Fc Fusion Protein is Mediated Through Variable Domain Exchange," Protein Engineering 14(12):1025-1033.
Ying, T. et al. (Jun. 1, 2012). "Soluble Monomeric IgG1 Fc," Journal of Biological Chemistry, 287(23):19399-19408.
Bentley, G.A. et al. (1995). "The Structure of the Antigen-Binding Site of Immunoglobulins and T Cell Receptors," Annual Review of Immunology 146:277-290.
Bixby, K.A. et al. (1999). "Zn2+-Binding and Molecular Determinants of Tetramerization in Voltage-Gated K+ Channels," Nature Structural Biology 6(1):38-43.
Breitling, F. et al. (Aug. 1991). "A Surface Expression Vector for Antibody Screening," Gene 104(2):147-153.
Burton, D.R. et al. (Nov. 1991). "A Large Array of Human Monoclonal Antibodies to Type I Human Immunodeficiency Virus From Combinatorial Libraries of Asymptomatic Seropositive Individuals," Proc. Nat. Acad. Sci. USA 88(22):10134-10137.
Chang, C.N. et al. (Nov. 15, 1991). "Expression of Antibody Fab Domains on Bacteriophage Surfaces. Potential Use for Antibody Selection," Journal of Immunology 147(10):3610-3614.
Chaudhary, V.K. et al. (Feb. 1990). "A Rapid Method of Cloning Functional Variable-Region Antibody Genes in *Escherichia coli* as Single-Chain Immunotoxins," Proc. Nat. Acad. Sci. USA 87(3):1066-1070.
Chiswell, D.J. et al. (Mar. 1992). "Phage Antibodies: Will New 'Coliclonal' Antibodies Replace Monoclonal Antibodies?" TIBTECH 10(3):80-84.
Clackson, T. et al. (Aug. 15, 1991). "Making Antibody Fragments Using Phage Display Libraries," Nature 352:624-628.
Davis, M.M. et al. (Aug. 4, 1988). "T-Cell Antigen Receptor Genes and T-Cell Recognition," Nature 334:395-402.
Ding, X.-F. et al. (2008). Characterization and Expression of a Human KCTD1 Gene Containing the BTB Domain, Which Mediates Transcriptional Repression and Homomeric Interactions, DNA and Cell Biology 27(5):257-265.
Fujiwara, Y. et al. (Nov. 21, 2008). "X-ray Crystal Structure of a TRPM Assembly Domain Reveals an Antiparallel Four Stranded Coiled-Coil," Journal of Molecular Biology 383(4):854 870, 28 pages.
Genbank Accession No. NG-023272.2, 38 pages.
Hawkins, R.E. et al. (Mar. 1992). "Cell Selection Strategies for Making Antibodies From Variable Gene Libraries: Trapping the Memory Pool," European Journal of Immunology 22(3):867-870.
Herrin, B.R. et al. (Aug. 1, 2010). "Alternative Adaptive Immunity in Jawless Vertebrates," J Immunol 185(3):1367-1374.
Hoogenboom, H.R. et al. (1991) "Multi-Subunit Proteins on the Surface of Filamentous Phage: Methodologies for Displaying Antibody (Fab) Heavy and Light Chains," Nucleic Acids Research 19(15):4133-4137.
Hosse, R.J. et al. (Jan. 2006). "A New Generation of Protein Display Scaffolds for Molecular Recognition," Protein Science 15(1):14-27.
Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
Irving, R.A. (Feb. 1, 2001). "Ribosome Display and Affinity Maturation: From Antibodies to Single V-Domains and Steps Towards Cancer Therapeutics," Journal of Immunological Methods 248(1-2):31-45.
Jeffrey, P.D. et al. (Mar. 1995). "Crystal structure of Tetramerization Domain of the p53 Tumor Suppressor at 1.7 Angstroms," Science 267(5203):1498-1502.
Kang, A.S. et al. (May 1991). "Linkage of Recognition and Replication Functions by Assembling Combinatorial Antibody Fab Libraries Along Phage Surfaces," Proc. Natl. Acad. Sci. USA, 88:4363-4366.

(56) References Cited

OTHER PUBLICATIONS

Kohl, A. et al. (Feb. 18, 2003, e-pub. Feb. 2, 2003). "Designed to be Stable: Crystal Structure of a Consensus Ankyrin Repeat Protein," Proc. Natl. Acad. Sci. USA 100(4):1700-1705.
Lerner, R.A. et al. (Nov. 20,1992). "Antibodies Without Immunization," Science 258(5086):1313-1314.
Liu, Y. et al. (Apr. 2006). "The Tetramer Structure of the Nervy Homology Two Domain, NHR2, is Critical for AML1/ETO's Activity," Cancer Cell 9(4):249-260.
Lowman, H.B. et al. (1991). "Selecting High-Affinity Binding Proteins by Monovalent Phage Display," Biochemistry 30(45):10832-10838.
Marks et al.,"Molecular evolution of proteins on filamentous phage. Mimicking the strategy of the immune system," J Biol Chem. (1992) 267(23): 16007-16010.
Marks, J.D. et al. (1991). "By-Passing Immunization Human Antibodies from V-gene Libraries Displayed on Phage," J. Mol. Biol. 222:581-597.
McCafferty, J. et al. (Dec. 6, 1990). "Phage Antibodies: Filamentous Phage Displaying Antibody Variable Domains," Nature 348:552-554.
Moysey, R. et al. (Mar. 15, 2004). "Amplification and One-Step Expression Cloning of Human T Cell Receptor Genes," Analytical Biochemistry 326(2):284-286.
Panowski, S. et al. (2014, e-pub. Nov. 1, 2013). "Site-Specific Antibody Drug Conjugates for Cancer Therapy," mAbs 6(1):34-45.
Parker, M.H. et al. (Sep. 2005, e-pub. Aug. 8, 2005). "Antibody Mimics Based on Human Fibronectin Type Three Domain Engineered for Thermostability and High-Affinity Binding to Vascular Endothelial Growth Factor Receptor Two," Protein Eng. Des. Sel. 18(9):435-444.
Perez, H.L. et al. (Jul. 2014). "Antibody-Drug Conjugates: Current Status and Future Directions," Drug Discovery Today 19(7):869-881.
Reddy Chichili, V.P. et al. (2013, e-pub. Dec. 6, 2012). "Linkers in the Structural Biology of Protein-Protein Interactions," Protein Science 22(2):153-167.
Shao, C.-Y. et al. (Jan. 2007, e-pub. Feb. 24, 2006). "Rapid Isolation of igNAR Variable Single Domain Antibody Fragments From a Shark Synthetic Library," Molecular Immunology 44(4):656-665.
Silverman, J. et al. (Dec. 2005, e-pub. Nov. 20, 2005). "Multivalent Avimer Proteins Evolved by Exon Shuffling of a Family of Human Receptor Domains," Nature Biotechnology 23(12):1556-1561.
Skerra, A. (Oct. 18, 2000). "Lipocalins as a Scaffold," Biochimica et Biophysica Acta (BBA) 1482(1-2):337-350.
Thie, H. et al. (Jul. 22, 2009). "Multimerization Domains for Antibody Phage Display and Antibody Production," New Biotech. 26(6):314-321.
Tonegawa, S. (1988). "Somatic Generation of Immune Diversity," Bioscience Reports 8(1):3-26.
Walchli, S. et al. (Nov. 21, 2011). "A Practical Approach to T-Cell Receptor Cloning and Expression," PLoS One 6(11):e27930.
Wikman, M. et al. (May 2004, e-pub. Jun. 18, 2004). "Selection and Characterization of HER2/Neu-Binding Affibody Ligands," Protein Eng. Des. Sel. 17(5):455-462.
Young, P.A. et al. (Oct. 2014). "Antibody-Cytokine Fusion Proteins for Treatment of Cancer: Engineering Cytokines for Improved Efficacy and Safety," Seminars in Oncology 41(5):623-636, 19 pages.
Zahnd, C. et al. (Jun. 15, 2007, e-pub. Mar. 20, 2007). "A Designed Ankyrin Repeat Protein Evolved to Picomolar Affinity to Her2," J. Mol. Biol. 369(4):1015-1028.
Zhang, J. et al. (May 2009, e-pub. Oct. 26, 2008). "Transient Expression and Purification of Chimeric Heavy Chain Antibodies," Protein Expression and Purification 65(1):77-82.
Liu, H. et al. (Jan. 26, 2017). "Fc engineering for Developing Therapeutic Bispecific Antibodies and Novel Scaffolds," 8(38):1-15.
Willuda, J. et al. (Apr. 27, 2001). "Tumor Targeting of Mono-, Di, and Tetravalent Anti-p185HER-2 Miniatibodies Multimerized by Self-Associating Peptides," The Journal of Biological Chemistry 276(17):14385-14392.

* cited by examiner

FIG. 5 ts-NY-ESO-1 TCR

α-chain

MGWSCIILFLVATATGVHSKQEVTQIPAALSVPEGENLVLNCSFTDSAI
YNLQWFRQDPGKGLTSLLLITPWQREQTSGRLNASLDKSSGRSTLYIAA
SQPGDSATYLCAVRPLLDGTYIPTFGRGTSLIVHPYIQNPDPAVYQLRD
SKSSDKSVCLFTDFDSQTNVSQSKDSDVYITDKTVLDMRSMDFKSNSAV
AWSNKSDFACANAFNNSIIPEDTFFPSPESSRTVAAPSVFIFPPSDEQL
KSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 131)

β-chain

MGWSCIILFLVATATGVHSNAGVTQTPKFQVLKTGQSMTLQCAQDMNH
EYMSWYRQDPGMGIRLIHYSVAIQTDQGEVPNGYNVSRSTIEDFPLRL
LSAAPSQTSVYFCASSYLGNTGELFFGEGSRLITVLEDLNKVFPPEVAV
FEPSEAEISHTQKATLVCLATGFFPDHVELSWWVNGKEVHSGVSTDPQ
PLKEQPALNDSRYALSSRLRVSATFWQDPRNHFRCQVQFYGLSENDEW
TQDRAKPVTQIVSAEAWGRADASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVGGGSGGGGSGGGGSGGGGSLIDRE
WAEEWKHLDHLLNCIMDMVEKTRRSLTVLRRQEADREELNYWIRRYS
DAEHHHHHH (SEQ ID NO: 132)

FIG. 6

α-NY-ESO-1 TCR

α-chain

MGWSCIILFLVATATGVHSKQEVTQIPAALSVPEGENLVLNCSFTDSAIY
NLQWFRQDPGKGLTLSLLITPWQREQTSGRLNASLDKSSGRSTLYIAASQ
PGDSATYLCAVRPLLDGTYIPTFGRGTSLIVHPYIQNPDPAVYQLRDSKS
SDKSVCLFTDFDSQTNVSQSKDSDVYITDKTVLDMRSMDFKSNSAVAWSN
KSDFACANAFNNSIIPEDTFFPSPESSRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC  (SEQ ID NO: 133)

β-chain

MGWSCIILFLVATATGVHSNAGVTQTPKFQVLKTGQSMTLQCAQDMNHEY
MSWYRQDPGMGLRLIHYSVAIQTDQGEVPNGYNVSRSTIEDFPLRLLSAA
PSQTSVYFCASSYLGNTGELFGEGSRLTVLEDLNKVFPPEVAVFEPSEA
EISHTQKATLVCLATGFFPDHVELSWWVNGKEVHSGVSTDPQPLKEQPAL
NDSRYALSSRLRVSATFWQDPRNHFRCQVQFYGLSENDEWTQDRAKPVTQ
IVSAEAWGRADCASTKGPSVFPLAPSSKSTSGGTAALGCLVKDYFPEPVTV
SWNSGALTSGVHTFPAVLQSSGLYSLSSVVTVPSSSLGTQTYICNVNHKP
SNTKVDKKVEPKSCDKTHTCPPCPGGGGSGGGGSGGGGSGGGGSLTDREW
AEEWKHLDLLNCIMDMVEKTRRSLTVLRRCQEADREELNYWIRRYSDAE
HHHHHH  (SEQ ID NO: 134)

FIG. 9 ts-NY-ESO-1 TCR-iL2

α-chain

MGWSCIILFLVATATGVHSKQEVTQIPAALSVPEGENLVLNCSFTDSAI
YNLQWFRQDPGKGLTSLLLITPWQREQTSGRLNASLDKSSGRSTLYIAA
SQPGDSATYLCAVRPLLDGTYIPTFGRGTSLIVHPYIQNPDPAVYQLRD
SKSSDKSVCLFTDFDSQTNVSQSKDSDVYITDKTVLDMRSMDFKSNSAV
AWSNKSDFACANAFNNSIIPEDTFFPSPESSRTVAAPSVFIFPPSDEQL
KSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 135)

β-chain

MGWSCIILFLVATATGVHSNAGVTQTPKFQVLKTGQSMTLQCAQDMNHE
YMSWYRQDPGMGLRLIHYSVAIQTDQGEVPNGYNVSRSTIEDFPLRLLS
AAPSQTSVYFCASSYLGNIGELFFGEGSRLTVLEDLNKVFPPEVAVFEP
SEAEISHTQKATLVCLATGFFPDHVELSWWVNGKEVHSGVSTDPQPLKE
QPALNDSRYALSSRLRVSATFWQDPRNHFRCQVQFYGLSENDEWTQDRA
KPVTQIVSAEAWGRADASTKGPSVFPLAPSSKSTSGGTAALGCLVKDYF
PEPVTVSWNSGALTSGVHTFPAVLQSSGLYSLSSVVTVPSSSLGTQTYI
CNVNHKPSNTKVDKKVGGGGSGGGGSGGGGSGGGGSLTDREWAEEWKHL
DHLLNCIMDMVEKTRRSLTVLRRCQEADREELNYWIRRYSDAEGGGSG
GGGSGGGGSGGGGSAPTSSSTKKTQLQLEHLLLDLQMILNGINNYKNPK
LTRMLTFKFYMPKKATELKHLQCLEEELKPLEEVLNLAQSKNFHLRPRD
LISNINVIVLELKGSETTFMCEYADETATIVEFLNRWITFCQSIISTLT
HHHHHH (SEQ ID NO: 136)

FIG. 10 os-NY-ESO-1 TCR-iL2

α-chain

MGWSCIIFLVATATGVHSKQEVTQIPAALSVPEGENLVLNCSFTDSA
IYNLQWFRQDPGKGLTSLLLITPWQREQTSGRLNASLDKSSGRSTLYI
AASQPGDSATYLCAVRPLLDGTYIPTFGRGTSLIVHPYIQNPDPAVYQ
LRDSKSSDKSVCLFTDFDSQTNVSQSKDSDVYITDKTVLDMRSMDFKS
NSAVAWSNKSDFACANAFNNSIIPEDTFFPSPESSRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC (SEQ ID NO: 137)

β-chain

MGWSCIIFLVATATGVHSNAGVTQTPKFQVLKTGQSMTLQCAQDMNH
EYMSWYRQDPGMGLRLIHYSVAIQTDQGEVPNGYNVSRSTIEDFPLRL
LSAAPSQTSVYFCASSYLGNTGELFFGEGSRLTVLEDLNKVFPPEVAV
FEPSEAEISHTQKATLVCLATGFFPDHVELSWWVNGKEVHSGVSTDPQ
PLKEQPALNDSRYALSSRLRVSATFWQDPRNHFRCQVQFYGLSENDEW
TQDRAKPVTQIVSAEAWGRADASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPGGGSGGGGS
GGGSGGGGSLTDREWAEENKHLDHLLNCIMDMVEKTRSLTVLRRCQ
EADREELNYWIRRYSDAEGGGGSGGGGSGGGGSGGGGSAPTSSSTKKT
QLQLEHLLLDLQMILNGINNYKNPKLTRMLTFKFYMPKKATELKHLQC
LEEELKPLEEVLNLAQSKNFHLRPRDLISNINVIVLELKGSETTFMCE
YADETATIVEFLNRWITFCQSIISTLTHHHHHH (SEQ ID NO: 138)

FIG. 15A: Quad 16

FIG. 15A continued.

FIG. 15B: Quad 17

FIG. 15B continued

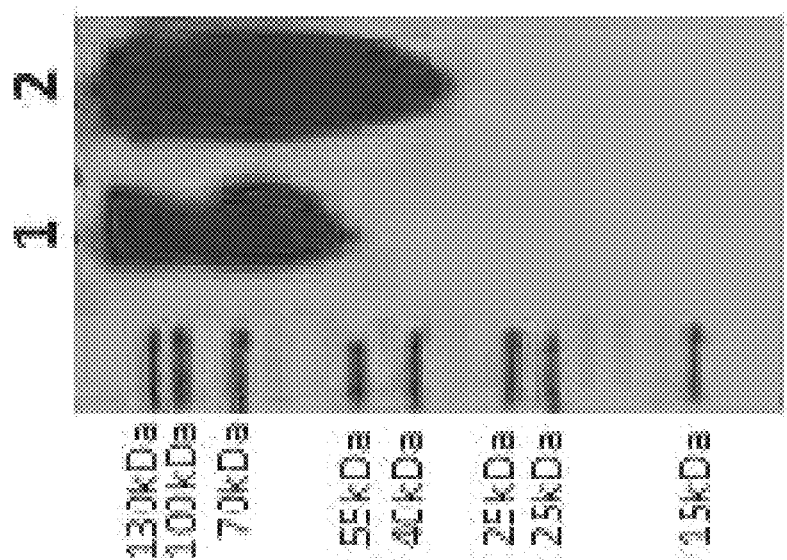
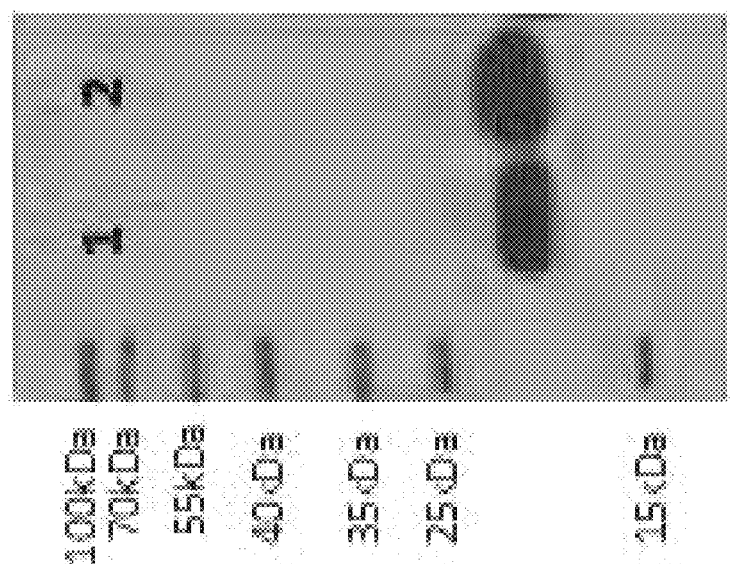
FIG. 20B
FIG. 20A

FIG. 21

| | | | | | | |
|---|---|---|---|---|---|---|
| Quad 1 | Leader | TRV$_b$ | TRC$_b$ | IgG1 CH1 | NHR2 TD | FLAG-HIS |
| Quad 2 | Leader | TRV$_b$ | TRC$_b$ | IgG1 CH1 | Linker$_{(G4S)}$ | NHR2 TD | FLAG-HIS |
| Quad 3 | Leader | TRV$_b$ | TRC$_b$* | IgG1 CH1 | NHR2 TD | FLAG-HIS |
| Quad 4 | Leader | TRV$_b$ | TRC$_b$* | IgG1 CH1 | Linker$_{(G4S)}$ | NHR2 TD | FLAG-HIS |
| Quad 5 | Leader | TRV$_b$ | TRC$_b$* | NHR2 TD | FLAG-HIS |
| Quad 6 | Leader | TRV$_b$ | TRC$_b$* | Linker$_{(G4S)}$ | NHR2 TD | FLAG-HIS |
| Quad 7 | Leader | TRV$_a$ | TRC$_a$ | C$_k$ |
| Quad 8 | Leader | TRV$_a$ | TRC$_a$* | C$_k$ |
| Quad 9 | Leader | TRV$_a$ | TRC$_a$* |
| Quad 10 | Leader | TRV$_b$ | TRC$_b$ | IgG1 CH1 | NHR2 TD | IL2 | FLAG-HIS |
| Quad 11 | Leader | TRV$_b$ | TRC$_b$ | IgG1 CH1 | Linker$_{(G4S)}$ | NHR2 TD | IL2 | FLAG-HIS |

FIG. 21 (continued)

| | | | | | | | | | | | | | |
|---|---|---|---|---|---|---|---|---|---|---|---|---|---|
| Quad 12 | Leader | TRV$_\beta$ | TRC$_\beta$ | IgG1 CH1 | Hinge | NHR2 TD | FLAG-HIS | | | | | | |
| Quad 13 | Leader | TRV$_\beta$ | TRC$_\beta$ | IgG1 CH1 | Hinge | Linker$_{(G4S)}$ | NHR2 TD | FLAG-HIS | | | | | |
| Quad 14 | Leader | VHH GFP | NHR2 TD | FLAG-HIS | | | | | | | | | |
| Quad 15 | Leader | VHH GFP | Linker$_{(G4S)}$ | NHR2 TD | FLAG-HIS | | | | | | | | |
| Quad 18 | Leader | VHH GFP | NHR2 TD | IL2 | FLAG-HIS | | | | | | | | |
| Quad 19 | Leader | VHH GFP | Linker$_{(G4S)}$ | NHR2 TD | IL2 | FLAG-HIS | | | | | | | |
| Quad 20 | Leader | TRV$_\alpha$ | TRC$_\alpha$ | IgG1 CH1 | NHR2* TD | FLAG-HIS | | | | | | | |
| Quad 21 | Leader | TRV$_\beta$ | TRC$_\beta$ | IgG1 CH1 | Linker$_{(G4S)}$ | NHR2* TD | FLAG-HIS | | | | | | |
| Quad 22 | Leader | TRV$_\alpha$ | TRC$_\alpha$ | C$_\kappa$ | | | | | | | | | |
| Quad 23 | Leader | VH | IgG1 CH1 | NHR2 TD | FLAG-HIS | | | | | | | | |
| Quad 24 | Leader | VH | IgG1 CH1 | Linker$_{(G4S)}$ | NHR2 TD | FLAG-HIS | | | | | | | |
| Quad 25 | Leader | V$_\kappa$ | CL | | | | | | | | | | |
| Quad 26 | Leader | VH | IgG1 CH1 | Hinge | NHR2 TD | FLAG-HIS | | | | | | | |

FIG. 21 (continued)

| | Leader | | | | | | | |
|---|---|---|---|---|---|---|---|---|
| Quad 27 | Leader | VH | IgG1 CH1 | Hinge | Linker(G4S) | NHR2 TD | FLAG-HIS | |
| Quad 28 | Leader | VH_Humira | IgG1 CH1 | NHR2* | FLAG-HIS | | | |
| Quad 29 | Leader | VH_Humira | IgG1 CH1 | Linker(G4S) | NHR2* | FLAG-HIS | | |
| Quad 30 | Leader | Vk_Humira | CL | | | | | |
| Quad 31 | Leader | VH_Humira | IgG1 CH1 | NHR2* | FLAG-HIS | | | |
| Quad 32 | Leader | VH_Humira | IgG1 CH1 | Linker(G4S) | NHR2* | FLAG-HIS | | |
| Quad 33 | Leader | Vk_Humira | CL | | | | | |
| Quad 34 | Leader | Vk_TNFa | Linker(G4S) | NHR2* | FLAG-HIS | | | |
| Quad 36 | Leader | VH_TNFR1 | Linker(G4S) | NHR2* | FLAG-HIS | | | |
| Quad 38 | Leader | Vk_EGFR | Linker(G4S) | NHR2* | FLAG-HIS | | | |
| Quad 40 | Leader | Vk_IGF1R | Linker(G4S) | NHR2* | FLAG-HIS | | | |
| Quad 42 | Leader | Vk_VEGF | Linker(G4S) | NHR2* | Vk_CD138 | FLAG-HIS | | |
| Quad 44 | Leader | Vk_CD138 | Linker(G4S) | NHR2* | FLAG-HIS | | | |
| Quad 46 | Leader | Vk_CD138 | Linker(G4S) | NHR2* | Vk_CD138 | FLAG-HIS | | |

SEQUENCE LISTING

<160> NUMBER OF SEQ ID NOS: 144

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser

```
225                 230                 235                 240
Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 2
<211> LENGTH: 341
<212> TYPE: PRT
<213> ORGANISM: Homo sapiens

<400> SEQUENCE: 2

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205
```

```
Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

Gln Lys Glu Asn Cys
            340

<210> SEQ ID NO 3
<211> LENGTH: 346
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240
```

```
Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser
            340                 345

<210> SEQ ID NO 4
<211> LENGTH: 354
<212> TYPE: PRT
<213> ORGANISM: Homo sapiens

<400> SEQUENCE: 4

Met Asp Asp Leu Met Leu Ser Pro Asp Ile Glu Gln Trp Phe Thr
1               5                   10                  15

Glu Asp Pro Gly Pro Asp Glu Ala Pro Arg Met Pro Glu Ala Ala Pro
                20                  25                  30

Pro Val Ala Pro Ala Pro Ala Ala Pro Thr Pro Ala Ala Pro Ala Pro
            35                  40                  45

Ala Pro Ser Trp Pro Leu Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
```

```
                        260                 265                 270
Thr Ser Ser Ser Pro Gln Pro Lys Lys Lys Pro Leu Asp Gly Glu Tyr
            275                 280                 285
Phe Thr Leu Gln Ile Arg Gly Arg Glu Arg Phe Glu Met Phe Arg Glu
            290                 295                 300
Leu Asn Glu Ala Leu Glu Leu Lys Asp Ala Gln Ala Gly Lys Glu Pro
305                 310                 315                 320
Gly Gly Ser Arg Ala His Ser Ser His Leu Lys Ser Lys Lys Gly Gln
                    325                 330                 335
Ser Thr Ser Arg His Lys Lys Leu Met Phe Lys Thr Glu Gly Pro Asp
                    340                 345                 350
Ser Asp

<210> SEQ ID NO 5
<211> LENGTH: 302
<212> TYPE: PRT
<213> ORGANISM: Homo sapiens

<400> SEQUENCE: 5

Met Asp Asp Leu Met Leu Ser Pro Asp Asp Ile Glu Gln Trp Phe Thr
1               5                   10                  15
Glu Asp Pro Gly Pro Asp Glu Ala Pro Arg Met Pro Glu Ala Ala Pro
                20                  25                  30
Pro Val Ala Pro Ala Pro Ala Ala Pro Thr Pro Ala Ala Pro Ala Pro
            35                  40                  45
Ala Pro Ser Trp Pro Leu Ser Ser Ser Val Pro Ser Gln Lys Thr Tyr
50                  55                  60
Gln Gly Ser Tyr Gly Phe Arg Leu Gly Phe Leu His Ser Gly Thr Ala
65                  70                  75                  80
Lys Ser Val Thr Cys Thr Tyr Ser Pro Ala Leu Asn Lys Met Phe Cys
                85                  90                  95
Gln Leu Ala Lys Thr Cys Pro Val Gln Leu Trp Val Asp Ser Thr Pro
                100                 105                 110
Pro Pro Gly Thr Arg Val Arg Ala Met Ala Ile Tyr Lys Gln Ser Gln
            115                 120                 125
His Met Thr Glu Val Val Arg Arg Cys Pro His His Glu Arg Cys Ser
            130                 135                 140
Asp Ser Asp Gly Leu Ala Pro Pro Gln His Leu Ile Arg Val Glu Gly
145                 150                 155                 160
Asn Leu Arg Val Glu Tyr Leu Asp Asp Arg Asn Thr Phe Arg His Ser
                165                 170                 175
Val Val Val Pro Tyr Glu Pro Pro Glu Val Gly Ser Asp Cys Thr Thr
                180                 185                 190
Ile His Tyr Asn Tyr Met Cys Asn Ser Ser Cys Met Gly Gly Met Asn
            195                 200                 205
Arg Arg Pro Ile Leu Thr Ile Ile Thr Leu Glu Asp Ser Ser Gly Asn
            210                 215                 220
Leu Leu Gly Arg Asn Ser Phe Glu Val Arg Val Cys Ala Cys Pro Gly
225                 230                 235                 240
Arg Asp Arg Arg Thr Glu Glu Asn Leu Arg Lys Lys Gly Glu Pro
                245                 250                 255
His His Glu Leu Pro Pro Gly Ser Thr Lys Arg Ala Leu Pro Asn Asn
            260                 265                 270
Thr Ser Ser Ser Pro Gln Pro Lys Lys Lys Pro Leu Asp Gly Glu Tyr
```

```
                275                 280                 285
Phe Thr Leu Gln Asp Gln Thr Ser Phe Gln Lys Glu Asn Cys
    290                 295                 300

<210> SEQ ID NO 6
<211> LENGTH: 307
<212> TYPE: PRT
<213> ORGANISM: Homo sapiens

<400> SEQUENCE: 6

Met Asp Asp Leu Met Leu Ser Pro Asp Ile Glu Gln Trp Phe Thr
1               5                   10                  15

Glu Asp Pro Gly Pro Asp Glu Ala Pro Arg Met Pro Glu Ala Ala Pro
                20                  25                  30

Pro Val Ala Pro Ala Pro Ala Ala Pro Thr Pro Ala Ala Pro Ala Pro
            35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
                100                 105                 110

Pro Pro Gly Thr Arg Val Arg Ala Met Ala Ile Tyr Lys Gln Ser Gln
            115                 120                 125

His Met Thr Glu Val Val Arg Arg Cys Pro His His Glu Arg Cys Ser
130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
            195                 200                 205

Arg Arg Pro Ile Leu Thr Ile Ile Thr Leu Glu Asp Ser Ser Gly Asn
210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
            275                 280                 285

Phe Thr Leu Gln Met Leu Leu Asp Leu Arg Trp Cys Tyr Phe Leu Ile
    290                 295                 300

Asn Ser Ser
305

<210> SEQ ID NO 7
<211> LENGTH: 261
<212> TYPE: PRT
<213> ORGANISM: Homo sapiens
```

<400> SEQUENCE: 7

```
Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
            115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
            195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp
            260
```

<210> SEQ ID NO 8
<211> LENGTH: 209
<212> TYPE: PRT
<213> ORGANISM: Homo sapiens

<400> SEQUENCE: 8

```
Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95
```

```
Cys Thr Thr Ile His Tyr Asn Tyr Met Cys Asn Ser Ser Cys Met Gly
                100                 105                 110

Gly Met Asn Arg Arg Pro Ile Leu Thr Ile Ile Thr Leu Glu Asp Ser
            115                 120                 125

Ser Gly Asn Leu Leu Gly Arg Asn Ser Phe Glu Val Arg Val Cys Ala
        130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Asp Gln Thr Ser Phe Gln Lys Glu Asn
        195                 200                 205

Cys

<210> SEQ ID NO 9
<211> LENGTH: 214
<212> TYPE: PRT
<213> ORGANISM: Homo sapiens

<400> SEQUENCE: 9

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
                100                 105                 110

Gly Met Asn Arg Arg Pro Ile Leu Thr Ile Ile Thr Leu Glu Asp Ser
            115                 120                 125

Ser Gly Asn Leu Leu Gly Arg Asn Ser Phe Glu Val Arg Val Cys Ala
        130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210

<210> SEQ ID NO 10
<211> LENGTH: 32
<212> TYPE: PRT
<213> ORGANISM: Homo sapiens
```

<400> SEQUENCE: 10

Gly Glu Tyr Phe Thr Leu Gln Ile Arg Gly Arg Glu Arg Phe Glu Met
1               5                   10                  15

Phe Arg Glu Leu Asn Glu Ala Leu Glu Leu Lys Asp Ala Gln Ala Gly
                20                  25                  30

<210> SEQ ID NO 11
<211> LENGTH: 50
<212> TYPE: PRT
<213> ORGANISM: Homo sapiens

<400> SEQUENCE: 11

Arg Ser Pro Asp Asp Glu Leu Leu Tyr Leu Pro Val Arg Gly Arg Glu
1               5                   10                  15

Thr Tyr Glu Met Leu Leu Lys Ile Lys Glu Ser Leu Glu Leu Met Gln
                20                  25                  30

Tyr Leu Pro Gln His Thr Ile Glu Thr Tyr Arg Gln Gln Gln Gln Gln
            35                  40                  45

Gln His
    50

<210> SEQ ID NO 12
<211> LENGTH: 42
<212> TYPE: PRT
<213> ORGANISM: Homo sapiens

<400> SEQUENCE: 12

Lys Lys Arg Arg His Gly Asp Glu Asp Thr Tyr Tyr Leu Gln Val Arg
1               5                   10                  15

Gly Arg Glu Asn Phe Glu Ile Leu Met Lys Leu Lys Glu Ser Leu Glu
                20                  25                  30

Leu Met Glu Leu Val Pro Gln Pro Leu Val
            35                  40

<210> SEQ ID NO 13
<211> LENGTH: 1290
<212> TYPE: DNA
<213> ORGANISM: Artificial Sequence
<220> FEATURE:
<223> OTHER INFORMATION: Synthetic Construct

<400> SEQUENCE: 13
atgagcctcg ggctcctgtg ctgtggggcc ttttctctcc tgtgggcagg tccagtgaat      60
gccggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttgcc atccagacaa ctgaccaagg agaagtcccc     240
aatggctaca atgtctccag atcaaccatc gaggatttcc cgctcaggct gctgtcggct     300
gctccctccc agacatctgt gtacttctgt gccagcagtt acctggggaa caccggggag     360
ctgtttttg gagaaggctc taggctgacc gtactggagg acctgaaaaa cgtgttccca     420
cccgaggtcg ctgtgtttga gccatcagaa gcagagatct cccacaccca aaaggccaca     480
ctggtgtgcc tggccacagg cttctacccc gaccatgtgg agctgagctg gtgggtgaat     540
gggaaggagg tgcacagtgg ggtcagcaca gacccgcagc cctcaaggag cagcccgcc     600
ctcaatgact ccagatacgc tctgagcagc cgcctgaggg tctcggccac cttctggcag     660
gaccccgcga accacttccg ctgtcaagtc cagttctacg ggctctcgga gaatgacgag     720

```
tggacccagg ataggGccaa acccgtcacc cagatcgtca gcgccgaggc ctggggtaga     780
gcagacgcca gcaccaaggg cccctctgtg ttccctctgg ccccttccag caagtccacc     840
tctggcggaa cagccgctct gggctgcctc gtgaaggact acttccccga gcctgtgacc     900
gtgtcctgga actctggcgc tctgaccagc ggagtgcaca ccttccctgc tgtgctgcag     960
tcctccggcc tgtactccct gtcctccgtc gtgaccgtgc cttccagctc tctgggcacc    1020
cagacctaca tctgcaacgt gaaccacaag ccctccaaca ccaaggtgga caagaaggtg    1080
ctaacagaca gagaatgggc agaagagtgg aaacatcttg accatctgtt aaactgcata    1140
atggacatgg tagaaaaaac aaggcgatct ctcaccgtac taaggcggtg tcaagaagca    1200
gaccgggaag aattgaatta ctggatccgg cggtacagtg acgccgagga ctacaaggac    1260
gacgacgaca agcaccacca ccatcaccac                                     1290

<210> SEQ ID NO 14
<211> LENGTH: 1305
<212> TYPE: DNA
<213> ORGANISM: Artificial Sequence
<220> FEATURE:
<223> OTHER INFORMATION: Synthetic Construct

<400> SEQUENCE: 14
atgagcctcg ggctcctgtg ctgtgggggcc ttttctctcc tgtgggcagg tccagtgaat      60
gccggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttgcc atccagacaa ctgaccaagg agaagtcccc    240
aatggctaca atgtctccag atcaaccatc gaggatttcc cgctcaggct gctgtcggct    300 gctcccctccc agacatctgt gtacttctgt gccagcagtt acctggggaa caccggggag    360 ctgtttttg gagaaggctc taggctgacc gtactggagg acctgaaaaa cgtgttccca    420
cccgaggtcg ctgtgtttga gccatcagaa gcagagatct cccacaccca aaaggccaca    480
ctggtgtgcc tggccacagg cttctacccc gaccatgtgg agctgagctg gtgggtgaat    540
gggaaggagg tgcacagtgg ggtcagcaca gaccgcagc ccctcaagga gcagcccgcc    600
ctcaatgact ccagatacgc tctgagcagc cgcctgaggg tctcggccac cttctggcag    660
gacccccgca accacttccg ctgtcaagtc cagttctacg gcctctcgga gaatgacgag    720
tggacccagg ataggGccaa acccgtcacc cagatcgtca gcgccgaggc ctggggtaga    780
gcagacgcca gcaccaaggg cccctctgtg ttccctctgg ccccttccag caagtccacc    840
tctggcggaa cagccgctct gggctgcctc gtgaaggact acttccccga gcctgtgacc    900
gtgtcctgga actctggcgc tctgaccagc ggagtgcaca ccttccctgc tgtgctgcag    960
tcctccggcc tgtactccct gtcctccgtc gtgaccgtgc cttccagctc tctgggcacc   1020
cagacctaca tctgcaacgt gaaccacaag ccctccaaca ccaaggtgga caagaaggtg   1080
ggaggaggtg ggagcctaac agacagagaa tgggcagaag agtggaaaca tcttgaccat   1140
ctgttaaact gcataatgga catggtagaa aaacaaggc gatctctcac cgtactaagg    1200
cggtgtcaag aagcagaccg ggaagaattg aattactgga tccggcggta cagtgacgcc   1260
gaggactaca aggacgacga cgacaagcac caccaccatc accac                   1305

<210> SEQ ID NO 15
<211> LENGTH: 1290
<212> TYPE: DNA
<213> ORGANISM: Artificial Sequence
```

<220> FEATURE:
<223> OTHER INFORMATION: Synthetic Construct

<400> SEQUENCE: 15

```
atgagcctcg ggctcctgtg ctgtggggcc ttttctctcc tgtgggcagg tccagtgaat    60
gccggtgtca ctcagacccc aaaattccag gtcctgaaga caggacagag catgacactg   120
cagtgtgccc aggatatgaa ccatgaatac atgtcctggt atcgacaaga cccaggcatg   180
gggctgaggc tgattcatta ctcagttgcc atccagacaa ctgaccaagg agaagtcccc   240
aatggctaca atgtctccag atcaaccatc gaggatttcc cgctcaggct gctgtcggct   300
gctcccctccc agacatctgt gtacttctgt gccagcagtt acctggggaa caccggggag   360
ctgttttttg gagaaggctc taggctgacc gtactggagg acctgaaaaa cgtgttccca   420
cccgaggtcg ctgtgtttga gccatcagaa gcagagatct cccacaccca aaaggccaca   480
ctggtgtgcc tggccacagg cttctacccc gaccatgtgg agctgagctg gtgggtgaat   540
gggaaggagg tgcacagtgg ggtctgcaca gacccgcagc ccctcaagga gcagcccgcc   600
ctcaatgact ccagatacgc tctgagcagc cgcctgaggg tctcggccac cttctggcag   660
gacccccgca accacttccg ctgtcaagtc cagttctacg gctctcgga gaatgacgag   720
tggacccagg atagggccaa acccgtcacc cagatcgtca gcgccgaggc tggggtaga   780
gcagacgcca gcaccaaggg cccctctgtg ttccctctgg cccctccag caagtccacc   840
tctggcggaa cagccgctct gggctgcctc gtgaaggact acttccccga gcctgtgacc   900
gtgtcctgga actctggcgc tctgaccagc ggagtgcaca ccttccctgc tgtgctgcag   960
tcctccggcc tgtactccct gtcctccgtc gtgaccgtgc cttccagctc tctgggcacc  1020
cagacctaca tctgcaacgt gaaccacaag ccctccaaca ccaaggtgga caagaaggtg  1080
ctaacagaca gagaatgggc agaagagtgg aaacatcttg accatctgtt aaactgcata  1140
atggacatgg tagaaaaaac aaggcgatct ctcaccgtac taaggcggtg tcaagaagca  1200
gaccgggaag aattgaatta ctggatccgg cggtacagtg acgccgagga ctacaaggac  1260
gacgacgaca agcaccacca ccatcaccac                                    1290
```

<210> SEQ ID NO 16
<211> LENGTH: 1305
<212> TYPE: DNA
<213> ORGANISM: Artificial Sequence
<220> FEATURE:
<223> OTHER INFORMATION: Synthetic Construct

<400> SEQUENCE: 16

```
atgagcctcg ggctcctgtg ctgtggggcc ttttctctcc tgtgggcagg tccagtgaat    60
gccggtgtca ctcagacccc aaaattccag gtcctgaaga caggacagag catgacactg   120
cagtgtgccc aggatatgaa ccatgaatac atgtcctggt atcgacaaga cccaggcatg   180
gggctgaggc tgattcatta ctcagttgcc atccagacaa ctgaccaagg agaagtcccc   240
aatggctaca atgtctccag atcaaccatc gaggatttcc cgctcaggct gctgtcggct   300
gctcccctccc agacatctgt gtacttctgt gccagcagtt acctggggaa caccggggag   360
ctgttttttg gagaaggctc taggctgacc gtactggagg acctgaaaaa cgtgttccca   420
cccgaggtcg ctgtgtttga gccatcagaa gcagagatct cccacaccca aaaggccaca   480
ctggtgtgcc tggccacagg cttctacccc gaccatgtgg agctgagctg gtgggtgaat   540
gggaaggagg tgcacagtgg ggtctgcaca gacccgcagc ccctcaagga gcagcccgcc   600
```

| | |
|---|---|
| ctcaatgact ccagatacgc tctgagcagc cgcctgaggg tctcggccac cttctggcag | 660 |
| gaccccgca accacttccg ctgtcaagtc cagttctacg ggctctcgga gaatgacgag | 720 |
| tggacccagg atagggccaa accgtcacc cagatcgtca gcgccgaggc ctggggtaga | 780 |
| gcagacgcca gcaccaaggg cccctctgtg ttccctctgg ccccttccag caagtccacc | 840 |
| tctggcggaa cagccgctct gggctgcctc gtgaaggact acttccccga gcctgtgacc | 900 |
| gtgtcctgga actctggcgc tctgaccagc ggagtgcaca ccttccctgc tgtgctgcag | 960 |
| tcctccggcc tgtactccct gtcctccgtc gtgaccgtgc cttccagctc tctgggcacc | 1020 |
| cagacctaca tctgcaacgt gaaccacaag ccctccaaca ccaaggtgga caagaaggtg | 1080 |
| ggaggaggtg ggagcctaac agacagagaa tgggcagaag agtggaaaca tcttgaccat | 1140 |
| ctgttaaact gcataatgga catggtagaa aaaacaaggc gatctctcac cgtactaagg | 1200 |
| cggtgtcaag aagcagaccg ggaagaattg aattactgga tccggcggta cagtgacgcc | 1260 |
| gaggactaca aggacgacga cgacaagcac caccaccatc accac | 1305 |

<210> SEQ ID NO 17
<211> LENGTH: 996
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| atgagcctcg ggctcctgtg ctgtgggcc ttttctctcc tgtgggcagg tccagtgaat | 60 |
| gccggtgtca ctcagacccc aaaattccag gtcctgaaga caggacagag catgacactg | 120 |
| cagtgtgccc aggatatgaa ccatgaatac atgtcctggt atcgacaaga cccaggcatg | 180 |
| gggctgaggc tgattcatta ctcagttgcc atccagacaa ctgaccaagg agaagtcccc | 240 |
| aatggctaca atgtctccag atcaaccatc gaggatttcc cgctcaggct gctgtcggct | 300 |
| gctcccctccc agacatctgt gtacttctgt gccagcagtt acctggggaa caccggggag | 360 |
| ctgttttttg gagaaggctc taggctgacc gtactggagg acctgaaaaa cgtgttccca | 420 |
| cccgaggtcg ctgtgtttga gccatcagaa gcagagatcc ccacaccca aaaggccaca | 480 |
| ctggtgtgcc tggccacagg cttctacccc gaccatgtgg agctgagctg gtgggtgaat | 540 |
| gggaaggagg tgcacagtgg ggtctgcaca gacccgcagc ccctcaagga gcagcccgcc | 600 |
| ctcaatgact ccagatacgc tctgagcagc cgcctgaggg tctcggccac cttctggcag | 660 |
| gaccccgca accacttccg ctgtcaagtc cagttctacg ggctctcgga gaatgacgag | 720 |
| tggacccagg atagggccaa accgtcacc cagatcgtca gcgccgaggc ctggggtaga | 780 |
| gcagacctaa cagacagaga atgggcagaa gagtggaaac atcttgacca tctgttaaac | 840 |
| tgcataatgg acatggtaga aaaaacaagg cgatctctca ccgtactaag gcggtgtcaa | 900 |
| gaagcagacc gggaagaatt gaattactgg atccggcggt acagtgacgc cgaggactac | 960 |
| aaggacgacg acgacaagca ccaccaccat caccac | 996 |

<210> SEQ ID NO 18
<211> LENGTH: 1011
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| atgagcctcg ggctcctgtg ctgtgggcc ttttctctcc tgtgggcagg tccagtgaat | 60 |

```
gccggtgtca ctcagacccc aaaattccag gtcctgaaga caggacagag catgacactg        120
cagtgtgccc aggatatgaa ccatgaatac atgtcctggt atcgacaaga cccaggcatg        180
gggctgaggc tgattcatta ctcagttgcc atccagacaa ctgaccaagg agaagtcccc        240
aatggctaca atgtctccag atcaaccatc gaggatttcc cgctcaggct gctgtcggct        300
gctccctccc agacatctgt gtacttctgt gccagcagtt acctggggaa caccggggag        360
ctgttttttg gagaaggctc taggctgacc gtactggagg acctgaaaaa cgtgttccca        420
cccgaggtcg ctgtgtttga gccatcagaa gcagagatct cccacaccca aaaggccaca        480
ctggtgtgcc tggccacagg cttctacccc gaccatgtgg agctgagctg gtgggtgaat        540
gggaaggagg tgcacagtgg ggtctgcaca gacccgcagc ccctcaagga gcagcccgcc        600
ctcaatgact ccagatacgc tctgagcagc gcctgaggg tctcggccac cttctggcag         660 gaccccgca accacttccg ctgtcaagtc cagttctacg ggctctcgga gaatgacgag         720
tggacccagg atagggccaa acccgtcacc cagatcgtca cgccgaggc ctggggtaga          780 gcagacggag gaggtgggag cctaacagac agagaatggg cagaagagtg gaaacatctt        840
gaccatctgt taaactgcat aatggacatg gtagaaaaaa caaggcgatc tctcaccgta        900
ctaaggcggt gtcaagaagc agaccgggaa gaattgaatt actggatccg gcggtacagt        960
gacgccgagg actacaagga cgacgacgac aagcaccacc accatcacca c                 1011
```

<210> SEQ ID NO 19
<211> LENGTH: 999
<212> TYPE: DNA
<213> ORGANISM: Artificial Sequence
<220> FEATURE:
<223> OTHER INFORMATION: Synthetic Construct

<400> SEQUENCE: 19

```
atggagaccc tcttgggcct gcttatcctt tggctgcagc tgcaatgggt gagcagcaaa         60
caggaggtga cacagattcc tgcagctctg agtgtcccag aaggagaaaa cttggttctc        120
aactgcagtt tcactgatag cgctatttac aacctccagt ggtttaggca ggaccctggg        180
aaaggtctca catctctgtt gcttattaca ccttggcaga gagagcaaac aagtggaaga        240
cttaatgcct cgctggataa atcatcagga cgtagtactt tatacattgc agcttctcag        300
cctggtgact cagccaccta cctctgtgct gtgaggcccc tgcttgacgg aacatacata        360
cctacatttg gaagaggaac cagccttatt gttcatccgt atatccagaa ccctgaccct        420
gccgtgtacc agctgagaga ctctaaatcc agtgacaagt ctgtctgcct attcaccgat        480
tttgattctc aaacaaatgt gtcacaaagt aaggattctg atgtgtatat cacagacaaa        540
actgtgctag acatgaggtc tatggacttc aagagcaaca gtgctgtggc ctggagcaac        600
aaatctgact ttgcatgtgc aaacgccttc aacaacagca ttattccaga agacaccttc        660
ttccccagcc agaaagttc acggtggcc gctccctccg tgttcatctt cccaccttcc          720
gacgagcagc tgaagtccgg caccgcttct gtcgtgtgcc tgctgaacaa cttctacccc        780
cgcgaggcca aggtgcagtg gaaggtggac aacgccctgc agtccggcaa ctcccaggaa        840
tccgtgaccg agcaggactc caaggacagc acctactccc tgtcctccac cctgaccctg        900
tccaaggccg actacgagaa gcacaaggtg tacgcctgcg aagtgaccca ccagggcctg        960
tctagccccg tgaccaagtc tttcaaccgg ggcgagtgt                                999
```

<210> SEQ ID NO 20

<211> LENGTH: 999
<212> TYPE: DNA
<213> ORGANISM: Artificial Sequence
<220> FEATURE:
<223> OTHER INFORMATION: Synthetic Construct

<400> SEQUENCE: 20

```
atggagaccc tcttgggcct gcttatcctt tggctgcagc tgcaatgggt gagcagcaaa    60
caggaggtga cacagattcc tgcagctctg agtgtcccag aaggagaaaa cttggttctc   120
aactgcagtt tcactgatag cgctatttac aacctccagt ggtttaggca ggaccctggg   180
aaaggtctca catctctgtt gcttattaca ccttggcaga gagagcaaac aagtggaaga   240
cttaatgcct cgctggataa atcatcagga cgtagtactt tatacattgc agcttctcag   300
cctggtgact cagccaccta cctctgtgct gtgaggcccc tgcttgacgg aacatacata   360
cctacatttg gaagaggaac cagccttatt gttcatccgt atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
tgtgtgctag acatgaggtc tatggacttc aagagcaaca gtgctgtggc ctggagcaac   600
aaatctgact ttgcatgtgc aaacgccttc aacaacagca ttattccaga agacaccttc   660
ttccccagcc agaaagttc acggtggcc gctccctccg tgttcatctt cccaccttcc   720
gacgagcagc tgaagtccgg caccgcttct gtcgtgtgcc tgctgaacaa cttctacccc   780
cgcgaggcca aggtgcagtg gaaggtggac aacgccctgc agtccggcaa ctcccaggaa   840
tccgtgaccg agcaggactc caaggacagc acctactccc tgtcctccac cctgaccctg   900
tccaaggccg actacgagaa gcacaaggtg tacgcctgcg aagtgaccca ccagggcctg   960
tctagccccg tgaccaagtc tttcaaccgg ggcgagtgt                          999
```

<210> SEQ ID NO 21
<211> LENGTH: 681
<212> TYPE: DNA
<213> ORGANISM: Artificial Sequence
<220> FEATURE:
<223> OTHER INFORMATION: Synthetic Construct

<400> SEQUENCE: 21

```
atggagaccc tcttgggcct gcttatcctt tggctgcagc tgcaatgggt gagcagcaaa    60
caggaggtga cacagattcc tgcagctctg agtgtcccag aaggagaaaa cttggttctc   120
aactgcagtt tcactgatag cgctatttac aacctccagt ggtttaggca ggaccctggg   180
aaaggtctca catctctgtt gcttattaca ccttggcaga gagagcaaac aagtggaaga   240
cttaatgcct cgctggataa atcatcagga cgtagtactt tatacattgc agcttctcag   300
cctggtgact cagccaccta cctctgtgct gtgaggcccc tgcttgacgg aacatacata   360
cctacatttg gaagaggaac cagccttatt gttcatccgt atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
tgtgtgctag acatgaggtc tatggacttc aagagcaaca gtgctgtggc ctggagcaac   600
aaatctgact ttgcatgtgc aaacgccttc aacaacagca ttattccaga agacaccttc   660
ttccccagcc agaaagttc c                                              681
```

<210> SEQ ID NO 22
<211> LENGTH: 1689

<212> TYPE: DNA
<213> ORGANISM: Artificial Sequence
<220> FEATURE:
<223> OTHER INFORMATION: Synthetic Construct

<400> SEQUENCE: 22

| | |
|---|---|
| atgagcctcg ggctcctgtg ctgtggggcc ttttctctcc tgtgggcagg tccagtgaat | 60 |
| gccggtgtca ctcagacccc aaaattccag gtcctgaaga caggacagag catgacactg | 120 |
| cagtgtgccc aggatatgaa ccatgaatac atgtcctggt atcgacaaga cccaggcatg | 180 |
| gggctgaggc tgattcatta ctcagttgcc atccagacaa ctgaccaagg agaagtcccc | 240 |
| aatggctaca atgtctccag atcaaccatc gaggatttcc cgctcaggct gctgtcggct | 300 |
| gctccctccc agacatctgt gtacttctgt gccagcagtt acctggggaa caccggggag | 360 |
| ctgttttttg gagaaggctc taggctgacc gtactggagg acctgaaaaa cgtgttccca | 420 |
| cccgaggtcg ctgtgtttga gccatcagaa gcagagatct cccacaccca aaaggccaca | 480 |
| ctggtgtgcc tggccacagg cttctacccc gaccatgtgg agctgagctg gtgggtgaat | 540 |
| gggaaggagg tgcacagtgg ggtcagcaca gacccgcagc ccctcaagga gcagcccgcc | 600 |
| ctcaatgact ccagatacgc tctgagcagc gcctgaggg tctcggccac cttctggcag | 660 |
| gaccccgca accacttccg ctgtcaagtc cagttctacg gctctcgga gaatgacgag | 720 |
| tggacccagg atagggccaa acccgtcacc cagatcgtca gcgccgaggc tggggtaga | 780 |
| gcagacgcca gcaccaaggg cccctctgtg ttccctctgg cccttccag caagtccacc | 840 |
| tctggcggaa cagccgctct gggctgcctc gtgaaggact acttcccga gcctgtgacc | 900 |
| gtgtcctgga actctggcgc tctgaccagc ggagtgcaca ccttccctgc tgtgctgcag | 960 |
| tcctccggcc tgtactccct gtcctccgtc gtgaccgtgc cttccagctc tctgggcacc | 1020 |
| cagacctaca tctgcaacgt gaaccacaag ccctccaaca ccaaggtgga caagaaggtg | 1080 |
| ctaacagaca gagaatgggc agaagagtgg aaacatcttg accatctgtt aaactgcata | 1140 |
| atggacatgg tagaaaaac aaggcgatct ctcaccgtac taaggcggtg tcaagaagca | 1200 |
| gaccgggaag aattgaatta ctggatccgg cggtacagtg acgccgaggc acctacttca | 1260 |
| agttctacaa agaaaacaca gctacaactg gagcatttac tgctggatt acagatgatt | 1320 |
| ttgaatggaa ttaataatta caagaatccc aaactcacca ggatgctcac atttaagttt | 1380 |
| tacatgccca agaaggccac agaactgaaa catcttcagt gtctagaaga gaactcaaa | 1440 |
| cctctggagg aagtgctaaa tttagctcaa agcaaaaact ttcacttaag acccagggac | 1500 |
| ttaatcagca atatcaacgt aatagttctg gaactaaagg gatctgaaac aacattcatg | 1560 |
| tgtgaatatg ctgatgagac agcaaccatt gtagaatttc tgaacagatg gattaccttt | 1620 |
| tgtcaaagca tcatctcaac actgactgac tacaaggacg acgacgacaa gcaccaccac | 1680 |
| catcaccac | 1689 |

<210> SEQ ID NO 23
<211> LENGTH: 1704
<212> TYPE: DNA
<213> ORGANISM: Artificial Sequence
<220> FEATURE:
<223> OTHER INFORMATION: Synthetic Construct

<400> SEQUENCE: 23

| | |
|---|---|
| atgagcctcg ggctcctgtg ctgtggggcc ttttctctcc tgtgggcagg tccagtgaat | 60 |
| gccggtgtca ctcagacccc aaaattccag gtcctgaaga caggacagag catgacactg | 120 |

| | |
|---|---|
| cagtgtgccc aggatatgaa ccatgaatac atgtcctggt atcgacaaga cccaggcatg | 180 |
| gggctgaggc tgattcatta ctcagttgcc atccagacaa ctgaccaagg agaagtcccc | 240 |
| aatggctaca atgtctccag atcaaccatc gaggatttcc cgctcaggct gctgtcggct | 300 |
| gctccctccc agacatctgt gtacttctgt gccagcagtt acctggggaa caccggggag | 360 |
| ctgttttttg gagaaggctc taggctgacc gtactggagg acctgaaaaa cgtgttccca | 420 |
| cccgaggtcg ctgtgtttga gccatcagaa gcagagatct cccacaccca aaaggccaca | 480 |
| ctggtgtgcc tggccacagg cttctacccc gaccatgtgg agctgagctg gtgggtgaat | 540 |
| gggaaggagg tgcacagtgg ggtcagcaca gacccgcagc ccctcaagga gcagcccgcc | 600 |
| ctcaatgact ccagatacgc tctgagcagc cgcctgaggg tctcggccac cttctggcag | 660 |
| gaccccgca accacttccg ctgtcaagtc cagttctacg gctctcgga gaatgacgag | 720 |
| tggacccagg atagggccaa accgtcacc cagatcgtca gcgccgaggc ctggggtaga | 780 |
| gcagacgcca gcaccaaggg cccctctgtg ttccctctgg cccctccag caagtccacc | 840 |
| tctggcggaa cagccgctct gggctgcctc gtgaaggact acttccccga gcctgtgacc | 900 |
| gtgtcctgga actctggcgc tctgaccagc ggagtgcaca ccttccctgc tgtgctgcag | 960 |
| tcctccggcc tgtactccct gtcctccgtc gtgaccgtgc cttccagctc tctgggcacc | 1020 |
| cagacctaca tctgcaacgt gaaccacaag ccctccaaca ccaaggtgga caagaaggtg | 1080 |
| ggaggaggtg ggagcctaac agacagagaa tgggcagaag agtggaaaca tcttgaccat | 1140 |
| ctgttaaact gcataatgga catggtagaa aaaacaaggc gatctctcac cgtactaagg | 1200 |
| cggtgtcaag aagcagaccg ggaagaattg aattactgga tccggcggta cagtgacgcc | 1260 |
| gaggcaccta cttcaagttc tacaaagaaa acacagctac aactggagca tttactgctg | 1320 |
| gatttacaga tgatttgaa tggaattaat aattacaaga atcccaaact caccaggatg | 1380 |
| ctcacatta agttttacat gcccaagaag gccacagaac tgaaacatct tcagtgtcta | 1440 |
| gaagaagaac tcaaacctct ggaggaagtg ctaaatttag ctcaaagcaa aaactttcac | 1500 |
| ttaagaccca gggacttaat cagcaatatc aacgtaatag ttctggaact aaagggatct | 1560 |
| gaaacaacat tcatgtgtga atatgctgat gagacagcaa ccattgtaga atttctgaac | 1620 |
| agatggatta ccttttgtca aagcatcatc tcaacactga ctgactacaa ggacgacgac | 1680 |
| gacaagcacc accaccatca ccac | 1704 |

<210> SEQ ID NO 24
<211> LENGTH: 1335
<212> TYPE: DNA
<213> ORGANISM: Artificial Sequence
<220> FEATURE:
<223> OTHER INFORMATION: Synthetic Construct

<400> SEQUENCE: 24

| | |
|---|---|
| atgagcctcg ggctcctgtg ctgtggggcc ttttctctcc tgtgggcagg tccagtgaat | 60 |
| gccggtgtca ctcagacccc aaaattccag gtcctgaaga caggacagag catgacactg | 120 |
| cagtgtgccc aggatatgaa ccatgaatac atgtcctggt atcgacaaga cccaggcatg | 180 |
| gggctgaggc tgattcatta ctcagttgcc atccagacaa ctgaccaagg agaagtcccc | 240 |
| aatggctaca atgtctccag atcaaccatc gaggatttcc cgctcaggct gctgtcggct | 300 |
| gctccctccc agacatctgt gtacttctgt gccagcagtt acctggggaa caccggggag | 360 |
| ctgttttttg gagaaggctc taggctgacc gtactggagg acctgaaaaa cgtgttccca | 420 |
| cccgaggtcg ctgtgtttga gccatcagaa gcagagatct cccacaccca aaaggccaca | 480 |

```
ctggtgtgcc tggccacagg cttctacccc gaccatgtgg agctgagctg gtgggtgaat    540
gggaaggagg tgcacagtgg ggtcagcaca gacccgcagc ccctcaagga gcagcccgcc    600
ctcaatgact ccagatacgc tctgagcagc cgcctgaggg tctcggccac cttctggcag    660
gacccccgca accacttccg ctgtcaagtc cagttctacg gctctcgga gaatgacgag     720
tggacccagg atagggccaa acccgtcacc cagatcgtca gcgccgaggc ctggggtaga    780
gcagacgcca gcaccaaggg ccctctgtg ttccctctgg cccttccag caagtccacc      840
tctggcggaa cagccgctct gggctgcctc gtgaaggact acttccccga gcctgtgacc    900
gtgtcctgga actctggcgc tctgaccagc ggagtgcaca ccttccctgc tgtgctgcag    960
tcctccggcc tgtactccct gtcctccgtc gtgaccgtgc cttccagctc tctgggcacc   1020
cagacctaca tctgcaacgt gaaccacaag ccctccaaca ccaaggtgga caagaaggtg   1080
gaacccaagt cctgcgacaa gacccacacc tgtcccccct tgtcctctaac agacagagaa  1140
tgggcagaag agtggaaaca tcttgaccat ctgttaaact gcataatgga catggtagaa   1200
aaaacaaggc gatctctcac cgtactaagg cggtgtcaag aagcagaccg ggaagaattg   1260
aattactgga tccggcggta cagtgacgcc gaggactaca aggacgacga cgacaagcac   1320
caccaccatc accac                                                    1335
```

<210> SEQ ID NO 25
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 25

```
atgagcctcg ggctcctgtg ctgtggggcc ttttctctcc tgtgggcagg tccagtgaat     60
gccggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttgcc atccagacaa ctgaccaagg agaagtcccc    240
aatggctaca atgtctccag atcaaccatc gaggatttcc cgctcaggct gctgtcggct    300
gctccctccc agacatctgt gtacttctgt gccagcagtt acctggggaa caccggggag    360
ctgtttttg gagaaggctc taggctgacc gtactgagg acctgaaaaa cgtgttccca     420
cccgaggtcg ctgtgtttga gccatcagaa gcagagatct cccacaccca aaaggccaca    480
ctggtgtgcc tggccacagg cttctacccc gaccatgtgg agctgagctg gtgggtgaat    540
gggaaggagg tgcacagtgg ggtcagcaca gacccgcagc ccctcaagga gcagcccgcc    600
ctcaatgact ccagatacgc tctgagcagc cgcctgaggg tctcggccac cttctggcag    660
gacccccgca accacttccg ctgtcaagtc cagttctacg gctctcgga gaatgacgag     720
tggacccagg atagggccaa acccgtcacc cagatcgtca gcgccgaggc ctggggtaga    780
gcagacgcca gcaccaaggg ccctctgtg ttccctctgg cccttccag caagtccacc      840
tctggcggaa cagccgctct gggctgcctc gtgaaggact acttccccga gcctgtgacc    900
gtgtcctgga actctggcgc tctgaccagc ggagtgcaca ccttccctgc tgtgctgcag    960
tcctccggcc tgtactccct gtcctccgtc gtgaccgtgc cttccagctc tctgggcacc   1020
cagacctaca tctgcaacgt gaaccacaag ccctccaaca ccaaggtgga caagaaggtg   1080
gaacccaagt cctgcgacaa gacccacacc tgtcccccct tgtcctggagg aggtgggagc  1140
```

| | |
|---|---|
| ctaacagaca gagaatgggc agaagagtgg aaacatcttg accatctgtt aaactgcata | 1200 |
| atggacatgg tagaaaaaac aaggcgatct ctcaccgtac taaggcggtg tcaagaagca | 1260 |
| gaccgggaag aattgaatta ctggatccgg cggtacagtg acgccgagga ctacaaggac | 1320 |
| gacgacgaca agcaccacca ccatcaccac | 1350 |

<210> SEQ ID NO 26
<211> LENGTH: 615
<212> TYPE: DNA
<213> ORGANISM: Artificial Sequence
<220> FEATURE:
<223> OTHER INFORMATION: Synthetic Construct

<400> SEQUENCE: 26

| | |
|---|---|
| atggagctgg ggctgagctg ggtggtcctg gctgctctac tacaaggtgt ccaggctcag | 60 |
| gttcagctgg ttgaaagcgg tggtgcactg gttcagcctg gtggtagcct gcgtctgagc | 120 |
| tgtgcagcaa gcggtttcc ggttaatcgt tatagcatgc gttggtatcg tcaggcaccg | 180 |
| ggtaaagaac gtgaatgggt tgcaggtatg agcagtgccg gtgatcgtag cagctatgaa | 240 |
| gatagcgtta aggtcgttt taccatcagc cgtgatgatg cacgtaatac cgtttatctg | 300 |
| caaatgaata gcctgaaacc ggaagatacc gcagtgtatt attgcaatgt taacgtgggc | 360 |
| tttgaatatt ggggtcaggg cacccaggtt accgttagca gcaaactaac agacagagaa | 420 |
| tgggcagaag agtggaaaca tcttgaccat ctgttaaact gcataatgga catggtagaa | 480 |
| aaaacaaggc gatctctcac cgtactaagg cggtgtcaag aagcagaccg ggaagaattg | 540 |
| aattactgga tccggcggta cagtgacgcc gaggactaca aggacgacga cgacaagcac | 600 |
| caccaccatc accac | 615 |

<210> SEQ ID NO 27
<211> LENGTH: 630
<212> TYPE: DNA
<213> ORGANISM: Artificial Sequence
<220> FEATURE:
<223> OTHER INFORMATION: Synthetic Construct

<400> SEQUENCE: 27

| | |
|---|---|
| atggagctgg ggctgagctg ggtggtcctg gctgctctac tacaaggtgt ccaggctcag | 60 |
| gttcagctgg ttgaaagcgg tggtgcactg gttcagcctg gtggtagcct gcgtctgagc | 120 |
| tgtgcagcaa gcggtttcc ggttaatcgt tatagcatgc gttggtatcg tcaggcaccg | 180 |
| ggtaaagaac gtgaatgggt tgcaggtatg agcagtgccg gtgatcgtag cagctatgaa | 240 |
| gatagcgtta aggtcgttt taccatcagc cgtgatgatg cacgtaatac cgtttatctg | 300 |
| caaatgaata gcctgaaacc ggaagatacc gcagtgtatt attgcaatgt taacgtgggc | 360 |
| tttgaatatt ggggtcaggg cacccaggtt accgttagca gcaaaggagg aggtgggagc | 420 |
| ctaacagaca gagaatgggc agaagagtgg aaacatcttg accatctgtt aaactgcata | 480 |
| atggacatgg tagaaaaaac aaggcgatct ctcaccgtac taaggcggtg tcaagaagca | 540 |
| gaccgggaag aattgaatta ctggatccgg cggtacagtg acgccgagga ctacaaggac | 600 |
| gacgacgaca agcaccacca ccatcaccac | 630 |

<210> SEQ ID NO 28
<211> LENGTH: 594
<212> TYPE: DNA
<213> ORGANISM: Artificial Sequence
<220> FEATURE:
<223> OTHER INFORMATION: Synthetic Construct

<400> SEQUENCE: 28

```
atggagctgg ggctgagctg ggtggtcctg gctgctctac tacaaggtgt ccaggctcag      60
gttcagctgg ttgaaagcgg tggtgcactg gttcagcctg gtggtagcct gcgtctgagc     120
tgtgcagcaa gcggttttcc ggttaatcgt tatagcatgc gttggtatcg tcaggcaccg     180
ggtaaagaac gtgaatgggt tgcaggtatg agcagtgccg gtgatcgtag cagctatgaa     240
gatagcgtta aggtcgttt taccatcagc cgtgatgatg cacgtaatac cgtttatctg     300
caaatgaata gcctgaaacc ggaagatacc gcagtgtatt attgcaatgt taacgtgggc     360
tttgaatatt ggggtcaggg cacccaggtt accgttagca gcaaactaac agacagagaa     420
tgggcagaag agtggaaaca tcttgaccat ctgttaaact gcataatgga catggtagaa     480
aaaacaaggc gatctctcac cgtactaagg cggtgtcaag aagcagaccg ggaagaattg     540
aattactgga tccggcggta cagtgacgcc gaggcaccta cttcaagttc taca           594
```

<210> SEQ ID NO 29
<211> LENGTH: 1029
<212> TYPE: DNA
<213> ORGANISM: Artificial Sequence
<220> FEATURE:
<223> OTHER INFORMATION: Synthetic Construct

<400> SEQUENCE: 29

```
atggagctgg ggctgagctg ggtggtcctg gctgctctac tacaaggtgt ccaggctcag      60
gttcagctgg ttgaaagcgg tggtgcactg gttcagcctg gtggtagcct gcgtctgagc     120
tgtgcagcaa gcggttttcc ggttaatcgt tatagcatgc gttggtatcg tcaggcaccg     180
ggtaaagaac gtgaatgggt tgcaggtatg agcagtgccg gtgatcgtag cagctatgaa     240
gatagcgtta aggtcgttt taccatcagc cgtgatgatg cacgtaatac cgtttatctg     300
caaatgaata gcctgaaacc ggaagatacc gcagtgtatt attgcaatgt taacgtgggc     360
tttgaatatt ggggtcaggg cacccaggtt accgttagca gcaaaggagg aggtgggagc     420
ctaacagaca gagaatgggc agaagagtgg aaacatcttg accatctgtt aaactgcata     480
atggacatgg tagaaaaaac aaggcgatct ctcaccgtac taaggcggtg tcaagaagca     540
gaccgggaag aattgaatta ctggatccgg cggtacagtg acgccgaggc acctacttca     600
agttctacaa agaaaacaca gctacaactg gagcatttac tgctggattt acagatgatt     660
ttgaatggaa ttaataatta caagaatccc aaactcacca ggatgctcac atttaagttt     720
tacatgccca agaaggccac agaactgaaa catcttcagt gtctagaaga gaactcaaa     780
cctctggagg aagtgctaaa tttagctcaa agcaaaaact ttcacttaag acccagggac     840
ttaatcagca atatcaacgt aatagttctg gaactaaagg gatctgaaac aacattcatg     900
tgtgaatatg ctgatgagac agcaaccatt gtagaatttc tgaacagatg gattaccttt     960
tgtcaaagca tcatctcaac actgactgac tacaaggacg acgacgacaa gcaccaccac    1020
catcaccac                                                            1029
```

<210> SEQ ID NO 30
<211> LENGTH: 1233
<212> TYPE: DNA
<213> ORGANISM: Artificial Sequence
<220> FEATURE:
<223> OTHER INFORMATION: Synthetic Construct

<400> SEQUENCE: 30

```
atggagaccc tcttgggcct gcttatcctt tggctgcagc tgcaatgggt gagcagcaaa    60
caggaggtga cacagattcc tgcagctctg agtgtcccag aaggagaaaa cttggttctc   120
aactgcagtt tcactgatag cgctatttac aacctccagt ggtttaggca ggaccctggg   180
aaaggtctca catctctgtt gcttattaca ccttggcaga gagagcaaac aagtggaaga   240
cttaatgcct cgctggataa atcatcagga cgtagtactt tatacattgc agcttctcag   300
cctggtgact cagccaccta cctctgtgct gtgaggcccc tgcttgacgg aacatacata   360
cctacatttg aagaggaac cagccttatt gttcatccgt atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
actgtgctag acatgaggtc tatggacttc aagagcaaca gtgctgtggc ctggagcaac   600
aaatctgact ttgcatgtgc aaacgccttc aacaacagca ttattccaga agacaccttc   660
ttccccagcc cagaaagttc cgccagcacc aagggcccct ctgtgttccc tctggcccct   720
tccagcaagt ccacctctgg cggaacagcc gctctgggct gcctcgtgaa ggactacttc   780
cccgagcctg tgaccgtgtc ctggaactct ggcgctctga ccagcggagt gcacaccttc   840
cctgctgtgc tgcagtcctc cggcctgtac tccctgtcct ccgtcgtgac cgtgccttcc   900
agctctctgg gcacccagac ctacatctgc aacgtgaacc acaagccctc caacaccaag   960
gtggacaaga aggtgttgca tggcacacgt caagaagaaa tgattgatca gactaacta  1020
gacagagaat gggcagaaga gtggaaacat cttgaccatc tgttaaactg cataatggac  1080
atggtagaaa aaacaaggcg atctctcacc gtactaaggc ggtgtcaaga agcagaccgg  1140
gaagaattga attactggat ccggcggtac agtgacgccg aggacttaaa agactacaag  1200
gacgacgacg acaagcacca ccaccatcac cac                              1233

<210> SEQ ID NO 31
<211> LENGTH: 1248
<212> TYPE: DNA
<213> ORGANISM: Artificial Sequence
<220> FEATURE:
<223> OTHER INFORMATION: Synthetic Construct

<400> SEQUENCE: 31
atggagaccc tcttgggcct gcttatcctt tggctgcagc tgcaatgggt gagcagcaaa    60
caggaggtga cacagattcc tgcagctctg agtgtcccag aaggagaaaa cttggttctc   120
aactgcagtt tcactgatag cgctatttac aacctccagt ggtttaggca ggaccctggg   180
aaaggtctca catctctgtt gcttattaca ccttggcaga gagagcaaac aagtggaaga   240
cttaatgcct cgctggataa atcatcagga cgtagtactt tatacattgc agcttctcag   300
cctggtgact cagccaccta cctctgtgct gtgaggcccc tgcttgacgg aacatacata   360
cctacatttg aagaggaac cagccttatt gttcatccgt atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
actgtgctag acatgaggtc tatggacttc aagagcaaca gtgctgtggc ctggagcaac   600
aaatctgact ttgcatgtgc aaacgccttc aacaacagca ttattccaga agacaccttc   660
ttccccagcc cagaaagttc cgccagcacc aagggcccct ctgtgttccc tctggcccct   720
tccagcaagt ccacctctgg cggaacagcc gctctgggct gcctcgtgaa ggactacttc   780
cccgagcctg tgaccgtgtc ctggaactct ggcgctctga ccagcggagt gcacaccttc   840
```

```
cctgctgtgc tgcagtcctc cggcctgtac tccctgtcct ccgtcgtgac cgtgccttcc      900
agctctctgg gcacccagac ctacatctgc aacgtgaacc acaagccctc aacaccaag      960 gtggacaaga aggtgggagg aggtgggagc ttgcatggca cacgtcaaga agaaatgatt     1020
gatcacagac taacagacag agaatgggca gaagagtgga acatcttga ccatctgtta     1080 aactgcataa tggacatggt agaaaaaaca aggcgatctc tcaccgtact aaggcggtgt     1140
caagaagcag accgggaaga attgaattac tggatccggc ggtacagtga cgccgaggac     1200
ttaaaagact acaaggacga cgacgacaag caccaccacc atcaccac                  1248

<210> SEQ ID NO 32
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 32
atgagcctcg ggctcctgtg ctgtggggcc ttttctctcc tgtgggcagg tccagtgaat       60
gccggtgtca ctcagacccc aaaattccag gtcctgaaga caggacagag catgacactg      120
cagtgtgccc aggatatgaa ccatgaatac atgtcctggt atcgacaaga cccaggcatg      180
gggctgaggc tgattcatta ctcagttgcc atccagacaa ctgaccaagg agaagtcccc      240
aatggctaca atgtctccag atcaaccatc gaggatttcc cgctcaggct gctgtcggct      300
gctccctccc agacatctgt gtacttctgt gccagcagtt acctggggaa caccggggag      360 ctgtttttg gagaaggctc taggctgacc gtactggagg acctgaaaaa cgtgttccca      420
cccgaggtcg ctgtgtttga gccatcagaa gcagagatct cccacaccca aaaggccaca      480
ctggtgtgcc tggccacagg cttctacccc gaccatgtgg agctgagctg gtgggtgaat      540
gggaaggagg tgcacagtgg ggtcagcaca gacccgcagc ccctcaagga gcagcccgcc      600
ctcaatgact ccagatacgc tctgagcagc cgcctgaggg tctcggccac cttctggcag      660
gacccccgca accacttccg ctgtcaagtc cagttctacg ggctctcgga gaatgacgag      720
tggacccagg atagggccaa accgtcacc cagatcgtca gcgccgaggc ctggggtaga      780
gcagacacgg tggccgctcc ctccgtgttc atcttcccac cttccgacga gcagctgaag      840
tccggcaccg cttctgtcgt gtgcctgctg aacaacttct accccgcga ggccaaggtg      900 cagtggaagg tggacaacgc cctgcagtcc ggcaactccc aggaatccgt gaccgagcag      960
gactccaagg acagcaccta ctccctgtcc tccaccctga cctgtccaa ggccgactac     1020 gagaagcaca aggtgtacgc ctgcgaagtg acccaccagg gcctgtctag ccccgtgacc     1080
aagtctttca ccggggcga gtgt                                              1104

<210> SEQ ID NO 33
<211> LENGTH: 912
<212> TYPE: DNA
<213> ORGANISM: Artificial Sequence
<220> FEATURE:
<223> OTHER INFORMATION: Synthetic Construct

<400> SEQUENCE: 33
atgaacttcg ggctcagctt gattttcctt gcccttattt taaaggtgt ccagtgtgag       60 gtgcaactgg tggagtctgg gggaggctta gtgaagcctg ggggtccct gaaactctcc      120 tgtgcagcct ctggactcac tttcagtagc tatgccatgt cttgggttcg ccagactcca      180
```

```
gagaagaggc tggagtgggt cgcatccatt agtagtggtg gtttcaccta ctatccagac    240
agtgtgaagg gccgattcac catctccaga gataatgcca ggaacatcct gtatctgcaa    300
atgagcagtc tgaggtctga ggacacggcc atgtattact gtgcaagaga cgaggtacgg    360
gggtacctcg atgtctgggg cgcagggacc acggtcaccg tttcctcggc cagcaccaag    420 ggccctctg tgttccctct ggccccttcc agcaagtcca cctctggcgg aacagccgct    480
ctgggctgcc tcgtgaagga ctacttcccc gagcctgtga ccgtgtcctg gaactctggc    540
gctctgacca gcggagtgca caccttccct gctgtgctgc agtcctccgg cctgtactcc    600
ctgtcctccg tcgtgaccgt gccttccagc tctctgggca cccagaccta catctgcaac    660
gtgaaccaca agccctccaa caccaaggtg gacaagaagg tgctaacaga cagagaatgg    720
gcagaagagt ggaaacatct tgaccatctg ttaaactgca taatggacat ggtagaaaaa    780
acaaggcgat ctctcaccgt actaaggcgg tgtcaagaag cagaccggga agaattgaat    840
tactggatcc ggcggtacag tgacgccgag gactacaagg acgacgacga caagcaccac    900
caccatcacc ac                                                        912

<210> SEQ ID NO 34
<211> LENGTH: 927
<212> TYPE: DNA
<213> ORGANISM: Artificial Sequence
<220> FEATURE:
<223> OTHER INFORMATION: Synthetic Construct

<400> SEQUENCE: 34
atgaacttcg ggctcagctt gattttcctt gcccttattt taaaaggtgt ccagtgtgag     60
gtgcaactgg tggagtctgg gggaggctta gtgaagcctg gggggtccct gaaactctcc    120
tgtgcagcct ctggactcac tttcagtagc tatgccatgt cttgggttcg ccagactcca    180
gagaagaggc tggagtgggt cgcatccatt agtagtggtg gtttcaccta ctatccagac    240
agtgtgaagg gccgattcac catctccaga gataatgcca ggaacatcct gtatctgcaa    300
atgagcagtc tgaggtctga ggacacggcc atgtattact gtgcaagaga cgaggtacgg    360
gggtacctcg atgtctgggg cgcagggacc acggtcaccg tttcctcggc cagcaccaag    420 ggccctctg tgttccctct ggccccttcc agcaagtcca cctctggcgg aacagccgct    480
ctgggctgcc tcgtgaagga ctacttcccc gagcctgtga ccgtgtcctg gaactctggc    540
gctctgacca gcggagtgca caccttccct gctgtgctgc agtcctccgg cctgtactcc    600
ctgtcctccg tcgtgaccgt gccttccagc tctctgggca cccagaccta catctgcaac    660
gtgaaccaca agccctccaa caccaaggtg gacaagaagg tgggaggagg tgggagccta    720
acagacagag aatgggcaga agagtggaaa catcttgacc atctgttaaa ctgcataatg    780
gacatggtag aaaaaacaag gcgatctctc accgtactaa ggcggtgtca agaagcagac    840
cgggaagaat tgaattactg gatccggcgg tacagtgacg ccgaggacta caaggacgac    900
gacgacaagc accaccacca tcaccac                                        927

<210> SEQ ID NO 35
<211> LENGTH: 717
<212> TYPE: DNA
<213> ORGANISM: Artificial Sequence
<220> FEATURE:
<223> OTHER INFORMATION: Synthetic Construct

<400> SEQUENCE: 35
atgaaatacc tattgcctac ggcagccgct ggattgttat tactcgcggc ccagccggcc     60
```

```
atggcggcct acaaagatat ccagatgaca cagactacat cctccctgtc tgcctctctg    120
ggagacagag tcaccatcag ttgcagtgca agtcagggca ttagcaatta tttaaactgg    180
tatcagcaga aaccagatgg aactgttaaa ctcctgatct attacacatc aagtttacac    240
tcaggagtcc catcaaggtt cagtggcagt gggtctggga cagattattc tctcaccatc    300
agcaacctgg aacctgaaga tattgccact tattattgtc agcagtatag caagcttccg    360
tacacgttcg gaggggggac caagctggaa ataaaacgta cggtggccgc tcccccgtg    420 ttcatcttcc caccttccga cgagcagctg aagtccggca ccgcttctgt cgtgtgcctg    480
ctgaacaact ctacccccg cgaggccaag gtgcagtgga aggtggacaa cgccctgcag    540
tccggcaact cccaggaatc cgtgaccgag caggactcca aggacagcac ctactccctg    600
tcctccaccc tgaccctgtc caaggccgac tacgagaagc acaaggtgta cgcctgcgaa    660
gtgacccacc agggcctgtc tagccccgtg accaagtctt tcaaccgggg cgagtgt      717

<210> SEQ ID NO 36
<211> LENGTH: 957
<212> TYPE: DNA
<213> ORGANISM: Artificial Sequence
<220> FEATURE:
<223> OTHER INFORMATION: Synthetic Construct

<400> SEQUENCE: 36
atgaacttcg ggctcagctt gattttcctt gcccttattt taaaggtgt ccagtgtgag     60 gtgcaactgg tggagtctgg gggaggctta gtgaagcctg ggggtccct gaaactctcc    120 tgtgcagcct ctggactcac tttcagtagc tatgccatgt cttgggttcg ccagactcca    180
gagaagaggc tggagtgggt cgcatccatt agtagtggtg gtttcaccta ctatccagac    240
agtgtgaagg gccgattcac catctccaga gataatgcca gaacatcct gtatctgcaa    300 atgagcagtc tgaggtctga ggacacggcc atgtattact gtgcaagaga cgaggtacgg    360
gggtacctcg atgtctgggg cgcagggacc acggtcaccg tttcctcggc cagcaccaag    420
ggcccctctg tgttccctct ggcccttcc agcaagtcca cctctggcgg aacagccgct    480
ctgggctgcc tcgtgaagga ctacttcccc gagcctgtga ccgtgtcctg gaactctggc    540
gctctgacca gcggagtgca caccttccct gctgtgctgc agtcctccgg cctgtactcc    600
ctgtcctccg tcgtgaccgt gccttccagc tctctgggca cccagaccta catctgcaac    660
gtgaaccaca agccctccaa caccaaggtg gacaagaagg tggaaccaa gtcctgcgac    720 aagacccaca cctgtccccc ttgtcctcta acagacagag aatgggcaga agagtggaaa    780
catcttgacc atctgttaaa ctgcataatg gacatggtag aaaaaacaag gcgatctctc    840
accgtactaa ggcggtgtca agaagcagac cgggaagaat tgaattactg gatccggcgg    900
tacagtgacg ccgaggacta caaggacgac gacgacaagc accaccacca tcaccac      957

<210> SEQ ID NO 37
<211> LENGTH: 972
<212> TYPE: DNA
<213> ORGANISM: Artificial Sequence
<220> FEATURE:
<223> OTHER INFORMATION: Synthetic Construct

<400> SEQUENCE: 37
atgaacttcg ggctcagctt gattttcctt gcccttattt taaaggtgt ccagtgtgag     60 gtgcaactgg tggagtctgg gggaggctta gtgaagcctg ggggtccct gaaactctcc    120
```

```
tgtgcagcct ctggactcac tttcagtagc tatgccatgt cttgggttcg ccagactcca    180
gagaagaggc tggagtgggt cgcatccatt agtagtggtg gtttcaccta ctatccagac    240
agtgtgaagg gccgattcac catctccaga gataatgcca ggaacatcct gtatctgcaa    300
atgagcagtc tgaggtctga ggacacggcc atgtattact gtgcaagaga cgaggtacgg    360
gggtacctcg atgtctgggg cgcagggacc acggtcaccg tttcctcggc cagcaccaag    420
ggcccctctg tgttccctct ggccccttcc agcaagtcca cctctggcgg aacagccgct    480
ctgggctgcc tcgtgaagga ctacttcccc gagcctgtga ccgtgtcctg aactctggc    540 gctctgacca gcggagtgca caccttccct gctgtgctgc agtcctccgg cctgtactcc    600
ctgtcctccg tcgtgaccgt gccttccagc tctctgggca cccagaccta catctgcaac    660
gtgaaccaca gcccctccaa caccaaggtg gacaagaagg tggaacccaa gtcctgcgac    720
aagacccaca cctgtccccc ttgtcctgga ggagtgggag cctaacaga cagagaatgg    780 gcagaagagt ggaaacatct tgaccatctg ttaaactgca taatggacat ggtagaaaaa    840
acaaggcgat ctctcaccgt actaaggcgg tgtcaagaag cagaccggga agaattgaat    900
tactggatcc ggcggtacag tgacgccgag gactacaagg acgacgacga caagcaccac    960
caccatcacc ac                                                         972

<210> SEQ ID NO 38
<211> LENGTH: 972
<212> TYPE: DNA
<213> ORGANISM: Artificial Sequence
<220> FEATURE:
<223> OTHER INFORMATION: Synthetic Construct

<400> SEQUENCE: 38
atgggatggt cttgtataat tctgttcctg gtggcaacag caacaggagt gcatagcgag     60
gtgcagctgg tggagtctgg gggaggcttg gtacagcccg gcaggtccct gagactctcc    120
tgtgcggcct ctggattcac ctttgatgat tatgccatgc actgggtccg gcaagctcca    180
gggaagggcc tggaatgggt ctcagctatc acttggaata gtggtcacat agactatgcg    240
gactctgtgg agggccgatt caccatctcc agagacaacg ccaagaactc cctgtatctg    300
caaatgaaca gtctgagagc tgaggatacg gccgtatatt actgtgcgaa agtctcgtac    360
cttagcaccg cgtcctccct tgactattgg ggccaaggta ccctggtcac cgtctcgagt    420
gccagcacca agggcccctc tgtgttccct ctggcccctt ccagcaagtc cacctctggc    480
ggaacagccg ctctgggctg cctcgtgaag gactacttcc ccgagcctgt gaccgtgtcc    540
tggaactctg gcgctctgac cagcggagtg cacaccttcc ctgctgtgct gcagtcctcc    600
ggcctgtact ccctgtcctc cgtcgtgacc gtgccttcca gctctctggg cacccagacc    660
tacatctgca acgtgaacca caagccctcc aacaccaagg tggacaagaa ggtgttgcat    720
ggcacacgtc aagaagaaat gattgatcac agactaacag acagaaatg gcagaagag    780 tggaaacatc ttgaccatct gttaaactgc ataatggaca tggtagaaaa acaaggcga    840 tctctcaccg tactaaggcg tgtcaagaa gcagaccggg aagaattgaa ttactggatc    900
cggcggtaca gtgacgccga ggacttaaaa gactacaagg acgacgacga caagcaccac    960
caccatcacc ac                                                         972

<210> SEQ ID NO 39
<211> LENGTH: 987
<212> TYPE: DNA
<213> ORGANISM: Artificial Sequence
```

<220> FEATURE:
<223> OTHER INFORMATION: Synthetic Construct

<400> SEQUENCE: 39

```
atgggatggt cttgtataat tctgttcctg gtggcaacag caacaggagt gcatagcgag      60
gtgcagctgg tggagtctgg gggaggcttg gtacagcccg gcaggtccct gagactctcc     120
tgtgcggcct ctggattcac ctttgatgat tatgccatgc actgggtccg gcaagctcca     180
gggaagggcc tggaatgggt ctcagctatc acttggaata gtggtcacat agactatgcg     240
gactctgtgg agggccgatt caccatctcc agagacaacg ccaagaactc cctgtatctg     300
caaatgaaca gtctgagagc tgaggatacg gccgtatatt actgtgcgaa agtctcgtac     360
cttagcaccg cgtcctccct tgactattgg ggccaaggta ccctggtcac cgtctcgagt     420
gccagcacca agggcccctc tgtgttccct ctggccccct ccagcaagtc cacctctggc     480
ggaacagccg ctctgggctg cctcgtgaag gactacttcc ccgagcctgt gaccgtgtcc     540
tggaactctg gcgctctgac cagcggagtg cacaccttcc ctgctgtgct gcagtcctcc     600
ggcctgtact ccctgtcctc cgtcgtgacc gtgccttcca gctctctggg cacccagacc     660
tacatctgca acgtgaacca caagccctcc aacaccaagg tggacaagaa ggtgggagga     720
ggtgggagct gcatggcac acgtcaagaa gaaatgattg atcacagact aacagacaga     780
gaatgggcag aagagtggaa acatcttgac catctgttaa actgcataat ggacatggta     840
gaaaaaacaa ggcgatctct caccgtacta aggcggtgtc aagaagcaga ccgggaagaa     900
ttgaattact ggatccggcg gtacagtgac gccgaggact aaaagactaa caaggacgac     960
gacgacaagc accaccacca tcaccac                                        987
```

<210> SEQ ID NO 40
<211> LENGTH: 708
<212> TYPE: DNA
<213> ORGANISM: Artificial Sequence
<220> FEATURE:
<223> OTHER INFORMATION: Synthetic Construct

<400> SEQUENCE: 40

```
atggacatga gggtccctgc tcagctcctg ggactcctgc tgctctggct cccagatacc      60
agatgtgaca tccagatgac ccagtctcca tcctccctgt ctgcatctgt aggggacaga     120
gtcaccatca cttgtcgggc aagtcagggc atcagaaatt acttagcctg gtatcagcaa     180
aaaccaggga agcccctaa gctcctgatc tatgctgcat ccactttgca atcaggggtc     240
ccatctcggt tcagtggcag tggatctggg acagatttca ctctcaccat cagcagccta     300
cagcctgaag atgttgcaac ttattactgt caaaggtata accgtgcacc gtatactttt     360
ggccagggga ccaaggtgga aatcaaacgt acggtggccg ctcccctccgt gttcatcttc     420
ccaccttccg acgagcagct gaagtccggc accgcttctg tcgtgtgcct gctgaacaac     480
ttctaccccc gcgaggccaa ggtgcagtgg aaggtggaca acgccctgca gtccggcaac     540
tcccaggaat ccgtgaccga gcaggactcc aaggacagca cctactccct gtcctccacc     600
ctgaccctgt ccaaggccga ctacgagaag cacaaggtgt acgcctgcga agtgacccac     660
cagggcctgt ctagccccgt gaccaagtct ttcaaccggg gcgagtgt                 708
```

<210> SEQ ID NO 41
<211> LENGTH: 978
<212> TYPE: DNA
<213> ORGANISM: Artificial Sequence
<220> FEATURE:

<223> OTHER INFORMATION: Synthetic Construct

<400> SEQUENCE: 41

| | | | | | |
|---|---|---|---|---|---|
| atgggatggt | cttgtataat | tctgttcctg | gtggcaacag | caacaggagt | gcatagcgag | 60 |
| gtccaacttg | tcgaaagtgg | cggcggtttg | gttcaacctg | gaggttcact | tcgactgtca | 120 |
| tgtgcagcga | gcggttatac | atttacgaat | tatggcatga | attgggttag | acaggcacca | 180 |
| ggaaagggac | tggagtgggt | aggctggatc | aatacctaca | caggagaacc | aacgtatgcc | 240 |
| gcagacttca | aacgacggtt | tacatttttcc | ttggatacct | ctaagtctac | agcgtatctc | 300 |
| caaatgaatt | cacttcgagc | ggaagatacc | gcggtctact | attgcgccaa | atacctcat | 360 |
| tattatgggt | catctcactg | gtatttcgat | gtctggggtc | agggaacact | ggtaaccgtg | 420 |
| tcatccgcca | gcaccaaggg | cccctctgtg | ttccctctgg | cccttccag | caagtccacc | 480 |
| tctggcggaa | cagccgctct | gggctgcctc | gtgaaggact | acttccccga | gcctgtgacc | 540 |
| gtgtcctgga | actctggcgc | tctgaccagc | ggagtgcaca | ccttccctgc | tgtgctgcag | 600 |
| tcctccggcc | tgtactccct | gtcctccgtc | gtgaccgtgc | cttccagctc | tctgggcacc | 660 |
| cagacctaca | tctgcaacgt | gaaccacaag | ccctccaaca | ccaaggtgga | caagaaggtg | 720 |
| ttgcatggca | cacgtcaaga | agaaatgatt | gatcacagac | taacagacag | agaatgggca | 780 |
| gaagagtgga | aacatcttga | ccatctgtta | aactgcataa | tggacatggt | agaaaaaaca | 840 |
| aggcgatctc | tcaccgtact | aaggcggtgt | caagaagcag | accggaaga | attgaattac | 900 |
| tggatccggc | ggtacagtga | cgccgaggac | ttaaaagact | acaaggacga | cgacgacaag | 960 |
| caccaccacc | atcaccac | | | | | 978 |

<210> SEQ ID NO 42
<211> LENGTH: 993
<212> TYPE: DNA
<213> ORGANISM: Artificial Sequence
<220> FEATURE:
<223> OTHER INFORMATION: Synthetic Construct

<400> SEQUENCE: 42

| | | | | | |
|---|---|---|---|---|---|
| atgggatggt | cttgtataat | tctgttcctg | gtggcaacag | caacaggagt | gcatagcgag | 60 |
| gtccaacttg | tcgaaagtgg | cggcggtttg | gttcaacctg | gaggttcact | tcgactgtca | 120 |
| tgtgcagcga | gcggttatac | atttacgaat | tatggcatga | attgggttag | acaggcacca | 180 |
| ggaaagggac | tggagtgggt | aggctggatc | aatacctaca | caggagaacc | aacgtatgcc | 240 |
| gcagacttca | aacgacggtt | tacatttttcc | ttggatacct | ctaagtctac | agcgtatctc | 300 |
| caaatgaatt | cacttcgagc | ggaagatacc | gcggtctact | attgcgccaa | atacctcat | 360 |
| tattatgggt | catctcactg | gtatttcgat | gtctggggtc | agggaacact | ggtaaccgtg | 420 |
| tcatccgcca | gcaccaaggg | cccctctgtg | ttccctctgg | cccttccag | caagtccacc | 480 |
| tctggcggaa | cagccgctct | gggctgcctc | gtgaaggact | acttccccga | gcctgtgacc | 540 |
| gtgtcctgga | actctggcgc | tctgaccagc | ggagtgcaca | ccttccctgc | tgtgctgcag | 600 |
| tcctccggcc | tgtactccct | gtcctccgtc | gtgaccgtgc | cttccagctc | tctgggcacc | 660 |
| cagacctaca | tctgcaacgt | gaaccacaag | ccctccaaca | ccaaggtgga | caagaaggtg | 720 |
| ggaggaggtg | ggagcttgca | tggcacacgt | caagaagaaa | tgattgatca | cagactaaca | 780 |
| gacagagaat | gggcagaaga | gtggaaacat | cttgaccatc | tgttaaactg | cataatggac | 840 |
| atggtagaaa | aaacaaggcg | atctctcacc | gtactaaggc | ggtgtcaaga | agcagaccgg | 900 |
| gaagaattga | attactggat | ccggcggtac | agtgacgccg | aggacttaaa | agactacaag | 960 |

```
gacgacgacg acaagcacca ccaccatcac cac                                993
```

<210> SEQ ID NO 43
<211> LENGTH: 708
<212> TYPE: DNA
<213> ORGANISM: Artificial Sequence
<220> FEATURE:
<223> OTHER INFORMATION: Synthetic Construct

<400> SEQUENCE: 43

```
atggacatga gggtccctgc tcagctcctg gggctcctgc agctctggct ctcaggtgcc    60
agatgtgaca tccaaatgac ccagagtcct tccagcctca gtgcgtcagt gggagatcga   120
gtgacgataa cgtgttctgc cagccaagac atttccaact atcttaattg gtaccagcag   180
aaaccgggaa aggccccgaa agtgctcata tactttacca gcagtcttca ctctggagtt   240
cctagccggt ttagcggctc aggtagtggc accgatttca ctctgaccat tagttctctt   300
caaccggaag attttgcaac ctactattgt cagcagtatt caacggtacc ttggaccttc   360
ggccaaggca ccaaagtcga gattaagcgt acggtggccg ctccctccgt gttcatcttc   420
ccaccttccg acgagcagct gaagtccggc accgcttctg tcgtgtgcct gctgaacaac   480
ttctaccccc gcgaggccaa ggtgcagtgg aaggtggaca cgccctgca gtccggcaac    540
tcccaggaat ccgtgaccga gcaggactcc aaggacagca cctactccct gtcctccacc   600
ctgaccctgt ccaaggccga ctacgagaag cacaaggtgt acgcctgcga agtgacccac   660
cagggcctgt ctagccccgt gaccaagtct ttcaaccggg gcgagtgt                708
```

<210> SEQ ID NO 44
<211> LENGTH: 660
<212> TYPE: DNA
<213> ORGANISM: Artificial Sequence
<220> FEATURE:
<223> OTHER INFORMATION: Synthetic Construct

<400> SEQUENCE: 44

```
atggatatgc gcgtcccggc acagctgctc ggcttgttgt tgctgtggtt gagagctagg    60
tgcgatatac agatgactca gtccccttcc agtctttcag ccagtgtcgg cgaccgggtt   120
accattactt gtcgggcaag tcaatctata gatagttatt tgcattggta tcaacaaaaa   180
ccaggcaaag cgcctaagtt gttgatatat tccgcatctg aactgcaatc aggcgttcct   240
tcacgctttt ctggaagcgg cagcggaacc gatttcactc ttaccataag tagtctccag   300
ccggaggatt ttgctacata ctattgtcaa caagtagtgt ggcgaccgtt caccttcgga   360
cagggggacaa aagtagaaat caagcgggga ggaggtggga gcttgcatgg cacacgtcaa   420
gaagaaatga ttgatcacag actaacagac agagaatggg cagaagagtg gaaacatctt   480
gaccatctgt taaactgcat aatggacatg gtagaaaaaa caaggcgatc tctcaccgta   540
ctaaggcggt gtcaagaagc agaccgggaa gaattgaatt actggatccg gcggtacagt   600
gacgccgagg acttaaaaga ctacaaggac gacgacgaca agcaccacca ccatcaccac   660
```

<210> SEQ ID NO 45
<211> LENGTH: 684
<212> TYPE: DNA
<213> ORGANISM: Artificial Sequence
<220> FEATURE:
<223> OTHER INFORMATION: Synthetic Construct

<400> SEQUENCE: 45

```
atggagtttg gcctcagttg gttgttttg gtagcgaaaa ttaaagtaca gtgtgaagtc      60
caactcctgg agagcggggg gggtctggta caaccaggcg gctcactgcg gcttagctgc    120
gcagcctccg ggttcacgtt cgcacatgaa acgatggtgt gggtgcgcca ggcaccgggg    180
aagggactcg aatgggtctc acatatacct cctgacggtc aggatccttt ttacgcggac    240
tctgtgaagg gacgattcac aataagtaga gacaatagta agaacaccct ttatttgcag    300
atgaacagtc tgcgggcgga agatacagca gtatatcatt gtgccctgct gcccaaacga    360
ggtccgtggt ttgactattg gggacagggg actctcgtta ctgtaagctc cggaggaggt    420
gggagcttgc atggcacacg tcaagaagaa atgattgatc acagactaac agacagagaa    480
tgggcagaag agtggaaaca tcttgaccat ctgttaaact gcataatgga catggtagaa    540
aaaacaaggc gatctctcac cgtactaagg cggtgtcaag aagcagaccg gaagaattg    600 aattactgga tccggcggta cagtgacgcc gaggacttaa aagactacaa ggacgacgac    660
gacaagcacc accaccatca ccac                                          684
```

<210> SEQ ID NO 46
<211> LENGTH: 657
<212> TYPE: DNA
<213> ORGANISM: Artificial Sequence
<220> FEATURE:
<223> OTHER INFORMATION: Synthetic Construct

<400> SEQUENCE: 46

```
atggacatga gggtccccgc tcagctcctg gggctcctgc tactctggct ccgagccaga     60
tgtgatatac agatgaccca atcaccaagc agcttgtccg cttcagtggg cgacagggta    120
actataacat gccgcgcaag ccaatggata ggtccagaac tctcatggta ccaacaaaaa    180
ccagggaaag cgccgaaact gcttatctat cacacaagca ttttgcaatc tggggtacct    240
agtcgattca gtggctctgg cagtgggact gactttacac tcaccataag ttctctccaa    300
ccagaggact ttgcaacata ctattgtcag caatatatgt ttcaaccacg cacctttgga    360
caaggcacaa agttgaaat ccgcggagga ggtgggagct tgcatggcac acgtcaagaa    420
gaaatgattg atcacagact aacagacaga gaatgggcag aagagtggaa acatcttgac    480
catctgttaa actgcataat ggacatggta gaaaaaacaa ggcgatctct caccgtacta    540
aggcggtgtc aagaagcaga ccggaagaa ttgaattact ggatccggcg gtacagtgac    600
gccgaggact aaaagactaa caaggacgac gacgacaagc accaccacca tcaccac      657
```

<210> SEQ ID NO 47
<211> LENGTH: 660
<212> TYPE: DNA
<213> ORGANISM: Artificial Sequence
<220> FEATURE:
<223> OTHER INFORMATION: Synthetic Construct

<400> SEQUENCE: 47

```
atggacatga gggtccccgc tcagctcctg gggctcctgc tactctggct ccgagccaga     60
tgtgatattc aaatgacaca gtcaccaacg agtctttccg cgagcgttgg ggaccgagtg    120
acaataactt gtcgagcctc tcagtggatt ggcaacttgc tggactggta tcagcaaaag    180
ccgggagaag ccccgaagct gctcatatac tatgcttcct tcctccagag tggagtacct    240
agcagattca gcgggggggg attcgggact gatttcactc ttacaatcag ctctcttcaa    300
cccgaggact cgcaacgta ctactgtcaa caagctaacc ctgcgccgct tactttcgga    360
caaggcacta aggtcgaaat taagcgagga ggaggtggga gcttgcatgg cacacgtcaa    420
```

```
gaagaaatga ttgatcacag actaacagac agagaatggg cagaagagtg gaaacatctt     480
gaccatctgt taaactgcat aatggacatg gtagaaaaaa caaggcgatc tctcaccgta     540
ctaaggcggt gtcaagaagc agaccgggaa gaattgaatt actggatccg gcggtacagt     600
gacgccgagg acttaaaaga ctacaaggac gacgacgaca agcaccacca ccatcaccac     660
```

<210> SEQ ID NO 48
<211> LENGTH: 996
<212> TYPE: DNA
<213> ORGANISM: Artificial Sequence
<220> FEATURE:
<223> OTHER INFORMATION: Synthetic Construct

<400> SEQUENCE: 48

```
atggacatga gggtccccgc tcagctcctg gggctcctgc tactctggct ccgagccaga      60
tgtgatatac agatgaccca atccaagag cagcttgtccg cttcagtggg cgacagggta     120
actataacat gccgcgcaag ccaatggata ggtccagaac tctcatggta ccaacaaaaa     180
ccagggaaag cgccgaaact gcttatctat cacacaagca ttttgcaatc tggggtacct     240
agtcgattca gtggctctgg cagtgggact gactttacac tcaccataag ttctctccaa     300
ccagaggact ttgcaacata ctattgtcag caatatatgt ttcaaccacg caccttgga      360 caaggcacaa aagttgaaat ccgcggagga ggtgggagct tgcatggcac acgtcaagaa     420
gaaatgattg atcacagact aacagacaga gaatgggcag aagagtggaa acatcttgac     480
catctgttaa actgcataat ggacatggta gaaaaaacaa ggcgatctct caccgtacta     540
aggcggtgtc aagaagcaga ccgggaagaa ttgaattact ggatccggcg gtacagtgac     600
gccgaggact aaaaggtgg aggaggtagc gatattcaaa tgacacagtc accaacgagt     660
ctttccgcga gcgttgggga ccgagtgaca ataacttgtc gagcctctca gtggattggc     720
aacttgctgg actggtatca gcaaaagccg gagaagccc cgaagctgct catatactat     780
gcttccttcc tccagagtgg agtacctagc agattcagcg gggggggatt cgggactgat     840
ttcactctta caatcagctc tcttcaaccc gaggacttcg caacgtacta ctgtcaacaa     900
gctaaccctg cgccgcttac tttcggacaa ggcactaagg tcgaaattaa gcagactac     960 aaggacgacg acgacaagca ccaccaccat caccac                               996
```

<210> SEQ ID NO 49
<211> LENGTH: 660
<212> TYPE: DNA
<213> ORGANISM: Artificial Sequence
<220> FEATURE:
<223> OTHER INFORMATION: Synthetic Construct

<400> SEQUENCE: 49

```
atggacatga gggtccccgc tcagctcctg gggctcctgc tactctggct ccgagccaga      60
tgtgacattc agatgactca gtcaccatcc tcattgtctg catcagttgg tgaccgagtt     120
acgatcacat gtcgagcaag ccaaaatata gattccagac tttcatggta ccagcagaag     180
cctggtaaag cgccgaaact cctcatatat cgcacgagcg tattgcaatc tggtgtgcct     240
tctcgatttt caggatctgg gtctggcact gacttcacct tgacaatatc ttctcttcag     300
cccgaagatt tcgctaccta ctactgccaa caatgggaca tgtttcctct gaccttcgga     360
cagggtacaa aggtcgagat taacggggga ggagtgggag gcttgcatgg cacacgtcaa     420
gaagaaatga ttgatcacag actaacagac agagaatggg cagaagagtg gaaacatctt     480
```

```
gaccatctgt taaactgcat aatggacatg gtagaaaaaa caaggcgatc tctcaccgta      540
ctaaggcggt gtcaagaagc agaccgggaa gaattgaatt actggatccg gcggtacagt      600
gacgccgagg acttaaaaga ctacaaggac gacgacgaca agcaccacca ccatcaccac      660
```

<210> SEQ ID NO 50
<211> LENGTH: 999
<212> TYPE: DNA
<213> ORGANISM: Artificial Sequence
<220> FEATURE:
<223> OTHER INFORMATION: Synthetic Construct

<400> SEQUENCE: 50

```
atggacatga gggtccccgc tcagctcctg gggctcctgc tactctggct ccgagccaga       60
tgtgacattc agatgactca gtcaccatcc tcattgtctg catcagttgg tgaccgagtt      120
acgatcacat gtcgagcaag ccaaaatata gattccgagc tttcatggta ccagcagaag      180
cctggtaaag cgccgaaact cctcatatat cgcacgagcg tattgcaatc tggtgtgcct      240
tctcgatttt caggatctgg gtctggcact gacttcaccc tgacaatatc ttctcttcag      300
cccgaagatt tcgctaccta ctactgccaa caatgggaca tgtttcctct gaccttcgga      360
cagggtacaa aggtcgagat taaacgggga ggaggtggga gcttgcatgg cacacgtcaa      420
gaagaaatga ttgatcacag actaacagac agagaatggg cagaagagtg gaaacatctt      480
gaccatctgt taaactgcat aatggacatg gtagaaaaaa caaggcgatc tctcaccgta      540
ctaaggcggt gtcaagaagc agaccgggaa gaattgaatt actggatccg gcggtacagt      600
gacgccgagg acttaaaagg tggaggaggt agcgatatac agatgactca atcccccttca      660 tccctctcag cttccgtagg ggacagagtt actataacgt gtcgagctag tcaagacata      720
ggtgatcgcc tgaggtggta tcagcaaaaa ccgggtaaag cacctaaact cctcatatat      780
catggttcca ggttggagtc aggcgtgccg tcacgattct ctgggtcacg ctctggcact      840
gacttcacat tgacgattag ttctctccag cccgaagact tcgccaccta ctactgtcaa      900
cagcaatggt ttcgcccgta cttttgggg cagggtacaa aggttgagat taaacgggac      960
tacaaggacg acgacgacaa gcaccaccac catcaccac                            999
```

<210> SEQ ID NO 51
<211> LENGTH: 121
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
```

<210> SEQ ID NO 52
<211> LENGTH: 108
<212> TYPE: PRT
<213> ORGANISM: Artificial Sequence
<220> FEATURE:
<223> OTHER INFORMATION: Synthetic Construct

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105
```

<210> SEQ ID NO 53
<211> LENGTH: 121
<212> TYPE: PRT
<213> ORGANISM: Artificial Sequence
<220> FEATURE:
<223> OTHER INFORMATION: Synthetic Construct

<400> SEQUENCE: 53

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120
```

<210> SEQ ID NO 54
<211> LENGTH: 107
<212> TYPE: PRT
<213> ORGANISM: Artificial Sequence
<220> FEATURE:
<223> OTHER INFORMATION: Synthetic Construct

<400> SEQUENCE: 54

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Asn Pro Pro Thr
                85                  90                  95

Phe Gly Gly Gly Thr Lys Leu Glu Ile Lys Arg
            100                 105
```

<210> SEQ ID NO 55
<211> LENGTH: 123
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 56
<211> LENGTH: 108
<212> TYPE: PRT
<213> ORGANISM: Artificial Sequence
<220> FEATURE:
<223> OTHER INFORMATION: Synthetic Construct

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
```

Glu Asp Phe Ala Thr Tyr Tyr Cys Gln Gln Tyr Ser Thr Val Pro Trp
65                  70                  75                  80
                    85                      90                  95

Thr Phe Gly Gln Gly Thr Lys Val Glu Ile Lys Arg
                100                 105

<210> SEQ ID NO 57
<211> LENGTH: 119
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 58
<211> LENGTH: 108
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Arg
                100                 105

<210> SEQ ID NO 59
<211> LENGTH: 119
<212> TYPE: PRT
<213> ORGANISM: Artificial Sequence
<220> FEATURE:

<223> OTHER INFORMATION: Synthetic Construct

<400> SEQUENCE: 59

Glu Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 60
<211> LENGTH: 108
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg
            100                 105

<210> SEQ ID NO 61
<211> LENGTH: 113
<212> TYPE: PRT
<213> ORGANISM: Artificial Sequence
<220> FEATURE:
<223> OTHER INFORMATION: Synthetic Construct

<400> SEQUENCE: 61

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val

```
                50              55              60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser

<210> SEQ ID NO 62
<211> LENGTH: 108
<212> TYPE: PRT
<213> ORGANISM: Artificial Sequence
<220> FEATURE:
<223> OTHER INFORMATION: Synthetic Construct

<400> SEQUENCE: 62

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg
                100                 105

<210> SEQ ID NO 63
<211> LENGTH: 118
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
             35                  40                  45

Thr Phe Ile Ser Tyr Asp Gly Asn Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
                100                 105                 110

Leu Val Thr Val Ser Ser
             115
```

<210> SEQ ID NO 64
<211> LENGTH: 109
<212> TYPE: PRT
<213> ORGANISM: Artificial Sequence
<220> FEATURE:
<223> OTHER INFORMATION: Synthetic Construct

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105

<210> SEQ ID NO 65
<211> LENGTH: 119
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 66
<211> LENGTH: 108
<212> TYPE: PRT
<213> ORGANISM: Artificial Sequence
<220> FEATURE:
<223> OTHER INFORMATION: Synthetic Construct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

```
Leu His Trp Tyr Gln Gln Lys Pro Gly Lys Ala Pro Lys Leu Leu Ile
            35                  40                  45

Tyr Ser Ala Ser Glu Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg
            100                 105

<210> SEQ ID NO 67
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Pro Glu
             20                  25                  30

Leu Ser Trp Tyr Gln Gln Lys Pro Gly Lys Ala Pro Lys Leu Leu Ile
            35                  40                  45

Tyr His Thr Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Phe Gln Pro Arg
                 85                  90                  95

Thr Phe Gly Gln Gly Thr Lys Val Glu Ile Arg
            100                 105

<210> SEQ ID NO 68
<211> LENGTH: 108
<212> TYPE: PRT
<213> ORGANISM: Artificial Sequence
<220> FEATURE:
<223> OTHER INFORMATION: Synthetic Construct

<400> SEQUENCE: 68

Asp Ile Gln Met Thr Gln Ser Pro Thr Ser Leu Ser Ala Ser Val Gly
 1               5                  10                  15

Asp Arg Val Thr Ile Thr Cys Arg Ala Ser Gln Trp Ile Gly Asn Leu
             20                  25                  30

Leu Asp Trp Tyr Gln Gln Lys Pro Gly Glu Ala Pro Lys Leu Leu Ile
            35                  40                  45

Tyr Tyr Ala Ser Phe Leu Gln Ser Gly Val Pro Ser Arg Phe Ser Gly
 50                  55                  60

Gly Gly Phe Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Pro Ala Pro Leu
                 85                  90                  95

Thr Phe Gly Gln Gly Thr Lys Val Glu Ile Lys Arg
            100                 105
```

```
<210> SEQ ID NO 69
<211> LENGTH: 108
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Ser Arg
            20                  25                  30

Leu Ser Trp Tyr Gln Gln Lys Pro Gly Lys Ala Pro Lys Leu Leu Ile
        35                  40                  45

Tyr Arg Thr Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Asp Met Phe Pro Leu
                85                  90                  95

Thr Phe Gly Gln Gly Thr Lys Val Glu Ile Lys Arg
            100                 105

<210> SEQ ID NO 70
<211> LENGTH: 108
<212> TYPE: PRT
<213> ORGANISM: Artificial Sequence
<220> FEATURE:
<223> OTHER INFORMATION: Synthetic Construct

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asp Arg
            20                  25                  30

Leu Arg Trp Tyr Gln Gln Lys Pro Gly Lys Ala Pro Lys Leu Leu Ile
        35                  40                  45

Tyr His Gly Ser Arg Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Phe Arg Pro Tyr
                85                  90                  95

Thr Phe Gly Gln Gly Thr Lys Val Glu Ile Lys Arg
            100                 105

<210> SEQ ID NO 71
<211> LENGTH: 115
<212> TYPE: PRT
<213> ORGANISM: Artificial Sequence
<220> FEATURE:
<223> OTHER INFORMATION: Synthetic Construct

<400> SEQUENCE: 71

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45
```

```
Leu Ile Thr Pro Trp Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Leu
                 85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72

Asn Ala Gly Val Thr Gln Thr Pro Lys Phe Gln Val Leu Lys Thr Gly
 1               5                  10                  15

Gln Ser Met Thr Leu Gln Cys Ala Gln Asp Met Asn His Glu Tyr Met
             20                  25                  30

Ser Trp Tyr Arg Gln Asp Pro Gly Met Gly Leu Arg Leu Ile His Tyr
         35                  40                  45

Ser Val Ala Ile Gln Thr Asp Gln Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asn Thr Gly Glu Leu Phe Phe Gly Glu Gly Ser Arg Leu Thr Val Leu
            100                 105                 110

<210> SEQ ID NO 73
<211> LENGTH: 133
<212> TYPE: PRT
<213> ORGANISM: Homo sapiens

<400> SEQUENCE: 73

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125
```

Ile Ser Thr Leu Thr
    130

<210> SEQ ID NO 74
<211> LENGTH: 115
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser
        115

<210> SEQ ID NO 75
<211> LENGTH: 108
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Lys His
            20                  25                  30

Leu Lys Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Arg Trp Pro Gln
                85                  90                  95

Thr Phe Gly Gln Gly Thr Lys Val Glu Ile Lys Arg
            100                 105

<210> SEQ ID NO 76
<211> LENGTH: 104
<212> TYPE: PRT
<213> ORGANISM: Homo sapiens

<400> SEQUENCE: 76

Ser Asp Thr Gly Arg Pro Phe Val Glu Met Tyr Ser Glu Ile Pro Glu
1               5                   10                  15

```
Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val
            100

<210> SEQ ID NO 77
<211> LENGTH: 101
<212> TYPE: PRT
<213> ORGANISM: Homo sapiens

<400> SEQUENCE: 77

Val Leu Ser Pro Ser His Gly Ile Glu Leu Ser Val Gly Glu Lys Leu
1               5                   10                  15

Val Leu Asn Cys Thr Ala Arg Thr Glu Leu Asn Val Gly Ile Asp Phe
            20                  25                  30

Asn Trp Glu Tyr Pro Ser Ser Lys His Gln His Lys Lys Leu Val Asn
        35                  40                  45

Arg Asp Leu Lys Thr Gln Ser Gly Ser Glu Met Lys Lys Phe Leu Ser
    50                  55                  60

Thr Leu Thr Ile Asp Gly Val Thr Arg Ser Asp Gln Gly Leu Tyr Thr
65                  70                  75                  80

Cys Ala Ala Ser Ser Gly Leu Met Thr Lys Lys Asn Ser Thr Phe Val
                85                  90                  95

Arg Val His Glu Lys
            100

<210> SEQ ID NO 78
<211> LENGTH: 431
<212> TYPE: PRT
<213> ORGANISM: Artificial Sequence
<220> FEATURE:
<223> OTHER INFORMATION: Synthetic Construct

<400> SEQUENCE: 78

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
```

115                 120                 125
Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430

<210> SEQ ID NO 79
<211> LENGTH: 31
<212> TYPE: PRT
<213> ORGANISM: Artificial Sequence
<220> FEATURE:
<223> OTHER INFORMATION: Synthetic Construct

<400> SEQUENCE: 79

His Ala Pro Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 80
<211> LENGTH: 34
<212> TYPE: PRT

<213> ORGANISM: Artificial Sequence
<220> FEATURE:
<223> OTHER INFORMATION: Synthetic Construct

<400> SEQUENCE: 80

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 81
<211> LENGTH: 39
<212> TYPE: PRT
<213> ORGANISM: Artificial Sequence
<220> FEATURE:
<223> OTHER INFORMATION: Synthetic Construct

<400> SEQUENCE: 81

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 82
<211> LENGTH: 275
<212> TYPE: PRT
<213> ORGANISM: Artificial Sequence
<220> FEATURE:
<223> OTHER INFORMATION: Synthetic Construct

<400> SEQUENCE: 82

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

```
Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly
        275

<210> SEQ ID NO 83
<211> LENGTH: 397
<212> TYPE: PRT
<213> ORGANISM: Artificial Sequence
<220> FEATURE:
<223> OTHER INFORMATION: Synthetic Construct

<400> SEQUENCE: 83

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270
```

```
Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
        290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Leu Thr Asp Arg Glu Trp Ala Glu Glu Trp Lys
            340                 345                 350

His Leu Asp His Leu Leu Asn Cys Ile Met Asp Met Val Glu Lys Thr
        355                 360                 365

Arg Arg Ser Leu Thr Val Leu Arg Arg Cys Gln Glu Ala Asp Arg Glu
370                 375                 380

Glu Leu Asn Tyr Trp Ile Arg Arg Tyr Ser Asp Ala Glu
385                 390                 395
```

<210> SEQ ID NO 84
<211> LENGTH: 402
<212> TYPE: PRT
<213> ORGANISM: Artificial Sequence
<220> FEATURE:
<223> OTHER INFORMATION: Synthetic Construct

<400> SEQUENCE: 84

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240
```

-continued

Arg Ala Asp Ala Ser Thr Lys Gly Pro Ser Val Phe Pro Leu Ala Pro
                    245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Gly Gly Gly Ser Leu Thr Asp Arg Glu Trp
            340                 345                 350

Ala Glu Glu Trp Lys His Leu Asp His Leu Leu Asn Cys Ile Met Asp
        355                 360                 365

Met Val Glu Lys Thr Arg Arg Ser Leu Thr Val Leu Arg Arg Cys Gln
    370                 375                 380

Glu Ala Asp Arg Glu Glu Leu Asn Tyr Trp Ile Arg Arg Tyr Ser Asp
385                 390                 395                 400

Ala Glu

<210> SEQ ID NO 85
<211> LENGTH: 397
<212> TYPE: PRT
<213> ORGANISM: Artificial Sequence
<220> FEATURE:
<223> OTHER INFORMATION: Synthetic Construct

<400> SEQUENCE: 85

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
            35                  40                  45

Ser Val Ala Ile Gln Thr Thr Asp Gln Gly Glu Val Pro Asn Gly Tyr
        50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg

```
            195                 200                 205
Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
                260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
        290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Leu Thr Asp Arg Glu Trp Ala Glu Glu Trp Lys
            340                 345                 350

His Leu Asp His Leu Leu Asn Cys Ile Met Asp Met Val Glu Lys Thr
        355                 360                 365

Arg Arg Ser Leu Thr Val Leu Arg Arg Cys Gln Glu Ala Asp Arg Glu
    370                 375                 380

Glu Leu Asn Tyr Trp Ile Arg Arg Tyr Ser Asp Ala Glu
385                 390                 395

<210> SEQ ID NO 86
<211> LENGTH: 402
<212> TYPE: PRT
<213> ORGANISM: Artificial Sequence
<220> FEATURE:
<223> OTHER INFORMATION: Synthetic Construct

<400> SEQUENCE: 86

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
```

```
            165                 170                 175
Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
            195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
            245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Gly Gly Gly Ser Leu Thr Asp Arg Glu Trp
            340                 345                 350

Ala Glu Glu Trp Lys His Leu Asp His Leu Leu Asn Cys Ile Met Asp
            355                 360                 365

Met Val Glu Lys Thr Arg Arg Ser Leu Thr Val Leu Arg Arg Cys Gln
370                 375                 380

Glu Ala Asp Arg Glu Glu Leu Asn Tyr Trp Ile Arg Arg Tyr Ser Asp
385                 390                 395                 400

Ala Glu

<210> SEQ ID NO 87
<211> LENGTH: 299
<212> TYPE: PRT
<213> ORGANISM: Artificial Sequence
<220> FEATURE:
<223> OTHER INFORMATION: Synthetic Construct

<400> SEQUENCE: 87

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
            35                  40                  45

Ser Val Ala Ile Gln Thr Thr Asp Gln Gly Glu Val Pro Asn Gly Tyr
            50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
            85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
            115                 120                 125
```

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Leu Thr Asp Arg Glu Trp Ala Glu Glu Trp Lys His Leu
                245                 250                 255

Asp His Leu Leu Asn Cys Ile Met Asp Met Val Glu Lys Thr Arg Arg
            260                 265                 270

Ser Leu Thr Val Leu Arg Arg Cys Gln Glu Ala Asp Arg Glu Glu Leu
        275                 280                 285

Asn Tyr Trp Ile Arg Arg Tyr Ser Asp Ala Glu
    290                 295

<210> SEQ ID NO 88
<211> LENGTH: 304
<212> TYPE: PRT
<213> ORGANISM: Artificial Sequence
<220> FEATURE:
<223> OTHER INFORMATION: Synthetic Construct

<400> SEQUENCE: 88

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
            195                 200                 205

Cys Gln Val Gln Phe Tyr Gly Leu Ser Glu Asn Asp Glu Trp Thr Gln
        210                 215                 220

Asp Arg Ala Lys Pro Val Thr Gln Ile Val Ser Ala Glu Ala Trp Gly
225                 230                 235                 240

Arg Ala Asp Gly Gly Gly Ser Leu Thr Asp Arg Glu Trp Ala Glu
                245                 250                 255

Glu Trp Lys His Leu Asp His Leu Leu Asn Cys Ile Met Asp Met Val
                260                 265                 270

Glu Lys Thr Arg Arg Ser Leu Thr Val Leu Arg Cys Gln Glu Ala
            275                 280                 285

Asp Arg Glu Glu Leu Asn Tyr Trp Ile Arg Arg Tyr Ser Asp Ala Glu
            290                 295                 300

<210> SEQ ID NO 89
<211> LENGTH: 314
<212> TYPE: PRT
<213> ORGANISM: Artificial Sequence
<220> FEATURE:
<223> OTHER INFORMATION: Synthetic Construct

<400> SEQUENCE: 89

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Thr Val Ala Ala Pro Ser Val Phe Ile Phe Pro Pro Ser Asp Glu Gln
    210                 215                 220

Leu Lys Ser Gly Thr Ala Ser Val Val Cys Leu Leu Asn Asn Phe Tyr
225                 230                 235                 240

Pro Arg Glu Ala Lys Val Gln Trp Lys Val Asp Asn Ala Leu Gln Ser
                245                 250                 255

Gly Asn Ser Gln Glu Ser Val Thr Glu Gln Asp Ser Lys Asp Ser Thr
            260                 265                 270

Tyr Ser Leu Ser Ser Thr Leu Thr Leu Ser Lys Ala Asp Tyr Glu Lys
        275                 280                 285

His Lys Val Tyr Ala Cys Glu Val Thr His Gln Gly Leu Ser Ser Pro
290                 295                 300

Val Thr Lys Ser Phe Asn Arg Gly Glu Cys
305                 310

<210> SEQ ID NO 90
<211> LENGTH: 314
<212> TYPE: PRT
<213> ORGANISM: Artificial Sequence
<220> FEATURE:
<223> OTHER INFORMATION: Synthetic Construct

<400> SEQUENCE: 90

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Thr Val Ala Ala Pro Ser Val Phe Ile Phe Pro Pro Ser Asp Glu Gln
    210                 215                 220

Leu Lys Ser Gly Thr Ala Ser Val Val Cys Leu Leu Asn Asn Phe Tyr
225                 230                 235                 240

Pro Arg Glu Ala Lys Val Gln Trp Lys Val Asp Asn Ala Leu Gln Ser
                245                 250                 255

Gly Asn Ser Gln Glu Ser Val Thr Glu Gln Asp Ser Lys Asp Ser Thr
            260                 265                 270

Tyr Ser Leu Ser Ser Thr Leu Thr Leu Ser Lys Ala Asp Tyr Glu Lys
        275                 280                 285

His Lys Val Tyr Ala Cys Glu Val Thr His Gln Gly Leu Ser Ser Pro
    290                 295                 300

```
Val Thr Lys Ser Phe Asn Arg Gly Glu Cys
305                 310

<210> SEQ ID NO 91
<211> LENGTH: 208
<212> TYPE: PRT
<213> ORGANISM: Artificial Sequence
<220> FEATURE:
<223> OTHER INFORMATION: Synthetic Construct

<400> SEQUENCE: 91

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 92
<211> LENGTH: 530
<212> TYPE: PRT
<213> ORGANISM: Artificial Sequence
<220> FEATURE:
<223> OTHER INFORMATION: Synthetic Construct

<400> SEQUENCE: 92

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
```

-continued

```
                85                  90                  95
Gly Asn Thr Gly Glu Leu Phe Phe Gly Glu Gly Ser Arg Leu Thr Val
            100                 105                 110
Leu Glu Asp Leu Lys Asn Val Phe Pro Pro Glu Val Ala Val Phe Glu
            115                 120                 125
Pro Ser Glu Ala Glu Ile Ser His Thr Gln Lys Ala Thr Leu Val Cys
            130                 135                 140
Leu Ala Thr Gly Phe Tyr Pro Asp His Val Glu Leu Ser Trp Trp Val
145                 150                 155                 160
Asn Gly Lys Glu Val His Ser Gly Val Ser Thr Asp Pro Gln Pro Leu
                165                 170                 175
Lys Glu Gln Pro Ala Leu Asn Asp Ser Arg Tyr Ala Leu Ser Ser Arg
            180                 185                 190
Leu Arg Val Ser Ala Thr Phe Trp Gln Asp Pro Arg Asn His Phe Arg
            195                 200                 205
Cys Gln Val Gln Phe Tyr Gly Leu Ser Glu Asn Asp Glu Trp Thr Gln
            210                 215                 220
Asp Arg Ala Lys Pro Val Thr Gln Ile Val Ser Ala Glu Ala Trp Gly
225                 230                 235                 240
Arg Ala Asp Ala Ser Thr Lys Gly Pro Ser Val Phe Pro Leu Ala Pro
                245                 250                 255
Ser Ser Lys Ser Thr Ser Gly Gly Thr Ala Ala Leu Gly Cys Leu Val
            260                 265                 270
Lys Asp Tyr Phe Pro Glu Pro Val Thr Val Ser Trp Asn Ser Gly Ala
            275                 280                 285
Leu Thr Ser Gly Val His Thr Phe Pro Ala Val Leu Gln Ser Ser Gly
            290                 295                 300
Leu Tyr Ser Leu Ser Ser Val Val Thr Val Pro Ser Ser Ser Leu Gly
305                 310                 315                 320
Thr Gln Thr Tyr Ile Cys Asn Val Asn His Lys Pro Ser Asn Thr Lys
                325                 330                 335
Val Asp Lys Lys Val Leu Thr Asp Arg Glu Trp Ala Glu Glu Trp Lys
            340                 345                 350
His Leu Asp His Leu Leu Asn Cys Ile Met Asp Met Val Glu Lys Thr
            355                 360                 365
Arg Arg Ser Leu Thr Val Leu Arg Arg Cys Gln Glu Ala Asp Arg Glu
            370                 375                 380
Glu Leu Asn Tyr Trp Ile Arg Arg Tyr Ser Asp Ala Glu Ala Pro Thr
385                 390                 395                 400
Ser Ser Ser Thr Lys Lys Thr Gln Leu Gln Leu Glu His Leu Leu Leu
                405                 410                 415
Asp Leu Gln Met Ile Leu Asn Gly Ile Asn Asn Tyr Lys Asn Pro Lys
            420                 425                 430
Leu Thr Arg Met Leu Thr Phe Lys Phe Tyr Met Pro Lys Lys Ala Thr
            435                 440                 445
Glu Leu Lys His Leu Gln Cys Leu Glu Glu Glu Leu Lys Pro Leu Glu
            450                 455                 460
Glu Val Leu Asn Leu Ala Gln Ser Lys Asn Phe His Leu Arg Pro Arg
465                 470                 475                 480
Asp Leu Ile Ser Asn Ile Asn Val Ile Val Leu Glu Leu Lys Gly Ser
                485                 490                 495
Glu Thr Thr Phe Met Cys Glu Tyr Ala Asp Glu Thr Ala Thr Ile Val
            500                 505                 510
```

```
Glu Phe Leu Asn Arg Trp Ile Thr Phe Cys Gln Ser Ile Ile Ser Thr
            515                 520                 525

Leu Thr
    530

<210> SEQ ID NO 93
<211> LENGTH: 535
<212> TYPE: PRT
<213> ORGANISM: Artificial Sequence
<220> FEATURE:
<223> OTHER INFORMATION: Synthetic Construct

<400> SEQUENCE: 93

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335
```

```
Val Asp Lys Lys Val Gly Gly Gly Ser Leu Thr Asp Arg Glu Trp
            340             345             350

Ala Glu Glu Trp Lys His Leu Asp His Leu Leu Asn Cys Ile Met Asp
        355             360             365

Met Val Glu Lys Thr Arg Arg Ser Leu Thr Val Leu Arg Arg Cys Gln
    370             375             380

Glu Ala Asp Arg Glu Glu Leu Asn Tyr Trp Ile Arg Arg Tyr Ser Asp
385             390             395             400

Ala Glu Ala Pro Thr Ser Ser Thr Lys Lys Thr Gln Leu Gln Leu
                405             410             415

Glu His Leu Leu Leu Asp Leu Gln Met Ile Leu Asn Gly Ile Asn Asn
                420             425             430

Tyr Lys Asn Pro Lys Leu Thr Arg Met Leu Thr Phe Lys Phe Tyr Met
            435             440             445

Pro Lys Lys Ala Thr Glu Leu Lys His Leu Gln Cys Leu Glu Glu Glu
        450             455             460

Leu Lys Pro Leu Glu Glu Val Leu Asn Leu Ala Gln Ser Lys Asn Phe
465             470             475             480

His Leu Arg Pro Arg Asp Leu Ile Ser Asn Ile Asn Val Ile Val Leu
                485             490             495

Glu Leu Lys Gly Ser Glu Thr Thr Phe Met Cys Glu Tyr Ala Asp Glu
            500             505             510

Thr Ala Thr Ile Val Glu Phe Leu Asn Arg Trp Ile Thr Phe Cys Gln
        515             520             525

Ser Ile Ile Ser Thr Leu Thr
    530             535

<210> SEQ ID NO 94
<211> LENGTH: 412
<212> TYPE: PRT
<213> ORGANISM: Artificial Sequence
<220> FEATURE:
<223> OTHER INFORMATION: Synthetic Construct

<400> SEQUENCE: 94

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160
```

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Glu Pro Lys Ser Cys Asp Lys Thr His Thr Cys
            340                 345                 350

Pro Pro Cys Pro Leu Thr Asp Arg Glu Trp Ala Glu Trp Lys His
        355                 360                 365

Leu Asp His Leu Leu Asn Cys Ile Met Asp Met Val Glu Lys Thr Arg
370                 375                 380

Arg Ser Leu Thr Val Leu Arg Arg Cys Gln Glu Ala Asp Arg Glu Glu
385                 390                 395                 400

Leu Asn Tyr Trp Ile Arg Arg Tyr Ser Asp Ala Glu
                405                 410

<210> SEQ ID NO 95
<211> LENGTH: 417
<212> TYPE: PRT
<213> ORGANISM: Artificial Sequence
<220> FEATURE:
<223> OTHER INFORMATION: Synthetic Construct

<400> SEQUENCE: 95

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Lys Val Glu Pro Lys Ser Cys Asp Lys Thr His Thr Cys
            340                 345                 350

Pro Pro Cys Pro Gly Gly Gly Ser Leu Thr Asp Arg Glu Trp Ala
        355                 360                 365

Glu Glu Trp Lys His Leu Asp His Leu Leu Asn Cys Ile Met Asp Met
    370                 375                 380

Val Glu Lys Thr Arg Arg Ser Leu Thr Val Leu Arg Arg Cys Gln Glu
385                 390                 395                 400

Ala Asp Arg Glu Glu Leu Asn Tyr Trp Ile Arg Arg Tyr Ser Asp Ala
                405                 410                 415

Glu

<210> SEQ ID NO 96
<211> LENGTH: 172
<212> TYPE: PRT
<213> ORGANISM: Artificial Sequence
<220> FEATURE:
<223> OTHER INFORMATION: Synthetic Construct

<400> SEQUENCE: 96

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

```
Ala Gly Met Ser Ser Ala Gly Asp Arg Ser Ser Tyr Glu Asp Ser Val
 50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
                100                 105                 110

Val Ser Ser Lys Leu Thr Asp Arg Glu Trp Ala Glu Trp Lys His
                115                 120                 125

Leu Asp His Leu Leu Asn Cys Ile Met Asp Met Val Glu Lys Thr Arg
130                 135                 140

Arg Ser Leu Thr Val Leu Arg Arg Cys Gln Glu Ala Asp Arg Glu Glu
145                 150                 155                 160

Leu Asn Tyr Trp Ile Arg Arg Tyr Ser Asp Ala Glu
                165                 170
```

<210> SEQ ID NO 97
<211> LENGTH: 177
<212> TYPE: PRT
<213> ORGANISM: Artificial Sequence
<220> FEATURE:
<223> OTHER INFORMATION: Synthetic Construct

<400> SEQUENCE: 97

```
Gln Val Gln Leu Val Glu Ser Gly Gly Ala Leu Val Gln Pro Gly Gly
 1                5                  10                  15

Ser Leu Arg Leu Ser Cys Ala Ala Ser Gly Phe Pro Val Asn Arg Tyr
                20                  25                  30

Ser Met Arg Trp Tyr Arg Gln Ala Pro Gly Lys Glu Arg Glu Trp Val
                35                  40                  45

Ala Gly Met Ser Ser Ala Gly Asp Arg Ser Ser Tyr Glu Asp Ser Val
 50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
                100                 105                 110

Val Ser Ser Lys Gly Gly Gly Ser Leu Thr Asp Arg Glu Trp Ala
                115                 120                 125

Glu Glu Trp Lys His Leu Asp His Leu Leu Asn Cys Ile Met Asp Met
130                 135                 140

Val Glu Lys Thr Arg Arg Ser Leu Thr Val Leu Arg Arg Cys Gln Glu
145                 150                 155                 160

Ala Asp Arg Glu Glu Leu Asn Tyr Trp Ile Arg Arg Tyr Ser Asp Ala
                165                 170                 175

Glu
```

<210> SEQ ID NO 98
<211> LENGTH: 305
<212> TYPE: PRT
<213> ORGANISM: Artificial Sequence
<220> FEATURE:
<223> OTHER INFORMATION: Synthetic Construct

<400> SEQUENCE: 98

```
Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
                100                 105                 110

Val Ser Ser Lys Leu Thr Asp Arg Glu Trp Ala Glu Trp Lys His
            115                 120                 125

Leu Asp His Leu Leu Asn Cys Ile Met Asp Met Val Glu Lys Thr Arg
    130                 135                 140

Arg Ser Leu Thr Val Leu Arg Cys Gln Glu Ala Asp Arg Glu Glu
145                 150                 155                 160

Leu Asn Tyr Trp Ile Arg Arg Tyr Ser Asp Ala Glu Ala Pro Thr Ser
                165                 170                 175

Ser Ser Thr Lys Lys Thr Gln Leu Gln Leu Glu His Leu Leu Leu Asp
            180                 185                 190

Leu Gln Met Ile Leu Asn Gly Ile Asn Asn Tyr Lys Asn Pro Lys Leu
        195                 200                 205

Thr Arg Met Leu Thr Phe Lys Phe Tyr Met Pro Lys Lys Ala Thr Glu
    210                 215                 220

Leu Lys His Leu Gln Cys Leu Glu Glu Glu Leu Lys Pro Leu Glu Glu
225                 230                 235                 240

Val Leu Asn Leu Ala Gln Ser Lys Asn Phe His Leu Arg Pro Arg Asp
                245                 250                 255

Leu Ile Ser Asn Ile Asn Val Ile Val Leu Glu Leu Lys Gly Ser Glu
                260                 265                 270

Thr Thr Phe Met Cys Glu Tyr Ala Asp Glu Thr Ala Thr Ile Val Glu
            275                 280                 285

Phe Leu Asn Arg Trp Ile Thr Phe Cys Gln Ser Ile Ile Ser Thr Leu
        290                 295                 300

Thr
305
```

<210> SEQ ID NO 99
<211> LENGTH: 310
<212> TYPE: PRT
<213> ORGANISM: Artificial Sequence
<220> FEATURE:
<223> OTHER INFORMATION: Synthetic Construct

<400> SEQUENCE: 99

```
Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45
```

Ala Gly Met Ser Ser Ala Gly Asp Arg Ser Ser Tyr Glu Asp Ser Val
    50              55                  60

Lys Gly Arg Phe Thr Ile Ser Arg Asp Asp Ala Arg Asn Thr Val Tyr
65              70                  75                  80

Leu Gln Met Asn Ser Leu Lys Pro Glu Asp Thr Ala Val Tyr Tyr Cys
            85                  90                  95

Asn Val Asn Val Gly Phe Glu Tyr Trp Gly Gln Gly Thr Gln Val Thr
            100                 105                 110

Val Ser Ser Lys Gly Gly Gly Ser Leu Thr Asp Arg Glu Trp Ala
            115                 120                 125

Glu Glu Trp Lys His Leu Asp His Leu Leu Asn Cys Ile Met Asp Met
130                 135                 140

Val Glu Lys Thr Arg Arg Ser Leu Thr Val Leu Arg Arg Cys Gln Glu
145                 150                 155                 160

Ala Asp Arg Glu Glu Leu Asn Tyr Trp Ile Arg Arg Tyr Ser Asp Ala
                165                 170                 175

Glu Ala Pro Thr Ser Ser Ser Thr Lys Lys Thr Gln Leu Gln Leu Glu
            180                 185                 190

His Leu Leu Leu Asp Leu Gln Met Ile Leu Asn Gly Ile Asn Asn Tyr
            195                 200                 205

Lys Asn Pro Lys Leu Thr Arg Met Leu Thr Phe Lys Phe Tyr Met Pro
210                 215                 220

Lys Lys Ala Thr Glu Leu Lys His Leu Gln Cys Leu Glu Glu Glu Leu
225                 230                 235                 240

Lys Pro Leu Glu Glu Val Leu Asn Leu Ala Gln Ser Lys Asn Phe His
                245                 250                 255

Leu Arg Pro Arg Asp Leu Ile Ser Asn Ile Asn Val Ile Val Leu Glu
                260                 265                 270

Leu Lys Gly Ser Glu Thr Thr Phe Met Cys Glu Tyr Ala Asp Glu Thr
            275                 280                 285

Ala Thr Ile Val Glu Phe Leu Asn Arg Trp Ile Thr Phe Cys Gln Ser
            290                 295                 300

Ile Ile Ser Thr Leu Thr
305                 310

<210> SEQ ID NO 100
<211> LENGTH: 378
<212> TYPE: PRT
<213> ORGANISM: Artificial Sequence
<220> FEATURE:
<223> OTHER INFORMATION: Synthetic Construct

<400> SEQUENCE: 100

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65              70                  75                  80

Gln Pro Gly Asp Ser Ala Thr Tyr Leu Cys Ala Val Arg Pro Leu Leu
                85                  90                  95

```
Asp Gly Thr Tyr Ile Pro Thr Phe Gly Arg Gly Ser Leu Ile Val
                100                 105                 110

His Pro Tyr Ile Gln Asn Pro Asp Pro Ala Val Tyr Gln Leu Arg Asp
            115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Ala Ser Thr Lys Gly Pro Ser Val Phe Pro Leu Ala Pro Ser Ser Lys
    210                 215                 220

Ser Thr Ser Gly Gly Thr Ala Ala Leu Gly Cys Leu Val Lys Asp Tyr
225                 230                 235                 240

Phe Pro Glu Pro Val Thr Val Ser Trp Asn Ser Gly Ala Leu Thr Ser
                245                 250                 255

Gly Val His Thr Phe Pro Ala Val Leu Gln Ser Ser Gly Leu Tyr Ser
            260                 265                 270

Leu Ser Ser Val Val Thr Val Pro Ser Ser Ser Leu Gly Thr Gln Thr
        275                 280                 285

Tyr Ile Cys Asn Val Asn His Lys Pro Ser Asn Thr Lys Val Asp Lys
    290                 295                 300

Lys Val Leu His Gly Thr Arg Gln Glu Glu Met Ile Asp His Arg Leu
305                 310                 315                 320

Thr Asp Arg Glu Trp Ala Glu Glu Trp Lys His Leu Asp His Leu Leu
                325                 330                 335

Asn Cys Ile Met Asp Met Val Glu Lys Thr Arg Arg Ser Leu Thr Val
            340                 345                 350

Leu Arg Arg Cys Gln Glu Ala Asp Arg Glu Glu Leu Asn Tyr Trp Ile
        355                 360                 365

Arg Arg Tyr Ser Asp Ala Glu Asp Leu Lys
    370                 375

<210> SEQ ID NO 101
<211> LENGTH: 383
<212> TYPE: PRT
<213> ORGANISM: Artificial Sequence
<220> FEATURE:
<223> OTHER INFORMATION: Synthetic Construct

<400> SEQUENCE: 101

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80
```

-continued

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Ala Ser Thr Lys Gly Pro Ser Val Phe Pro Leu Ala Pro Ser Ser Lys
    210                 215                 220

Ser Thr Ser Gly Gly Thr Ala Ala Leu Gly Cys Leu Val Lys Asp Tyr
225                 230                 235                 240

Phe Pro Glu Pro Val Thr Val Ser Trp Asn Ser Gly Ala Leu Thr Ser
                245                 250                 255

Gly Val His Thr Phe Pro Ala Val Leu Gln Ser Ser Gly Leu Tyr Ser
            260                 265                 270

Leu Ser Ser Val Val Thr Val Pro Ser Ser Ser Leu Gly Thr Gln Thr
        275                 280                 285

Tyr Ile Cys Asn Val Asn His Lys Pro Ser Asn Thr Lys Val Asp Lys
    290                 295                 300

Lys Val Gly Gly Gly Ser Leu His Gly Thr Arg Gln Glu Glu Met
305                 310                 315                 320

Ile Asp His Arg Leu Thr Asp Arg Glu Trp Ala Glu Glu Trp Lys His
                325                 330                 335

Leu Asp His Leu Leu Asn Cys Ile Met Asp Met Val Glu Lys Thr Arg
            340                 345                 350

Arg Ser Leu Thr Val Leu Arg Arg Cys Gln Glu Ala Asp Arg Glu Glu
        355                 360                 365

Leu Asn Tyr Trp Ile Arg Arg Tyr Ser Asp Ala Glu Asp Leu Lys
    370                 375                 380

<210> SEQ ID NO 102
<211> LENGTH: 349
<212> TYPE: PRT
<213> ORGANISM: Artificial Sequence
<220> FEATURE:
<223> OTHER INFORMATION: Synthetic Construct

<400> SEQUENCE: 102

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 103
<211> LENGTH: 291
<212> TYPE: PRT
<213> ORGANISM: Artificial Sequence
<220> FEATURE:
<223> OTHER INFORMATION: Synthetic Construct

<400> SEQUENCE: 103

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Leu His Gly Thr Arg
            210                 215                 220

Gln Glu Glu Met Ile Asp His Arg Leu Thr Asp Arg Glu Trp Ala Glu
225                 230                 235                 240

Glu Trp Lys His Leu Asp His Leu Leu Asn Cys Ile Met Asp Met Val
                245                 250                 255

Glu Lys Thr Arg Arg Ser Leu Thr Val Leu Arg Arg Cys Gln Glu Ala
                260                 265                 270

Asp Arg Glu Glu Leu Asn Tyr Trp Ile Arg Arg Tyr Ser Asp Ala Glu
            275                 280                 285

Asp Leu Lys
        290

<210> SEQ ID NO 104
<211> LENGTH: 296
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Gly Gly Gly Gly Ser
    210                 215                 220

Leu His Gly Thr Arg Gln Glu Glu Met Ile Asp His Arg Leu Thr Asp
225                 230                 235                 240

Arg Glu Trp Ala Glu Glu Trp Lys His Leu Asp His Leu Leu Asn Cys
                245                 250                 255

Ile Met Asp Met Val Glu Lys Thr Arg Arg Ser Leu Thr Val Leu Arg
                260                 265                 270

Arg Cys Gln Glu Ala Asp Arg Glu Glu Leu Asn Tyr Trp Ile Arg Arg
            275                 280                 285

Tyr Ser Asp Ala Glu Asp Leu Lys
    290                 295

<210> SEQ ID NO 105
<211> LENGTH: 214
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 106
<211> LENGTH: 293
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65              70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Leu His Gly
    210                 215                 220

Thr Arg Gln Glu Glu Met Ile Asp His Arg Leu Thr Asp Arg Glu Trp
225                 230                 235                 240

Ala Glu Glu Trp Lys His Leu Asp His Leu Leu Asn Cys Ile Met Asp
                245                 250                 255

Met Val Glu Lys Thr Arg Arg Ser Leu Thr Val Leu Arg Cys Gln
            260                 265                 270

Glu Ala Asp Arg Glu Glu Leu Asn Tyr Trp Ile Arg Arg Tyr Ser Asp
        275                 280                 285

Ala Glu Asp Leu Lys
    290

<210> SEQ ID NO 107
<211> LENGTH: 298
<212> TYPE: PRT
<213> ORGANISM: Artificial Sequence
<220> FEATURE:
<223> OTHER INFORMATION: Synthetic Construct

<400> SEQUENCE: 107
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Gly Gly Gly
    210                 215                 220

Gly Ser Leu His Gly Thr Arg Gln Glu Glu Met Ile Asp His Arg Leu
225                 230                 235                 240

Thr Asp Arg Glu Trp Ala Glu Glu Trp Lys His Leu Asp His Leu Leu
                245                 250                 255

Asn Cys Ile Met Asp Met Val Glu Lys Thr Arg Arg Ser Leu Thr Val
            260                 265                 270

Leu Arg Arg Cys Gln Glu Ala Asp Arg Glu Glu Leu Asn Tyr Trp Ile
        275                 280                 285

Arg Arg Tyr Ser Asp Ala Glu Asp Leu Lys
    290                 295
```

```
<210> SEQ ID NO 108
<211> LENGTH: 214
<212> TYPE: PRT
<213> ORGANISM: Artificial Sequence
<220> FEATURE:
<223> OTHER INFORMATION: Synthetic Construct

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 109
<211> LENGTH: 185
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Asp Ser Tyr
                 20                  25                  30

Leu His Trp Tyr Gln Gln Lys Pro Gly Lys Ala Pro Lys Leu Leu Ile
             35                  40                  45

Tyr Ser Ala Ser Glu Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg Gly Gly Gly Gly
            100                 105                 110

Ser Leu His Gly Thr Arg Gln Glu Glu Met Ile Asp His Arg Leu Thr
            115                 120                 125

Asp Arg Glu Trp Ala Glu Trp Lys His Leu Asp His Leu Leu Asn
130                 135                 140

Cys Ile Met Asp Met Val Glu Lys Thr Arg Arg Ser Leu Thr Val Leu
145                 150                 155                 160

Arg Arg Cys Gln Glu Ala Asp Arg Glu Glu Leu Asn Tyr Trp Ile Arg
                165                 170                 175

Arg Tyr Ser Asp Ala Glu Asp Leu Lys
            180                 185

<210> SEQ ID NO 110
```

```
<211> LENGTH: 196
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser Gly Gly Gly Ser Leu His Gly Thr
        115                 120                 125

Arg Gln Glu Glu Met Ile Asp His Arg Leu Thr Asp Arg Glu Trp Ala
    130                 135                 140

Glu Glu Trp Lys His Leu Asp His Leu Leu Asn Cys Ile Met Asp Met
145                 150                 155                 160

Val Glu Lys Thr Arg Arg Ser Leu Thr Val Leu Arg Arg Cys Gln Glu
                165                 170                 175

Ala Asp Arg Glu Glu Leu Asn Tyr Trp Ile Arg Arg Tyr Ser Asp Ala
            180                 185                 190

Glu Asp Leu Lys
        195

<210> SEQ ID NO 111
<211> LENGTH: 184
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Gly Gly Gly Gly Ser
            100                 105                 110

Leu His Gly Thr Arg Gln Glu Glu Met Ile Asp His Arg Leu Thr Asp
```

```
              115                 120                 125
Arg Glu Trp Ala Glu Trp Lys His Leu Asp His Leu Leu Asn Cys
    130                 135                 140

Ile Met Asp Met Val Glu Lys Thr Arg Arg Ser Leu Thr Val Leu Arg
145                 150                 155                 160

Arg Cys Gln Glu Ala Asp Arg Glu Glu Leu Asn Tyr Trp Ile Arg Arg
                165                 170                 175

Tyr Ser Asp Ala Glu Asp Leu Lys
                180

<210> SEQ ID NO 112
<211> LENGTH: 185
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Gly Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg Gly Gly Gly Gly
            100                 105                 110

Ser Leu His Gly Thr Arg Gln Glu Glu Met Ile Asp His Arg Leu Thr
        115                 120                 125

Asp Arg Glu Trp Ala Glu Glu Trp Lys His Leu Asp His Leu Leu Asn
    130                 135                 140

Cys Ile Met Asp Met Val Glu Lys Thr Arg Arg Ser Leu Thr Val Leu
145                 150                 155                 160

Arg Arg Cys Gln Glu Ala Asp Arg Glu Glu Leu Asn Tyr Trp Ile Arg
                165                 170                 175

Arg Tyr Ser Asp Ala Glu Asp Leu Lys
            180                 185

<210> SEQ ID NO 113
<211> LENGTH: 297
<212> TYPE: PRT
<213> ORGANISM: Artificial Sequence
<220> FEATURE:
<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45
```

Tyr His Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Gly Gly Gly Ser
            100                 105                 110

Leu His Gly Thr Arg Gln Glu Met Ile Asp His Arg Leu Thr Asp
            115                 120                 125

Arg Glu Trp Ala Glu Trp Lys His Leu Asp His Leu Leu Asn Cys
130                 135                 140

Ile Met Asp Met Val Glu Lys Thr Arg Arg Ser Leu Thr Val Leu Arg
145                 150                 155                 160

Arg Cys Gln Glu Ala Asp Arg Glu Leu Asn Tyr Trp Ile Arg Arg
                165                 170                 175

Tyr Ser Asp Ala Glu Asp Leu Lys Gly Gly Gly Ser Asp Ile Gln
            180                 185                 190

Met Thr Gln Ser Pro Thr Ser Leu Ser Ala Ser Val Gly Asp Arg Val
            195                 200                 205

Thr Ile Thr Cys Arg Ala Ser Gln Trp Ile Gly Asn Leu Leu Asp Trp
210                 215                 220

Tyr Gln Gln Lys Pro Gly Glu Ala Pro Lys Leu Leu Ile Tyr Tyr Ala
225                 230                 235                 240

Ser Phe Leu Gln Ser Gly Val Pro Ser Arg Phe Ser Gly Gly Phe
                245                 250                 255

Gly Thr Asp Phe Thr Leu Thr Ile Ser Ser Leu Gln Pro Glu Asp Phe
            260                 265                 270

Ala Thr Tyr Tyr Cys Gln Gln Ala Asn Pro Ala Pro Leu Thr Phe Gly
        275                 280                 285

Gln Gly Thr Lys Val Glu Ile Lys Arg
        290                 295

<210> SEQ ID NO 114
<211> LENGTH: 185
<212> TYPE: PRT
<213> ORGANISM: Artificial Sequence
<220> FEATURE:
<223> OTHER INFORMATION: Synthetic Construct

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Ser Arg
            20                  25                  30

Leu Ser Trp Tyr Gln Gln Lys Pro Gly Lys Ala Pro Lys Leu Leu Ile
        35                  40                  45

Tyr Arg Thr Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Asp Met Phe Pro Leu
                85                  90                  95

Thr Phe Gly Gln Gly Thr Lys Val Glu Ile Lys Arg Gly Gly Gly Gly
            100                 105                 110

Ser Leu His Gly Thr Arg Gln Glu Glu Met Ile Asp His Arg Leu Thr
            115                 120                 125

Asp Arg Glu Trp Ala Glu Glu Trp Lys His Leu Asp His Leu Leu Asn
        130                 135                 140

Cys Ile Met Asp Met Val Glu Lys Thr Arg Arg Ser Leu Thr Val Leu
145                 150                 155                 160

Arg Arg Cys Gln Glu Ala Asp Arg Glu Glu Leu Asn Tyr Trp Ile Arg
                165                 170                 175

Arg Tyr Ser Asp Ala Glu Asp Leu Lys
            180                 185

<210> SEQ ID NO 115
<211> LENGTH: 298
<212> TYPE: PRT
<213> ORGANISM: Artificial Sequence
<220> FEATURE:
<223> OTHER INFORMATION: Synthetic Construct

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Ser Arg
            20                  25                  30

Leu Ser Trp Tyr Gln Gln Lys Pro Gly Lys Ala Pro Lys Leu Leu Ile
        35                  40                  45

Tyr Arg Thr Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Asp Met Phe Pro Leu
                85                  90                  95

Thr Phe Gly Gln Gly Thr Lys Val Glu Ile Lys Arg Gly Gly Gly Gly
            100                 105                 110

Ser Leu His Gly Thr Arg Gln Glu Glu Met Ile Asp His Arg Leu Thr
        115                 120                 125

Asp Arg Glu Trp Ala Glu Glu Trp Lys His Leu Asp His Leu Leu Asn
    130                 135                 140

Cys Ile Met Asp Met Val Glu Lys Thr Arg Arg Ser Leu Thr Val Leu
145                 150                 155                 160

Arg Arg Cys Gln Glu Ala Asp Arg Glu Glu Leu Asn Tyr Trp Ile Arg
                165                 170                 175

Arg Tyr Ser Asp Ala Glu Asp Leu Lys Gly Gly Gly Ser Asp Ile
            180                 185                 190

Gln Met Thr Gln Ser Pro Ser Ser Leu Ser Ala Ser Val Gly Asp Arg
        195                 200                 205

Val Thr Ile Thr Cys Arg Ala Ser Gln Asp Ile Gly Asp Arg Leu Arg
    210                 215                 220

Trp Tyr Gln Gln Lys Pro Gly Lys Ala Pro Lys Leu Leu Ile Tyr His
225                 230                 235                 240

Gly Ser Arg Leu Glu Ser Gly Val Pro Ser Arg Phe Ser Gly Ser Arg
                245                 250                 255

Ser Gly Thr Asp Phe Thr Leu Thr Ile Ser Ser Leu Gln Pro Glu Asp
            260                 265                 270

Phe Ala Thr Tyr Tyr Cys Gln Gln Gln Trp Arg Pro Tyr Thr Phe
        275                 280                 285

Gly Gln Gly Thr Lys Val Glu Ile Lys Arg
       290                 295

<210> SEQ ID NO 116
<211> LENGTH: 168
<212> TYPE: DNA
<213> ORGANISM: Homo sapiens

<400> SEQUENCE: 116
ctaacagaca gagaatgggc agaagagtgg aaacatcttg accatctgtt aaactgcata      60
atggacatgg tagaaaaaac aaggcgatct ctcaccgtac taaggcggtg tcaagaagca     120
gaccgggaag aattgaatta ctggatccgg cggtacagtg acgccgag                  168

<210> SEQ ID NO 117
<211> LENGTH: 216
<212> TYPE: DNA
<213> ORGANISM: Artificial Sequence
<220> FEATURE:
<223> OTHER INFORMATION: Synthetic Construct

<400> SEQUENCE: 117
ttgcatggca cacgtcaaga agaaatgatt gatcacagac taacagacag agaatgggca      60
gaagagtgga aacatcttga ccatctgtta aactgcataa tggacatggt agaaaaaaca     120
aggcgatctc tcaccgtact aaggcggtgt caagaagcag accgggaaga attgaattac     180
tggatccggc ggtacagtga cgccgaggac ttaaaa                              216

<210> SEQ ID NO 118
<211> LENGTH: 201
<212> TYPE: DNA
<213> ORGANISM: Artificial Sequence
<220> FEATURE:
<223> OTHER INFORMATION: Synthetic Construct

<400> SEQUENCE: 118
ggcacacgtc aagaagaaat gattgatcac agactaacag acagagaatg gcagaagag       60 tggaaacatc ttgaccatct gttaaactgc ataatggaca tggtagaaaa aacaaggcga     120
tctctcaccg tactaaggcg tgtcaagaa gcagaccggg aagaattgaa ttactggatc     180
cggcggtaca gtgacgccga g                                              201

<210> SEQ ID NO 119
<211> LENGTH: 141
<212> TYPE: DNA
<213> ORGANISM: Artificial Sequence
<220> FEATURE:
<223> OTHER INFORMATION: Synthetic Construct

<400> SEQUENCE: 119
caagaagaaa tgattgatca cagactaaca gacagagaat gggcagaaga gtggaaacat      60
cttgaccatc tgttaaactg cataatggac atggtagaaa aacaaggcg atctctcacc     120 gtactaaggc ggtgtcaaga a                                              141

<210> SEQ ID NO 120
<211> LENGTH: 56
<212> TYPE: PRT
<213> ORGANISM: Homo sapiens

<400> SEQUENCE: 120

Leu Thr Asp Arg Glu Trp Ala Glu Glu Trp Lys His Leu Asp His Leu
1               5                   10                  15

Leu Asn Cys Ile Met Asp Met Val Glu Lys Thr Arg Arg Ser Leu Thr
                20                  25                  30

Val Leu Arg Arg Cys Gln Glu Ala Asp Arg Glu Leu Asn Tyr Trp
            35                  40                  45

Ile Arg Arg Tyr Ser Asp Ala Glu
    50                  55

<210> SEQ ID NO 121
<211> LENGTH: 72
<212> TYPE: PRT
<213> ORGANISM: Artificial Sequence
<220> FEATURE:
<223> OTHER INFORMATION: Synthetic Construct

<400> SEQUENCE: 121

Leu His Gly Thr Arg Gln Glu Glu Met Ile Asp His Arg Leu Thr Asp
1               5                   10                  15

Arg Glu Trp Ala Glu Glu Trp Lys His Leu Asp His Leu Leu Asn Cys
                20                  25                  30

Ile Met Asp Met Val Glu Lys Thr Arg Arg Ser Leu Thr Val Leu Arg
            35                  40                  45

Arg Cys Gln Glu Ala Asp Arg Glu Leu Asn Tyr Trp Ile Arg Arg
        50                  55                  60

Tyr Ser Asp Ala Glu Asp Leu Lys
65                  70

<210> SEQ ID NO 122
<211> LENGTH: 67
<212> TYPE: PRT
<213> ORGANISM: Artificial Sequence
<220> FEATURE:
<223> OTHER INFORMATION: Synthetic Construct

<400> SEQUENCE: 122

Gly Thr Arg Gln Glu Glu Met Ile Asp His Arg Leu Thr Asp Arg Glu
1               5                   10                  15

Trp Ala Glu Glu Trp Lys His Leu Asp His Leu Leu Asn Cys Ile Met
                20                  25                  30

Asp Met Val Glu Lys Thr Arg Arg Ser Leu Thr Val Leu Arg Arg Cys
            35                  40                  45

Gln Glu Ala Asp Arg Glu Leu Asn Tyr Trp Ile Arg Arg Tyr Ser
        50                  55                  60

Asp Ala Glu
65

<210> SEQ ID NO 123
<211> LENGTH: 47
<212> TYPE: PRT
<213> ORGANISM: Artificial Sequence
<220> FEATURE:
<223> OTHER INFORMATION: Synthetic Construct

<400> SEQUENCE: 123

Gln Glu Glu Met Ile Asp His Arg Leu Thr Asp Arg Glu Trp Ala Glu
1               5                   10                  15

Glu Trp Lys His Leu Asp His Leu Leu Asn Cys Ile Met Asp Met Val
                20                  25                  30

Glu Lys Thr Arg Arg Ser Leu Thr Val Leu Arg Arg Cys Gln Glu
            35                  40                  45

<210> SEQ ID NO 124
<211> LENGTH: 126
<212> TYPE: DNA
<213> ORGANISM: Homo sapiens

<400> SEQUENCE: 124

```
aagaagaaac cactggatgg agaatatttc acccttcaga tccgtgggcg tgagcgcttc      60
gagatgttcc gagagctgaa tgaggccttg gaactcaagg atgcccaggc tgggaaggag     120
ccaggg                                                                126
```

<210> SEQ ID NO 125
<211> LENGTH: 96
<212> TYPE: DNA
<213> ORGANISM: Artificial Sequence
<220> FEATURE:
<223> OTHER INFORMATION: Synthetic Construct

<400> SEQUENCE: 125

```
ggagaatatt tcacccttca gatccgtggg cgtgagcgct tcgagatgtt ccgagagctg      60
aatgaggcct tggaactcaa ggatgcccag gctggg                                96
```

<210> SEQ ID NO 126
<211> LENGTH: 42
<212> TYPE: PRT
<213> ORGANISM: Homo sapiens

<400> SEQUENCE: 126

Lys Lys Lys Pro Leu Asp Gly Glu Tyr Phe Thr Leu Gln Ile Arg Gly
1               5                   10                  15

Arg Glu Arg Phe Glu Met Phe Arg Glu Leu Asn Glu Ala Leu Glu Leu
            20                  25                  30

Lys Asp Ala Gln Ala Gly Lys Glu Pro Gly
        35                  40

<210> SEQ ID NO 127
<211> LENGTH: 593
<212> TYPE: PRT
<213> ORGANISM: Artificial Sequence
<220> FEATURE:
<223> OTHER INFORMATION: Synthetic Construct

<400> SEQUENCE: 127

Cys Ala Cys Gly Thr Gly Ala Thr Gly Gly Ala Gly Cys Thr Gly Gly
1               5                   10                  15

Gly Gly Cys Thr Gly Ala Gly Cys Thr Gly Gly Gly Thr Gly Gly Thr
            20                  25                  30

Cys Cys Thr Gly Gly Cys Thr Gly Cys Thr Cys Thr Ala Cys Thr Ala
        35                  40                  45

Cys Ala Ala Gly Gly Thr Gly Thr Cys Ala Gly Gly Cys Thr Cys
    50                  55                  60

Ala Gly Gly Thr Thr Cys Ala Gly Cys Thr Gly Thr Thr Gly Thr Ala
65                  70                  75                  80

Ala Ala Gly Cys Gly Gly Thr Gly Gly Thr Gly Cys Ala Cys Thr Gly
                85                  90                  95

Gly Thr Thr Cys Ala Gly Cys Cys Thr Gly Gly Thr Gly Gly Thr Ala
                100                 105                 110

Gly Cys Cys Thr Gly Cys Gly Thr Cys Thr Gly Ala Gly Cys Thr Gly
                115                 120                 125

```
Thr Gly Cys Ala Gly Cys Ala Ala Gly Cys Gly Gly Thr Thr Thr Thr
    130                 135                 140

Cys Cys Gly Gly Thr Thr Ala Ala Thr Cys Gly Thr Thr Ala Thr Ala
145                 150                 155                 160

Gly Cys Ala Thr Gly Cys Gly Thr Thr Gly Gly Thr Ala Thr Cys Gly
                165                 170                 175

Thr Cys Ala Gly Gly Cys Ala Cys Cys Gly Gly Gly Thr Ala Ala Ala
            180                 185                 190

Gly Ala Ala Cys Gly Thr Gly Ala Ala Thr Gly Gly Gly Thr Thr Gly
        195                 200                 205

Cys Ala Gly Gly Thr Ala Thr Gly Ala Gly Cys Ala Gly Thr Gly Cys
    210                 215                 220

Cys Gly Gly Thr Gly Ala Thr Cys Gly Thr Ala Gly Cys Ala Gly Cys
225                 230                 235                 240

Thr Ala Thr Gly Ala Ala Gly Ala Thr Ala Gly Cys Gly Thr Thr Ala
                245                 250                 255

Ala Ala Gly Gly Thr Cys Gly Thr Thr Thr Thr Ala Cys Cys Ala Thr
            260                 265                 270

Cys Ala Gly Cys Cys Gly Thr Gly Ala Thr Gly Ala Thr Gly Cys Ala
        275                 280                 285

Cys Gly Thr Ala Ala Thr Ala Cys Cys Gly Thr Thr Thr Ala Thr Cys
    290                 295                 300

Thr Gly Cys Ala Ala Ala Thr Gly Ala Ala Thr Ala Gly Cys Cys Thr
305                 310                 315                 320

Gly Ala Ala Ala Cys Cys Gly Gly Ala Ala Gly Ala Thr Ala Cys Cys
                325                 330                 335

Gly Cys Ala Gly Thr Gly Thr Ala Thr Thr Ala Thr Thr Gly Cys Ala
            340                 345                 350

Ala Thr Gly Thr Thr Ala Ala Cys Gly Thr Gly Gly Gly Cys Thr Thr
        355                 360                 365

Thr Gly Ala Ala Thr Ala Thr Thr Gly Gly Gly Gly Thr Cys Ala Gly
    370                 375                 380

Gly Gly Cys Ala Cys Cys Cys Ala Gly Gly Thr Thr Ala Cys Cys Gly
385                 390                 395                 400

Thr Thr Ala Gly Cys Ala Gly Cys Ala Ala Ala Ala Ala Gly Ala Ala
                405                 410                 415

Gly Ala Ala Ala Cys Cys Ala Cys Thr Gly Gly Ala Thr Gly Gly Ala
            420                 425                 430

Gly Ala Ala Thr Ala Thr Thr Thr Cys Ala Cys Cys Cys Thr Thr Cys
        435                 440                 445

Ala Gly Ala Thr Cys Cys Gly Thr Gly Gly Gly Cys Gly Thr Gly Ala
    450                 455                 460

Gly Cys Gly Cys Thr Thr Cys Gly Ala Gly Ala Thr Gly Thr Thr Cys
465                 470                 475                 480

Cys Gly Ala Gly Ala Gly Cys Thr Gly Ala Ala Thr Gly Ala Gly Gly
                485                 490                 495

Cys Cys Thr Thr Gly Gly Ala Ala Cys Thr Cys Ala Ala Gly Gly Ala
            500                 505                 510

Thr Gly Cys Cys Cys Ala Gly Gly Cys Thr Gly Gly Gly Ala Ala Gly
        515                 520                 525

Gly Ala Gly Cys Cys Ala Gly Gly Gly Gly Ala Cys Thr Ala Cys Ala
    530                 535                 540

Ala Gly Gly Ala Cys Gly Ala Cys Gly Ala Cys Gly Ala Cys Ala Ala

```
                545                 550                 555                 560
Gly Cys Ala Cys Cys Ala Cys Cys Ala Cys Cys Ala Thr Cys Ala Cys
                    565                 570                 575

Cys Ala Cys Thr Gly Ala Thr Ala Ala Gly Cys Gly Gly Cys Cys Gly
                    580                 585                 590

Cys

<210> SEQ ID NO 128
<211> LENGTH: 193
<212> TYPE: PRT
<213> ORGANISM: Artificial Sequence
<220> FEATURE:
<223> OTHER INFORMATION: Synthetic Construct

<400> SEQUENCE: 128

His Val Met Glu Leu Gly Leu Ser Trp Val Val Leu Ala Ala Leu Leu
1               5                   10                  15

Gln Gly Val Gln Ala Gln Val Gln Leu Val Glu Ser Gly Gly Ala Leu
                20                  25                  30

Val Gln Pro Gly Gly Ser Leu Arg Leu Ser Cys Ala Ala Ser Gly Phe
            35                  40                  45

Pro Val Asn Arg Tyr Ser Met Arg Trp Tyr Arg Gln Ala Pro Gly Lys
        50                  55                  60

Glu Arg Glu Trp Val Ala Gly Met Ser Ser Ala Gly Asp Arg Ser Ser
65                  70                  75                  80

Tyr Glu Asp Ser Val Lys Gly Arg Phe Thr Ile Ser Arg Asp Asp Ala
                85                  90                  95

Arg Asn Thr Val Tyr Leu Gln Met Asn Ser Leu Lys Pro Glu Asp Thr
            100                 105                 110

Ala Val Tyr Tyr Cys Asn Val Asn Val Gly Phe Glu Tyr Trp Gly Gln
        115                 120                 125

Gly Thr Gln Val Thr Val Ser Ser Lys Lys Lys Pro Leu Asp Gly
    130                 135                 140

Glu Tyr Phe Thr Leu Gln Ile Arg Gly Arg Glu Arg Phe Glu Met Phe
145                 150                 155                 160

Arg Glu Leu Asn Glu Ala Leu Glu Leu Lys Asp Ala Gln Ala Gly Lys
                165                 170                 175

Glu Pro Gly Asp Tyr Lys Asp Asp Asp Lys His His His His
            180                 185                 190

His

<210> SEQ ID NO 129
<211> LENGTH: 608
<212> TYPE: PRT
<213> ORGANISM: Artificial Sequence
<220> FEATURE:
<223> OTHER INFORMATION: Synthetic Construct

<400> SEQUENCE: 129

Cys Ala Cys Gly Thr Gly Ala Thr Gly Gly Ala Gly Cys Thr Gly Gly
1               5                   10                  15

Gly Gly Cys Thr Gly Ala Gly Cys Thr Gly Gly Thr Gly Gly Thr Thr
                20                  25                  30

Cys Cys Thr Gly Gly Cys Thr Gly Cys Thr Cys Thr Ala Cys Thr Ala
            35                  40                  45

Cys Ala Ala Gly Gly Thr Gly Thr Cys Cys Ala Gly Gly Cys Thr Cys
        50                  55                  60
```

```
Ala Gly Gly Thr Thr Cys Ala Gly Cys Thr Gly Thr Thr Gly Ala
 65                  70                  75                  80

Ala Ala Gly Cys Gly Thr Gly Gly Thr Gly Cys Ala Cys Thr Gly
             85                  90                  95

Gly Thr Thr Cys Ala Gly Cys Cys Thr Gly Thr Gly Gly Thr Ala
            100                 105                 110

Gly Cys Cys Thr Gly Cys Gly Thr Cys Thr Gly Ala Gly Cys Thr Gly
            115                 120                 125

Thr Gly Cys Ala Gly Cys Ala Ala Gly Cys Gly Gly Thr Thr Thr Thr
    130                 135                 140

Cys Cys G

```
Cys Gly Cys Thr Thr Cys Gly Ala Gly Ala Thr Gly Thr Cys Cys
                485                 490                 495

Gly Ala Gly Ala Gly Cys Thr Gly Ala Ala Thr Gly Ala Gly Gly Cys
            500                 505                 510

Cys Thr Thr Gly Gly Ala Ala Cys Thr Cys Ala Ala Gly Gly Ala Thr
            515                 520                 525

Gly Cys Cys Cys Ala Gly Gly Cys Thr Gly Gly Ala Ala Gly Gly
            530                 535                 540

Ala Gly Cys Cys Ala Gly Gly Gly Ala Cys Thr Ala Cys Ala Ala
545                 550                 555                 560

Gly Gly Ala Cys Gly Ala Cys Gly Ala Cys Gly Ala Cys Ala Ala Gly
            565                 570                 575

Cys Ala Cys Cys Ala Cys Cys Ala Cys Cys Ala Thr Cys Ala Cys Cys
            580                 585                 590

Ala Cys Thr Gly Ala Thr Ala Ala Gly Cys Gly Gly Cys Cys Gly Cys
            595                 600                 605

<210> SEQ ID NO 130
<211> LENGTH: 198
<212> TYPE: PRT
<213> ORGANISM: Artificial Sequence
<220> FEATURE:
<223> OTHER INFORMATION: Synthetic Construct

<400> SEQUENCE: 130

His Val Met Glu Leu Gly Leu Ser Trp Val Leu Ala Ala Leu Leu
1               5                   10                  15

Gln Gly Val Gln Ala Gln Val Gln Leu Val Glu Ser Gly Gly Ala Leu
                20                  25                  30

Val Gln Pro Gly Gly Ser Leu Arg Leu Ser Cys Ala Ala Ser Gly Phe
            35                  40                  45

Pro Val Asn Arg Tyr Ser Met Arg Trp Tyr Arg Gln Ala Pro Gly Lys
        50                  55                  60

Glu Arg Glu Trp Val Ala Gly Met Ser Ser Ala Gly Asp Arg Ser Ser
65                  70                  75                  80

Tyr Glu Asp Ser Val Lys Gly Arg Phe Thr Ile Ser Arg Asp Asp Ala
                85                  90                  95

Arg Asn Thr Val Tyr Leu Gln Met Asn Ser Leu Lys Pro Glu Asp Thr
            100                 105                 110

Ala Val Tyr Tyr Cys Asn Val Asn Val Gly Phe Glu Tyr Trp Gly Gln
        115                 120                 125

Gly Thr Gln Val Thr Val Ser Ser Lys Gly Gly Gly Ser Lys Lys
    130                 135                 140

Lys Pro Leu Asp Gly Glu Tyr Phe Thr Leu Gln Ile Arg Gly Arg Glu
145                 150                 155                 160

Arg Phe Glu Met Phe Arg Glu Leu Asn Glu Ala Leu Glu Leu Lys Asp
                165                 170                 175

Ala Gln Ala Gly Lys Glu Pro Gly Asp Tyr Lys Asp Asp Asp Lys
            180                 185                 190

His His His His His His
        195

<210> SEQ ID NO 131
<211> LENGTH: 334
<212> TYPE: PRT
<213> ORGANISM: Artificial Sequence
<220> FEATURE:
```

<223> OTHER INFORMATION: Synthetic Construct

<400> SEQUENCE: 131

```
Met Gly Trp Ser Cys Ile Ile Leu Phe Leu Val Ala Thr Ala Thr Gly
1               5                   10                  15

Val His Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Thr Pro Trp Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Leu Asp Gly Thr Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
    290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330
```

<210> SEQ ID NO 132
<211> LENGTH: 441
<212> TYPE: PRT
<213> ORGANISM: Artificial Sequence
<220> FEATURE:
<223> OTHER INFORMATION: Synthetic Construct

<400> SEQUENCE: 132

```
Met Gly Trp Ser Cys Ile Ile Leu Phe Leu Val Ala Thr Ala Thr Gly
1               5                   10                  15
```

```
Val His Ser Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Ala Ile Gln Thr Asp Gln Gly Glu Val Pro Asn
65                  70                  75                  80

Gly Tyr Asn Val Ser Arg Ser Thr Ile Glu Asp Phe Pro Leu Arg Leu
                85                  90                  95

Leu Ser Ala Ala Pro Ser Gln Thr Ser Val Tyr Phe Cys Ala Ser Ser
            100                 105                 110

Tyr Leu Gly Asn Thr Gly Glu Leu Phe Phe Gly Glu Gly Ser Arg Leu
        115                 120                 125

Thr Val Leu Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Ala Leu Ser
        195                 200                 205

Ser Arg Leu Arg Val Ser Ala Thr Phe Trp Gln Asp Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Ala Ser Thr Lys Gly Pro Ser Val Phe Pro Leu
            260                 265                 270

Ala Pro Ser Ser Lys Ser Thr Ser Gly Gly Thr Ala Ala Leu Gly Cys
        275                 280                 285

Leu Val Lys Asp Tyr Phe Pro Glu Pro Val Thr Val Ser Trp Asn Ser
    290                 295                 300

Gly Ala Leu Thr Ser Gly Val His Thr Phe Pro Ala Val Leu Gln Ser
305                 310                 315                 320

Ser Gly Leu Tyr Ser Leu Ser Ser Val Val Thr Val Pro Ser Ser Ser
                325                 330                 335

Leu Gly Thr Gln Thr Tyr Ile Cys Asn Val Asn His Lys Pro Ser Asn
            340                 345                 350

Thr Lys Val Asp Lys Lys Val Gly Gly Gly Ser Gly Gly Gly Gly
        355                 360                 365

Ser Gly Gly Gly Gly Ser Gly Gly Gly Gly Ser Leu Thr Asp Arg Glu
    370                 375                 380

Trp Ala Glu Glu Trp Lys His Leu Asp His Leu Leu Asn Cys Ile Met
385                 390                 395                 400

Asp Met Val Glu Lys Thr Arg Arg Ser Leu Thr Val Leu Arg Arg Cys
                405                 410                 415

Gln Glu Ala Asp Arg Glu Glu Leu Asn Tyr Trp Ile Arg Arg Tyr Ser
            420                 425                 430
```

Asp Ala Glu His His His His His His
             435                 440

<210> SEQ ID NO 133
<211> LENGTH: 334
<212> TYPE: PRT
<213> ORGANISM: Artificial Sequence
<220> FEATURE:
<223> OTHER INFORMATION: Synthetic Construct

<400> SEQUENCE: 133

Met Gly Trp Ser Cys Ile Ile Leu Phe Leu Val Ala Thr Ala Thr Gly
1               5                   10                  15

Val His Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Thr Pro Trp Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Leu Asp Gly Thr Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
    290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 134
<211> LENGTH: 456

```
<212> TYPE: PRT
<213> ORGANISM: Artificial Sequence
<220> FEATURE:
<223> OTHER INFORMATION: Synthetic Construct

<400> SEQUENCE: 134

Met Gly Trp Ser Cys Ile Ile Leu Phe Leu Val Ala Thr Ala Thr Gly
1               5                   10                  15

Val His Ser Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Ala Ile Gln Thr Asp Gln Gly Glu Val Pro Asn
65                  70                  75                  80

Gly Tyr Asn Val Ser Arg Ser Thr Ile Glu Asp Phe Pro Leu Arg Leu
                85                  90                  95

Leu Ser Ala Ala Pro Ser Gln Thr Ser Val Tyr Phe Cys Ala Ser Ser
            100                 105                 110

Tyr Leu Gly Asn Thr Gly Glu Leu Phe Phe Gly Glu Gly Ser Arg Leu
        115                 120                 125

Thr Val Leu Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Ala Leu Ser
        195                 200                 205

Ser Arg Leu Arg Val Ser Ala Thr Phe Trp Gln Asp Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Ala Ser Thr Lys Gly Pro Ser Val Phe Pro Leu
            260                 265                 270

Ala Pro Ser Ser Lys Ser Thr Ser Gly Gly Thr Ala Ala Leu Gly Cys
        275                 280                 285

Leu Val Lys Asp Tyr Phe Pro Glu Pro Val Thr Val Ser Trp Asn Ser
290                 295                 300

Gly Ala Leu Thr Ser Gly Val His Thr Phe Pro Ala Val Leu Gln Ser
305                 310                 315                 320

Ser Gly Leu Tyr Ser Leu Ser Ser Val Val Thr Val Pro Ser Ser Ser
                325                 330                 335

Leu Gly Thr Gln Thr Tyr Ile Cys Asn Val Asn His Lys Pro Ser Asn
            340                 345                 350

Thr Lys Val Asp Lys Lys Val Glu Pro Lys Ser Cys Asp Lys Thr His
        355                 360                 365

Thr Cys Pro Pro Cys Pro Gly Gly Gly Ser Gly Gly Gly Ser
        370                 375                 380
```

Gly Gly Gly Gly Ser Gly Gly Gly Ser Leu Thr Asp Arg Glu Trp
385                 390                 395                 400

Ala Glu Glu Trp Lys His Leu Asp His Leu Leu Asn Cys Ile Met Asp
            405                 410                 415

Met Val Glu Lys Thr Arg Arg Ser Leu Thr Val Leu Arg Arg Cys Gln
            420                 425                 430

Glu Ala Asp Arg Glu Glu Leu Asn Tyr Trp Ile Arg Arg Tyr Ser Asp
            435                 440                 445

Ala Glu His His His His His His
    450                 455

<210> SEQ ID NO 135
<211> LENGTH: 334
<212> TYPE: PRT
<213> ORGANISM: Artificial Sequence
<220> FEATURE:
<223> OTHER INFORMATION: Synthetic Construct

<400> SEQUENCE: 135

Met Gly Trp Ser Cys Ile Ile Leu Phe Leu Val Ala Thr Ala Thr Gly
1               5                   10                  15

Val His Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Thr Pro Trp Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Leu Asp Gly Thr Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

```
Lys Asp Ser Thr Tyr Ser Leu Ser Ser Thr Leu Thr Leu Ser Lys Ala
        290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 136
<211> LENGTH: 594
<212> TYPE: PRT
<213> ORGANISM: Artificial Sequence
<220> FEATURE:
<223> OTHER INFORMATION: Synthetic Construct

<400> SEQUENCE: 136

Met Gly Trp Ser Cys Ile Ile Leu Phe Leu Val Ala Thr Ala Thr Gly
1               5                   10                  15

Val His Ser Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
50                  55                  60

Ile His Tyr Ser Val Ala Ile Gln Thr Asp Gln Gly Glu Val Pro Asn
65                  70                  75                  80

Gly Tyr Asn Val Ser Arg Ser Thr Ile Glu Asp Phe Pro Leu Arg Leu
                85                  90                  95

Leu Ser Ala Ala Pro Ser Gln Thr Ser Val Tyr Phe Cys Ala Ser Ser
            100                 105                 110

Tyr Leu Gly Asn Thr Gly Glu Leu Phe Phe Gly Glu Gly Ser Arg Leu
        115                 120                 125

Thr Val Leu Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Ala Leu Ser
        195                 200                 205

Ser Arg Leu Arg Val Ser Ala Thr Phe Trp Gln Asp Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Ala Ser Thr Lys Gly Pro Ser Val Phe Pro Leu
            260                 265                 270

Ala Pro Ser Ser Lys Ser Thr Ser Gly Gly Thr Ala Ala Leu Gly Cys
        275                 280                 285

Leu Val Lys Asp Tyr Phe Pro Glu Pro Val Thr Val Ser Trp Asn Ser
290                 295                 300

Gly Ala Leu Thr Ser Gly Val His Thr Phe Pro Ala Val Leu Gln Ser
305                 310                 315                 320
```

```
Ser Gly Leu Tyr Ser Leu Ser Ser Val Val Thr Val Pro Ser Ser Ser
                325                 330                 335

Leu Gly Thr Gln Thr Tyr Ile Cys Asn Val Asn His Lys Pro Ser Asn
            340                 345                 350

Thr Lys Val Asp Lys Lys Val Gly Gly Gly Ser Gly Gly Gly Gly
        355                 360                 365

Ser Gly Gly Gly Ser Gly Gly Gly Ser Leu Thr Asp Arg Glu
    370                 375                 380

Trp Ala Glu Glu Trp Lys His Leu Asp His Leu Leu Asn Cys Ile Met
385                 390                 395                 400

Asp Met Val Glu Lys Thr Arg Arg Ser Leu Thr Val Leu Arg Arg Cys
                405                 410                 415

Gln Glu Ala Asp Arg Glu Leu Asn Tyr Trp Ile Arg Arg Tyr Ser
            420                 425                 430

Asp Ala Glu Gly Gly Gly Ser Gly Gly Gly Ser Gly Gly
        435                 440                 445

Gly Ser Gly Gly Gly Ser Ala Pro Thr Ser Ser Thr Lys Lys
    450                 455                 460

Thr Gln Leu Gln Leu Glu His Leu Leu Leu Asp Leu Gln Met Ile Leu
465                 470                 475                 480

Asn Gly Ile Asn Asn Tyr Lys Asn Pro Lys Leu Thr Arg Met Leu Thr
                485                 490                 495

Phe Lys Phe Tyr Met Pro Lys Lys Ala Thr Glu Leu Lys His Leu Gln
            500                 505                 510

Cys Leu Glu Glu Glu Leu Lys Pro Leu Glu Glu Val Leu Asn Leu Ala
            515                 520                 525

Gln Ser Lys Asn Phe His Leu Arg Pro Arg Asp Leu Ile Ser Asn Ile
            530                 535                 540

Asn Val Ile Val Leu Glu Leu Lys Gly Ser Glu Thr Thr Phe Met Cys
545                 550                 555                 560

Glu Tyr Ala Asp Glu Thr Ala Thr Ile Val Glu Phe Leu Asn Arg Trp
                565                 570                 575

Ile Thr Phe Cys Gln Ser Ile Ile Ser Thr Leu Thr His His His His
            580                 585                 590

His His

<210> SEQ ID NO 137
<211> LENGTH: 334
<212> TYPE: PRT
<213> ORGANISM: Artificial Sequence
<220> FEATURE:
<223> OTHER INFORMATION: Synthetic Construct

<400> SEQUENCE: 137

Met Gly Trp Ser Cys Ile Ile Leu Phe Leu Val Ala Thr Ala Thr Gly
1               5                   10                  15

Val His Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Thr Pro Trp Gln Arg Glu Gln Thr Ser Gly Arg
65                  70                  75                  80

Leu Asn Ala Ser Leu Asp Lys Ser Ser Gly Arg Ser Thr Leu Tyr Ile
```

```
                    85                  90                  95
Ala Ala Ser Gln Pro Gly Asp Ser Ala Thr Tyr Leu Cys Ala Val Arg
                100                 105                 110

Pro Leu Leu Asp Gly Thr Tyr Ile Pro Thr Phe Gly Arg Gly Thr Ser
            115                 120                 125

Leu Ile Val His Pro Tyr Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
    290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330
```

<210> SEQ ID NO 138
<211> LENGTH: 609
<212> TYPE: PRT
<213> ORGANISM: Artificial Sequence
<220> FEATURE:
<223> OTHER INFORMATION: Synthetic Construct

<400> SEQUENCE: 138

```
Met Gly Trp Ser Cys Ile Ile Leu Phe Leu Val Ala Thr Ala Thr Gly
1               5                   10                  15

Val His Ser Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Ala Ile Gln Thr Asp Gln Gly Glu Val Pro Asn
65                  70                  75                  80

Gly Tyr Asn Val Ser Arg Ser Thr Ile Glu Asp Phe Pro Leu Arg Leu
                85                  90                  95

Leu Ser Ala Ala Pro Ser Gln Thr Ser Val Tyr Phe Cys Ala Ser Ser
            100                 105                 110

Tyr Leu Gly Asn Thr Gly Glu Leu Phe Phe Gly Glu Gly Ser Arg Leu
```

-continued

```
            115                 120                 125
Thr Val Leu Glu Asp Leu Asn Lys Val Phe Pro Pro Glu Val Ala Val
        130                 135                 140
Phe Glu Pro Ser Glu Ala Glu Ile Ser His Thr Gln Lys Ala Thr Leu
145                 150                 155                 160
Val Cys Leu Ala Thr Gly Phe Phe Pro Asp His Val Glu Leu Ser Trp
                165                 170                 175
Trp Val Asn Gly Lys Glu Val His Ser Gly Val Ser Thr Asp Pro Gln
                180                 185                 190
Pro Leu Lys Glu Gln Pro Ala Leu Asn Asp Ser Arg Tyr Ala Leu Ser
                195                 200                 205
Ser Arg Leu Arg Val Ser Ala Thr Phe Trp Gln Asp Pro Arg Asn His
        210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Ala Ser Thr Lys Gly Pro Ser Val Phe Pro Leu
            260                 265                 270
Ala Pro Ser Ser Lys Ser Thr Ser Gly Gly Thr Ala Ala Leu Gly Cys
            275                 280                 285
Leu Val Lys Asp Tyr Phe Pro Glu Pro Val Thr Val Ser Trp Asn Ser
        290                 295                 300
Gly Ala Leu Thr Ser Gly Val His Thr Phe Pro Ala Val Leu Gln Ser
305                 310                 315                 320
Ser Gly Leu Tyr Ser Leu Ser Ser Val Val Thr Val Pro Ser Ser Ser
                325                 330                 335
Leu Gly Thr Gln Thr Tyr Ile Cys Asn Val Asn His Lys Pro Ser Asn
                340                 345                 350
Thr Lys Val Asp Lys Lys Val Glu Pro Lys Ser Cys Asp Lys Thr His
        355                 360                 365
Thr Cys Pro Pro Cys Pro Gly Gly Gly Gly Ser Gly Gly Gly Gly Ser
    370                 375                 380
Gly Gly Gly Gly Ser Gly Gly Gly Gly Ser Leu Thr Asp Arg Glu Trp
385                 390                 395                 400
Ala Glu Glu Trp Lys His Leu Asp His Leu Leu Asn Cys Ile Met Asp
                405                 410                 415
Met Val Glu Lys Thr Arg Arg Ser Leu Thr Val Leu Arg Arg Cys Gln
            420                 425                 430
Glu Ala Asp Arg Glu Glu Leu Asn Tyr Trp Ile Arg Arg Tyr Ser Asp
        435                 440                 445
Ala Glu Gly Gly Gly Gly Ser Gly Gly Gly Gly Ser Gly Gly Gly Gly
        450                 455                 460
Ser Gly Gly Gly Gly Ser Ala Pro Thr Ser Ser Ser Thr Lys Lys Thr
465                 470                 475                 480
Gln Leu Gln Leu Glu His Leu Leu Asp Leu Gln Met Ile Leu Asn
                485                 490                 495
Gly Ile Asn Asn Tyr Lys Asn Pro Lys Leu Thr Arg Met Leu Thr Phe
                500                 505                 510
Lys Phe Tyr Met Pro Lys Lys Ala Thr Glu Leu Lys His Leu Gln Cys
        515                 520                 525
Leu Glu Glu Glu Leu Lys Pro Leu Glu Glu Val Leu Asn Leu Ala Gln
        530                 535                 540
```

```
Ser Lys Asn Phe His Leu Arg Pro Arg Asp Leu Ile Ser Asn Ile Asn
545                 550                 555                 560

Val Ile Val Leu Glu Leu Lys Gly Ser Glu Thr Thr Phe Met Cys Glu
                565                 570                 575

Tyr Ala Asp Glu Thr Ala Thr Ile Val Glu Phe Leu Asn Arg Trp Ile
            580                 585                 590

Thr Phe Cys Gln Ser Ile Ile Ser Thr Leu Thr His His His His His
        595                 600                 605

His
```

```
<210> SEQ ID NO 139
<211> LENGTH: 593
<212> TYPE: DNA
<213> ORGANISM: Artificial Sequence
<220> FEATURE:
<223> OTHER INFORMATION: Synthetic Construct

<400> SEQUENCE: 139
gcggccgctt atcagtggtg atggtggtgg tgcttgtcgt cgtcgtcctt gtagtcccct    60
ggctccttcc cagcctgggc atccttgagt tccaaggcct cattcagctc tcggaacatc   120
tcgaagcgct cacgcccacg gatctgaagg gtgaaatatt ctccatccag tggtttcttc   180
tttttgctgc taacggtaac ctgggtgccc tgacccccaat attcaaagcc acgttaaca   240 ttgcaataat acactgcggt atcttccggt ttcaggctat tcatttgcag ataaacggta   300
ttacgtgcat catcacggct gatggtaaaa cgacctttaa cgctatcttc atagctgcta   360
cgatcaccgg cactgctcat acctgcaacc cattcacgtt ctttaccccgg tgcctgacga   420 taccaacgca tgctataacg attaaccgga aaaccgcttg ctgcacagct cagacgcagg   480
ctaccaccag gctgaaccag tgcaccaccg ctttcaacca gctgaacctg agcctggaca   540
ccttgtagta gagcagccag gaccacccag ctcagcccca gctccatcac gtg          593
```

```
<210> SEQ ID NO 140
<211> LENGTH: 608
<212> TYPE: DNA
<213> ORGANISM: Artificial Sequence
<220> FEATURE:
<223> OTHER INFORMATION: Synthetic Construct

<400> SEQUENCE: 140
gcggccgctt atcagtggtg atggtggtgg tgcttgtcgt cgtcgtcctt gtagtcccct    60
ggctccttcc cagcctgggc atccttgagt tccaaggcct cattcagctc tcggaacatc   120
tcgaagcgct cacgcccacg gatctgaagg gtgaaatatt ctccatccag tggtttcttc   180
ttgctcccac ctcctccttt gctgctaacg gtaacctggg tgccctgacc ccaatattca   240
aagcccacgt taacattgca ataatacact gcggtatctt ccggtttcag gctattcatt   300
tgcagataaa cggtattacg tgcatcatca cggctgatgg taaaacgacc tttaacgcta   360
tcttcatagc tgctacgatc accggcactg ctcatacctg caacccattc acgttcttta   420
cccggtgcct gacgatacca acgcatgcta taacgattaa ccggaaaacc gcttgctgca   480
cagctcagac gcaggctacc accaggctga accagtgcac caccgctttc aaccagctga   540
acctgagcct ggacaccttg tagtagagca gccaggacca cccagctcag ccccagctcc   600
atcacgtg                                                           608
```

```
<210> SEQ ID NO 141
```

<211> LENGTH: 9
<212> TYPE: PRT
<213> ORGANISM: Artificial Sequence
<220> FEATURE:
<223> OTHER INFORMATION: Synthetic Construct

<400> SEQUENCE: 141

Ser Leu Leu Met Trp Ile Thr Gln Cys
1               5

<210> SEQ ID NO 142
<211> LENGTH: 19
<212> TYPE: PRT
<213> ORGANISM: Artificial Sequence
<220> FEATURE:
<223> OTHER INFORMATION: Synthetic Construct

<400> SEQUENCE: 142

Met Gly Trp Ser Cys Ile Ile Leu Phe Leu Val Ala Thr Ala Thr Gly
1               5                   10                  15

Val His Ser

<210> SEQ ID NO 143
<211> LENGTH: 593
<212> TYPE: DNA
<213> ORGANISM: Artificial Sequence
<220> FEATURE:
<223> OTHER INFORMATION: Synthetic Construct

<400> SEQUENCE: 143
cacgtgatgg agctggggct gagctgggtg gtcctggctg ctctactaca aggtgtccag      60
gctcaggttc agctggttga aagcggtggt gcactggttc agcctggtgg tagcctgcgt     120
ctgagctgtg cagcaagcgg ttttccggtt aatcgttata gcatgcgttg gtatcgtcag     180
gcaccgggta agaacgtga atgggttgca ggtatgagca gtgccggtga tcgtagcagc     240
tatgaagata gcgttaaagg tcgttttacc atcagccgtg atgatgcacg taataccgtt     300
tatctgcaaa tgaatagcct gaaaccggaa gataccgcag tgtattattg caatgttaac     360
gtgggctttg aatattgggg tcagggcacc caggttaccg ttagcagcaa aaagaagaaa     420
ccactggatg gagaatattt caccttcag atccgtgggc gtgagcgctt cgagatgttc       480
cgagagctga atgaggcctt ggaactcaag gatgcccagg ctgggaagga gccaggggac     540
tacaaggacg acgacgacaa gcaccaccac catcaccact gataagcggc cgc             593

<210> SEQ ID NO 144
<211> LENGTH: 608
<212> TYPE: DNA
<213> ORGANISM: Artificial Sequence
<220> FEATURE:
<223> OTHER INFORMATION: Synthetic Construct

<400> SEQUENCE: 144
cacgtgatgg agctggggct gagctgggtg gtcctggctg ctctactaca aggtgtccag      60
gctcaggttc agctggttga aagcggtggt gcactggttc agcctggtgg tagcctgcgt     120
ctgagctgtg cagcaagcgg ttttccggtt aatcgttata gcatgcgttg gtatcgtcag     180
gcaccgggta agaacgtga atgggttgca ggtatgagca gtgccggtga tcgtagcagc     240
tatgaagata gcgttaaagg tcgttttacc atcagccgtg atgatgcacg taataccgtt     300
tatctgcaaa tgaatagcct gaaaccggaa gataccgcag tgtattattg caatgttaac     360
gtgggctttg aatattgggg tcagggcacc caggttaccg ttagcagcaa aggaggaggt     420

```
gggagcaaga agaaaccact ggatggagaa tatttcaccc ttcagatccg tgggcgtgag    480
cgcttcgaga tgttccgaga gctgaatgag gccttggaac tcaaggatgc ccaggctggg    540
aaggagccag gggactacaa ggacgacgac gacaagcacc accaccatca ccactgataa    600
gcggccgc                                                             608
```

MULTIMERS, TETRAMERS AND OCTAMERS

CROSS REFERENCE TO RELATED APPLICATIONS

This application is a national stage application under 35 U.S.C. § 371 of International Application No. PCT/EP2017/073527, filed internationally on Sep. 18, 2017, which claims priority benefit to United Kingdom Application No. 1615768.7, filed Sep. 15, 2016, United Kingdom Application No. 1713342.2, filed Aug. 20, 2017, and United Kingdom Application No. 1713351.3, filed Aug. 21, 2017, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165132000100SEQLIST.TXT, date recorded: Mar. 7, 2019, size: 245 KB).

TECHNICAL FIELD

The invention relates to multimers such as tetramers of polypeptides and tetramers and octamers of effector domains, such as antigen binding sites (eg, antibody or TCR binding sites that specifically bind to antigen or pMHC, or variable domains thereof) or peptides such as incretin, insulin or hormone peptides.

BACKGROUND

Multimers of effector domains have recognized utility in medical and non-medical applications for combining and multiplying the activity and presence of effector domains, eg, to provide for higher avidity of antigen binding (for effector domains that are antibody or TCR binding domains, for example) or for enhancing biological or binding activity, such as for providing bi- or multi-specific targeting or interaction with target ligands in vivo or in vitro.

Multimerisation domains which cause self-assembly of protein monomers into multimers are known in the art. Examples include domains found in transcription factors such as p53, p63 and p73, as well as domains found in ion channels such as TRP cation channels. The transcription factor p53 can be divided into different functional domains: an N-terminal transactivation domain, a proline-rich domain, a DNA-binding domain, a tetramerization domain and a C-terminal regulatory region. The tetramerization domain of human p53 extends from residues 325 to 356, and has a 4-helical bundle fold (Jeffrey et al., Science (New York, N.Y.) 1995, 267(5203):1498-1502). The TRPM tetramerization domain is a short anti-parallel coiled-coil tetramerization domain of the transient receptor potential cation channel subfamily M member proteins 1-8. It is held together by extensive core packing and interstrand polar interactions (Fujiwara et al., Journal of Molecular Biology 2008, 383(4):854-870). Transient receptor potential (TRP) channels comprise a large family of tetrameric cation-selective ion channels that respond to diverse forms of sensory input. Another example is the potassium channel BTB domain. This domain can be found at the N terminus of voltage-gated potassium channel proteins, where represents a cytoplasmic tetramerization domain (Ti) involved in assembly of alpha-subunits into functional tetrameric channels (Bixby et al., Nature Structural Biology 1999, 6(1):38-43). This domain can also be found in proteins that are not potassium channels, like KCTD1 (potassium channel tetramerization domain-containing protein 1; Ding et al., DNA and Cell Biology 2008, 27(5):257-265).

Multimeric antibody fragments have been produced using a variety of multimerisation techniques, including biotin, dHLX, ZIP and BAD domains, as well as p53 (Thie et al., Nature Boitech., 2009:26, 314-321). Biotin, which is efficient in production, is a bacterial protein which induces immune reactions in humans.

Human p53 (UniProtKB—P04637 (P53_HUMAN)) acts as a tumor suppressor in many tumor types, inducing growth arrest or apoptosis depending on the physiological circumstances and cell type. It is involved in cell cycle regulation as a trans-activator that acts to negatively regulate cell division by controlling a set of genes required for this process. Human p53 is found in increased amounts in a wide variety of transformed cells. It is frequently mutated or inactivated in about 60% of cancers. Human p53 defects are found in Barrett metaplasia a condition in which the normally stratified squamous epithelium of the lower esophagus is replaced by a metaplastic columnar epithelium. The condition develops as a complication in approximately 10% of patients with chronic gastroesophageal reflux disease and predisposes to the development of esophageal adenocarcinoma.

Nine isoforms of p53 naturally occur and are expressed in a wide range of normal tissues but in a tissue-dependent manner. Isoform 2 is expressed in most normal tissues but is not detected in brain, lung, prostate, muscle, fetal brain, spinal cord and fetal liver. Isoform 3 is expressed in most normal tissues but is not detected in lung, spleen, testis, fetal brain, spinal cord and fetal liver. Isoform 7 is expressed in most normal tissues but is not detected in prostate, uterus, skeletal muscle and breast. Isoform 8 is detected only in colon, bone marrow, testis, fetal brain and intestine. Isoform 9 is expressed in most normal tissues but is not detected in brain, heart, lung, fetal liver, salivary gland, breast or intestine.

SUMMARY OF THE INVENTION

The invention provides:—
In a First Configuration
A protein multimer of at least first, second, third and fourth copies of an effector domain (eg, a protein domain or a peptide), wherein the multimer is multimerised by first, second, third and fourth self-associating tetramerization domains (TDs) which are associated together, wherein each tetramerization domain is comprised by a respective engineered polypeptide comprising one or more copies of said protein domain or peptide.
In a Second Configuration
An isolated tetramer or octamer of a TCR binding site, insulin peptide, incretin peptide or peptide hormone; or a plurality of said tetramers or octamers.
An isolated tetramer or octamer of an antibody binding site or an antibody variable domain (eg, a single variable domain); or a plurality of said tetramers or octamers.
In an example the tetramer or octamer is soluble in aqueous solution (eg, aqueous eukaryotic cell culture medium). In an example the tetramer or octamer is expressible in a eukaryotic cell. Exemplification is provided below.

In a Third Configuration

A tetramer or octamer of (a) TCR V domains or TCR binding sites, wherein the tetramer or octamer is soluble in aqueous solution (eg, an aqueous eukaryotic cell growth medium or buffer);
(b) antibody single variable domains, wherein the tetramer or octamer is soluble in aqueous solution (eg, an aqueous eukaryotic cell growth medium or buffer);
(c) TCR V domains or TCR binding sites, wherein the tetramer or octamer is capable of being intracellularly and/or extracellularly expressed by HEK293 cells; or
(d) antibody variable domains (eg, antibody single variable domains), wherein the tetramer or octamer is capable of being intracellularly and/or extracellularly expressed by HEK293 cells.

In a Fourth Configuration

An engineered polypeptide or monomer of a multimer, tetramer or octamer of the invention.

In a Fifth Configuration

An engineered (and optionally isolated) engineered polypeptide (P1) which comprises (in N- to C-terminal direction):—

(a) TCR V1-TCR C1—antibody CH1 (eg, IgG CH1)—optional linker—TD, wherein
   (i) V1 is a Vα and C1 is a Cα;
   (ii) V1 is a Vβ and C1 is a Cβ;
   (iii) V1 is a Vγ and C1 is a Cγ; or
   (iv) V1 is a Vδ and C1 is a Cδ; or
(b) TCR V1—antibody CH1 (eg, IgG CH1)—optional linker—TD, wherein
   (i) V1 is a Vα;
   (ii) V1 is a Vβ;
   (iii) V1 is a Vγ; or
   (iv) V1 is a Vδ; or
(c) antibody V1—antibody CH1 (eg, IgG CH1)—optional linker—TD, wherein
   (i) V1 is a VH; or
   (ii) V1 is a VL (eg, a Vλ or a Vκ); or
(d) antibody V1—optional antibody CH1 (eg, IgG CH1)—antibody Fc (eg, an IgG Fc)—optional linker—TD, wherein
   (i) V1 is a VH; or
   (ii) V1 is a VL (eg, a Vλ or a Vκ); or
(e) antibody V1—antibody CL (eg, a Cλ or a Cκ)—optional linker—TD, wherein
   (i) V1 is a VH; or
   (ii) V1 is a VL (eg, a Vλ or a Vκ); or
(f) TCR V1-TCR C1—optional linker—TD, wherein
   (i) V1 is a Vα and C1 is a Cα;
   (ii) V1 is a Vβ and C1 is a Cβ;
   (iii) V1 is a Vγ and C1 is a Cγ; or
   (iv) V1 is a Vδ and C1 is a Cδ.

In a Sixth Configuration

A nucleic acid encoding an engineered polypeptide or monomer of the invention, optionally wherein the nucleic acid is comprised by an expression vector for expressing the polypeptide.

In a Seventh Configuration

Use of a nucleic acid or vector of the invention in a method of manufacture of protein multimers for producing intracellularly expressed and/or secreted multimers, wherein the method comprises expressing the multimers in and/or secreting the multimers from eukaryotic cells comprising the nucleic acid or vector.

In an Eighth Configuration

A method producing (a) TCR V domain multimers, the method comprising the soluble and/or intracellular expression of TCR V-TD (eg, NHR2 TD or TCR V-p53 TD) fusion proteins expressed in eukaryotic cells, the method optionally comprising isolating a plurality of said multimers;
(b) antibody V domain multimers, the method comprising the soluble and/or intracellular expression of antibody V (eg, a single variable domain)—TD (eg, V-NHR2 TD or V-p53 TD) fusion proteins expressed in eukaryotic cells, the method optionally comprising isolating a plurality of said multimers;
(c) incretin peptide (eg, GLP-1, GIP or insulin) multimers, the method comprising the soluble and/or intracellular expression of incretin peptide-TD (eg, incretin peptide-NHR2 TD or incretin peptide-p53 TD) fusion proteins expressed in eukaryotic cells, such as HEK293T cells; the method optionally comprising isolating a plurality of said multimers; or
(d) peptide hormone multimers, the method comprising the soluble and/or intracellular expression of peptide hormone-TD (eg, peptide hormone-NHR2 TD or peptide hormone-p53 TD) fusion proteins expressed in eukaryotic cells, such as HEK293T cells; the method optionally comprising isolating a plurality of said multimers.

In a Ninth Configuration

Use of a nucleic acid or vector of the invention in a method of manufacture of protein multimers for producing glycosylated multimers in eukaryotic cells comprising the nucleic acid or vector.

In a Tenth Configuration

Use of self-associating tetramerization domains (TD) (eg, NHR2 TD, p53 TD, p63 TD or p73 TD or a homologue or orthologue thereof) in a method of the manufacture of a tetramer of polypeptides, for producing a higher yield of tetramers versus monomer and/or dimer polypeptides.

In a Eleventh Configuration

Use of an engineered polypeptide in a method of the manufacture of a tetramer of a polypeptide comprising multiple copies of a protein domain or peptide, for producing a higher yield of tetramers versus monomer and/or dimer polypeptides, wherein the engineered polypeptide comprises one or more copies of said protein domain or peptide and further comprises a self-associating tetramerization domains (TD) (eg, NHR2 TD, p53 TD, p63 TD or p73 TD or a homologue or orthologue).

In a Twelfth Configuration

Use of self-associating tetramerization domains (TD) (eg, NHR2 TD, p53 TD, p63 TD or p73 TD or a homologue or orthologue thereof) in a method of the manufacture of a tetramer of a polypeptide, for producing a plurality of tetramers that are not in mixture with monomers, dimers or trimers.

In a Thirteenth Configuration

A eukaryotic host cell comprising the nucleic acid or vector for intracellular and/or secreted expression of the multimer, tetramer, octamer, engineered polypeptide or monomer of the invention.

In a Fourteenth Configuration

Use of an engineered polypeptide in a method of the manufacture of a tetramer of a polypeptide comprising multiple copies of a protein domain or peptide, for producing a plurality of tetramers that are not in mixture with monomers, dimers or trimers, wherein the engineered polypeptide comprises one or more copies of said protein domain or peptide and further comprises a self-associating tetramerization domains (TD) (eg, NHR2 TD, p53 TD, p63 TD or p73 TD or a homologue or orthologue).

In a fifteenth Configuration

A multivalent heterodimeric soluble T cell receptor capable of binding pMHC complex comprising:
(i) TCR extracellular domains;
(ii) immunoglobulin constant domains; and
(iii) an NHR2 multimerisation domain of ETO.

In a Sixteenth Configuration

A multimeric immunoglobulin, comprising
(i) immunoglobulin variable domains; and
(ii) an NHR2 multimerisation domain of ETO.

In a Seventeenth Configuration

A method for assembling a soluble, multimeric polypeptide, comprising:
(a) providing a monomer of the said multimeric polypeptide, fused to an NHR2 domain of ETO;
(b) causing multiple copies of said monomer to associate, thereby obtaining a multimeric, soluble polypeptide.

In an Eighteenth Configuration

A mixture comprising (i) a cell line (eg, a eukaryotic, mammalian cell line, eg, a HEK293, CHO or Cos cell line) encoding a polypeptide of the invention; and (ii) tetramers of the invention.

In a Nineteenth Configuration

A method for enhancing the yield of tetramers of an protein effector domain (eg, an antibody variable domain or binding site), the method comprising expressing from a cell line (eg, a mammalian cell, CHO, HEK293 or Cos cell line) tetramers of a polypeptide, wherein the polypeptide is a polypeptide of the invention and comprises one or more effector domains; and optionally isolating said expressed tetramers.

The invention also provides a pharmaceutical composition, cosmetic, foodstuff, beverage, cleaning product, detergent comprising the multimer(s), tetramer(s) or octamer(s) of the invention.

BRIEF DESCRIPTION OF THE DRAWINGS

FIG. 5: Amino acid sequence of the α and β chain of the ts-NY-ESO-1 TCR protein complex. Amino acid sequences of alternate domains are underlined.

FIG. 6: Amino acid sequence of the α and β chain of the os-NY-ESO-1 TCR protein complex. Amino acid sequences of alternate domains are underlined.

FIG. 9: Amino acid sequence of the α and β chain of the ts-NY-ESO-1 TCR-IL2 fusion protein complex. Amino acid sequences of alternate domains are underlined.

FIG. 10: Amino acid sequence of the α and β chain of the os-NY-ESO-1 TCR-IL2 fusion protein complex. Amino acid sequences of alternate domains are underlined.

FIG. 15A shows Quad16 monomer sequence and configuration, and FIG. 15B shows Quad 17 monomer sequence and configuration.

(FIG. 16A) a PAGE gel under SDS denatured conditions—16=Quad16; 17=Quad17; and (FIG. 16B) a PAGE gel under native (ie, non-denatured) conditions—16=Quad16; 17=Quad17.

(FIG. 17B) Protein samples from Quads 12 and 13 were prepared from whole cell extracts and loaded in lanes 1 and 2 respectively. The expected Mw for Quads 12 and 13 are 47.8 and 48.1 kDa respectively.

(FIG. 18B) Protein samples from Quads 12 and 13 were prepared by concentrating cell supernatant and loaded in lanes 1 and 2 respectively. The expected Mw for Quads 12 and 13 are 47.8 and 48.1 kDa respectively.

(FIG. 19B) Protein samples from Quads 23, 24, 26 and 27 were prepared from whole cell extracts and loaded in lanes 1-4, respectively. The expected Mw for Quads 23, 24, 26 and 27 are 32.1, 32.4, 33.7 and 34.0 kDa respectively. (FIG. 19C) Protein samples from Quads 34, and 38 were prepared from whole cell extracts and loaded in lanes 1-2, respectively. The expected Mw for Quads 34, and 38 are 25.5 and 25.4 kDa respectively. (FIG. 19D) Protein samples from Quads 40, 42, 44 and 46 were prepared from whole cell extracts and loaded in lanes 1-4, respectively. The expected Mw for Quads 40, 42, 44 and 46 are 25.4, 37.6, 25.5 and 38.0 kDa respectively. Lane U contains concentrated serum prepared from untransfected HEK293T cells (negative control) and C is a His-tagged protein used as a positive control for the anti-His HRP detection antibody. Serum anti-His background band is highlighted by a black arrow, which can be consistently detected in all for blots.

FIGS. 20A-20B: Western blot prepared from denaturing SDS-PAGE gel (FIG. 20A) and probed with anti-human IgG HRP detection antibody. Protein samples from Quads 14 and 15 were prepared from whole cell extracts and loaded in lanes 1 and 2, respectively. The expected Mw for Quads 14 and 15 are 22.0 and 22.3 kDa respectively. (FIG. 20B) Western blot prepared from Native PAGE gels and probed with anti-human IgG HRP detection antibody. Lanes 1 and 2 contains protein samples from Quads 14 and 15 prepared from whole cell extract.

FIG. 21: Quad polyeptides fused to leader and tag sequences. Where linker is present, the linker is G4S (only 1 G4S). * denotes TCR constant domains with introduced cysteine residue allowing S—S bond formation between TCR alpha and beta chain. Human IgG1 hinge was used. All C regions are human. The TCR V domains are specific for NY-ESO-1. GFP=green fluorescent protein.

Figure 1:
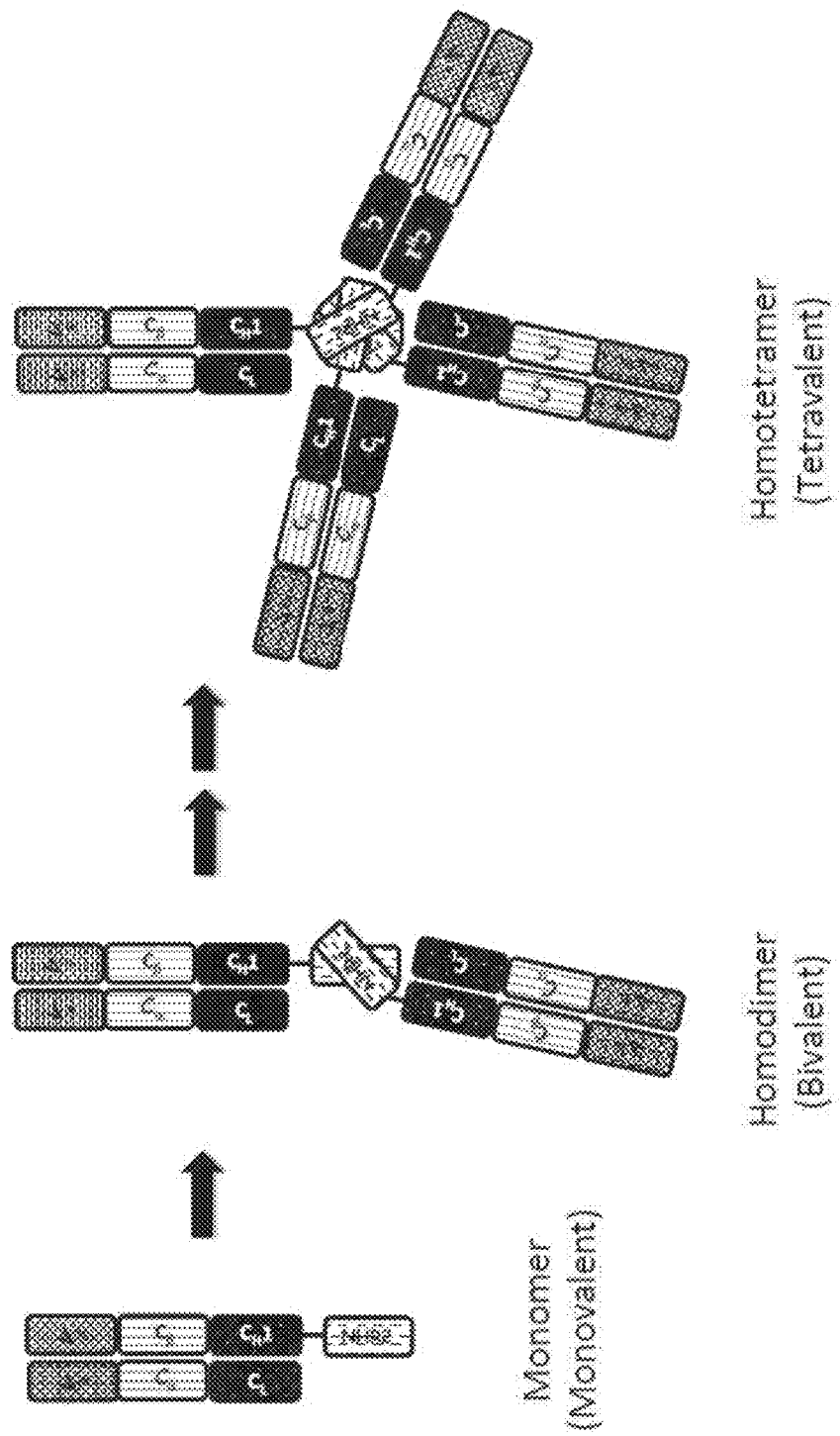
FIG. 1. A schematic drawing representing the stepwise self-assembly of an tetravalent heterodimeric soluble TCR protein complex via a monomer and homodimer, which is aided by NHR2 tetramerization domain.

All polypeptide schematics and amino acid sequences herein are written N- to C-terminal. All nucleotide sequences herein are written 5' to 3'.

DETAILED DESCRIPTION

The invention relates to multimers such as tetramers of polypeptides and tetramers and octamers of effector domains (such as antigen binding sites (eg, antibody or TCR binding sites that specifically bind to antigen or pMHC, or variable domains thereof)) or peptides such as incretin, insulin or hormone peptides. In embodiments, multimers of the invention are usefully producible in eurkaryotic systems and can be secreted from eukaryotic cells in soluble form, which is useful for various industrial applications, such as producing pharmaceuticals, diagnostics, as imaging agents, detergents etc. Higher order multimers, such as tetramers or octamers of effector domains or peptides are useful for enhancing antigen or pMHC binding avidity. This may be useful for producing an efficacious medicine or for enhancing the sensitivity of a diagnostic reagent comprising the multimer, tetramer or octamer. An additional or alternative benefit is enhanced half-life in vivo when the multimers of the invention are administered to a human or animal subject, eg, for treating or preventing a disease or condition in the subject. Usefully, the invention can also provide for multi-specific (eg, bi- or tri-specific) multivalent binding proteins. Specificity may related to specificity of antigen or pMHC binding. By using a single engineered polypeptide comprising binding domains or peptides, the invention in certain examples usefully provides a means for producing multivalent (eg, bi-specific) proteins at high purity. Use of a single species of engineered polypeptide monomer avoids the problem of mixed products seen when 2 or more different polypeptide species are used to produce multi- (eg, bi-) specific or multivalent proteins.

The invention provides the following Clauses, Aspects and Concepts. Any Clause herein can be combined with any Aspect or Concept herein. Any Aspect herein can be combined with any Concept herein.

Aspects:
1. A protein multimer of at least first, second, third and fourth copies of an effector domain (eg, a protein domain) or a peptide, wherein the multimer is multimerised by first, second, third and fourth self-associating tetramerization domains (TDs) which are associated together, wherein each tetramerization domain is comprised by a respective engineered polypeptide comprising one or more copies of said protein domain or peptide.

In an example, each TD is a TD of any one of proteins 1 to 119 listed in Table 2. In an example, each TD is a p53 TD or a homologue or orthologue thereof. In an example, each TD is a NHR2 TD or a homologue or orthologue thereof. In an example, each TD is a p63 TD or a homologue or orthologue thereof. In an example, each TD is a p73 TD or a homologue or orthologue thereof. In an example, each TD is not a NHR2 TD. In an example, each TD is not a p53 TD. In an example, each TD is not a p63 TD. In an example, each TD is not a p73 TD. In an example, each TD is not a p53, 63 or 73 TD. In an example, each TD is not a NHR2, p53, 63 or 73 TD.

By being "associated together", the TDs in Aspect 1 multimerise first, second, third and fourth copies of the engineered polypeptide to provide a multimer protein, for example, a multimer that can be expressed intracellularly in a eukaryotic or mammalian cell (eg, a HEK293 cell) and/or which can be extracellularly secreted from a eukaryotic or mammalian cell (eg, a HEK293 cell) and/or which is soluble in an aqueous medium (eg, a eukaryotic or mammalian cell (eg, a HEK293 cell) culture medium). Examples are NHR TD, p53 TD, p63 TD and p73 TD (eg, human NHR TD, p53 TD, p63 TD and p73 TD) or an orthologue or homologue thereof.

In an example, the TD is not a p53 TD (or homologue or orthologue thereof), eg, it is not a human p53 TD (or homologue or orthologue thereof). In an example, the TD is a NHR2 TD or a homologue or orthologue thereof, but excluding a p53 TD or a homologue or orthologue thereof. In an example, the TD is a human NHR2 TD or a homologue or orthologue thereof, but excluding a human p53 TD or a homologue or orthologue thereof. In an example, the TD is human NHR2. In an example, the amino acid sequence of the TD is at least 80, 85, 90, 95, 96, 97, 98 or 99% identical to the sequence of human NHR2. In an example, the domain or peptide is not naturally comprised by a polypeptide that also comprise a NHR2 TD.

In an example, all of the domains of the polypeptide are human.

The engineered polypeptide may comprise one or more copies of said domain or peptide N-terminal to a copy of said TD. Additionally or alternatively, the engineered polypeptide may comprise one or more copies of said domain or peptide C-terminal to a copy of said TD. In an example, the engineered polypeptide comprises a first said domain or peptide and a TD, wherein the first domain or peptide is spaced by at least 10, 20, 30, 40, 50, 60, 70, 80, 90, 100, 200, 300, 400, 500, 600, 700, 800, 900 or 1000 contiguous amino acids from the TD, wherein there is no further said domain or peptide between the first domain or peptide and the TD.

In an example, the multimer (eg, tetramer of said engineered polypeptide) comprises 4 (but no more than 4) TDs (eg, identical TDs) and 4, 8, 12 or 16 (but no more than said 4, 8, 12 or 16 respectively) copies of said domain or peptide. In an example, each TD and each said domain or peptide is human.

In an example, the multimer, tetramer or octamer comprises first, second, third and fourth identical copies of an engineered polypeptide, the polypeptide comprising a TD and one (but no more than one), two (but no more than two), or more copies of the said protein domain or peptide.

In some embodiments, by requiring just one type of engineered polypeptide to form the multimer, tetramer or octamer of the invention, the invention advantageously provides a format that can be readily isolated in pure (or highly pure, ie >90, 95, 96, 97, 98 or 99% purity) format, as well as a method for producing such a format in pure (or highly pure) form. Purity is indicated by the multimer of the invention not being in mixture in a composition with any other multimer or polypeptide monomer, or wherein the multimer of the invention comprises >90, 95, 96, 97, 98 or 99% of species in a composition comprising the multimer of the invention and other multimers and/or polypeptide monomers which comprise the engineered polypeptide. Thus, mixtures of different types of polypeptide in these embodiments are avoided or minimised. This advantageously also provides, therefore, plurality of multimers (eg, a plurality of tetramers or octamers) that comprise only one (and no more than one) type of engineered polypeptide, wherein the multimers are monospecific (but multivalent) for antigen binding, or alternatively bi- or multi-specific for antigen binding. Thus, the invention provides a plurality of multimers (eg, a plurality of tetramers or octamers, each polypeptide being at least tetra-valent for antigen binding and (i) bi-specific (ie, capable of specifically binding to 2 different antigens) or (ii) mono-specific and at least tetravalent for antigen binding. Herein, where antigen binding is mentioned this can instead be pMHC binding when the domain is a TCR V domain. Advantageously, the plurality is in pure form (ie, not mixed with multimers (eg, tetramers or octamers) that comprise more than one type of polypeptide monomer. In an example, the multimer comprises at least 2 different types of antigen binding site. In an example, the multimer is bi-specific, tri-specific or tetra-specific. In an example, the multimer has an antigen binding site or pMHC binding site valency of 4, 6, 8, 10 or 12, preferably 4 or 8.

In an example, a peptide MHC (pMHC) is a class I or class II pMHC.

By the term "specifically binds," as used herein, eg, with respect to a domain, antibody or binding site, is meant a domain, antibody or binding site which recognises a specific antigen (or pMHC) with a binding affinity of 1 mM or less as determined by SPR Target binding ability, specificity and affinity (KD (also termed Kd), $K_{off}$ and/or $K_{on}$) can be determined by any routine method in the art, eg, by surface plasmon resonance (SPR). The term "KD", as used herein, is intended to refer to the equilibrium dissociation constant of a particular binding site/ligand, receptor/ligand or antibody/antigen interaction. In one embodiment, the surface plasmon resonance (SPR) is carried out at 25° C. In another embodiment, the SPR is carried out at 37° C. In one embodiment, the SPR is carried out at physiological pH, such as about pH7 or at pH7.6 (eg, using Hepes buffered saline at pH7.6 (also referred to as HBS-EP)). In one embodiment, the SPR is carried out at a physiological salt level, eg, 150 mM NaCl. In one embodiment, the SPR is carried out at a detergent level of no greater than 0.05% by volume, eg, in the presence of P20 (polysorbate 20; eg, Tween-20™) at 0.05% and EDTA at 3 mM. In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022). In an example, the affinity (eg, of a VH/VL binding site) is determined using SPR by using any standard SPR apparatus, such as by Biacore™ or using the ProteOn XPR36™ (Bio-Rad®). The binding data can be fitted to 1:1 model inherent using standard techniques, eg, using a model inherent to the ProteOn XPR36™ analysis software.

In an example, a multimer, tetramer or octamer of the invention is an isolated multimer, tetramer or octamer. In an example, a multimer, tetramer or octamer of the invention consists of copies of said engineered polypeptide. Optionally the multimer, tetramer or octamer of the invention comprises 4 or 8 but not more than 4 or 8 copies respectively of the engineered polypeptide.

By "engineered" is meant that the polypeptide is not naturally-occurring, for example the protein domain or peptide is not naturally comprised by a polypeptide that also comprises said TD.

Each said protein domain or peptide may be a biologically active domain or peptide (eg, biologically active in humans or animals), such as a domain that specifically binds to an antigen or peptide-MHC (pMHC), or wherein the domain is comprised by an antigen or pMHC binding site. In an alternative, the domain or peptide is a carbohydrate, glucose or sugar-regulating agent, such as an incretin or an insulin peptide. In an alternative, the domain or peptide is an inhibitor or an enzyme or an inhibitor of a biological function or pathway in humans or animals. In an alternative, the domain or peptide is an iron-regulating agent. Thus, in an example, each protein domain or peptide is selected from an antigen or pMHC binding domain or peptide; a hormone; a carbohydrate, glucose or sugar-regulating agent; an iron-regulating agent; and an enzyme inhibitor.

2. The multimer of any preceding Aspect, wherein the multimer is a tetramer or an octamer of said domain or peptide.

3. The multimer of any Aspect 1 or 2, comprising a tetramer or octamer of animmunoglobulin superfamily binding site (eg, an antibody or TCR binding site, such as a scFv or scTCR).

The immunoglobulin superfamily (IgSF) is a large protein superfamily of cell surface and soluble proteins that are involved in the recognition, binding, or adhesion processes of cells. Molecules are categorized as members of this superfamily based on shared structural features with immunoglobulins (also known as antibodies); they all possess a domain known as an immunoglobulin domain or fold. Members of the IgSF include cell surface antigen receptors, co-receptors and costimulatory molecules of the immune system, molecules involved in antigen presentation to lymphocytes, cell adhesion molecules, certain cytokine receptors and intracellular muscle proteins. They are commonly associated with roles in the immune system.

T-cell receptor (TCR) domains can be Vα (eg. paired with a Vβ), Vβ (eg. paired with a Vα), Vγ (eg, paired with a Vδ) or Vδ (eg, paired with a Vγ).

4. The multimer of Aspect 3, wherein the binding site comprises a first variable domain paired with a second variable domain.

In a first example, the first and second variable domains are comprised by the engineered polypeptide. In another example, the first domain is comprised by the engineered polypeptide and the second domain is comprised a by a further polypeptide that is different from the engineered polypeptide (and optionally comprises a TD or is devoid of a TD).

In the alternative, the domains are constant region domains. In an alternative, the domains are FcAbs. In an alternative, the domains are non-Ig antigen binding sites or comprises by a non-Ig antigen binding site, eg, an affibody.

Antigen Binding Sites & Effector Domains

In an example, the or each antigen binding site (or effector domain) is selected from the group consisting of an antibody variable domain (eg, a VL or a VH, an antibody single variable domain (domain antibody or dAb), a camelid VHH antibody single variable domain, a shark immunoglobulin single variable domain (NA V), a Nanobody™ or a camelised VH single variable domain); a T-cell receptor binding domain; an immunoglobulin superfamily domain; an agnathan variable lymphocyte receptor (J Immunol; 2010 Aug. 1; 185(3):1367-74; "Alternative adaptive immunity in jawless vertebrates; Herrin B R & Cooper M D.); a fibronectin domain (eg, an Adnectin™); an scFv; an (scFv)$_2$; an sc-diabody; an scFab; a centyrin and an antigen binding site derived from a scaffold selected from CTLA-4 (Evibody™); a lipocalin domain; Protein A such as Z-domain of Protein A (eg, an Affibody™ or SpA); an A-domain (eg, an Avimer™ or Maxibody™); a heat shock protein (such as and epitope binding domain derived from GroEI and GroES); a transferrin domain (eg, a trans-body); ankyrin repeat protein (eg, a DARPin™); peptide aptamer; C-type lectin domain (eg, Tetranectin™); human γ-crystallin or human ubiquitin (an affilin); a PDZ domain; scorpion toxin; and a kunitz type domain of a human protease inhibitor.

Further sources of antigen binding sites are variable domains and VH/VL pairs of antibodies disclosed in WO2007024715 at page 40, line 23 to page 43, line 23. This specific disclosure is incorporated herein by reference as though explicitly written herein to provide basis for epitope binding moieties for use in the present invention and for possible inclusion in claims herein.

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain The phrase "immunoglobulin single variable domain" or "antibody single variable domain" refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH immunoglobulin single variable domains. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein "VH includes camelid VHH domains. NA V are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A. CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001). Lipocalins are a family of extracellular proteins which transport small hydrophobic molecules such as steroids, bilins, retinoids and lipids. They have a rigid β-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1. Avimers™ are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins™) are derived from ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a α-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins™ consist of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796. Other epitope binding moieties and domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006).

5. The multimer of any preceding Aspect, wherein each polypeptide comprises first and second copies of said protein domain or peptide, wherein the polypeptide comprises in (N- to C-terminal direction) (i) a first of said copies—TD—the second of said copies; (ii) TD—and the first and second copies; or (iii) said first and second copies—TD.

6. The multimer of any preceding Aspect, wherein the TDs are NHR2 TDs and the domain or peptide is not a NHR2 domain or peptide; or wherein the TDs are p53 TDs and the domain or peptide is not a p53 domain or peptide.

7. The multimer of any preceding Aspect, wherein the engineered polypeptide comprises one or more copies of a second type of protein domain or peptide, wherein the second type of protein domain or peptide is different from the first protein domain or peptide.

For example, the polypeptide comprises in N-terminal direction (i) P1-TD-P2; or (ii) TD-P1-P2, wherein P1=a copy of a domain or peptide of the first type (ie, the type of domain or peptide of the multimer of Aspect 1); and P2=a copy of a domain or peptide of said second type.

8. The multimer of any preceding Aspect, wherein the domains are immunoglobulin superfamily domains.

9. The multimer of any preceding Aspect, wherein the domain or peptide is an antibody variable or constant domain (eg, an antibody single variable domain), a TCR variable or constant domain, an incretin, an insulin peptide, or a hormone peptide.

10. The multimer of any preceding Aspect, wherein the multimer comprises first, second, third and fourth identical copies of a said engineered polypeptide, the polypeptide comprising a TD and one (but no more than one), two (but no more than two) or more copies of the said protein domain or peptide.

11. The multimer of any preceding Aspect, wherein the engineered polypeptide comprises an antibody or TCR variable domain (V1) and a NHR2 TD.

12. The multimer of Aspect 11, wherein the polypeptide comprises (in N- to C-terminal direction) (i) V1—an optional linker-NHR2 TD; (ii) V1—an optional linker-NHR2 TD-optional linker-V2; or (iii) V1—an optional linker-V2—optional linker—NHR2 TD, wherein V1 and V2 are TCR variable domains and are the same or different, or wherein V1 and V2 are antibody variable domains and are the same or different.

13. The multimer of Aspect 12, wherein V1 and V2 are antibody single variable domains.

14. The multimer of aspect 11, wherein each engineered polypeptide comprises (in N- to C-terminal direction) V1—an optional linker-NHR2 TD, wherein V1 is an antibody or TCR variable domain and each engineered polypeptide is paired with a respective second engineered polypeptide that comprises V2, wherein V2 is a an antibody or TCR variable domain respectively that pairs with V1 to form an antigen or pMHC binding site, and optionally one polypeptide comprises an antibody Fc, or comprises antibody CH1 and the other polypeptide comprises an antibody CL that pairs with the CH1.

15. The multimer of any preceding Aspect, wherein the TD comprises (i) an amino acid sequence identical to SEQ ID NO: 10 or 126 or at least 80% identical thereto; or (ii) an amino acid sequence identical to SEQ ID NO: 120 or 123 or at least 80% identical thereto.

16. The multimer of any preceding Aspect, wherein the multimer comprises a tetramer or octamer of an antigen binding site of an antibody selected from the group consisting of REOPRO®; Abciximab; RITUXAN®; Rituximab; ZENAPAX®; Daclizumab; SIMULECT®; Basiliximab; SYNAGIS®; Palivizumab; REMICADE®; Infliximab; HERCEPTIN®; MYLOTARG®; Gemtuzumab; CAMPATH®; Alemtuzumab; ZEVALIN®; Ibritumomab; HUMIRA®; Adalimumab; XOLAIR®; Omalizumab; BEXXAR®; Tositumomab; RAPTIVA™; Efalizumab; ERBITUX®; Cetuximab; AVASTIN®; Bevacizumab; TYSABRI®; Natalizumab; ACTEMRA®; Tocilizumab;-VECTIBIX®; Panitumumab; LUCENTIS®; Ranibizumab; SOLIRIS®; Eculizumab; CIMZIA®; Certolizumab; SIMPONI®; Golimumab, ILARIS®; Canakinumab; STELARA®; Ustekinumab;-ARZERRA®; Ofatumumab; PROLIA®; Denosumab; NUMAX™; Motavizumab; ABTHRAX™; Raxibacumab; BENLYSTA®; Belimumab; YERVOY®; Ipilimumab; ADCETRIS®; Brentuximab Vedotin; PERJETA®; Pertuzumab; KADCYLA®; Ado-trastuzumab;-KEYTRUDA®, OPDIVO®, GAZYVA® and Obinutuzumab.

For example, a said protein domain of the engineered polypeptide is a V domain (a VH or VL) of an antibody binding site of an antibody selected from said group, wherein the multimer comprises a further V domain (a VL or VH respectively) that pairs with the V domain of the engineered polypeptide to form the antigen binding site of the selected antibody. Advantageously, therefore, the invention provides tetramers or octamers of a binding site of said selected antibody, which beneficially may have improved affinity, avidity and/or efficacy for binding its cognate antigen or for treating or preventing a disease or condition in a human or animal wherein the multimer is administered thereto to bind the cognate antigen in vivo.

For example, the multimer, tetramer or octamer comprises 4 copies of an antigen binding site of an antibody, wherein the antibody is adalimumab, sarilumab, dupilumab, bevacizumab (eg, AVASTIN™), cetuximab (eg, ERBITUX™), tocilizumab (eg, ACTEMRA™) or trastuzumab (HERCEPTIN™). In an alternative the antibody is an anti-CD38 antibody, an anti-TNFa antibody, an anti-TNFR antibody, an anti-IL-4Ra antibody, an anti-IL-6R antibody, an anti-IL-6 antibody, an anti-VEGF antibody, an anti-EGFR antibody, an anti-PD-1 antibody, an anti-PD-L1 antibody, an anti-CTLA4 antibody, an anti-PCSK9 antibody, an anti-CD3 antibody, an anti-CD20 antibody, an anti-CD138 antibody, an anti-IL-1 antibody. In an alternative the antibody is selected from the antibodies disclosed in WO2007024715 at page 40, line 23 to page 43, line 23, the disclosure of which is incorporated herein by reference.

A binding site herein may, for example, be a ligand (eg, cytokine or growth factor, eg, VEGF or EGFR) binding site of a receptor (eg, KDR or Flt). A binding site herein may, for example, be a binding site of Eyelea™, Avastin™ or Lucentis™, eg, for ocular or oncological medical use in a human or animal. When the ligand or antigen is VEGF, the mutlimer, tetramer or octamer may be for treatment or prevention of a caner or ocular condition (eg, wet or dry AMD or diabetic retinopathy) or as an inhibitor of neovascularisation in a human or animal subject.

17. An isolated tetramer or octamer of a TCR binding site, insulin peptide, incretin peptide or peptide hormone; or a plurality of said tetramers or octamers.

Several important peptide hormones are secreted from the pituitary gland. The anterior pituitary secretes three hormones: prolactin, which acts on the mammary gland; adrenocorticotropic hormone (ACTH), which acts on the adrenal cortex to regulate the secretion of glucocorticoids; and growth hormone, which acts on bone, muscle, and the liver. The posterior pituitary gland secretes antidiuretic hormone, also called vasopressin, and oxytocin. Peptide hormones are produced by many different organs and tissues, however, including the heart (atrial-natriuretic peptide (ANP) or atrial natriuretic factor (ANF)) and pancreas (glucagon, insulin and somatostatin), the gastrointestinal tract (cholecystokinin, gastrin), and adipose tissue stores (leptin). In an example, the peptide hormone of the invention is selected from prolactin, ACTH, growth hormone (somatotropin), vasopressin, oxytocin, glucagon, insulin, somatostatin, cholecystokinin, gastrin and leptin (eg, selected from human prolactin, ACTH, growth hormone, vasopressin, oxytocin, glucagon, insulin, somatostatin, cholecystokinin, gastrin and leptin).

In an example, the incretin is a GLP-1, GIP or exendin-4 peptide.

The invention provides, in embodiments, the following engineered tetramers and octamers:—

An isolated tetramer or octamer of an incretin.
An isolated tetramer or octamer of an insulin peptide.
An isolated tetramer or octamer of a GLP-1 (glucagon-like peptide-1 (GLP-1) peptide.
An isolated tetramer or octamer of a GIP (glucose-dependent insulinotropic polypeptide) peptide.
An isolated tetramer or octamer of an exendin (eg, exendin-4) peptide.
An isolated tetramer or octamer of a peptide hormone.
An isolated tetramer or octamer of a prolactin or prolactin peptide.
An isolated tetramer or octamer of a ACTH or ACTH peptide.
An isolated tetramer or octamer of a growth hormone or growth hormone peptide.
An isolated tetramer or octamer of a vasopressin or vasopressin peptide.
An isolated tetramer or octamer of an oxytocin or oxytocin peptide.
An isolated tetramer or octamer of a glucagon or glucagon peptide.
An isolated tetramer or octamer of a insulin or insulin peptide.
An isolated tetramer or octamer of a somatostatin or somatostatin peptide.
An isolated tetramer or octamer of a cholecystokinin or cholecystokinin peptide.
An isolated tetramer or octamer of a gastrin or gastrin peptide.
An isolated tetramer or octamer of a leptin or leptin peptide.
An isolated tetramer or octamer of an antibody binding site (eg, a scFv or Fab).
An isolated tetramer or octamer of a TCR binding site (eg, a scTCR).
An isolated tetramer or octamer of a TCR Vα/Vβ binding site.
An isolated tetramer or octamer of a TCR Vγ/Vδ binding site.
An isolated tetramer or octamer of an antibody single variable domain binding site.
An isolated tetramer or octamer of an FcAb binding site.

In an example of any of these tetramers or octamers, the domain or peptide is human. In an example of any of these tetramers or octamers, the tetramer or octamer comprises a NHR2 TD (eg, a human NHR2). In an example of any of these tetramers or octamers, the tetramer or octamer comprises a p53 TD (eg, a human p53 TD). In an example of any of these tetramers or octamers, the tetramer or octamer comprises a p63 TD (eg, a human p63 TD). In an example of any of these tetramers or octamers, the tetramer or octamer comprises a p73 TD (eg, a human p73 TD). In an example of any of these tetramers or octamers, the tetramer or octamer comprises a tetramer of TDs (eg, human NHR2 TDs), whereby the domains or peptides form a multimer of 4 or 8 domains or peptides.

In an example, the plurality is pure, eg, is not in mixture with multimers of said binding site or peptide wherein the multimers comprise more than one type of polypeptide monomer.

18. The multimer, tetramer or octamer of any preceding Aspect, wherein the mulitmer, tetrameror octamer is
    (a) soluble in aqueous solution (eg, an aqueous eukaryotic cell growth medium or buffer);
    (b) secretable from a eukaryotic cell; and/or
    (c) an expression product of a eukaryotic cell.

In an example the multimer, tetramer or octamer is secretable from a HEK293T (or other eukaryotic, mammalian, CHO or Cos) cell in stable form as indicated by a single band at the molecular weight expected for said multimer, tetramer or octamer on a PAGE gel using a sample of supernatant from such cells and detected using Western Blot.

19. A tetramer or octamer of
    (a) TCR V domains or TCR binding sites, wherein the tetramer or octamer is soluble in aqueous solution (eg, an aqueous eukaryotic cell growth medium or buffer);
    (b) antibody single variable domains, wherein the tetramer or octamer is soluble in aqueous solution (eg, an aqueous eukaryotic cell growth medium or buffer);
    (c) TCR V domains or TCR binding sites, wherein the tetramer or octamer is capable of being intracellularly and/or extracellularly expressed by HEK293 cells; or
    (d) antibody variable domains (eg, antibody single variable domains), wherein the tetramer or octamer is capable of being intracellularly and/or extracellularly expressed by HEK293 cells.

An example of the medium is SFMII growth medium supplemented with L-glutamine (eg, complete SFMII growth medium supplemented with 4 mM L-glutamine). In an example, the medium is serum-free HEK293 cell culture medium. In an example, the medium is serum-free CHO cell culture medium.

For example, a cell herein is a human cell, eg, a HEK293 cell (such as a HEK293T cell).

20. The multimer, tetramer or octamer of any preceding Aspect, wherein the tetramer or octamer is bi-specific for antigen or pMHC binding.
21. The multimer, tetramer or octamer of any preceding Aspect, wherein the domains are identical.
22. The multimer, tetramer or octamer of any preceding Aspect, wherein the multimer, tetrameror octamer comprises eukaryotic cell glycosylation.

For example the glycosylation is CHO cell glycosylation. For example the glycosylation is HEK (eg, HEK293, such as HEK293T) cell glycosylation. For example the glycosylation is Cos cell glycosylation. For example the glycosylation is *Picchia* cell glycosylation. For example the glycosylation is *Sacchaaromyces* cell glycosylation.

23. The multimer, tetramer or octamer of Aspect 22, wherein the cell is a HEK293 cell.
24. A plurality of multimers, tetramers or octamers of any preceding Aspect.
25. A pharmaceutical composition comprising the multimer(s), tetramer(s) or octamer(s) of any preceding Aspect and a pharmaceutically acceptable carrier, diluent or excipient.
26. A cosmetic, foodstuff, beverage, cleaning product, detergent comprising the multimer(s), tetramer(s) or octamer(s) of any one of Aspects 1 to 24.
27. A said engineered (and optionally isolated) polypeptide or a monomer (optionally isolated) of a multimer, tetramer or octamer of any preceding Aspect.

The monomer is an engineered polypeptide as disclosed herein, comprising a said protein domain or peptide and further comprising a TD.

Optionally, the engineered polypeptide comprises (in N- to C-terminal direction) a variable domain (V1)—a constant domain (C) (eg, a CH1 or Fc)—optional linker—TD.

28. An engineered (and optionally isolated) engineered polypeptide (P1) which comprises (in N- to C-terminal direction):—
    (a) TCR V1-TCR C1—antibody C (eg, CH, CH1 (such as IgG CH1) or CL (such as Cλ or a Cκ))—optional linker—TD, wherein
        (i) V1 is a Vα and C1 is a Cα;
        (ii) V1 is a Vβ and C1 is a Cβ;
        (iii) V1 is a Vγ and C1 is a Cγ; or
        (iv) V1 is a Vδ and C1 is a Cδ;
        or
    (b) TCR V1—antibody C (eg, CH, CH1 (such as IgG CH1) or CL (such as Cλ or a Cκ))—optional linker—TD, wherein
        (i) V1 is a Vα;
        (ii) V1 is a Vβ;
        (iii) V1 is a Vγ; or
        (iv) V1 is a Vδ;
        or
    (c) antibody V1—antibody C (eg, CH, CH1 (such as IgG CH1) or CL (such as Cλ or a Cκ))—optional linker—TD, wherein
        (i) V1 is a VH; or
        (ii) V1 is a VL (eg, a Vλ or a Vκ);
        or
    (d) antibody V1—optional antibody C (eg, CH, CH1 (such as IgG CH1) or CL (such as Cλ or a Cκ))—antibody Fc (eg, an IgG Fc)—optional linker—TD, wherein
        (i) V1 is a VH; or
        (ii) V1 is a VL (eg, a Vλ or a Vκ);
        or
    (e) antibody V1—antibody CL (eg, a Cλ or a Cκ)—optional linker—TD, wherein
        (i) V1 is a VH; or
        (ii) V1 is a VL (eg, a Vλ or a Vκ);
        or
    (f) TCR V1-TCR C1—optional linker—TD, wherein
        (i) V1 is a Vα and C1 is a Cα;
        (ii) V1 is a Vβ and C1 is a Cβ;
        (iii) V1 is a Vγ and C1 is a Cγ; or
        (iv) V1 is a Vδ and C1 is a Cδ.

In (a) or (b), in an example, the TCR V is comprised by an single chain TCR binding site (scTCR) that specifically binds to a pMHC, wherein the binding site comprises TCR V-linker—TCRV. In an example, the engineered polypeptide comprises (in N- to C-terminal direction) (i) V1-linker—V—optional C—optional linker—TD, or (ii) Va—linker—V1—optional C—optional linker—TD, wherein Va is a TCR V domain and C is an antibody C domain (eg, a CH1 or CL) or a TCR C.

Preferably, the antibody C is CH1 (eg, IgG CH1).

In an example the multimer, tetramer or octamer has a size of no more than 155 kDa, eg, wherein said protein domain is an antibody variable domain comprising a CDR3 of at least 16, 17, 18, 19, 20, 21 or 22 amino acids, such as a Camelid CDR3 or bovine CDR3.

In an example, the multimer, tetramer or octamer comprises TCR binding sites and antibody binding sites. For example, each polypeptide comprises a TCR V (eg, comprised by a scTCR that specifically binds a pMHC) and an antibody V (eg, comprised by a scFv or paired with a second V domain comprised by a said second polypeptide to form a V/V paired binding site that specifically binds to an antigen). In an example, the pMHC comprises a RAS peptide. In an example the antigen is selected from the group consisting of PD-1, PD-L1 or any other antigen disclosed herein. For example, the antigen is PD-1 and the pMHC comprises a RAS peptide.

29. The polypeptide of Aspect 28, wherein the engineered polypeptide P1 is paired with a further polypeptide (P2), wherein P2 comprises (in N- to C-terminal direction):—
    (g) TCR V2-TCR C2—antibody CL (eg, a Cλ or a Cκ), wherein P1 is according to (a) recited in Aspect 28 and
        (i) V2 is a Vα and C2 is a Cα when P1 is according to (a)(ii);
        (ii) V2 is a Vβ and C2 is a Cβ when P1 is according to (a)(i);
        (iii) V2 is a Vγ and C2 is a Cγ when P1 is according to (a)(iv); or
        (iv) V2 is a Vδ and C2 is a Cδ when P1 is according to (a)(iii);
        or
    (h) TCR V2—antibody CL (eg, a Cλ or a Cκ), wherein P1 is according to (b) recited in Aspect 28 and
        (i) V2 is a Vα when P1 is according to (b)(ii);
        (ii) V2 is a Vβ when P1 is according to (b)(i);
        (iii) V2 is a Vγ when P1 is according to (b)(iv); or
        (iv) V2 is a Vδ when P1 is according to (b)(iii);

or
(i) Antibody V2—CL (eg, a Cλ or a Cκ), wherein P1 is according to (c) recited in Aspect 28 and
   (i) V2 is a VH when P1 is according to (c)(ii); or
   (ii) V2 is a VL (eg, a Vλ or a Vκ) when P1 is according to (c)(i);
or
(j) Antibody V2—optional CL (eg, a Cλ or a Cκ), wherein P1 is according to (d) recited in Aspect 28 and
   (i) V2 is a VH when P1 is according to (d)(ii); or
   (ii) V2 is a VL (eg, a Vλ or a Vκ) when P1 is according to (d)(i);
or
(k) Antibody V2—CH1 (eg, IgG CH1), wherein P1 is according to (e) recited in Aspect 28 and
   (i) V2 is a VH when P1 is according to (e)(ii); or
   (ii) V2 is a VL (eg, a Vλ or a Vκ) when P1 is according to (e)(i);
or
(l) TCR V2-TCR C2, wherein P1 is according to (f) recited in Aspect 28 and
   (i) V2 is a Vα and C2 is a Cα when P1 is according to (f)(ii);
   (ii) V2 is a Vβ and C2 is a Cβ when P1 is according to (f)(i);
   (iii) V2 is a Vγ and C2 is a Cγ when P1 is according to (f)(iii); or
   (iv) V2 is a Vδ and C2 is a Cδ when P1 is according to (f)(iv).

Optionally, V1 and V2 form a paired variable domain binding site that is capable of specifically binding to an antigen or pMHC. In an example, V1 and V2 are variable domains of an antibody, eg, selected from the group consisting of REOPRO®; Abciximab; RITUXAN®; Rituximab; ZENAPAX®; Daclizumab; SIMULECT®; Basiliximab; SYNAGIS®; Palivizumab; REMICADE®; Infliximab; HERCEPTIN®; MYLOTARG®; Gemtuzumab; CAMPATH®; Alemtuzumab; ZEVALIN®; Ibritumomab; HUMIRA®; Adalimumab; XOLAIR®; Omalizumab; BEXXAR®; Tositumomab; RAPTIVA™; Efalizumab; ERBITUX®; Cetuximab; AVASTIN®; Bevacizumab; TYSABRI®; Natalizumab; ACTEMRA®; Tocilizumab;-VECTIBIX®; Panitumumab; LUCENTIS®; Ranibizumab; SOLIRIS®; Eculizumab; CIMZIA®; Certolizumab; SIMPONI®; Golimumab, ILARIS®; Canakinumab; STELARA®; Ustekinumab;-ARZERRA®; Ofatumumab; PROLIA®; Denosumab; NUMAX™; Motavizumab; ABTHRAX™; Raxibacumab; BENLYSTA®; Belimumab; YERVOY®; Ipilimumab; ADCETRIS®; Brentuximab Vedotin; PERJETA®; Pertuzumab; KADCYLA®; Ado-trastuzumab;-KEYTRUDA®, OPDIVO®, GAZYVA® and Obinutuzumab In one embodiment, the antibody is AVASTIN®.
In one embodiment, the antibody is ACTEMRA®.
In one embodiment, the antibody is ERBITUX®.
In one embodiment, the antibody is LUCENTIS®.
In one embodiment, the antibody is sarilumab
In one embodiment, the antibody is dupilumab
In one embodiment, the antibody is alirocumab
In one embodiment, the antibody is evolocumab
In one embodiment, the antibody is pembrolizumab
In one embodiment, the antibody is nivolumab
In one embodiment, the antibody is ipilimumab
In one embodiment, the antibody is remicade
In one embodiment, the antibody is golimumab
In one embodiment, the antibody is ofatumumab
In one embodiment, the antibody is BENLYSTA®.
In one embodiment, the antibody is CAMPATH®.
In one embodiment, the antibody is rituximab
In one embodiment, the antibody is HERCEPTIN®.
In one embodiment, the antibody is durvalumab
In one embodiment, the antibody is daratumumab In an example, V1 is capable (itself when a single variable domain, or when paired with V2) of specifically binding to an antigen selected from the group consisting of ABCF1; ACVR1; ACVR1B; ACVR2; ACVR2B; ACVRL1; ADORA2A; Aggrecan; AGR2; AICDA; AWI; AIG1; AKAP1; AKAP2; AIYIH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BM P1; BMP2; BMP3B (GDFIO); BMP4; BMP6; BM P8; BMPRIA; BMPRIB; BM PR2; BPAG1 (plectin); BRCA1; CI9orflO (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-id); CCL16 (HCC-4); CCL17 (TARC); CCL18 (PARC); CCL19 (M IP-3b); CCL2 (MCP-1); MCAF; CCL20 (MIP-3a); CCL21 (MIP-2); SLC; exodus-2; CCL22 (MDC/STC-1); CCL23 (M PIF-1); CCL24 (MPIF-2 I eotaxin-2); CCL25 (TECK); CCL26 (eotaxin-3); CCL27 (CTACK/ILC); CCL28; CCL3 (MIP-1a); CCL4 (M IP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CM KBR5/ChemR13); CCR6 (CMKBR6/CKR-L3/STRL22/DRY6); CCR7 (CKR7/EBI1); CCR8 (CM KBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p2IWap1/Cip1); CDKN1B (p27Kipl); CDKNIC; CDKN2A (pl6INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYDi); CX3CR1 (V28); CXCL1 (GROl); CXCLIO (IP-10); CXCL11 (1-TAC/IP-9); CXCL12 (SDF1); CXCL13; CXCL14; CXCL16; CXCL2 (GR02); CXCL3 (GR03); CXCL5 (ENA-78 I LIX); CXCL6 (GCP-2); CXCL9 (MIG); CXCR3 (GPR9/CKR-L2); CXCR4; CXCR6 (TYMSTR ISTRL33 I Bonzo); CYB5; CYC1; CYSLTR1; DAB2IP; DES; DKFZp451J0118; DNCL1; DPP4; E2F1; ECGF1; EDG1; EFNAI; EFNA3; EFNB2; EGF; EGFR; ELAC2; ENG; EN01; EN02; EN03; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FU12584; FU25530; FLRT1 (fibronectin); FLT1; FOS; FOSL1 (FRA-I); FY (DARC); GABRP (GABAa); GAGEB 1; GAGEC1; GALNAC4S-65T; GATA3; GDF5; GFI1; GGT1; GM-CSF; GNAS1;

GNRH1; GPR2 (CCRIO); GPR31; GPR44; GPR81 (FKSG80); GRCCIO (CIO); GRP; GSN (Gelsolin); GSTP1; HAVCR2; HDAC4; EDAC5; HDAC7A; HDAC9; HGF; HIF1A; HIP1;

histamine and histamine receptors; HLA-A; HLA-DRA; HM74; HMOX1; HUMCYT2A; ICEBERG; ICOSL; 1D2; IFN-α; IFNA1; IFNA2; IFNA4; IFNA5; IFNA6; IFNA7; IFNB1; IFNgamma; TFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; 1L13; IL13RA1; IL13RA2; 1L14; 1L15; IL15RA; IL16; 1L17; IL17B; IL17C; IL17R; 1L18; IL18BP; IL18R1; IL18RAP; 1L19; ILIA; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; 1L2; 1L20; IL20RA; IL21R; 1L22; 1L22R; 1L22RA2; 1L23; 1L24; 1L25; 1L26; 1L27; 1L28A; 1L28B; 1L29; IL2RA; IL2RB; IL2RG; 1L3; 1L30; IL3RA; 1L4; IL4R; 1L5; IL5RA; 1L6; IL6R; IL6ST (glycoprotein 130); 1L7; TL7R; 1L8; IL8RA; IL8RB; IL8RB; 1L9; IL9R; ILK; INHA; INHBA; INSL3; INSL4; IRAKI; IRAK2; ITGA1; ITGA2; 1TGA3; ITGA6 (a6 integrin); ITGAV; ITGB3; ITGB4 (b 4 integrin); JAG1; JAK1; JAK3; JUN; K6HF; KAI1; KDR; MTLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; M IB1; midkine; M IF; M IP-2; MK167 (Ki-67); MMP2; M MP9; MS4A1; MSMB; MT3 (metallothionectin-ifi); MTSS 1; M UC 1 (mucin); MYC; MYD88; NCK2; neurocan; NFKB 1; NFKB2; NGFB (NGF); NGFR; NgR-Lingo; NgR-Nogo66 (Nogo); NgR-p75; NgR-Troy; NM E1 (NM23A); NOX5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PARTI; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p2IRac2); RARB; RGS1; RGS13; RGS3; RNF110 (ZNF144); ROB02; S100A2; SCGB1D2 (lipophilin B); SCGB2A1 (mamma-globin 2); SCGB2A2 (mammaglobin 1); SCYE1 (endothelial Monocyte-activating cytokine); SDF2; SERPINAl; SERPINIA3; SERPINB5 (maspin); SERPINE1 (PAT-i); SERPINFi; SHBG; SLA2; SLC2A2; SLC33A1; SLC43A1; SLIT2; SPPl; SPRRIB (Spri); ST6GAL1; STABi; STAT6; STEAP; STEAP2; TB4R2; TBX21; TCPIO; TDGF1; TEK; TGFA; TGFB1; TGFB1I1; TGFB2; TGFB3; TGFBI; TGFBR1; TGFBR2; TGFBR3; TH1L; THBS1(thrombospondin-1); THBS2; THBS4; THPO; TIE (Tie-i); T]MP3; tissue factor; TLRIO; TLR2; TLR3; TLR4; TLR5; TLR6; TLR7; TLR8; TLR9; TNF; TNF-α; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEM-L); TNFSF15 (VEGI); TNFSF18; TNFSF4 (0×40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM 1; TPM2; TRADD; TRAF1; TRAF2; TRAF3; TRAF4; TRAF5; TRAF6; TREM 1; TREM2; TRPCδ; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

For example in any configuration of the invention, the multimer, tetramer or octamer specifically binds to first and second epitopes or antigens, each of which is selected from the group consisting of EpCAM and CD3; CD19 and CD3; VEGF and VEGFR2; VEGF and EGFR; CD138 and CD20; CD138 and CD40; CD20 and CD3; CD38 and CD138; CD38 and CD20; CD38 and CD40; CD40 and CD20; CD19 and CD20; CD-8 and IL-6; PDL-1 and CTLA-4; CTLA-4 and BTN02; CSPGs and RGM A; IGF1 and IGF2; IGF1 and/or 2 and Erb2B; IL-12 and IL-18; IL-12 and TWEAK; IL-13 and ADAM8; IL-13 and CL25; IL-13 and IL-1beta; IL-13 and IL-25; IL-13 and IL-4; IL-13 and IL-5; IL-13 and IL-9; IL-13 and LHR agonist; IL-13 and MDC; IL-13 and MIF; IL-13 and PED2; IL-13 and SPRR2a; IL-13 and SPRR2b; IL-13 and TARC; IL-13 and TGF-beta; IL-1 alpha and IL-1 beta; MAG and RGM A; NgR and RGM A; NogoA and RGM A; OMGp and RGM A; RGM A and RGM B; Te38 and TNF alpha; TNF alpha and IL-12; TNF alpha and IL-12p40; TNF alpha and IL-13; TNF alpha and IL-15; TNF alpha and IL-17; TNF alpha and IL-18; TNF alpha and IL-1 beta; TNF alpha and IL-23; TNF alpha and M IF; TNF alpha and PEG2; TNF alpha and PGE4; TNF alpha and VEGF; and VEGFR and EGFR; TNF alpha and RANK ligand; TNF alpha and Blys; TNF alpha and GP130; TNF alpha and CD-22; and TNF alpha and CTLA-4

For example, the first epitope or antigen is selected from the group consisting of CD3; CD16; CD32; CD64; and CD89; and the second epitope or antigen is selected from the group consisting of EGFR; VEGF; IGF-1R; Her2; c-Met (aka HGF); HER3; CEA; CD33; CD79a; CD19; PSA; EpCAM; CD66; CD30; HAS; PSMA; GD2; ANG2; IL-4; IL-13; VEGFR2; andVEGFR3.

In an example, V1 is capable (itself when a single variable domain, or when paired with V2) of specifically binding to an antigen selected from the group consisting of human IL-1A, IL-13, IL-1RN, IL-6, BLys, APRIL, activin A, TNF alpha, a BMP, BMP2, BMP7, BMP9, BMP10, GDF8, GDF11, RANKL, TRAIL, VEGFA, VEGFB or PGF; optionally the multimer comprises a cytokine amino acid sequence (eg, C-terminal to a TD), such as IL-2 or an IL2-peptide; and the multimer, tetramer or octamer is for treating or preventing a cancer in a human subject. In an example the said effector or protein domain is capable of binding to such an antigen; optionally the multimer comprises a cytokine amino acid sequence (eg, C-terminal to a TD), such as IL-2 or an IL2-peptide; and the multimer, tetramer or octamer is for treating or preventing a cancer in a human subject.

30. A multimer (eg, a dimer, trimer, tetramer or octamer) of P1 as defined in Aspect 28; or of P1 paired with P2 as defined in Aspect 29; or a plurality of said multimers, optionally wherein the multimer is according to any one of aspects 1 to 24.

Preferably the multimer is a tetramer of the engineered polypeptide and/or effector domain. In one example, the plurality of tetramers are not in mixture with monomers, dimers or trimers of the polypeptide, In one example the multimer, eg, tetramer, is a capable of specifically binding to two different pMHC.

31. A nucleic acid encoding an engineered polypeptide or monomer of any one of Aspects 27 to 29, optionally wherein the nucleic acid is comprised by an expression vector for expressing the polypeptide.

In an example, the nucleic acid is a DNA, optionally operably connected to or comprising a promoter for expression of the polypeptide or monomer. In another example the nucleic acid is a RNA (eg, mRNA).

32. A eukaryotic host cell comprising the nucleic acid or vector of Aspect 31 for intracellular and/or secreted expression of the multimer, tetramer, octamer, engineered polypeptide or monomer of any one of Aspects 1 to 24.
33. Use of a nucleic acid or vector according to aspect 31 in a method of manufacture of protein multimers for producing intracellularly expressed and/or secreted multimers, wherein the method comprises expressing the multimers in and/or secreting the multimers from eukaryotic cells comprising the nucleic acid or vector.
34. Use of a nucleic acid or vector according to aspect 31 in a method of manufacture of protein multimers for producing glycosylated multimers in eukaryotic cells comprising the nucleic acid or vector.

Mammalian glycosylation of the invention is useful for producing medicines comprising or consisting of the multimers, tetramers or octamers of the invention for medical treatment or prevention of a disease or condition in a mammal, eg, a human. The invention thus provides such a method of use as well as the multimer, tetramer or octamer of the invention for this purpose. Similarly, intracellular and/or secreted expression in one or more host cells (or cell lines thereof) that are mammalian according to the invention is useful for producing such medicines. Particularly useful is such expression in HEK293, CHO or Cos cells as these are commonly used for production of medicaments.

In an embodiment, the invention comprises a detergent or personal healthcare product comprising a multimer, tetramer or octamer of the invention. In an embodiment, the invention comprises a foodstuff or beverage comprising a multimer, tetramer or octamer of the invention.

In an example, the multimer, monomer, dimer, trimer, tetramer, octamer, polypeptide, composition, mixture, use or method of the present invention is for an industrial or domestic use, or is used in a method for such use. For example, it is for or used in agriculture, oil or petroleum industry, food or drink industry, clothing industry, packaging industry, electronics industry, computer industry, environmental industry, chemical industry, aeorspace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry or steel industry.

35. A mixture comprising (i) a eukaryotic cell line encoding an engineered polypeptide according to any one of Aspects 27 to 29; and (ii) multimers, tetramers or octamers as defined in any one of Aspects 1 to 24.
36. The mixture of Aspect 35, wherein the cell line is in a medium comprising secretion products of the cells, wherein the secretion products comprise said multimers, tetramers or octamers.
37. The multimer, tetramer or octamer of any one of aspects 1 to 24 for medical use.
38. A method producing
    (a) TCR V domain multimers, the method comprising the soluble and/or intracellular expression of TCR V-NHR2 TD or TCR V-p53 TD fusion proteins expressed in eukaryotic cells, the method optionally comprising isolating a plurality of said multimers;
    (b) antibody V domain multimers, the method comprising the soluble and/or intracellular expression of antibody V (eg, a single variable domain)—NHR2 TD or V-p53 TD fusion proteins expressed in eukaryotic cells, the method optionally comprising isolating a plurality of said multimers;
    (c) incretin peptide (eg, GLP-1, GIP or insulin) multimers, the method comprising the soluble and/or intracellular expression of incretin peptide-NHR2 TD or incretin peptide-p53 TD fusion proteins expressed in eukaryotic cells, such as HEK293T cells; the method optionally comprising isolating a plurality of said multimers; or
    (d) peptide hormone multimers, the method comprising the soluble and/or intracellular expression of peptide hormone-NHR2 TD or peptide hormone-p53 TD fusion proteins expressed in eukaryotic cells, such as HEK293T cells; the method optionally comprising isolating a plurality of said multimers.
39. Use of self-associating tetramerization domains (TD) (eg, NHR2 TD, p53 TD, p63 TD or p73 TD or a homologue or orthologue thereof) in a method of the manufacture of a tetramer of polypeptides, for producing a higher yield of tetramers versus monomer and/or dimer polypeptides.
40. Use of an engineered polypeptide in a method of the manufacture of a tetramer of a polypeptide comprising multiple copies of a protein domain or peptide, for producing a higher yield of tetramers versus monomer and/or dimer polypeptides, wherein the engineered polypeptide comprises one or more copies of said protein domain or peptide and further comprises a self-associating tetramerization domains (TD) (eg, NHR2 TD, p53 TD, p63 TD or p73 TD or a homologue or orthologue).
41. Use of self-associating tetramerization domains (TD) (eg, NHR2 TD, p53 TD, p63 TD or p73 TD or a homologue or orthologue thereof) in a method of the manufacture of a tetramer of a polypeptide, for producing a plurality of tetramers that are not in mixture with monomers, dimers or trimers.
42. Use of an engineered polypeptide in a method of the manufacture of a tetramer of a polypeptide comprising multiple copies of a protein domain or peptide, for producing a plurality of tetramers that are not in mixture with monomers, dimers or trimers, wherein the engineered polypeptide comprises one or more copies of said protein domain or peptide and further comprises a self-associating tetramerization domains (TD) (eg, NHR2 TD, p53 TD, p63 TD or p73 TD or a homologue or orthologue).
43. The use of any one of Aspects 39 to 42, wherein the yield of tetramers is at least 10, 20, 30, 40 or 50× the yield of monomers and/or dimers.
44. The use of any one of Aspects 39 to 43, wherein the ratio of tetramers produced:monomers and/or dimers produced in the method is at least 90:10 (eg, at least 95:5 or 98:2, or 99:1).
45. The use of any one of Aspects 39 to 44, wherein each monomer has a size of no more than 40, 35, 30, 25 or 20 kDa.
46. The use of any one of Aspects 39 to 45, wherein each tetramer has a size of no more than 200, 160, 155 or 150 kDa.
47. The use of any one of Aspects 39 to 46, wherein the method comprises expressing the tetramers from a eukaryotic cell line.

48. A multivalent heterodimeric soluble T cell receptor capable of binding pMHC complex comprising:
   (i) TCR extracellular domains;
   (ii) immunoglobulin constant domains; and
   (iii) an NHR2 multimerisation domain of ETO.
49. A multimeric immunoglobulin, comprising
   (i) immunoglobulin variable domains; and
   (ii) an NHR2 multimerisation domain of ETO.
50. A method for assembling a soluble, multimeric polypeptide, comprising:
   (a) providing a monomer of the said multimeric polypeptide, fused to an NHR2 domain of ETO;
   (b) causing multiple copies of said monomer to associate, thereby obtaining a multimeric, soluble polypeptide.

Figure 2:
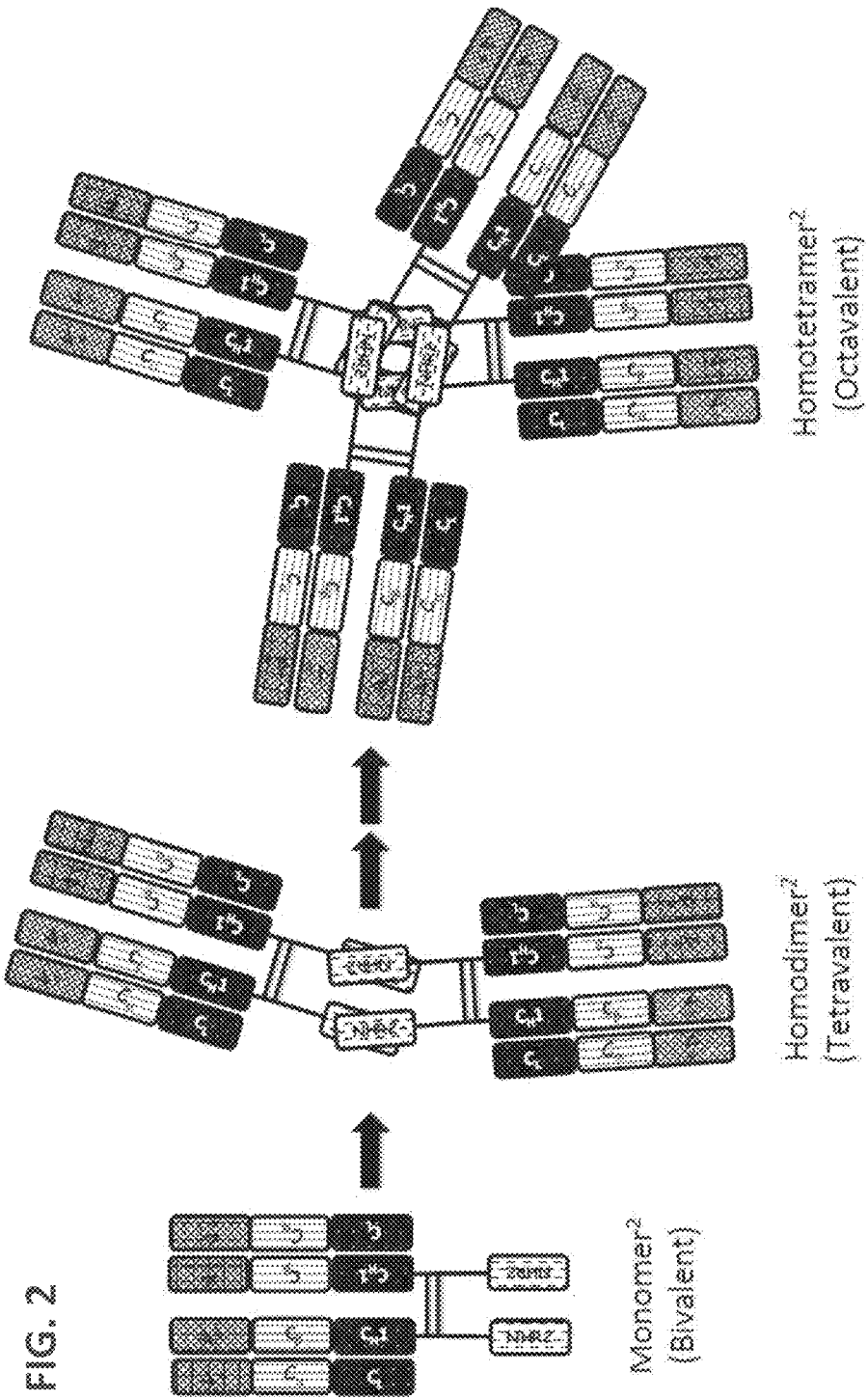
FIG. 2. A schematic drawing representing the stepwise self-assembly of a octavalent heterodimeric soluble TCR protein complex via a monomer$^2$ and homodimer$^2$, which is aided by NHR2 tetramerization domain and immunoglobulin hinge domain.
Figure 11A:
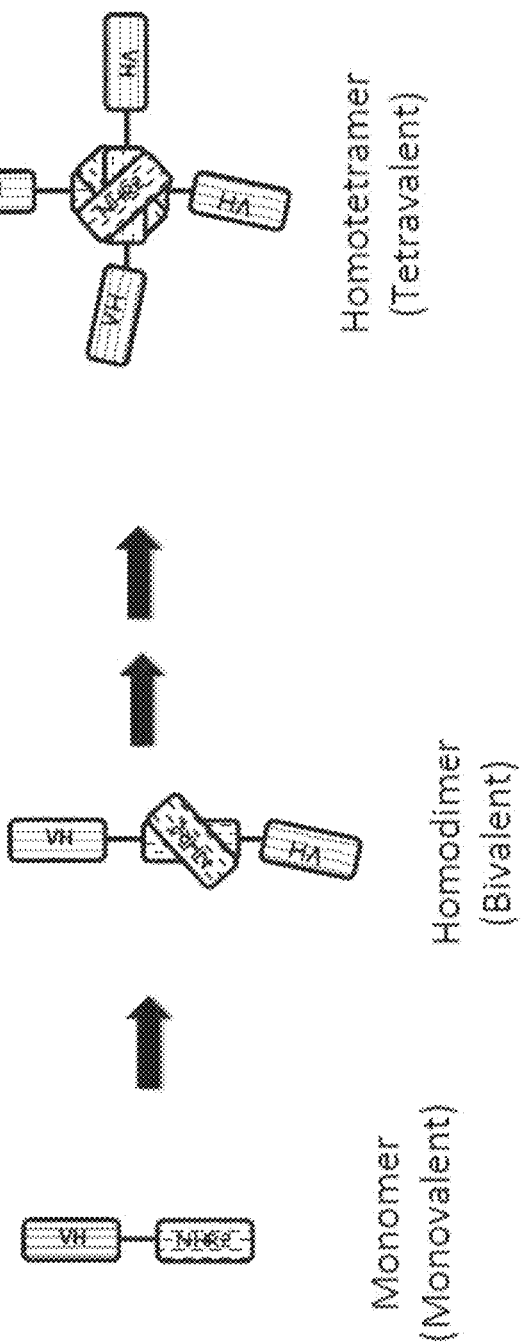
FIG. 11A: A schematic drawing representing the stepwise self-assembly of a tetravalent single domain antibody (dAb) complex via a monomer and homodimer, which is aided by NHR2 tetramerization domain.
Figure 12A:
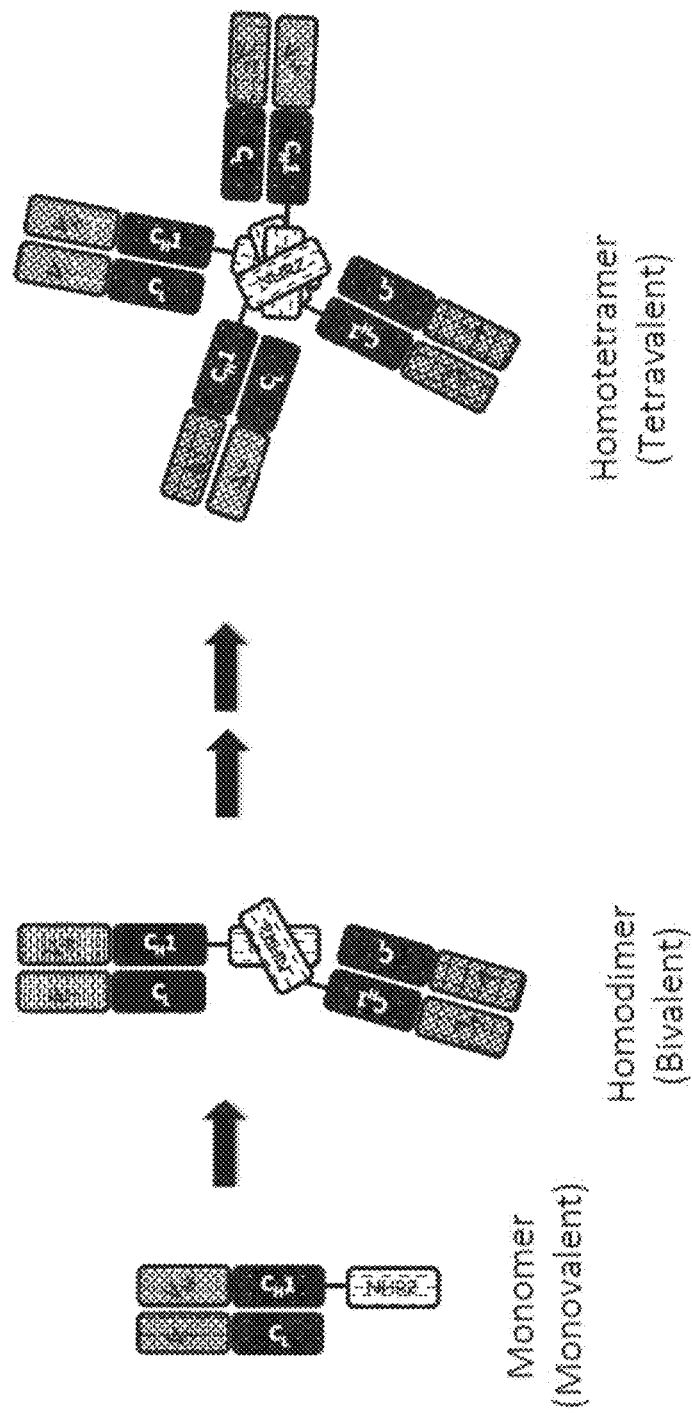
FIG. 12A: A schematic drawing representing the stepwise self-assembly of a tetravalent Fab complex via a monomer and homodimer, which is aided by NHR2 tetramerization domain.
Figure 13A:
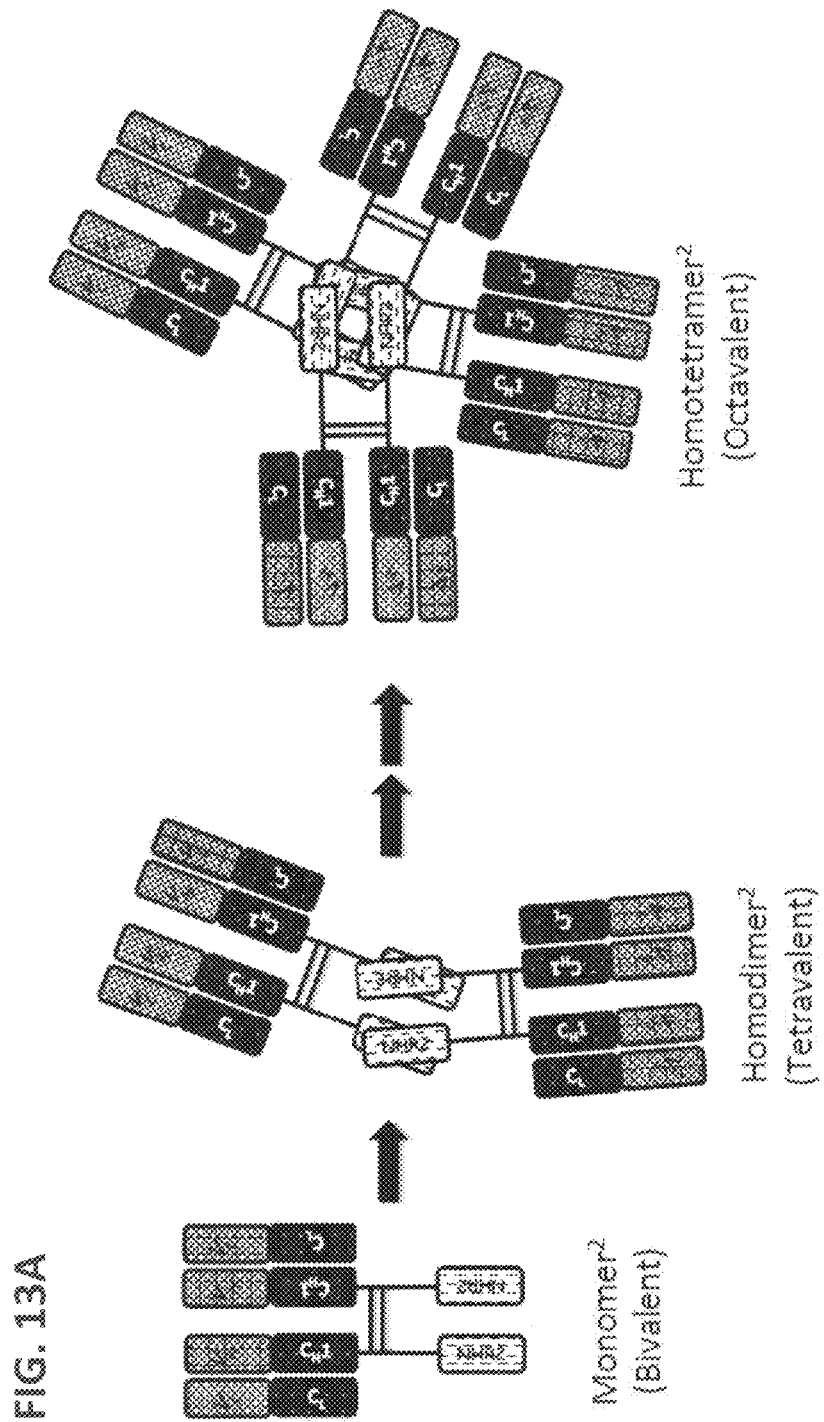
FIG. 13A: A schematic drawing representing the stepwise self-assembly of an octavalent Fab complex via a monomer and homodimer, which is aided by NHR2 tetramerization domain and an antibody hinge region linked to CH1 domain.

The invention further provides
   (i) A monomer as shown in FIG. 1;
   (ii) A homodimer as shown in FIG. 1;
   (iii) A homotetramer as shown in FIG. 1;
   (iv) A monomer$^2$ as shown in FIG. 2;
   (v) A homodimer$^2$ as shown in FIG. 2;
   (vi) A homotetramer$^2$ as shown in FIG. 2;
   (vii) A monomer as shown in FIG. 11A;
   (viii) A homodimer as shown in FIG. 11A;
   (ix) A homotetramer as shown in FIG. 11A;
   (x) A monomer as shown in FIG. 12A;
   (xi) A homodimer as shown in FIG. 12A;
   (xii) A homotetramer as shown in FIG. 12A;
   (xiii) A monomer$^2$ as shown in FIG. 13A;
   (xiv) A homodimer$^2$ as shown in FIG. 13A;
   (xv) A homotetramer$^2$ as shown in FIG. 13A; or
   (xvi) A multimeric protein comprising any one of (i) to (xv) (eg, any one of Quads 3, 4, 12, 13, 14, 15, 16 and 17) or a multimer of any protein shown in FIG. 21 (excluding any leader or tag).
   (xvii) A plurality of multimers of (xvi); or
   (xviii) A pharmaceutical composition comprising any one of (i) to (xvii) and a pharmaceutically acceptable carrier, diluent or excipient.

The invention also provides
   (i) A tetravalent or octavalent antibody V molecule;
   (ii) A tetravalent or octavalent antibody Fab molecule;
   (iii) A tetravalent or octavalent antibody dAb molecule;
   (iv) A tetravalent or octavalent antibody scFv molecule;
   (v) A tetravalent or octavalent antibody TCR V molecule; or
   (vi) A tetravalent or octavalent antibody scFv molecule;
Wherein the Molecule is
   (a) soluble in aqueous solution (eg, a solution or cell culture medium disclosed herein) and/or;
   (b) capable of being intracellularly and/or extracellularly expressed by HEK293 cells.

The invention provides a claim multimer (eg, tetramer) of NHR2 or p53 (or another TD disclosed herein) fused at its N- and/or C-terminus to an amino acid sequence (eg, a peptide, protein domain or protein) that is not an NHR2 sequence. For example, sequence is selected from a TCR (eg, TCRα, TCRβ, Cα or Cβ), cytokine (eg, interleukin, eg, IL-2, IL-12, IL-12 and IFN), antibody fragments (eg, scFv, dAb or Fab) and a antibody domain (eg, V or C domain, eg, VH, VL, Vκ, Vλ, CH, CH1, CH2, CH3, hige, Cκ or Cλ domain). Optionally, the multimer is the molecule is
   (i) soluble in aqueous solution (eg, a solution or cell culture medium disclosed herein) and/or;
   (ii) capable of being intracellularly and/or extracellularly expressed by HEK293 cells.

The invention provides:—
   (i) Use of NHR2 or p53 (or another TD disclosed herein) for the manufacture of a polypeptide for soluble expression of a multimer of the polypeptide from a cell, eg, a eukaryotic cell, eg, a mammalian, HEK293, CHO or Cos cell.
   (ii) Use of NHR2 or p53 (or another TD disclosed herein) for the manufacture of a polypeptide for intracellular expression of a multimer of the polypeptide in a cell, eg, a eukaryotic cell, eg, a mammalian, HEK293, CHO or Cos cell.
   (iii) A cell comprising an intracellular expression product, wherein the product comprises a multimer of a polypeptide comprising NHR2 or p53 (or another TD disclosed herein) fused at its N- and/or C-terminus to an amino acid sequence (eg, a peptide, protein domain or protein) that is not an NHR2 sequence.
   (iv) Use of NHR2 as a promiscuous tetramerization domain for tetramerising peptides, protein domains, polypeptides or proteins in the manufacture of multimers that are intracellularly and/or solubly expressed from host cell.

Optionally, the amino acid is an amino acid sequence of a human peptide, protein domain or protein, eg, a TCR (eg, TCRα, TCRβ, Cα or Cβ), cytokine (eg, interleukin, eg, IL-2, IL-12, IL-12 and IFN), antibody fragments (eg, scFv, dAb or Fab), or an antibody domain (eg, V or C domain, eg, VH, VL, Vκ, Vλ, CH, CH1, CH2, CH3, hige, Cκ or Cλ domain).

Optionally, the or each polypeptide comprises a polypeptide selected from the group consisting of Quad 1-46 (ie, a polypeptide as shown in FIG. 21 but excluding any leader or tag sequence). Optionally, the invention provides a multimer (eg, a dimer, trimer, tetramer, pentamer, hexamer, septamer or octamer, preferably a tetramer or octamer) of a polypeptide selected from the group consisting of such Quad 1-46, eg, for medical or diagnostic use, eg, medical use for treating or preventing a disease or condition in a human or animal (eg, a human).

Optionally, the or each polypeptide comprises a polypeptide (excluding any leader or tag sequence) that is encoded by a nucleotide sequence selected from the group consisting of SEQ ID NOs: 13-50. Optionally, the or each polypeptide comprises a polypeptide (excluding any leader or tag sequence) that comprises an amino acid sequence selected from the group consisting of SEQ ID NOs: 83-115. Optionally, the invention provides a multimer (eg, a dimer, trimer, tetramer, pentamer, hexamer, septamer or octamer, preferably a tetramer or octamer) of such a polypeptide, eg, for medical or diagnostic use, eg, medical use for treating or preventing a disease or condition in a human or animal (eg, a human).

In an example, the TD is a TD comprised by any one of SEQ ID NOs: 1-9. In an example, the TD is a TD comprising SEQ ID NO: 10 or 126. In an example, the TD is encoded by SEQ ID NO: 124 or 125. In an example, the amino acid sequence of each TD is SEQ ID NO: 10 or 126 or is at least 80, 85, 90, 95, 96m 97, 98 or 99% identical to the SEQ ID NO: 10 or 126.

In an example, the TD is a TD comprising SEQ ID NO: 120 or 123. In an example, the TD is encoded by SEQ ID NO: 116 or 119. In an example, the amino acid sequence of each TD is SEQ ID NO: 120 or 123 or is at least 80, 85, 90, 95, 96m 97, 98 or 99% identical to the SEQ ID NO: 120 or 123.

Optionally, the domain or peptide comprised by the engineered polypeptide or monomer comprises an amino acid selected from SEQ ID NOs: 51-82.

High Purity Tetramers

As exemplified herein, the invention in one configuration is based on the surprising realization that tetramerization domains (TD), eg, p53 tetramerization domain (p53 TD), can be used to preferentially produce tetramers of effector domains over the production of lower-order structures such as dimers and monomers. This is particularly useful for secretion of tetramers is desirable yields from mammalian expression cell lines, such as CHO, HEK293 and Cos cell lines. The invention is also particularly useful for the production of tetramers no more than 200, 160, 155 or 150 kDa in size.

Thus, the invention provides the following Concepts:—
Concepts
1. Use of a tetramerization domain (TD) (eg, p53 tetramerization domain (p53 TD) or NHR2 TD) or a homologue or orthologue thereof in a method of the manufacture of a tetramer of polypeptides, for producing a higher yield of tetramers versus monomer and/or dimer polypeptides.

The monomers and dimers comprise one or two copies of the TD, homologue or orthologue respectively In an example, the TD, orthologue or homologue is a human domain In an example, the yield of tetramers is higher than the yield of monomers; In an example, the yield of tetramers is higher than the yield of dimers; In an example, the yield of tetramers is higher than the yield of trimers; In an example, the yield of tetramers is higher than the yield of monomers and dimers; In an example, the yield of tetramers is higher than the yield of monomers and trimers; In an example, the yield of tetramers is higher than the yield of monomers, dimers and trimers For example, the TD is the TD of p53 isoform 1. In an example, the TD comprises or consists of an amino acid sequence that is identical to positions 325 to 356 (or 319-360; or 321-359) of human p53 (eg, isoform 1). Optionally, the TD, orthologue or homologue comprises or consists of an amino acid sequence that is at least 80, 85, 90, 95, 96, 97, 98 or 99% identical to SEQ ID NO: 10, 126, 11 or 12. For example the sequence is identical to said selected sequence. Optionally, the TD, orthologue or homologue comprises or consists of an amino acid sequence that is at least 80, 85, 90, 95, 96, 97, 98 or 99% identical to SEQ ID NO: 120, 121, 122 or 123. For example the sequence is identical to said selected sequence.

2. The use of Concept 1, wherein first, second, third and fourth copies of an identical TD or homologue or orthologue thereof is used.

3. The use of any preceding Concept, wherein the TD is a NHR2, p53, p63 or p73 tetramerization domain.

For example, the TD is a p53 TD. In an example, the TD is an orthologue or homologue of a p53 TD, eg, a human p53 TD.

4. The use of any preceding Concept, wherein the yield of tetramers is at least 10× the yield of monomers and/or dimers.

Optionally, the yield is at least 2×3×, 4×, 5×, 6×, 7×, 8×, 9×, or 10× the yield of monomers and/or dimers. Optionally, the ratio of tetramers produced:monomers and/or dimers is at least 90:10, eg, at least 95:5; or 96:4; or 97:3; or 98:2; or 99:1. Optionally only tetramers are produced.

In an embodiment, each domain comprised by each monomer, dimer or tetramer is a human domain; and optionally the monomer, dimer or tetramer does not comprise non-human amino acid sequences or linkers.

5. The use of any preceding Concept, wherein the ratio of tetramers produced:monomers and/or dimers produced in the method is at least 90:10 (ie, 9× the amount of monomers; 9× the amount of dimers; or 9× the amount of the combination of monomers and dimers).

6. The use of Concept 4 or 5, wherein the yield or ratio is determinable or determined by obtaining a sample of the product of the tetramer manufacture method, using a protein separation technique on the sample to resolve tetramers, monomers and dimers and comparing the amount of tetramers with the amount of monomers and dimers.

Amounts of tetramers, monomers, dimers and trimers can be determined, for example, using Western Blot analysis of a gel described herein, eg, a native gel, ie, a gel not under denatured conditions, such as in the absence of SDS.

7. The use of Concept 4 or 5, wherein the yield or ratio is determinable or determined by
  (a) Obtaining a sample of the product of the tetramer manufacture method;
  (b) Carrying out polyacrylamide gel electrophoresis (PAGE) under non-reducing conditions to resolve the sample into a band corresponding to said tetramers and a band corresponding to said monomers and/or a band corresponding to said dimers; and
  (c) Comparing the tetramer band with the monomer and/or dimer band(s) to determine said yield or ratio, eg, by comparing the relative band intensities and/or band sizes.

8. The use of Concept 4 or 5, wherein the yield or ratio is determinable or determined by
  (d) Obtaining a sample of the product of the tetramer manufacture method;
  (e) Carrying out polyacrylamide gel electrophoresis (PAGE) under non-reducing conditions to resolve the sample into a band corresponding to said tetramers, eg, wherein the gel is under non-denatured conditions (eg, in the absence of sodium dodecylsuphate (SDS);
  (f) Determining that there is no band corresponding to said monomers and/or no band corresponding to said dimers.

9. The use of Concept 7 or 8, comprising
  (g) Obtaining a second sample of the product of the tetramer manufacture method;
  (h) Carrying out polyacrylamide gel electrophoresis (PAGE) under reducing conditions to resolve the second sample into a band corresponding to said monomers and/or a band corresponding to said dimers, eg, wherein the gel is under non-denatured conditions (eg, in the absence of sodium dodecylsuphate (SDS); and
  (i) Comparing the gel produced by step (h) with the gel of step (b) or (e) to determine the position of monomer and/or dimer band(s) in the gel of step (b) or where such gels would be expected in the gel of step (e).

10. The use of any preceding Concept, wherein each monomer has a size of no more than 40 kDa.
  For example, the monomer has a size of no more than 35, 30, 25, 24, 23, 22, 21 or 20 kDa 11. The use of any preceding Concept, wherein each tetramer has a size of no more than 150 kDa.
  For example, the tetramer has a size of no more than 80, 90, 100, 110, 120, 130 or 140 kDa.

12. The use of any preceding Concept, wherein the method comprises expressing the tetramers from a mammalian cell line, eg, a HEK293, CHO or Cos cell line.
  For example, the cell line is a HEK293 (eg, HEK293T) cell line. In the alternative, the cell line is a yeast (eg, *Saccharomyces* or *Pichia*, eg, *P. pastoris*) or bacterial cell line.

13. The use of any preceding Concept, wherein the method comprises secreting the tetramers from a mammalian cell line, eg, a HEK293, CHO or Cos cell line.

Thus, advantageously in an example, the use or tetramer is for expression from a mammalian cell line (eg, a HEK293, CHO or Cos cell line) or a eukaryotic cell line. This is useful for large-scale manufacture of the products, eg, tetramers, of the invention.

For example, the cell line is a HEK293 (eg, HEK293T) cell line. In the alternative, the cell line is a yeast (eg, *Saccharomyces* or *Pichia*, eg, *P. pastoris*) or bacterial cell line.

14. The use of any preceding Concept, wherein each polypeptide or monomer comprises a said TD, homologue or orthologue and one or more protein effector domains, such as one or more antibody domains, eg, one or more antibody domains forming an antigen binding site.
15. The use of Concept 14, wherein the polypeptide comprises one or more of
    (i) an antibody single variable domain (dAb or VHH or Nanobody™) that is capable of specifically binding an antigen;
    (ii) an scFv that is capable of binding an antigen or an scTCR that is capable of binding pMHC;
    (iii) a Fab that is capable of binding an antigen; or
    (iv) a TCR variable domain or pMHC binding site.
16. The use of any preceding Concept, wherein each polypeptide or monomer comprises a said TD, homologue or orthologue and one or more incretin, insulin, GLP-1 or Exendin-4 domains.
17. The use of any preceding Concept, wherein each polypeptide or monomer comprises a said TD, homologue or orthologue; and first and second antigen binding sites.
18. The use of Concept 17, wherein each binding site is provided by
    (i) an antibody single variable domain (dAb or VHH or Nanobody™) that is capable of specifically binding an antigen;
    (ii) an scFv that is capable of binding an antigen or an scTCR that is capable of binding pMHC;
    (iii) a Fab that is capable of binding an antigen; or
    (iv) a TCR variable domain or pMHC binding site.
19. The use of Concept 18, wherein each binding site is provided by an antibody single variable domain.
20. The use of any one of Concepts 14 to 18, wherein the TD, homologue or orthologue is directly fused to said further domain(s).
21. The use of Concept 20, wherein each monomer or polypeptide comprises the TD, homologue or orthologue fused directly or via a peptide linker to the C-terminal of a said further domain.
22. A tetramer of polypeptides, wherein each polypeptide comprises
    (i) a tetramerization domain (TD) (eg, a p53 TD or a NHR2 TD) or a homologue or orthologue thereof;
    (ii) one or more protein effector domains; and
    (iii) optionally a linker linking (i) to (ii) (eg, linking the C-terminus of (ii) to the N-terminus of (i));
wherein optionally each tetramer has a size of no more than 150 or 200 kDa.

For example, the tetramer has a size of no more than 80, 90, 100, 110, 120, 130 or 140 kDa. In an example, any multimer, dimer, trimer, tetramer or octamer herein has a size of at least 60 or 80 kDa; this may be useful for example to increase half-life in a human or animal subject administered with the multimer, dimer, trimer, tetramer or octamer (eg, to treat or prevent a disease or condition in the subject). Sizes in these ranges may be above the renal filtration size.

In an alternative, the invention provides a monomer, dimer, tetramer or octamer instead of a tetramer.

23. The tetramer of Concept 22, wherein each polypeptide comprises one or more of
    (i) an antibody single variable domain (dAb or VHH or Nanobody™) that is capable of specifically binding an antigen;
    (ii) an scFv that is capable of binding an antigen or an scTCR that is capable of binding pMHC;
    (iii) a Fab that is capable of binding an antigen; or
    (iv) a TCR variable domain or pMHC binding site.
24. The tetramer of Concept 22 or 23, wherein each polypeptide comprises a said TD, homologue or orthologue and one or more incretin, insulin, GLP-1 or Exendin-4 domains.
25. The tetramer of Concept 22 or 23, wherein each polypeptide comprises a said TD, homologue or orthologue; and first and second antigen binding sites.
26. The tetramer of Concept 25, wherein each binding site is provided by
    (i) an antibody single variable domain (dAb or VHH or Nanobody™) that is capable of specifically binding an antigen;
    (ii) an scFv that is capable of binding an antigen or an scTCR that is capable of binding pMHC;
    (iii) a Fab that is capable of binding an antigen; or
    (iv) a TCR variable domain or pMHC binding site.
27. The tetramer of Concept 26, wherein each binding site is provided by an antibody single variable domain.
28. The tetramer of any one of Concepts 22 to 27, wherein the TD, homologue or orthologue is directly fused to said effector domain(s).
29. The tetramer of any one of Concepts 22 to 27, wherein each polypeptide comprises the TD, homologue or orthologue fused directly or via a peptide linker to the C-terminal of a said effector domain.

In an embodiment, each polypeptide comprises only 2 (ie, only a first and a second, but not a third) effector domains or only 2 dAbs, VHH, scFvs, scTCRs, Fabs or antigen binding sites.

30. A pharmaceutical composition comprising a tetramer of any one of Concepts 22 to 29 and a pharmaceutically acceptable carrier, diluent or excipient.

Optionally the composition is comprised by a sterile medical container or device, eg, a syringe, vial, inhaler or injection device.

31. A cosmetic, foodstuff, beverage, cleaning product, detergent comprising a tetramer of any one of Concepts 22 to 29.
32. A mixture comprising a cell line (eg, a mammalian cell line, eg, a HEK293, CHO or Cos cell line) encoding a polypeptide as recited in any preceding Concept; and tetramers as defined in any preceding Concept.

Optionally, the mixture is comprised by a sterile container.

33. The mixture of Concept 32, wherein the cell line is in a medium comprising secretion products of the cells, wherein the secretion products comprise said tetramers.
34. The mixture of Concept 33, wherein the secretion products do not comprise monomers and/or dimers as defined in any one of Concepts 1 to 31.
35. The mixture of Concept 33, wherein the secretion products comprise said tetramers in an amount of at least 10× the amount of monomers and/or dimers.

36. The mixture of Concept 33, wherein the secretion products comprise said tetramers in a ratio of tetramers:monomers and/or dimers of at least 90:10.

37. A method for enhancing the yield of tetramers of an protein effector domain (eg, an antibody variable domain or binding site), the method comprising expressing from a cell line (eg, a mammalian cell, CHO, HEK293 or Cos cell line) tetramers of a polypeptide, wherein the polypeptide is as defined in any preceding Concept and comprises one or more effector domains; and optionally isolating said expressed tetramers.

The homologue, orthologue or equivalent has tetramerization function.

Homologue:

A gene, nucleotide or protein sequence related to a second gene, nucleotide or protein sequence by descent from a common ancestral DNA or protein sequence. The term, homologue, may apply to the relationship between genes separated by the event of or to the relationship between genes separated by the event of genetic duplication.

Orthologue:

Orthologues are genes, nucleotide or protein sequences in different species that evolved from a common ancestral gene, nucleotide or protein sequence by speciation. Normally, orthologues retain the same function in the course of evolution.

In an example, the TD, orthologue or homologue is a TD of any one of proteins 1 to 119 listed in Table 2. In an example, the orthologue or homologue is an orthologue or homologue of a TD of any one of proteins 1 to 119 listed in Table 2. In an embodiment, instead of the use of a p53 tetramerization domain (p53-TD) or a homologue or orthologue thereof, all aspects of the invention herein instead can be read to relate to the use or inclusion in a polypeptide, monomer, dimer, trimer or tetramer of a TD of any one of proteins 1 to 119 listed in Table 2 or a homologue or orthologue thereof. The TD may be a NHR2 (eg, a human NHR2) TD or an orthologue or homologue thereof. The TD may be a p63 (eg, a human p63) TD or an orthologue or homologue thereof. The TD may be a p73 (eg, a human p73) TD or an orthologue or homologue thereof. This may have one or more advantages as follows:—

- secretion of tetramers from mammalian or other eukaryotic cells, eg, a mammalian cell disclosed herein such as CHO, HEK293 or Cos;
- enhanced yield of secreted tetramers versus monomers;
- enhanced yield of secreted tetramers versus dimers;
- enhanced yield of secreted tetramers versus trimers;
- enhanced yield of secreted tetramers versus monomers and dimers combined;
  - enhanced yield of secreted tetramers versus monomers, dimers and trimers combined;
  - enhanced affinity or avidity of antigen binding in tetramers comprising antigen binding sites;
  - enhanced tetramer production and/or expression, wherein the tetramer is no more than 200 or no more than 160 or 150 kDa in size.

In an embodiment, each polypeptide or monomer comprises one or more VH, VL or VH/VL binding sites of an antibody selected from REOPRO®; Abciximab; RITUXAN®; Rituximab; ZENAPAX®; Daclizumab; SIMULECT®; Basiliximab; SYNAGIS®; Palivizumab; REMICADE®; Infliximab; HERCEPTIN®; Trastuzumab; MYLOTARG®; Gemtuzumab; CAMPATH®; Alemtuzumab; ZEVALIN®; Ibritumomab; HUMIRA®; Adalimumab; XOLAIR®; Omalizumab; BEXXAR®; Tositumomab; RAPTIVA™; Efalizumab; ERBITUX®; Cetuximab; AVASTIN®; Bevacizumab; TYSABRI®; Natalizumab; ACTEMRA®; Tocilizumab;-VECTIBIX®; Panitumumab; LUCENTIS®; Ranibizumab; SOLIRIS®; Eculizumab; CIMZIA®; Certolizumab; SIMPONI®; Golimumab, ILARIS®; Canakinumab; STELARA®; Ustekinumab;-ARZERRA®; Ofatumumab; PROLIA®; Denosumab; NUMAX™; Motavizumab; ABTHRAX™; Raxibacumab; BENLYSTA®; Belimumab; YERVOY®; Ipilimumab; ADCETRIS®; Brentuximab Vedotin; PERJETA®; Pertuzumab; KADCYLA®; Ado-trastuzumab;-KEYTRUDA®, OPDIVO®, GAZYVA® and Obinutuzumab. In an alternative, (eg, for treating or preventing a cancer in a human) each polypeptide or monomer comprise one or more VH, VL or VH/VL binding sites of an antibody selected from ipilimumab (or YERVOY™), tremelimumab, nivolumab (or OPDIVO®), pembrolizumab (or KEYTRUDA™), pidilizumab, BMS-936559, durvalumab and atezolizumab.

In an example, the tetramer comprises 4 copies of the antigen binding site of a first antibody selected from the group consisting of ipilimumab (or YERVOY™), tremelimumab, nivolumab (or OPDIVO™), pembrolizumab (or KEYTRUDA™), pidilizumab, BMS-936559, durvalumab and atezolizumab and optionally 4 copies of the antigen binding site of a second antibody selected from said group, wherein the first and second antibodies are different. For example, the first antibody is ipilimumab (or YERVOY™) and optionally the second antibody is nivolumab (or OPDIVO™) or pembrolizumab (or KEYTRUDA™). This is useful for treating or preventing a cancer in a human.

In an example, the tetramer comprises 4 copies of the antigen binding site of AVASTIN®. In an example, the tetramer comprises 4 copies of the antigen binding site of HUMIRA®. In an example, the tetramer comprises 4 copies of the antigen binding site of ERBITUX®. In an example, the tetramer comprises 4 copies of the antigen binding site of ACTEMRA®. In an example, the tetramer comprises 4 copies of the antigen binding site of sarilumab. In an example, the tetramer comprises 4 copies of the antigen binding site of dupilumab. In an example, the tetramer comprises 4 copies of the antigen binding site of alirocumab or evolocumab. In an example, the tetramer comprises 4 copies of the antigen binding site of In an example, the tetramer comprises 4 copies of the antigen binding site of REMICADE®. In an example, the tetramer comprises 4 copies of the antigen binding site of LUCENTIS®. In an example, the tetramer comprises 4 copies of the antigen binding site of EYLEA®. Such tetramers are useful for administering to a human to treat or prevent a cancer. Such tetramers are useful for administering to a human to treat or prevent an ocular condition (eg, wet AMD or diabetic retinopathy, eg, when the binding site is an AVASTIN®, LUCENTIS® or EYLEA® site). Such tetramers are useful for administering to a human to treat or prevent angiogenesis.

In an example, the tetramer comprises 4 copies of insulin. In an example, the tetramer comprises 4 copies of GLP-1. In an example, the tetramer comprises 4 copies of GIP. In an example, the tetramer comprises 4 copies of Exendin-4. In an example, the tetramer comprises 4 copies of insulin and 4 copies of GLP-1. In an example, the tetramer comprises 4 copies of insulin and 4 copies of GIP. In an example, the tetramer comprises 4 copies of insulin and 4 copies of Exendin-4. In an example, the tetramer comprises 4 copies of GLP-1 and 4 copies of Exendin-4. Such tetramers are useful for administering to a human to treat or prevent diabetes (eg, Type II diabetes) or obesity.

Diseases and Conditions

The monomer or multimer (eg, dimer, trimer, tetramer or octamer) of the invention can be used in a method for administration to a human or animal subject to treat or prevent a disease or condition in the subject.

Optionally, the disease or condition is selected from
(a) A neurodegenerative disease or condition;
(b) A brain disease or condition;
(c) A CNS disease or condition;
(d) Memory loss or impairment;
(e) A heart or cardiovascular disease or condition, eg, heart attack, stroke or atrial fibrillation;
(f) A liver disease or condition;
(g) A kidney disease or condition, eg, chronic kidney disease (CKD);
(h) A pancreas disease or condition;
(i) A lung disease or condition, eg, cystic fibrosis or COPD;
(j) A gastrointestinal disease or condition;
(k) A throat or oral cavity disease or condition;
(l) An ocular disease or condition;
(m) A genital disease or condition, eg, a vaginal, labial, penile or scrotal disease or condition;
(n) A sexually-transmissible disease or condition, eg, gonorrhea, HIV infection, syphilis or *Chlamydia* infection;
(o) An ear disease or condition;
(p) A skin disease or condition;
(q) A heart disease or condition;
(r) A nasal disease or condition
(s) A haematological disease or condition, eg, anaemia, eg, anaemia of chronic disease or cancer;
(t) A viral infection;
(u) A pathogenic bacterial infection;
(v) A cancer;
(w) An autoimmune disease or condition, eg, SLE;
(x) An inflammatory disease or condition, eg, rheumatoid arthritis, psoriasis, eczema, asthma, ulcerative colitis, colitis, Crohn's disease or IBD;
(y) Autism;
(z) ADHD;
(aa) Bipolar disorder;
(bb) ALS [Amyotrophic Lateral Sclerosis];
(cc) Osteoarthritis;
(dd) A congenital or development defect or condition;
(ee) Miscarriage;
(ff) A blood clotting condition;
(gg) Bronchitis;
(hh) Dry or wet AMD;
(ii) Neovascularisation (eg, of a tumour or in the eye);
(jj) Common cold;
(kk) Epilepsy;
(ll) Fibrosis, eg, liver or lung fibrosis;
(mm) A fungal disease or condition, eg, thrush;
(nn) A metabolic disease or condition, eg, obesity, anorexia, diabetes, Type I or Type II diabetes.
(oo) Ulcer(s), eg, gastric ulceration or skin ulceration;
(pp) Dry skin;
(qq) Sjogren's syndrome;
(rr) Cytokine storm;
(ss) Deafness, hearing loss or impairment;
(tt) Slow or fast metabolism (ie, slower or faster than average for the weight, sex and age of the subject);
(uu) Conception disorder, eg, infertility or low fertility;
(vv) Jaundice;
(ww) Skin rash;
(xx) Kawasaki Disease;
(yy) Lyme Disease;
(zz) An allergy, eg, a nut, grass, pollen, dust mite, cat or dog fur or dander allergy;
(aaa) Malaria, typhoid fever, tuberculosis or cholera;
(bbb) Depression;
(ccc) Mental retardation;
(ddd) Microcephaly;
(eee) Malnutrition;
(fff) Conjunctivitis;
(ggg) Pneumonia;
(hhh) Pulmonary embolism;
(iii) Pulmonary hypertension;
(jjj) A bone disorder;
(kkk) Sepsis or septic shock;
(lll) Sinusitis;
(mmm) Stress (eg, occupational stress);
(nnn) Thalassaemia, anaemia, von Willebrand Disease, or haemophilia;
(ooo) Shingles or cold sore;
(ppp) Menstruation;
(qqq) Low sperm count.

Neurodegenerative or CNS Diseases or Conditions for Treatment or Prevention

In an example, the neurodegenerative or CNS disease or condition is selected from the group consisting of Alzheimer disease, geriopsychosis, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease. For example, the disease is Alzheimer disease. For example, the disease is Parkinson syndrome.

In an example, wherein the method of the invention is practised on a human or animal subject for treating a CNS or neurodegenerative disease or condition, the method causes downregulation of Treg cells in the subject, thereby promoting entry of systemic monocyte-derived macrophages and/or Treg cells across the choroid plexus into the brain of the subject, whereby the disease or condition (eg, Alzheimer's disease) is treated, prevented or progression thereof is reduced. In an embodiment the method causes an increase of IFN-gamma in the CNS system (eg, in the brain and/or CSF) of the subject. In an example, the method restores nerve fibre and/or reduces the progression of nerve fibre damage. In an example, the method restores nerve myelin and/or reduces the progression of nerve myelin damage. In an example, the method of the invention treats or prevents a disease or condition disclosed in WO2015136541 and/or the method can be used with any method disclosed in WO2015136541 (the disclosure of this document is incorporated by reference herein in its entirety, eg, for providing disclosure of such methods, diseases, conditions and potential therapeutic agents that can be administered to the subject for effecting treatment and/or prevention of CNS and neurodegenerative diseases and conditions, eg, agents such as immune checkpoint inhibitors, eg, anti-PD-1, anti-PD-L1, anti-TIM3 or other antibodies disclosed therein).

Cancers for Treatment or Prevention

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated with the invention include, but are not limited to, carcinoma, blastoma, and sarcoma, and certain leukaemia or lymphoid malignancies, benign and malignant tumours, and malignancies e.g., sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyeiocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous eel! carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, bladder carcinoma, melanoma, and CNS tumours (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

Autoimmune Diseases for Treatment or Prevention
  Acute Disseminated Encephalomyelitis (ADEM)
  Acute necrotizing hemorrhagic leukoencephalitis
  Addison's disease
  Agammaglobulinemia
  Alopecia areata
  Amyloidosis
  Ankylosing spondylitis
  Anti-GBM/Anti-TBM nephritis
  Antiphospholipid syndrome (APS)
  Autoimmune angioedema
  Autoimmune aplastic anemia
  Autoimmune dysautonomia
  Autoimmune hepatitis
  Autoimmune hyperlipidemia
  Autoimmune immunodeficiency
  Autoimmune inner ear disease (AIED)
  Autoimmune myocarditis
  Autoimmune oophoritis
  Autoimmune pancreatitis
  Autoimmune retinopathy
  Autoimmune thrombocytopenic purpura (ATP)
  Autoimmune thyroid disease
  Autoimmune urticaria
  Axonal & neuronal neuropathies
  Balo disease
  Behcet's disease
  Bullous pemphigoid
  Cardiomyopathy
  Castleman disease
  Celiac disease
  Chagas disease
  Chronic fatigue syndrome
  Chronic inflammatory demyelinating polyneuropathy (CIDP)
  Chronic recurrent multifocal ostomyelitis (CRMO)
  Churg-Strauss syndrome
  Cicatricial pemphigoid/benign mucosal pemphigoid
  Crohn's disease
  Cogans syndrome
  Cold agglutinin disease
  Congenital heart block
  Coxsackie myocarditis
  CREST disease
  Essential mixed cryoglobulinemia
  Demyelinating neuropathies
  Dermatitis herpetiformis
  Dermatomyositis
  Devic's disease (neuromyelitis optica)
  Discoid lupus
  Dressler's syndrome
  Endometriosis
  Eosinophilic esophagitis
  Eosinophilic fasciitis
  Erythema nodosum
  Experimental allergic encephalomyelitis
  Evans syndrome
  Fibromyalgia
  Fibrosing alveolitis
  Giant cell arteritis (temporal arteritis)
  Giant cell myocarditis
  Glomerulonephritis
  Goodpasture's syndrome
  Granulomatosis with Polyangiitis (GPA) (formerly called Wegener's Granulomatosis)
  Graves' disease
  Guillain-Barre syndrome
  Hashimoto's encephalitis
  Hashimoto's thyroiditis
  Hemolytic anemia
  Henoch-Schonlein purpura
  Herpes gestationis
  Hypogammaglobulinemia
  Idiopathic thrombocytopenic purpura (ITP)
  IgA nephropathy
  IgG4-related sclerosing disease
  Immunoregulatory lipoproteins
  Inclusion body myositis
  Interstitial cystitis
  Juvenile arthritis
  Juvenile diabetes (Type 1 diabetes)
  Juvenile myositis
  Kawasaki syndrome
  Lambert-Eaton syndrome
  Leukocytoclastic vasculitis
  Lichen planus
  Lichen sclerosus
  Ligneous conjunctivitis
  Linear IgA disease (LAD)
  Lupus (SLE)
  Lyme disease, chronic Meniere's disease
Microscopic polyangiitis
Mixed connective tissue disease (MCTD)
Mooren's ulcer
Mucha-Habermann disease
Multiple sclerosis
Myasthenia gravis
Myositis
Narcolepsy
Neuromyelitis optica (Devic's)
Neutropenia
Ocular cicatricial pemphigoid
Optic neuritis
Palindromic rheumatism
PANDAS (Pediatric Autoimmune Neuropsychiatric Disorders Associated with *Streptococcus*)
Paraneoplastic cerebellar degeneration
Paroxysmal nocturnal hemoglobinuria (PNH)
Parry Romberg syndrome
Parsonnage-Turner syndrome
Pars planitis (peripheral uveitis)
Pemphigus
Peripheral neuropathy
Perivenous encephalomyelitis
Pernicious anemia
POEMS syndrome
Polyarteritis *nodosa*
Type I, II, & III autoimmune polyglandular syndromes
Polymyalgia rheumatica
Polymyositis
Postmyocardial infarction syndrome
Postpericardiotomy syndrome
Progesterone dermatitis
Primary biliary cirrhosis
Primary sclerosing cholangitis
Psoriasis
Psoriatic arthritis
Idiopathic pulmonary fibrosis
Pyoderma gangrenosum
Pure red cell aplasia
Raynauds phenomenon
Reactive Arthritis
Reflex sympathetic dystrophy
Reiter's syndrome
Relapsing polychondritis
Restless legs syndrome
Retroperitoneal fibrosis
Rheumatic fever
Rheumatoid arthritis
Sarcoidosis
Schmidt syndrome
Scleritis
Scleroderma
Sjogren's syndrome
Sperm & testicular autoimmunity
Stiff person syndrome
Subacute bacterial endocarditis (SBE)
Susac's syndrome
Sympathetic ophthalmia
Takayasu's arteritis
Temporal arteritis/Giant cell arteritis
Thrombocytopenic purpura (TTP)
Tolosa-Hunt syndrome
Transverse myelitis
Type 1 diabetes
Ulcerative colitis
Undifferentiated connective tissue disease (UCTD)
Uveitis
Vasculitis
Vesiculobullous dermatosis
Vitiligo
Wegener's granulomatosis (now termed Granulomatosis with Polyangiitis (GPA).
Inflammatory Diseases for Treatment or Prevention
Alzheimer's
ankylosing spondylitis
arthritis (osteoarthritis, rheumatoid arthritis (RA), psoriatic arthritis)
asthma
atherosclerosis
Crohn's disease
colitis
dermatitis
diverticulitis
fibromyalgia
hepatitis
irritable bowel syndrome (IBS)
systemic lupus erythematous (SLE)
nephritis
Parkinson's disease
ulcerative colitis.

Multivalent Soluble TCR

The present configuration relates to a multivalent soluble TCR protein. In one aspect, the invention relates to tetravalent and octavalent soluble TCR analogues. The TCR proteins of the invention are capable of self-assembly from monomers and are entirely of human origin. The proteins are multimers which comprise an ETO NHR2 multimerisation domain. The invention also relates to methods of constructing multimeric soluble TCRs, and methods of using such proteins.

Attempts to exploit alternative soluble TCR formats as therapeutic molecules have lagged far behind compared to the plethora of antibody formats. This is largely due to TCR, a heterodimeric transmembrane protein having the intrinsic problem of solubility once the extracellular TCR ca/3 chains are dissociated from their transmembrane and cytoplasmic domain. Secondly the intrinsiclow affinity and avidity of these molecules for their cognate ligand at the target site has to a large degree hampered their development as a therapeutic molecule.

In order to overcome these drawbacks, the present configuration of the invention provides a TCR protein which is both multivalent and soluble. Multivalency increases the avidity of the TCR for cognate pMHC, and solubility allows the TCR to be used outside of a transmembrane environment. Accordingly, in a first aspect there is provided a multivalent heterodimeric soluble T cell receptor capable of binding pMHC complex comprising:
(i) TCR extracellular domains;
(ii) (ii) immunoglobulin constant domains; and
(iii) (iii) an NHR2 multimerisation domain of ETO.

The use of Ig constant domains provides the TCR extracellular domains with stability and solubility; multimerisation via the NHR2 domains provides multivalency and increased avidity. Advantageously, all of the domains are of human origin or conform to human protein sequences.

Using the Ig constant domain to stabilise and render soluble the TCR avoids the use of non-native disulphide bonds. Advantageously, therefore, the TCR of the invention does not comprise a non-native disulphide bond.

In one embodiment, said complex comprises a heavy chain and a light chain, and each light chain comprises a TCR V$\alpha$ domain and an immunoglobulin C$_\alpha$ domain, and each heavy chain comprises a TCR Vβ domain and an immunoglobulin $C_H1$ domain.

In one embodiment, each light chain additionally comprises a TCR Cα domain, and each heavy chain additionally comprises a TCR Cβ domain.

In embodiments, the TCR and immunoglobulin domains can be separated by a flexible linker.

The NHR2 multimerisation domain is advantageously attached to the C-terminus of an immunoglobulin domain. Thus, each dimer of heavy and light chains will be attached to one multimerisation domain, so that the heavy chain-light chain dimers associate into multivalent oligomers.

In embodiments, the multimerisation domain and the immunoglobulin domain are separated by a flexible linker. In certain embodiments, this allows the multimerisation domain to multimerise without hindrance from the immunoglobulin domain(s).

In embodiments, the TCR protein may further comprise an immunoglobulin hinge domain. Hinge domains allow dimerization of heavy chain-light chain dimers; this allows further multimerisation of the TCR proteins. For example, a multimerisation domain which forms tetramers can, using an immunoglobulin hinge domain, form multimers up to octamers. Likewise, a dimerising multimerisation domain can form tetramers in the presence of a hinge domain.

In embodiments, the TCR protein of the invention is tetravalent.

In embodiments, the TCR protein of the invention is octavalent

The present invention provides a soluble TCR where it is stably assembled in a tetravalent heterodimeric format using the nervy homology region 2 (NHR2) domain found in the ETO family protein in humans (Liu et al. 2006). The NHR2 domain is found naturally to form homotetramer, which is formed from pairing of two NHR2 homodimers. NHR2 linked operably to the extracellular TCRα or TCRβ chain will preferentially form tetravalent heterodimeric soluble TCR protein molecules sequentially self-assembled from a monomer followed by a homodimer (FIG. 1).

TCR proteins assembling into octamers can be created using the NHR2 domain, by employing immunoglobulin hinge domains.

In a further aspect, the TCR proteins of the invention can be coupled to biologically active polypeptides/effector molecules. Examples of such polypeptides can include immunologically active moieties such as cytokines, binding proteins such as antibodies or targeted polypeptides, and the like.

The invention further relates to methods for making tetravalent and octavalent heterodimeric soluble TCR, the DNA vectors encoding the proteins used for transfecting host cells of interests and the use of these novel highly sensitive multivalent soluble TCR protein molecules. Applications for use could include but not limited to, therapeutics, diagnostics and drug discovery.

In a further aspect, the invention provides a method for constructing multivalent immunoglobulin molecules in an efficient manner, without employing non-human construct components.

Accordingly, there is provided a multimeric immunoglobulin comprising
(i) immunoglobulin variable domains; and
(ii) an NHR2 multimerisation domain of ETO.

The immunoglobulin variable domains are preferably antibody variable domains. Such domains are fused to the ETO NHR2 multimerisation domain, which provides means for forming tetramers of the immunoglobulin variable domains.

The ETO NHR2 domain is more efficient than p53 and similar multimerisation domains in the production of immunoglobulin multimers, and permits the production of multimeric immunoglobulin molecules without the use of non-human components in the construct.

Also provided is a method for producing a multimeric immunoglobulin, comprising expressing immunoglobulin variable domains in fusion with an NHR2 domain of ETO, and allowing the variable domains to assemble into multimers.

Preferably, the immunoglobulin variable domains are attached to one or more immunoglobulin constant domains.

Advantageously, the immunoglobulin domains are antibody domains. For example, the variable domains can be $V_H$ and $V_L$ antibody domains. For example, the constant domains are antibody CH1 domains.

In one embodiment, the multimeric immunoglobulin molecules according to the invention, both TCR and non-TCR immunoglobulins, are produced for screening by phage display or another display technology. For example, therefore, the multivalent immunoglobulins are produced as fusions with a phage coat protein. For each immunoglobulin produced fused to a coat protein, other immunoglobulin molecules are produced without a coat protein, such that they can assemble on the phage surface as a result of NHR2 multimerisation.

The present configuration of the invention as detailed above relates to the nucleic acid sequences and methods for producing novel multivalent, for example tetravalent and octavalent, soluble proteins. In one aspect in particular the soluble protein is a TCR assembled into a tetravalent heterodimeric format that can bind four pMHC with high sensitivity, affinity and specificity. The soluble tetravalent heterodimeric TCR is a unique protein molecule composed from either the entire or in part the extracellular TCR α/β chains. The extracellular TCR α/β chains are linked to immunoglobulin $C_H1$ and $C_L$ (either Cκ or Cλ) domains. This linkage allows stable formation of heterodimeric TCR α/β. In the context of soluble tetravalent TCR the unique feature is the NHR2 homotetramer domain of the ETO family of proteins, which is operably linked to the C-terminus of $C_H1$ or the C-terminus of $C_L$. Linkage of the NHR2 domain to the heterodimeric α/β TCR in this manner allows it to self-assemble into a tetravalent format inside cells and be subsequently secreted into the supernatant as a soluble protein.

TCR Extracellular Domains

TCR extracellular domains are composed of variable and constant regions. These domains are present in T-cell receptors in the same way as they are present in antibodies and other immunoglobulin domains. The TCR repertoire has extensive diversity created by the same gene rearrangement mechanisms used in antibody heavy and light chain genes (Tonegawa, S. (1988) *Biosci. Rep.* 8:3-26). Most of the diversity is generated at the junctions of variable (V) and joining (J) (or diversity, D) regions that encode the complementarity determining region 3 (CDR3) of the α and β chains (Davis and Bjorkman (1988) *Nature* 334:395-402). Databases of TCR genes are available, such as the IMGT LIGM database, and methods for cloning TCRs are known in the art—for example, see Bentley and Mariuzza (1996) *Ann. Rev. Immunol.* 14:563-590; Moysey et al., Anal Biochem. 2004 Mar. 15; 326(2):284-6; Walchli, et al. (2011)

A Practical Approach to T-Cell Receptor Cloning and Expression. PLoS ONE 6(11): e27930.

Immunoglobulin Variable Domains

Antibody variable domains are known in the art and available from a wide variety of sources. Databases of sequences of antibody variable domains exist, such as IMGT and Kabat, and variable domains can be produced by cloning and expression of natural sequences, or synthesis of artificial nucleic acids according to established techniques.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. USA.,* 88: 4363; Clackson et al. (1991) *Nature*, 352: 624; Lowman et al. (1991) *Biochemistry*, 30: 10832; Burton et al. (1991) *Proc. Natl. Acad Sci USA.,* 88: 10134; Hoogenboom et al. (1991) Nucleic Acids Res., 19: 4133; Chang et al. (1991) *J Immunol.,* 147: 3610; Breitling et al. (1991) *Gene*, 104: 147; Marks et al. (1991) supra; Barbas et al. (1992) supra; Hawkins and Winter (1992) *J Immunol.,* 22: 867; Marks et al., 1992, *J Bioi. Chem.,* 267: 16007; Lerner et al. (1992) *Science*, 258: 1313, incorporated herein by reference).

One particularly advantageous approach has been the use of scFv phage-libraries (Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) *Nature*, 352: 624; Marks et al. (1991) *J Mol. Bioi.,* 222: 581; Chiswell et al. (1992) Trends Biotech., 10: 80; Marks et al. (1992) *J Bioi. Chem.,* 267). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference.

Such techniques can be adapted for the production of multimeric immunoglobulins by the fusion of NHR2 multimerisation domains to the antibody variable domains Immunoglobulin Constant Domains An immunoglobulin constant domain, as referred to herein, is preferably an antibody constant domain. Constant domains do vary in sequence between antibody subtypes; preferably, the constant domains are IgG constant domains. Preferably, the constant domains are CH1 constant domains. Antibody constant domains are well known in the art and available from a number of sources and databases, including the IMGT and Kabat databases.

The fusion of antibody constant domains to immunoglobulin variable domains is also known in the art, for example in the construction of engineered Fab antibody fragments.

Linkers

Flexible linkers can be used to connect TCR variable domain—Ig constant domain to the NHR2 multimerisation domain. This allows the TCR domains and the multimerisation domain to function without steric hindrance from each other or other molecules in the multimeric complex. Suitable linkers comprise, for example, glycine repeats, glycine-alanine repeats, Gly(4)Ser linkers, or flexible polypeptide linkers as set forth in Reddy Chichili et al., 2012 Protein Science 22:153-167.

Immunoglobulin Hinge Domain

The Ig Hinge domain, herein preferably an antibody hinge domain, is the domain which links antibody constant regions in a natural antibody. This domain therefore provides for natural dimerization of molecules which include an antibody constant domain. It is present, for example, in a F(ab)2 antibody fragment, as well as whole antibodies such as IgG. This region comprises two natural interchain disulphide bonds, which connect the two CH1 constant domains together.

The multimerisation domain, in one embodiment, may be attached to the Ig constant domain or to the hinge domain. If a hinge domain is present, the multimerisation domain will form a TRC octamer, comprising four dimers of TCR variable-Ig Constant domains joined at a hinge region. Without the hinge region, the multimerisation domain will lead to the formation of a tetramer. Preferably, the multimerisation domain is attached to the C-terminal end of the constant domain or the hinge region.

Biologically Active Molecule

One or more biologically active molecules or effector molecules (EM) can be attached to the multimer, eg, multimeric TCR proteins, of the present invention. Such molecules may be, for example, antibodies, especially antibodies which may assist in immune recognition and functioning of the TCR, such as anti-CD3 antibodies or antibody fragments.

In some aspects, the biologically active molecule can be a cytotoxic drug, toxin or a biologically active molecule such as a cytokine, as described in more detail below. Examples of biologically active molecules include chemokines such as MIP-1b, cytokines such as IL-2, growth factors such as GM-CSF or G-CSF, toxins such as ricin, cytotoxic agents, such as doxorubicin or taxanes, labels including radioactive and fluorescent labels, and the like. For examples of biologically active molecules conjugatable to TCRs, see US20110071919.

In other aspects, the biologically active molecule is, for example, selected from the group consisting of: a group capable of binding to a molecule which extends the half-life of the polypeptide ligand in vivo, and a molecule which extends the half-life of the polypeptide ligand in vivo. Such a molecule can be, for instance, HSA or a cell matrix protein, and the group capable of binding to a molecule which extends the half-life of the TCR molecule in vivo is an antibody or antibody fragment specific for HSA or a cell matrix protein.

In one embodiment, the biologically active molecule is a binding molecule, for example an antibody fragment. 2, 3, 4, 5 or more antibody fragments may be joined together using suitable linkers. The specificities of any two or more of these antibody fragments may be the same or different; if they are the same, a multivalent binding structure will be formed, which has increased avidity for the target compared to univalent antibody fragments.

The biologically active molecule can moreover be an effector group, for example an antibody Fc region.

Attachments to the N or C terminus may be made prior to assembly of the TCR molecule or engineered polypeptide into multimers, or afterwards. Thus, the TCR fusion with an Ig Constant domain may be produced (synthetically, or by expression of nucleic acid) with an N or C terminal biologically active molecule already in place. In certain aspects, however, the addition to the N or C terminus takes place after the TCR fusion has been produced. For example, Fluorenylmethyloxycarbonyl chloride can be used to introduce the Fmoc protective group at the N-terminus of the TCR fusion. Fmoc binds to serum albumins including HSA with high affinity, and Fmoc-Trp or FMOC-Lys bind with an increased affinity. The peptide can be synthesised with the Fmoc protecting group left on, and then coupled with the scaffold through the cysteines. An alternative is the palmitoyl moiety which also binds HSA and has, for example been used in Liraglutide to extend the half-life of this GLP-1 analogue.

Alternatively, the TCR fusion can be modified at the N-terminus, for example with the amine- and sulfhydryl-reactive linker N-e-maleimidocaproyloxy)succinimide ester (EMCS). Via this linker the TCR can be linked to other polypeptides, for example an antibody Fc fragment.

The NHR2 Domain

AML1/ETO is the fusion protein resulting from the t(8; 21) found in acute myeloid leukemia (AML) of the M2 subtype. AML1/ETO contains the N-terminal 177 amino acids of RUNX1 fused in frame with most (575 aa) of ETO. The nervy homology domain 2 of ETO is responsible for many of the biological activities associated with AML1/ETO, including oligomerisation and protein-protein interactions. This domain is characterised in detail in Liu et al (2006). See Genbank accession number NG_023272.2.

In one aspect of the present invention, the protein assembled into a soluble multivalent format is a TCR composed of either in part or all of the extracellular domains of the TCR α and β chains. The TCR α and β chains are stabilized by immunoglobulin $C_H1$ and $C_L$ domains and could be arranged in the following configurations:
1. Vα-$C_L$ and Vβ$C_H1$
2. Vα-$C_H1$ and Vβ-$C_L$
3. VαCα-$C_L$ and VβCβ-$C_H1$
4. VαCα$C_H1$ and VβCβ$C_L$ In one aspect of this invention, the extracellular TCR domains are linked to immunoglobulin $C_H1$ and $C_L$ domains via an optional peptide linker (L) to promote protein flexibility and facilitate optimal protein folding.
1. Vα-(L)-$C_L$ and Vβ-(L)-$C_H1$
2. Vα-(L)-$C_H1$ and Vβ-(L)-$C_L$
3. VαCα-(L)-$C_L$ and VβCβ-(L)-$C_H1$
4. VαCα-(L)-$C_H1$ and VβCβ-(L)-$C_L$ In another aspect of this invention, a tetramerization domain (TD) such as NHR2 homotetramer domain is linked to the C-terminus of either the immunoglobulin $C_H1$ or $C_L$ domain, which is linked to the extracellular TCR α and β chain. The NHR2 domain could be optionally linked to $C_H1$ or $C_L$ domain via a peptide linker. The resulting tetravalent heterodimeric TCR protein could be arranged in the following configurations where (L) is an optional peptide linker:
1. Vα-(L)-$C_L$ and Vβ-(L)-$C_H1$-(L)-TD
2. Vα-(L)-$C_H1$-(L)-TD and Vβ-(L)-$C_L$
3. VαCα-(L)-$C_L$ and VβCβ-(L)-$C_H1$-(L)-TD
4. VαCα-(L)-$C_H1$-(L)-TD and VβCβ-(L)-$C_L$
5. Vα-(L)-$C_L$-(L)-TD and Vβ-(L)-$C_H1$
6. Vα-(L)-$C_H1$ and Vβ-(L)-$C_L$-(L)-TD
7. VαCα-(L)-$C_L$-(L)-TD and VβCβ-(L)-$C_H1$
8. VαCα-(L)-$C_H1$ and VβCβ-(L)-$C_L$-(L)-TD The sensitivity of the soluble TCR for its cognate pMHC can be enhanced by increasing the avidity effect. This is achieved by increasing the number of antigen binding sites, facilitated by the tetramerization domain. This in turn also increases the molecular weight of the protein molecule compared to a monovalent soluble TCR and thus extends serum retention in circulation. Increasing the serum half-life also enhances the likelihood of these molecules interacting with their cognate target antigens.

The tetravalent heterodimeric soluble TCR protein molecule is capable of binding simultaneously to one, two, three or four pMHC displayed on a single cell or bind simultaneously to one, two, three or four different cells displaying its cognate pMHC.

TCR α and β chain sequences used in this invention could be from a known TCR specific for a particular pMHC or identified de novo by screening using techniques known in the art, such as phage display. Furthermore, TCR sequences are not limited to α and β chain in this invention but can also incorporate TCRδ and γ or ε chain and sequence variations thereof either directly cloned from human T cells or identified by directed evolution using recombinant DNA technology.

In another aspect to this invention, the tetravalent heterodimeric soluble TCR protein molecules are preferentially produced in mammalian cells for optimal production of soluble, stable and correctly folded protein molecules.

Multimer (eg, tetramer or octamer), or multivalent TCR according to the present invention may be expressed in cells, such as mammalian cells, using any suitable vector system. The pTT5 expression vector is one example of an expression system is used to express multivalent soluble TCR. The pTT5 expression system allows for high-level transient production of recombinant proteins in suspension-adapted HEK293 EBNA cells (Zhang et al. 2009). It contains origin of replication (oriP) that is recognized by the viral protein Epstein-Barr Nuclear Antigen 1 (EBNA-1), which together with the host cell replication factor mediates episomal replication of the DNA plasmid allowing enhanced expression of recombinant protein. Other suitable vector system for mammalian cell expression known in the art and commercially available can be used with this invention.

The tetravalent heterodimeric soluble TCR protein molecules or other multimers can be produced by transiently expressing genes from an expression vector.

In another embodiment, tetravalent heterodimeric soluble TCR protein molecules or other multimers can be produced from an engineered stable cell line. Cell lines can be engineered to produce the protein molecule using genome-engineering techniques known in the art where the gene(s) encoding for the protein molecule is integrated into the genome of the host cells either as a single copy or multiple copies. The site of DNA integration can be a defined location within the host genome or randomly integrated to yield maximum expression of the desired protein molecule. Genome engineering techniques could include but not limited to, homologous recombination, transposon mediated gene transfer such as PiggyBac transposon system, site specific recombinases including recombinase-mediated cassette exchange, endonuclease mediated gene targeting such as CRISPR/Cas9, TALENs, Zinc-finger nuclease, meganuclease and virus mediated gene transfer such as Lentivirus.

Also in another aspect to the invention, the tetravalent heterodimeric soluble TCR protein molecule or other multimer is produced by overexpression in the cytoplasm of *E. coli* as inclusion bodies and refolded in vitro after purification by affinity chromatography to produce functional protein molecules capable of correctly binding to its cognate pMHC or antigen.

In another aspect to the invention, expression of the tetravalent heterodimeric soluble TCR protein molecule or other multimer is not limited to mammalian or bacterial cells but can also be expressed and produced in insect cells, plant cells and lower eukaryotic cells such as yeast cells.

In another aspect to this invention, the heterodimeric soluble TCR molecule or other multimer is produced as an octavalent protein complex, eg, having up to eight binding sites for its cognate pMHC (FIG. 2). The multiple antigen binding sites allow this molecule to bind up to eight pMHC displayed on one cell or bind pMHC displayed on up to eight different cells thus creating a highly sensitive soluble TCR.

The heterodimeric soluble TCR portion of the molecule is made into a bivalent molecule by fusing the immunoglobulin hinge domain to the C-terminus of either the $C_H1$ or $C_L$ domain, which is linked itself either to TCR α or β chain. The hinge domain allows for the connection of two heavy chains giving a structure similar to IgG. To the C-terminus of the hinge domain, a tetramerization domain such as NHR2 is linked via an optional peptide linker. By joining immunoglobulin hinge to C- and N-terminus of Ig CH1 or CL domain and NHR2 domain respectively, it allows for the assembly of two NHR2 monomers referred to as monomer$^2$. In this conformation we predict the two NHR2 domains will most likely not form a homodimer by an antiparallel association due to structural constraints unless a long flexible linker is provided between the hinge and NHR2 domain. Linkage of the tetramerization and the hinge domain to the to the heterodimeric soluble TCR via immunoglobulin $C_H1$ or $C_L$ domain allows for the stepwise self-assembly of an octavalent soluble TCR formed through a NHR2 homotetramer$^2$. The self-assembly of the octavalent soluble TCR is via NHR2 monomer$^2$ and homodimer$^2$ intermediate protein complexes (FIG. 2). The resulting octavalent heterodimeric soluble TCR protein molecule will have superior sensitivity for its cognate pMHC thus giving it a distinctive advantage of identifying unknown antigen or pMHC without having to affinity mature the TCR for its pMHC ligand much beyond affinities seen naturally. In particular it would be useful for identifying pMHC recognized by uncharacterized tumour-specific T cells and T cells involved in other diseases such as autoimmune diseases. A number of different configurations of the octavalent heterodimeric soluble TCR protein molecules can be produced. Some examples are shown below.

1. Vα-(L)-$C_L$ and Vβ-(L)-$C_H1$-Hinge-(L)-TD
2. Vα-(L)-$C_H1$-Hinge-(L)-TD and Vβ-(L)-$C_L$
3. Vα-Cα-(L)-$C_L$ and Vβ-Cβ-(L)-$C_H1$-Hinge-(L)-TD
4. VαCα(L)-$C_H1$-Hinge-(L)-TD and VβCβ-(L)-$C_L$
5. Vα-(L)-$C_L$-(L)-TD and Vβ-(L)-$C_H1$-Hinge
6. Vα-(L)-$C_H1$-Hinge and Vβ-(L)-$C_L$-(L)-TD
7. Vα-Cα-(L)-$C_L$-(L)-TD and Vβ-Cβ(L)-$C_H1$-Hinge
8. Vα-Cα-(L)-$C_H1$-Hinge and Vβ-Cβ-(L)-$C_L$-(L)-TD In another aspect to this invention, the self-assembled multivalent protein preferentially tetravalent and octavalent heterodimeric soluble TCR are fused or conjugated to biologically active agent/effector molecule thus allowing these molecules to be guided to the desired cell population such as cancers cells and exert their therapeutic effect specifically. The tumour targeting ability of monoclonal antibodies to guide an effector molecule such as a cytotoxic drug, toxins or a biologically active molecule such as cytokines is well established (Perez et al. 2014; Young et al. 2014). In a similar manner the multivalent soluble TCR molecules outlined in this invention can also be fused with effector proteins and polypeptide or conjugated to cytotoxic agents. Examples of effector protein molecules suitable for use as a fusion protein with the multivalent protein complexes outlined in this invention include but are not limited to, IFNα, IFNβ, IFNγ, IL-2, IL-11, IL-13, granulocyte colony-stimulating factor [G-CSF], granulocyte-macrophage colony-stimulating factor [GM-CSF], and tumor necrosis factor [TNF]α, IL-7, IL-10, IL-12, IL-15, IL-21, CD40L, and TRAIL, the costimulatory ligand is B7.1 or B7.2, chemokines DC-CK1, SDF-1, fractalkine, lyphotactin, IP-10, Mig, MCAF, MIP-1a, MIP-1/3, IL-8, NAP-2, PF-4, and RANTES or an active fragment thereof. Examples of toxic agent suitable for use as a fusion protein or conjugated to the multivalent protein complexes described in this invention include but not limited to, toxins such as diphtheria toxin, ricin, *Pseudomonas* exotoxin, cytotoxic drugs such as auristatin, maytansines, calicheamicin, anthracyclines, duocarmycins, pyrrolobenzodiazepines. The cytotoxic drug can be conjugated by a select linker, which is either non-cleavable or cleavable by protease or is acid-labile.

To eliminate heterogeneity and improve conjugate stability the cytotoxic drug can be conjugated in a site-specific manner. By engineering specific cysteine residues or using enzymatic conjugation through glycotransferases and transglutaminases can achieve this (Panowski et al. 2014).

In another aspect of the invention, the multivalent protein complex is covalently linked to molecules allowing detection, such as fluorescent, radioactive or electron transfer agents.

In another aspect of the invention, an effector molecule (EM) is fused to the multivalent protein complex via the C-terminus of the tetramerization domain such as NHR2 via an optional peptide linker. Fusion via the NHR2 domain can be arranged to produce multivalent protein complexes in a number of different configurations. Examples of some of the protein configurations that can be produced using the tetravalent heterodimeric soluble TCR is shown below:

1. Vα-(L)-$C_L$ and Vβ-(L)-$C_H1$-(L)-TD-(L)-EM
2. Vα-(L)-$C_H1$-(L)-TD-(L)-EM and Vβ-(L)-$C_L$
3. Vα-Cα-(L)-$C_L$ and Vβ-Cβ-(L)-$C_H1$-(L)-TD-(L)-EM
4. Vα-Cα-(L)-$C_H1$-(L)-TD-(L)-EM and Vβ-Cβ-(L)-$C_L$
5. Vα-(L)-$C_L$-(L)-TD-(L)-EM and Vβ-(L)-$C_H1$
6. Vα-(L)-$C_H1$ and Vβ-(L)-$C_L$-(L)-TD-(L)-EM
7. Vα-Cα-(L)-$C_L$-(L)-TD-(L)-EM and Vβ-Cβ-(L)-$C_H1$
8. Vα-Cα-(L)-$C_H1$ and Vβ-Cβ-(L)-$C_L$-(L)-TD-(L)-EM In another aspect of the invention, the effector molecule (EM) is fused to the multivalent protein complex at the C-terminus of either the immunoglobulin CH1 or CL1 domain via an optional peptide linker. Fusion of the EM via the immunoglobulin domain can be arranged to produce multivalent protein complexes in a number of different configurations. Examples of some of the protein configurations that can be produced using the tetravalent heterodimeric soluble TCR is shown below:

9. Vα-(L)-$C_L$-(L)-EM and Vβ-(L)-$C_H1$-(L)-TD
10. Vα-(L)-$C_H1$-(L)-TD and Vβ-(L)-$C_L$-(L)-EM
11. Vα-Cα-(L)-$C_L$-(L)-EM and Vβ-Cβ-(L)-$C_H1$-(L)-TD
12. Vα-Cα-(L)-$C_H1$-(L)-TD and Vβ-Cβ-(L)-$C_L$-(L)-EM
13. Vα-(L)-$C_L$-(L)-TD and Vβ-(L)-$C_H1$-(L)-EM
14. Vα-(L)-$C_H1$-(L)-EM and Vβ-(L)-$C_L$-(L)-TD
15. Vα-Cα-(L)-$C_L$-(L)-TD and Vβ-Cβ-(L)-$C_H1$-(L)-EM
16. Vα-Cα-(L)-$C_H1$-(L)-EM and Vβ-Cβ-(L)-$C_L$-(L)-TD In another aspect of the invention, effector molecules (EM) are fused to the multivalent protein complex at the C-terminus of either the immunoglobulin CH1 or CL1 domain and also the C-terminus of the tetramerization domain (e.g. NHR2) via an optional peptide linkers. This approach allows for the fusion of two effector molecules to be fused per TCR heterodimer complex. Fusion of the EM via the immunoglobulin domain and the tetramerization domain can be arranged to produce multivalent protein complexes in a number of different configurations. Examples of some of the protein configurations that can be produced using the tetravalent heterodimeric soluble TCR is shown below:

17. Vα-(L)-$C_L$-(L)-EM and Vβ-(L)-$C_H1$-(L)-TD-(L)-EM
18. Vα-(L)-$C_H1$-(L)-TD-(L)-EM and Vβ-(L)-$C_L$-(L)-EM
19. Vα-Cα-(L)-$C_L$-(L)-EM and VβCβ-(L)-$C_H1$-(L)-TD-(L)-EM 20. Vα-Cα-(L)-$C_H$1-(L)-TD-(L)-EM and Vβ-Cβ-(L)-$C_L$-(L)-EM
21. Vα-(L)-$C_L$-(L)-TD-(L)-EM and Vβ-(L)-$C_H$1-(L)-EM
22. Vα-(L)-$C_H$1-(L)-EM and Vβ-(L)-$C_L$-(L-)TD-(L)-EM
23. Vα-Cα-(L)-$C_L$-(L)-TD-(L)-EM and Vβ-Cβ-(L)-$C_H$1-(L)-EM
24. Vα-(L)-$C_H$1-(L)-EM and Vβ-Cβ-(L)-$C_L$-(L)-TD-(L)-EM In another aspect of the invention, the multivalent protein complex is fused to a protein tag to facilitate purification. Purification tags are known in the art and they include, without being limited to, the following tags: His, GST, TEV, MBP, Strep, FLAG.

Non-TCR Multimers

The present invention provides a unique method for assembling proteins in a soluble multivalent format with potential to bind multiple interacting domains or antigens. The protein can be a monomer, homodimer, heterodimer or oligomer preferentially involved either directly or indirectly in the immune system, or having the potential to regulate immune responses. Examples include, but not limited to, TCR, peptide MHC class I and class II, antibodies or antigen-binding portions thereof and binding proteins having alternative non-antibody protein scaffolds.

In another aspect of the invention, the interacting domains or antigens could be any cell surface expressed or secreted proteins, peptide-associated with MHC Class I or II or any proteins associated with pathogens including viral and bacterial proteins.

Non-TCR multimers may be multimers of antibodies or antibody fragments, such as dAbs of Fabs. Examples of dAbs and Fabs in accordance with the invention include the following:

Examples of Multivalent Dabs
25. VH-(L)-NHR2
26. VL(λ or κ)-(L)-NHR2
27. VH-(L)-NHR2-(L)-EM
28. VL(λ or κ)-(L)-NHR2-(L)-EM
29. VH-CH1-(L)-NHR2
30. VL(λ or κ)-CL-(L)-NHR2
31. VH-CH1-(L)-NHR2-(L)-EM
32. VL(λ or κ)-CL-(L)-NHR2-(L)-EM Examples of Multivalent Fabs
33. VH-CH1-(L)-NHR2 and VL(λ or κ)-CL
34. VL(λ or κ)-CL-(L)-NHR2 and VH-CH1
35. VH-CH1-Hinge-(L)-NHR2 and VL(λ or κ)-CL
36. VL(λ or κ)-CL-Hinge-(L)-NHR2 and VH-CH1
37. VH-CH1-(L)-NHR2-(L)-EM and VL(λ or κ)-CL
38. VL(λ or κ)-CL-(L)-NHR2-(L)-EM and VH-CH1
39. VH-CH1-Hinge-(L)-NHR2-(L)-EM and VL(λ or κ)-CL
40. VL(λ or κ)-CL-Hinge-(L)-NHR2-(L)-EM and VH-CH1
41. VH-CH1-(L)-NHR2 and VL(λ or κ)-CL-(L)-EM
42. VL(λ or κ)-CL-(L)-NHR2 and VH-CH1-(L)-EM
43. VH-CH1-Hinge-(L)-NHR2 and VL(λ or κ)-CL-(L)-EM
44. VL(λ or κ)-CL-Hinge-(L)-NHR2 and VH-CH1-(L)-EM In the examples above, (L) denotes an optional peptide linker, whilst EM denotes a biologically active agent or effector molecule such as toxins, drugs or cytokines, and including binding molecules such as antibodies, Fabs and ScFv.

The variable light chain can be either Vλ or Vκ.

In one aspect of the invention, the assembled tetramerized protein molecule in one example could be a human pMHC for the application in drug discovery using animal drug discovery platforms (e.g. mice, rats, rabbits, chicken). In such a context, the tetramerization domain is preferentially expressed and produced from genes originating from the animal species it is intended for. One example of such drug discovery applications would be the use of the tetramerized human pMHC as an antigen for immunization in rats for example. Once rats are immunized with pMHC the immune response is directed specifically towards the human pMHC and not the tetramerization domain of the protein complex.

Multivalent antibodies can be produced, for example using single domain antibody sequences, fused to the NHR2 multimerisation domain.

In a related aspect to the invention, the tetravalent protein can be a peptide used as a probe for molecular imaging of tumour antigens. The multivalent binding of such a probe will have distinctive advantage over monovalent molecular probes as it will have enhanced affinity, avidity and retention time in vivo and this in turn will enhance in vivo tumour targeting.

The multimerisation domain is the NHR2 domain set forth above. Preferably, polypeptides are stabilized and/or rendered soluble by the use of Ig constant domains fused to the polypeptides, such that the fusions provide tetramers of polypeptides. Ig hinge domains can be used to provide octamers.

Uses of Multimers

Multimeric TCR proteins according to the invention are useful in any application in which soluble TCR proteins are indicated. Particular advantages of the TCR proteins of the invention include increased avidity for the selected target, and/or the ability to bind a plurality of targets.

Thus, in one aspect, the multivalent heterodimeric soluble TCR protein molecules of the invention can be used for selectively inhibiting immune responses, for example suppression of an autoimmune response. The multivalent, for example tetravalent, nature of these soluble protein molecules gives it exquisite sensitivity and binding affinity to compete antigen-specific interactions between T cells and antigen presenting cells. This kind of neutralization effect can be therapeutically beneficial in autoimmune diseases such as rheumatoid arthritis, systemic lupus erythematosus, psoriasis, inflammatory bowel diseases, graves disease, vasculitis and type 1 diabetes.

Similarly, the tetravalent heterodimeric soluble TCR protein molecules can be used to prevent tissue transplant rejection by selectively suppressing T cell recognition of specific transplantation antigen and self antigens binding to target molecule and thus inhibiting cell-to-cell interaction.

In another aspect of the invention, the tetravalent heterodimeric soluble TCR protein molecules can be used in clinical studies such as toxicity, infectious disease studies, neurological studies, behavior and cognition studies, reproduction, genetics and xenotransplantation studies.

The tetravalent heterodimeric soluble TCR protein molecules with enhanced sensitivity for cognate pMHC can be used for the purpose of diagnostics using biological samples obtained directly from human patients. The enhanced sensitivity of the tetravalent heterodimeric soluble TCRs allows detection of potential disease-associated peptides displayed on MHC, which are naturally found to be expressed at low density. These molecules can also be used for patient stratification for enrolling patient onto relevant clinical trials.

In another aspect of the invention, octavalent heterodimeric soluble TCR protein molecules can be used in pharmaceutical preparations for the treatment of various diseases.

In another related aspect to this invention, octavalent heterodimeric soluble TCR protein molecules can be used as a probe for tumour molecular imaging or prepared as a therapeutic protein.

EXAMPLES

Example 1: Generation of Tetravalent and Octavalent Soluble Heterodimeric NY-ESO-1 TCR Molecules This example demonstrates a method for generating tetravalent and octavalent soluble heterodimeric TCR molecules referred to as ts-NY-ESO-1 TCR and os-NY-ESO-1 TCR respectively. These formats overcome the problems associated with solubility and avidity for cognate ligand at the target site.

To exemplify ts-NY-ESO-1 TCR and os-NY-ESO-1 TCR as stable and soluble molecules, TCR αu variable sequences with high affinity for NY-ESO-1 together with immunoglobulin constant domains and the NHR2 tetramerization domain are used in this example.

The high-affinity NY-ESO TCR αu chains (composing of TCR Vα-Cα and Vβ-Cβ respectively) specific for SLL-MWITQC(SEQ ID NO: 141)-HLA-A*0201 used in this example is as reported in WO 2005/113595 A2 with the inclusion of a signal peptide sequence (MGWSCIILFL-VATATGVHS; SEQ ID NO: 142). To aid protein purification, a histidine tag was incorporated to the C-terminus of NHR2 domain.

Figure 3:
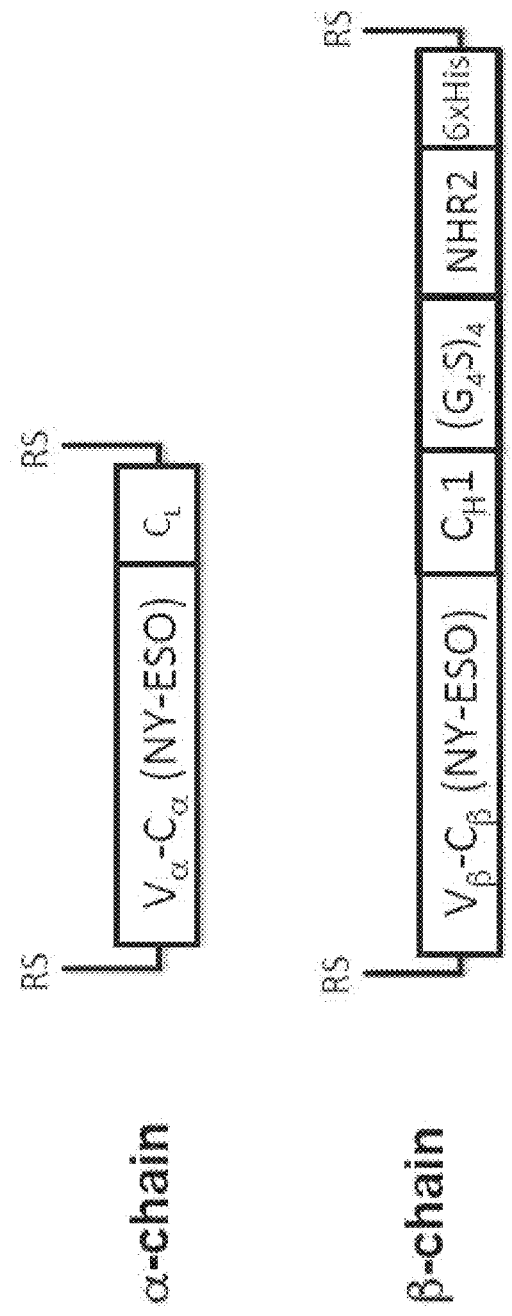
FIG. 3: A schematic drawing of the domain arrangements in the α and β chain used for expressing and assembling ts-NY-ESO-1 TCR.
Figure 4:
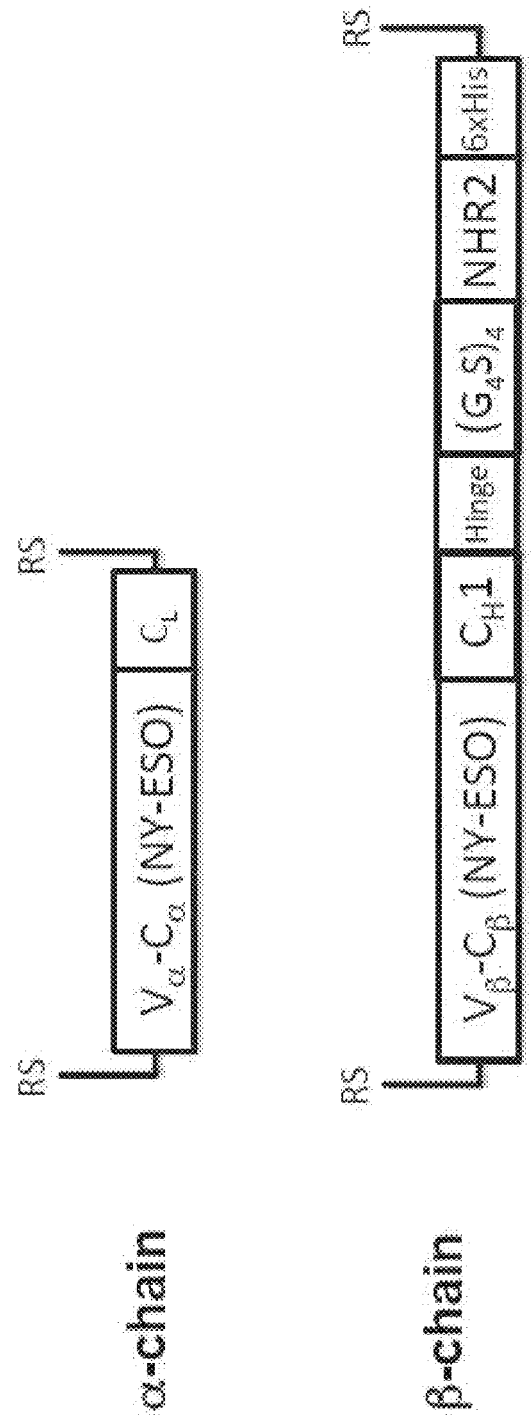
FIG. 4: A schematic drawing of the domain arrangements in the α and β chain used for expressing and assembling os-NY-ESO-1 TCR.

DNA constructs encoding components of ts-NY-ESO-1 TCR and os-NY-ESO-1 TCR are synthetically constructed as a two-vector system to allow for their soluble expression and functional assembly in mammalian cells. A schematic representation of the two assembled TCR chains (a and 3 chains) whose DNA sequences are synthesized for cloning into the expression vector are shown in FIGS. 3 and 4 and their amino acid sequences are shown in FIGS. 5 and 6.

The pTT5 vector system allows for high-level transient production of recombinant proteins in suspension-adapted HEK293 EBNA cells (Zhang et al., 2009). It contains origin of replication (oriP) that is recognized by the viral protein Epstein-Barr Nuclear Antigen 1 (EBNA-1), which together with the host cell replication factor mediates episomal replication of the DNA plasmid allowing enhanced expression of recombinant protein. Therefore the pTT5 expression vector is selected for cloning the components for the ts-NY-ESO-1 TCR and os-NY-ESO-1 TCR molecules.

Synthesized DNA fragments containing the TCR αβ chains are digested with restriction enzymes at the restriction sites (RS) (FastDigest, Fermantas) and the DNA separated out on a 1% agarose gel. The correct size DNA fragments is excised and the DNA purified using Qiagen gel extraction kit. The pTT5 vector was also digested with the same restriction enzymes and the linearized plasmid DNA is purified from excised agarose gel. The digested TCR αβ chains is cloned into the digested pTT5 vector to give four expression vectors (pTT5-ts-NY-ESO-1-TCR, pTT5-ts-ESO-1-TCRβ, pTT5-os-NY-ESO-1-TCRα and pTT5-os-ESO-1-TCRβ).

Expression of Tetravalent and Octavalent Soluble NY-ESO TCR

Functional expression of ts-NY-ESO-1 TCR and os-NY-ESO-1 TCR is carried out in suspension-adapted HEK293 EBNA cells. HEK293-EBNA cells are cultured in serum-free Dulbecco's Modified Eagle Medium (DMEM, high glucose (4.5 g/L) with 2 mM L-glutamine) at 37° C., 5% $CO_2$ and 95% humidity.

For each transfection, HEK293-EBNA cells ($3\times10^7$ cells) are freshly seeded into 250 mL Erlenmeyer shaker Flask (Corning) from ~60% confluent cells. Transfections are carried out using FreeStyle MAX cationic lipid base reagent (Life Technologies) according to the supplier's guidelines. For expression of ts-NY-ESO-1 TCR, 37.5 μg of total plasmid DNA (18.75 μg plasmid DNA each of pTT5-ts-NY-ESO-1-TCRα and pTT5-ts-ESO-1-TCRβ vectors are used or varying amounts of the two expression plasmids) are used per transfection. Similarly for expression of os-NY-ESO-1 TCR, 18.75 μg plasmid DNA each of pTT5-os-NY-ESO-1-TCRα and pTT5-os-ESO-1-TCRβ is are used for transfection. Following transfection, cells were recovered in fresh medium and cultivated at 37° C. with 5% $CO_2$ in an orbital shaker at 110 rpm for between 4-8 days. Smaller scale transfections are done similarly in 6 well or 24 well plates.

Analysis of Expressed Soluble $eTCR^2$-BiTE

The ts-NY-ESO-1 TCR and os-NY-ESO-1 TCR protein molecules secreted into the supernatant are analyzed either directly by sodium dodecyl sulfate (SDS) polyacrylamide gel electrophoresis (PAGE) or after protein purification. Protein samples and standards are prepared under both reducing and non-reducing conditions. SDS-PAGE was performed using cast mini gels for protein electrophoresis in a Mini-PROTEAN Tetra cell electrophoresis system (Bio-Rad). Coomassie blue dye was used to stain proteins in SDS-PAGE gel.

Purification of Ts-NY-ESO-1 TCR and Os-NY-ESO-1 TCR Protein Molecules

Soluble ts-NY-ESO-1 TCR and os-NY-ESO-1 TCR from cell supernatant are purified in two steps. In the first step immobilized metal affinity chromatography (IMAC) are used with nitrilotriacetic acid (NTA) agarose resin loaded with nickel (HisPur Ni-NTA Superflow agarose—Thermo fisher). The binding and washing buffer consists of Tris-buffer saline (TBS) at pH7.2 containing low concentration of imidazole (10-25 mM). Elution and recovery of the His-tagged ts-NY-ESO-1 TCR and os-NY-ESO-1 TCR from the IMAC column are achieved by washing with high concentration of imidazole (>200 mM). The eluted protein fractions are analysed by SDS-PAGE and the fractions containing the protein of interest are pooled. The pooled protein fraction is used directly in binding assays or further purified in a second step involving size-exclusion chromatography (SEC). Superdex 200 increase prepacked column (Gelifesciences) are used to separate out monomer, oligomer and any aggregated forms of the target protein.

Surface Plasmon Resonance

Figure 7:
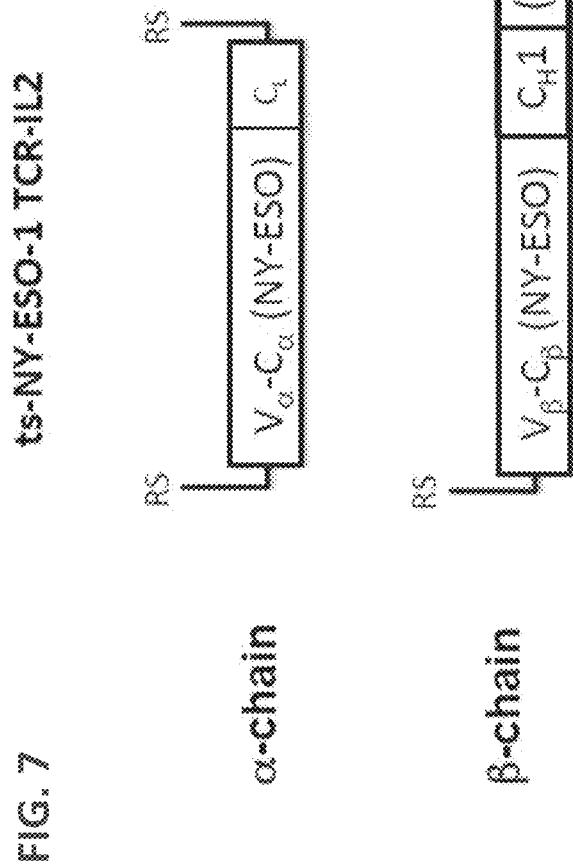
FIG. 7: A schematic drawing of the domain arrangements in the α and β chain used for expressing and assembling ts-NY-ESO-1 TCR-IL2 fusion protein complex.
Figure 8:
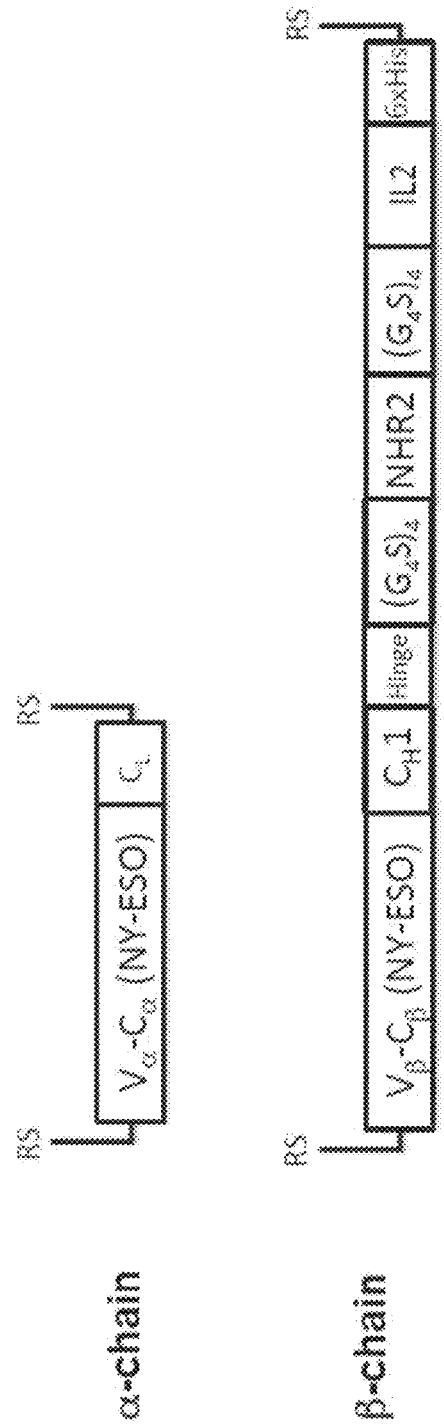
FIG. 8: A schematic drawing of the domain arrangements in the α and β chain used for expressing and assembling os-NY-ESO-1 TCR-IL2 fusion protein complex.

The specific binding and affinity analysis of ts-NY-ESO-1 TCR and os-NY-ESO-1 TCR to its pMHC is performed using BIAcore. Briefly, the purified Histidine-tagged ts-NY-ESO-1 TCR and os-NY-ESO-1 TCR proteins are captured onto sensor surface via $Ni^{2+}$ chelation of nitrilotriacetic acid (NTA). Varying concentration of the analyte solution containing NY-ESO pep$_{(SLLMWITQV)}$-MHC (ProImmune) is injected and the binding signals were monitored Example 2: Generation of Tetravalent and Octavalent Soluble NY-ESO TCR-IL2 Fusion Molecule The DNA encoding the domains required for expressing ts-NY-ESO-1 TCR-IL2 and os-NY-ESO-1 TCR-IL2 protein complexes are synthesized and cloned into the expression vector pTT5 as described above. A schematic representation of the domains within the TCR αβ chains for ts-NY-ESO-1 TCR-IL2 and os-NY-ESO-1 TCR-IL2 are shown in FIGS. 7 and 8 and the amino acids sequences are shown in FIGS. 9 and 10.

Expression, purification and characterization of ts-NY-ESO-1 TCR-IL2 and os-NY-ESO-1 TCR-IL2 are carried out as described above.

Example 3: High Yield Tetramer Secretion

Figure 14:
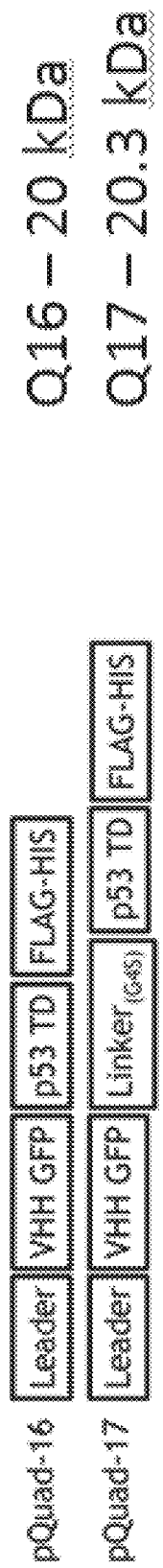
FIG. 14 is a schematic of Quad 16 and Quad 17.
Figure 15A:
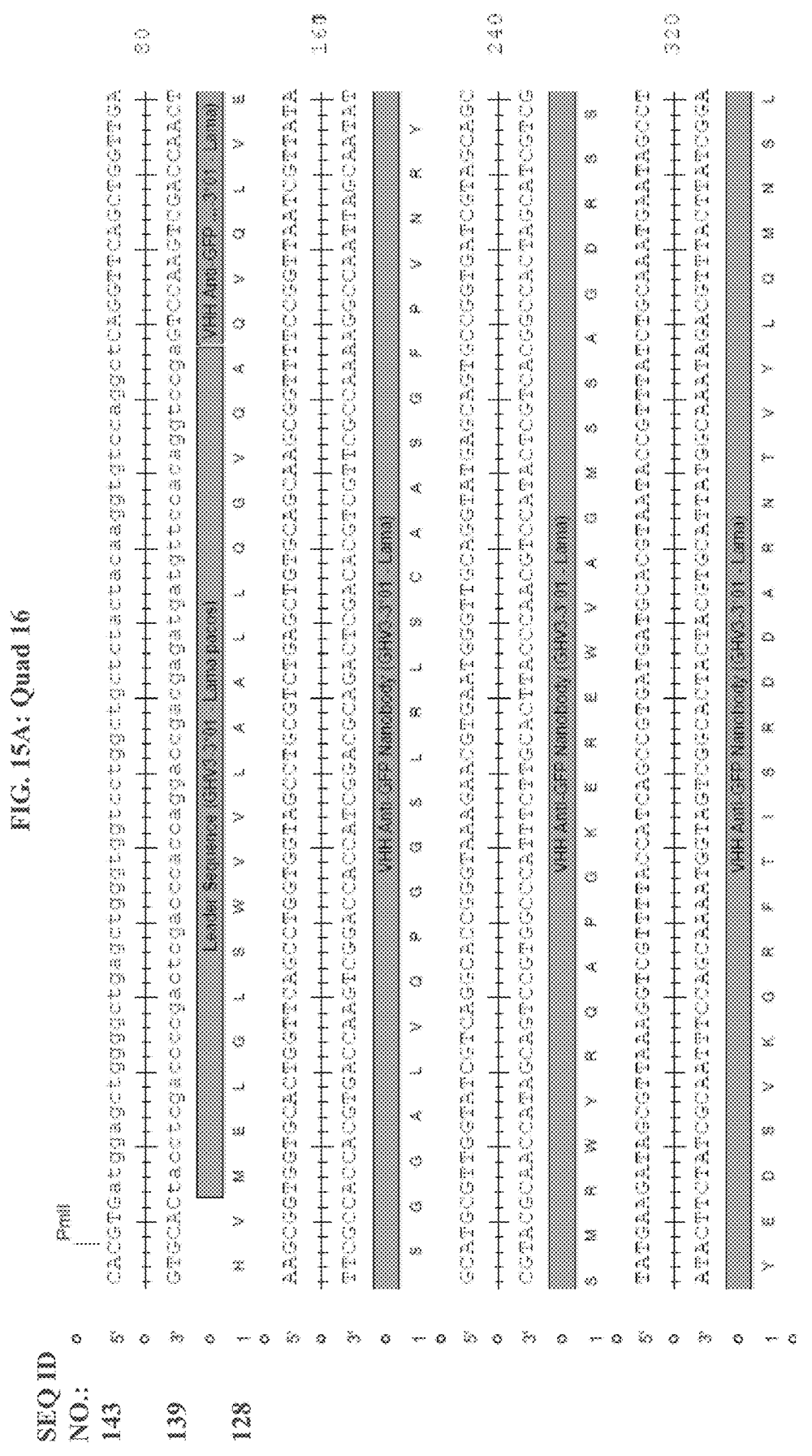
Figure 15A:
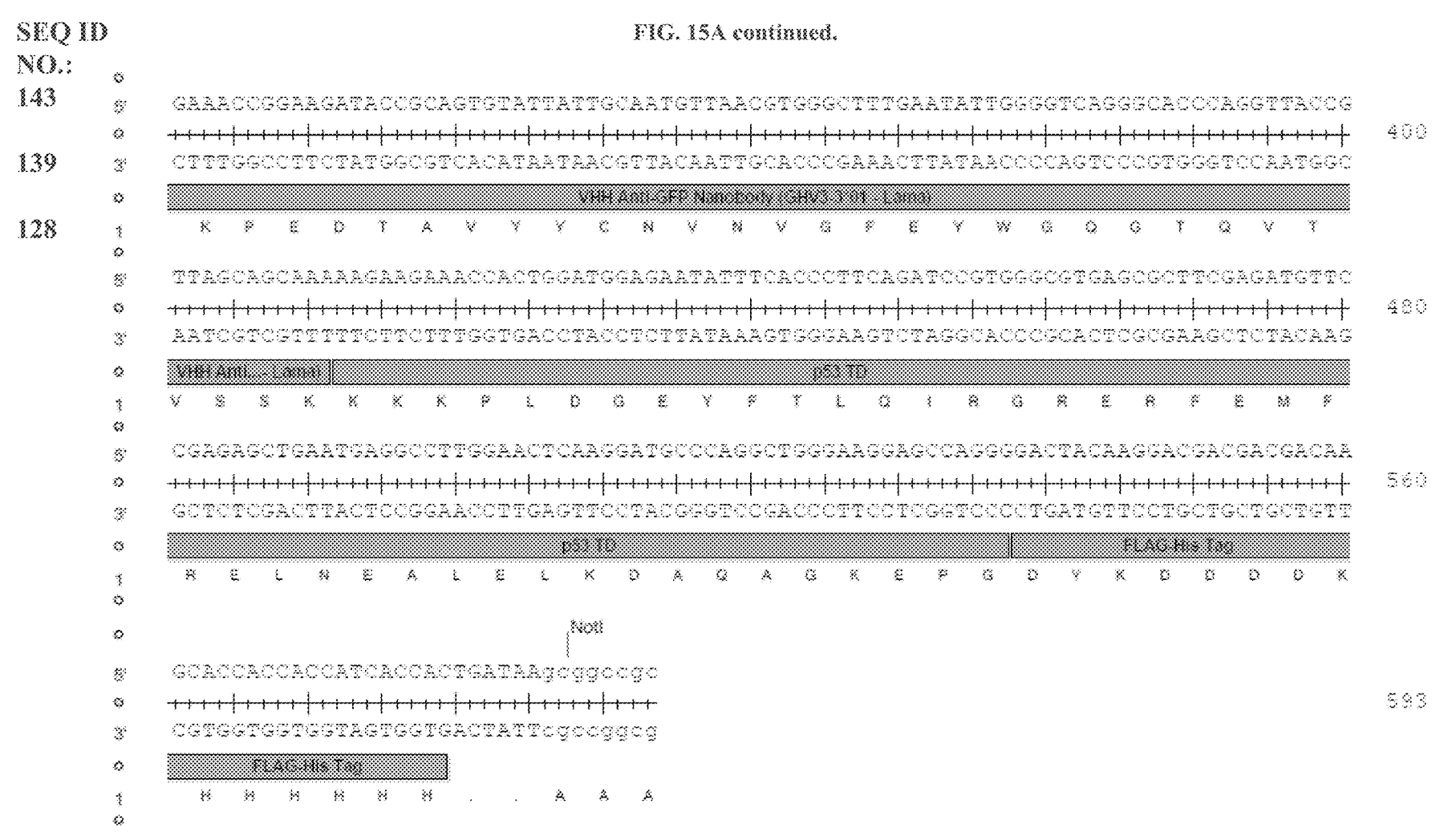
Figure 15B:
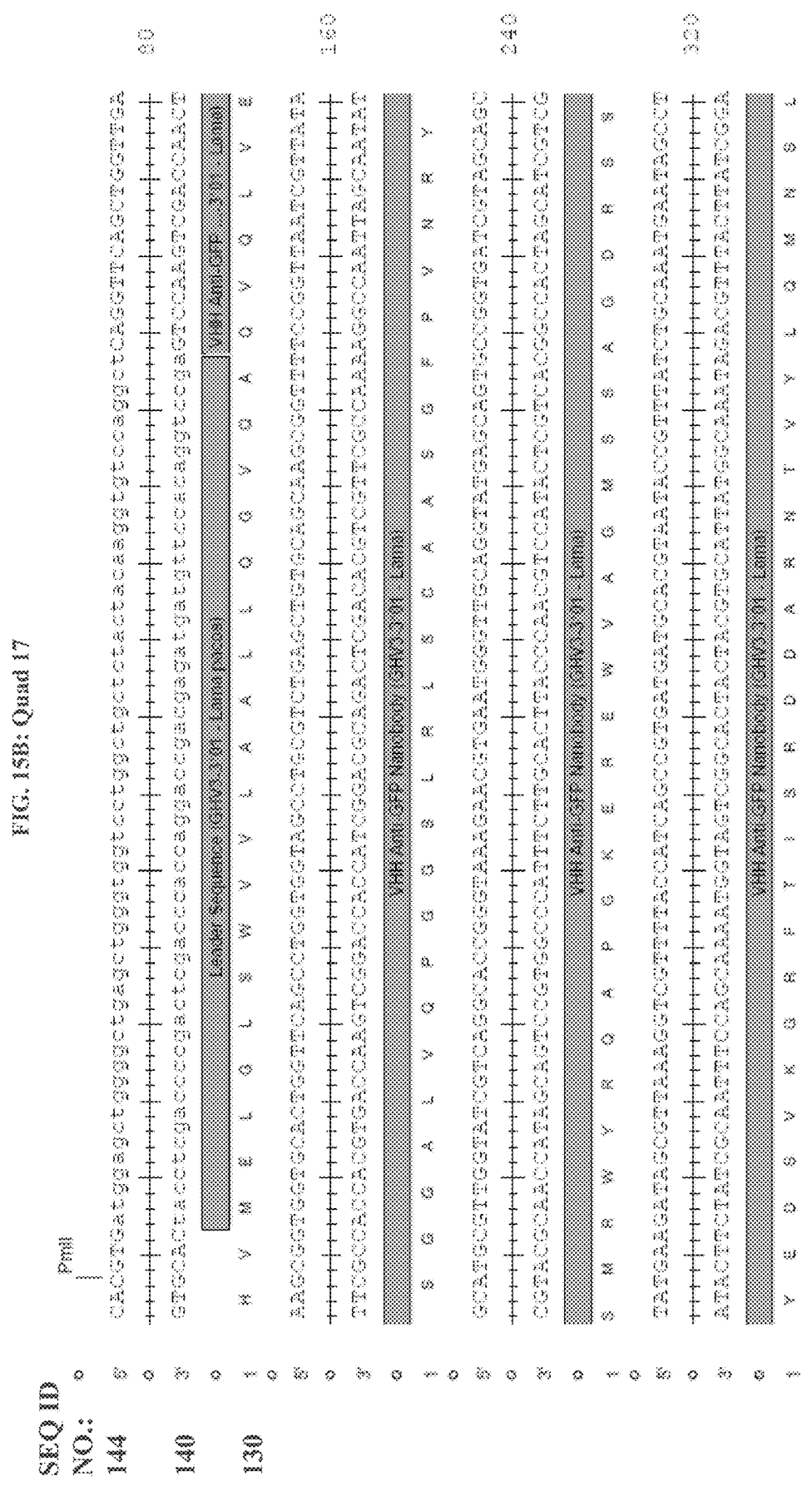
Figure 15B:
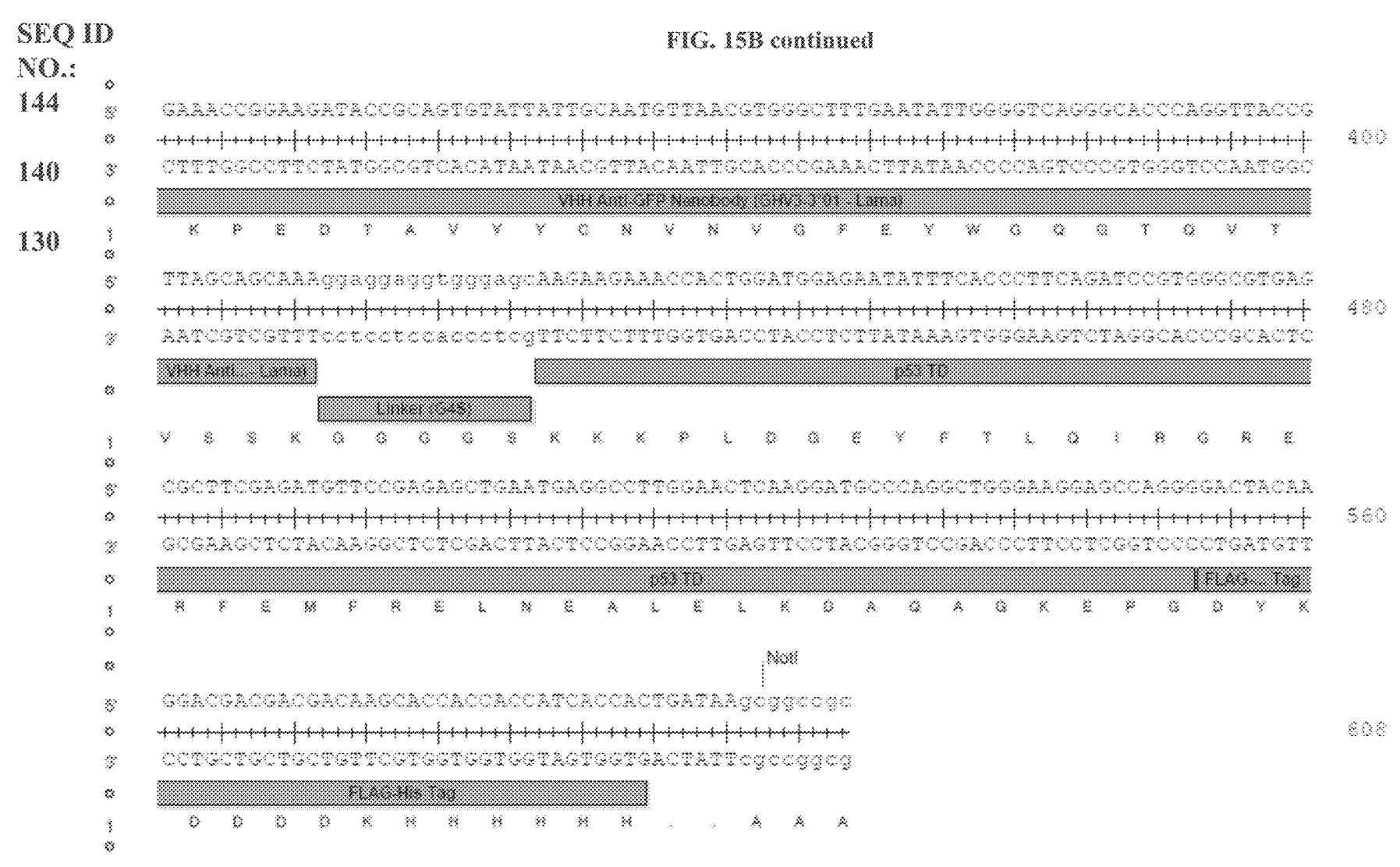

Briefly, using conventional genetic engineering techniques, a HEK293-T cell line was made that encodes Quad 16 (FIGS. 14 and 15A) and another HEK293-T cell line was made that encodes Quad 17 (FIGS. 14 and 15B).

Protein expression took place and protein was secreted from the cell lines. Samples of the medium in which the cells were incubated were subjected to PAGE under denaturing conditions (SDS-PAGE) or under native conditions (no SDS). The former was further under reduced conditions (using mercaptoethanol), whereas the latter was not.

Figures 16A, 16B:
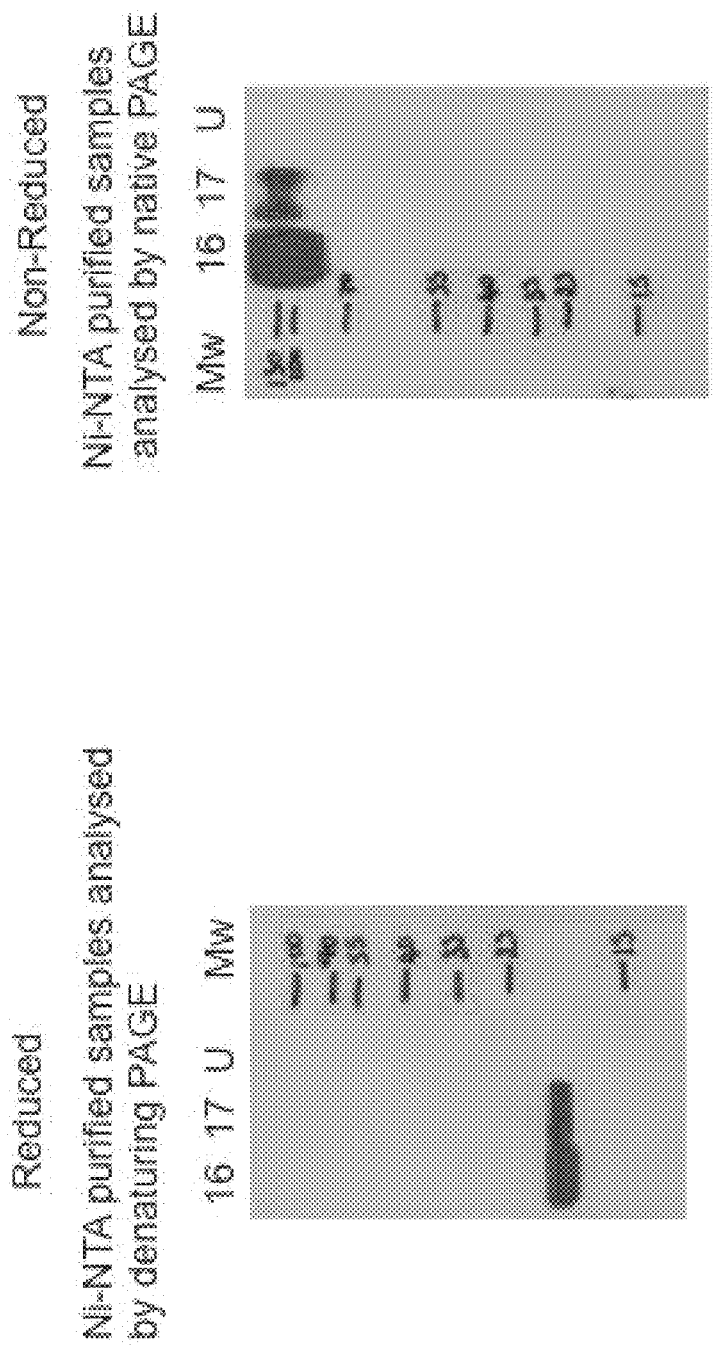
FIGS. 16A-16B show analysis of secreted proteins using anti-Ig Western Blot.

The reduced gel showed a distinct banding (FIG. 16A) at the expected monomer size. Surprisingly, the unreduced, native gel showed no detectable banding at the monomer, dimer or trimer size, but instead heavy banding was seen at the tetramer size indicating that a very high yield of tetramer had been obtained, and this was confirmed by SEC to be of high purity.

For Quad 16, the tetramer peak from SEC was run on SDS-PAGE and the obtained band was cut out for mass spectrometry. The data were obtained with trypsin digests and p53 was detected in 100% of the protein. This was conclusive evidence that the secreted Quad 16 was multimerised Example 4: Intracellular Protein Expression of Extracellular Portion of TCR Fused to NHR2 TD Expression Vector All DNA fragments were synthesized and cloned into the expression vector, pEF/myc/cyto (Invitrogen) by Twist Bioscience (California). Schematics and sequences of the synthesized DNA fragments and Quad polypeptides are shown in FIG. 21, and the sequence tables herein.

DNA Preparation

Lyophilised plasmid DNA synthesized by Twist Bioscience, were resuspended with MQ water to a concentration of 50 ng/μl. 50 ng of DNA was transformed into 50 μl of competent DH5c cells using a conventional heat shock method. The cells were plated on LB agar plates containing 100 μg/mL ampicillin and grown overnight at 37° C. Individual colonies were picked and grown overnight at 37° C., 220 rpm. The DNA was purified from the cells using the QIAprep Spin Miniprep Kit, according to the manufacturers instructions (Qiagen).

Transfections in HEK293T Cell

Briefly, HEK293T cells were maintained in high glucose DMEM supplemented with 10% FBS and Pen/Strep. Cells were seeded at $6 \times 10^5$ cells per well of a 6-well plate in 2 ml media and were allowed to adhere overnight at 37° C., 5% $CO_2$. 7.5 μl of Lipofectamine 2000 was diluted in 150 μl of OptiMem and incubated at room temperature for 5 mins. Plasmid DNA (2.5 μg) was diluted in 150 μl of OptiMem. Diluted DNA was combined with the diluted Lipofectamine 2000, mixed gently and incubated at R.T. for 20 mins. The 300 μl of complexes were added to one well of the 6-well plates. When analysis required the media to be serum free, the media was aspirated and replaced with CD293 media 6 hours post-transfection. The cells were incubated for 48 hours at 37° C., 5% $CO_2$ prior to analysis.

Accordingly, different formats of TCR-linked NHR2 tetramerization domain (TD) constructs (Quads) were transfected into HEK293T cells. Quads 3 & 4 resembling a TCR tetravalent format (structure schematically represented in FIGS. 1 & 3) and Quads 12 & 13 resembling a TCR octavalent format (Structure schematically represented in FIGS. 2 & 4) were transfected for protein expression analysis. Protein samples were prepared from transfected HEK293T cells as follows to check for intracellularly expressed protein. Briefly cells were washed once with 2 ml PBS, which was subsequently aspirated. 150 μl of Trypsin-EDTA (0.05%) was added to each well and the cells were incubated at R.T. for ~1 min. The plate was tapped to lift any strongly adhering cells. 850 μl of media was added to each well to inactivate the trypsin. The cells were transferred to a 1.5 ml eppendorf and spun at 1,000 rpm for 5 mins. The supernatant was aspirated and the pellets stored on ice. The cells were resuspended in 400 μl cell lysis buffer (10 mM Tris pH 7.5, 1% SDS) containing Protease Inhibitor Cocktail Set III (Calbiochem), diluted 1/200. The samples were vortexed vigorously and incubated on ice for 20 mins. The cells were sonicated using a Branson Ultrasonics Sonifier™ (Thermo Fisher Scientific). The amplitude was set to 30% and the cells were sonicated for a total of 24 seconds (6 secs on, 3 secs off×4). The total protein concentration was quantified using the Pierce BCA Protein Assay Kit™, according to the manufacturer's instructions. 100 g was diluted with MQ water to give a volume of 80 μl. 20 μl of 5×SDS loading buffer was then added giving samples of 1 mg/ml. Samples were incubated at 95° C. for 5 min prior to SDS-PAGE and Western blot analysis.

Protein samples were separated on SDS-PAGE under denaturing condition. Typically, 25 μg of whole cell lysate (25 μl) were loaded on to the gel for Western blot analysis. 5 μl of PageRule Prestained 10-180 kDa Protein Ladder was loaded into the gel alongside the protein samples. The gels were run in Tris-Glycine buffer containing 0.1% SDS. A constant voltage of 150 volts was used and the gels were run for ~70 mins until the dye front has migrated fully.

SDS-PAGE (15% Bis-Tris) gels were prepared using the following resolving and stacking gels.

Resolving Gel:
5 ml 30% Bis-Acrylamide
2.6 ml 1.5 M Tris (pH 8.8)
50 μl 20% SDS
100 μl 10% APS
10 μl TEMED
2.2 ml MQ Water Stacking Gel:
0.75 ml 30% Bis-Acrylamide
1.25 ml 1.5 M Tris (pH 8.8)
25 μl 20% SDS
50 μl 10% APS
5 μl TEMED
2.9 ml MQ Water Western blotting was performed for the specific and sensitive detection of protein expression of TCR-NHR2 TD fusion proteins from Quads 3, 4, 12 and 13. Proteins separated out on SDS-PAGE were transferred onto Amersham Hybond™ 0.45 μM PVDF membrane as follows. Briefly, Amersham Hybond 0.45 μM PVDF membrane was activated with MeOH for ~1 min and rinsed with transfer buffer (25 mM Tris, 190 mM Glycine, 20% MeOH) before use. The sponge, filter paper, gel, membrane, filter paper, sponge stack was prepared and placed in the cassette for transfer. Transfer was carried out on ice at 280 mA for 75 mins. The membrane was incubated for ~2 hours in blocking buffer (TBST, 5% milk powder). The membrane was washed briefly with TBST before being incubated at 4° C. overnight with anti-human IgG HRP (Thermo, 31410) diluted 1/2500 in TBST, 1% milk powder. The membrane was washed thoroughly (three washes of TBST, 15 mins each) before being developed using the Pierce ECL Western Blotting Substrate.

Figure 17B:
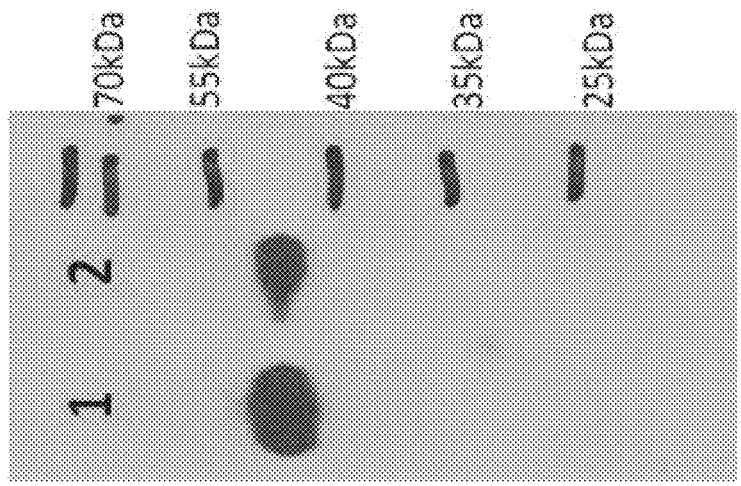
FIGS. 17A-17B: Western blots prepared from denaturing SDS-PAGE gel probed with anti-human IgG HRP detection antibody (FIG. 17A) Protein samples from Quads 3 and 4 were prepared from whole cell extracts and loaded in lanes 1 and 2 respectively. The expected Mw for Quads 3 and 4 are 46.1 and 46.4 kDa respectively.
Figure 17A:
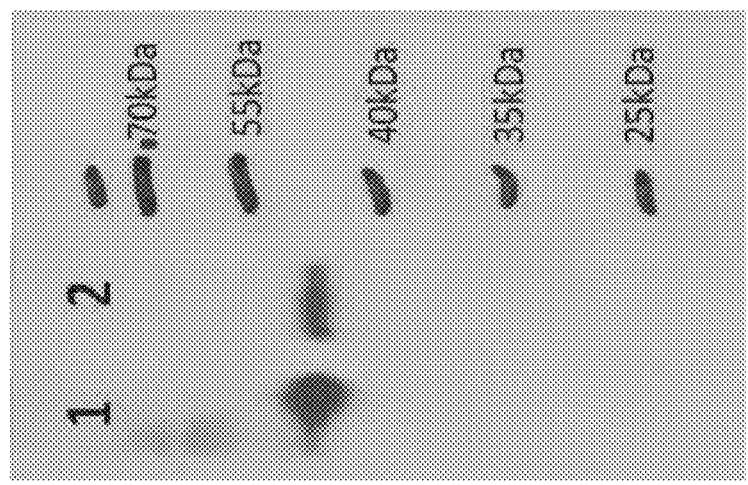

Using anti-human IgG detection antibody to probe Western blots, specific protein band at the expected molecular weight can be detected from samples prepared from Quads 3 (46.1 kDa), 4 (46.4 kDa), 12 (47.8 kDa) and 13 (48.1 kDa) (FIGS. 17A and 17B). These data confirm intracellular protein expression of TCR-NHR2 TD fusion proteins in HEK293T cells.

For all of the Quads analysed, a clear single band can be detected indicating TRVβ-TRCβ-IgG1-CH1 (+/−IgG hinge domain) fusions with the NHR2 TD are stable. These expression data also confirm the possibility of assembling tetravalent (Quads 3 & 4) and octavalent (Quads 12 & 13) molecules as exemplified in this example.

The difference between Quads 3 and 4 is the presence of a small peptide linker (G4S) located between the IgG1 CH1 domain and NHR2 TD. This is also true for Quads 12 and 13 where Q13 contains a peptide linker between the IgG1 CH1 domain and NHR2 TD. From the expression data, it can be seen the peptide linker does not effect protein expression. However, it may be desirable to include a peptide linker to aid antigen binding and or stabilizing the multimerisation complex in these TCR-NHR2 TD formats.

Example 5: Soluble Protein Expression of Extracellular Portion of TCR Fused to NHR2 TD TCR-NHR2 TD fusion proteins were shown in Example 4 to be expressed intracellularly in HEK293T cells. Here again Quads 3, 4, 12 and 13 were used to demonstrate soluble expression of these fusion proteins. As described above, Quads 3, 4, 12 and 13 were transfected into HEK293T cells and soluble proteins from the cell supernatant were concentrated. Briefly, the media was harvested 48 hours post-transfection and centrifuged at 2,000 rpm for 5 mins to remove any cells or debris. Typically, 500 µl of media was concentrated to 100 µl using Amicon™ Ultra 0.5 Centrifugal Units with a MWCO of 10 kDa. 25 µl of 5×SDS loading buffer was added to the sample, which was then incubated at 95° C. for 5 mins prior to gel/Western blot analysis. Concentrated protein samples were separated out on SDS-PAGE gel and transferred onto Amersham Hybond 0.45 µM PVDF membrane. Western blotting and protein detection was done using anti-human IgG HRP using the methods described above.

Figure 18B:
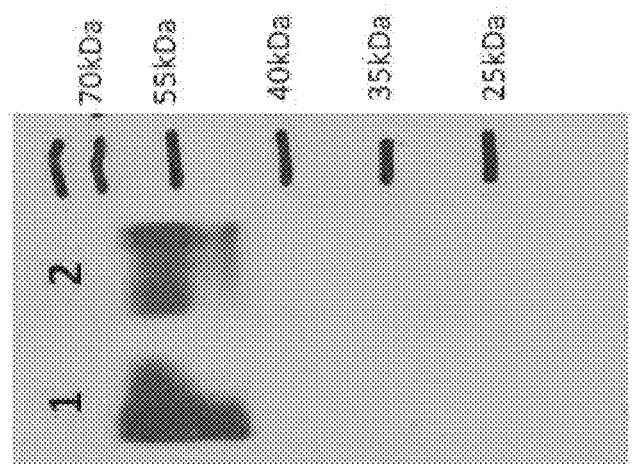
FIGS. 18A-18B: Western blots prepared from denaturing SDS-PAGE gel probed with anti-human IgG HRP detection antibody (FIG. 18A) Protein samples from Quads 3 and 4 were prepared by concentrating cell supernatant and loaded in lanes 1 and 2 respectively. The expected Mw for Quads 3 and 4 are 46.1 and 46.4 kDa respectively.
Figure 18A:
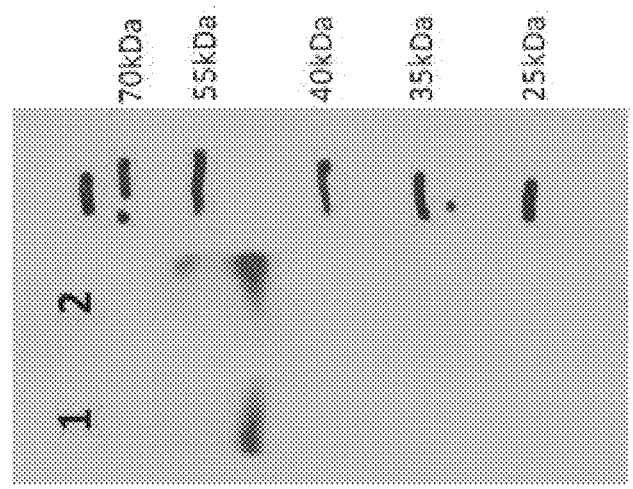
Figure 19B:
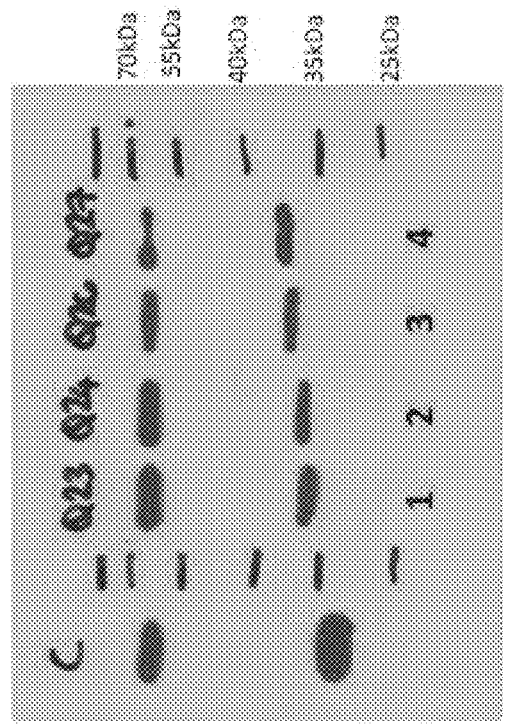
FIGS. 19A-19D: Western blots prepared from denaturing SDS-PAGE gel probed with anti-HIS HRP detection antibody (FIG. 19A) Protein samples from Quads 14, 15, 18 and 19 were prepared from whole cell extracts and loaded in lanes 1-4, respectively. The expected Mw for Quads 14, 15, 18 and 19 are 22.0, 22.3, 37.4 and 37.7 kDa respectively.
Figure 19A:
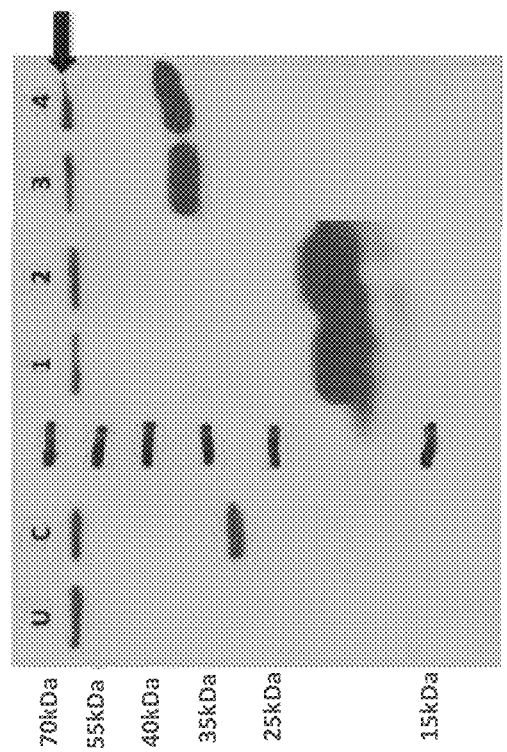
Figure 19D:
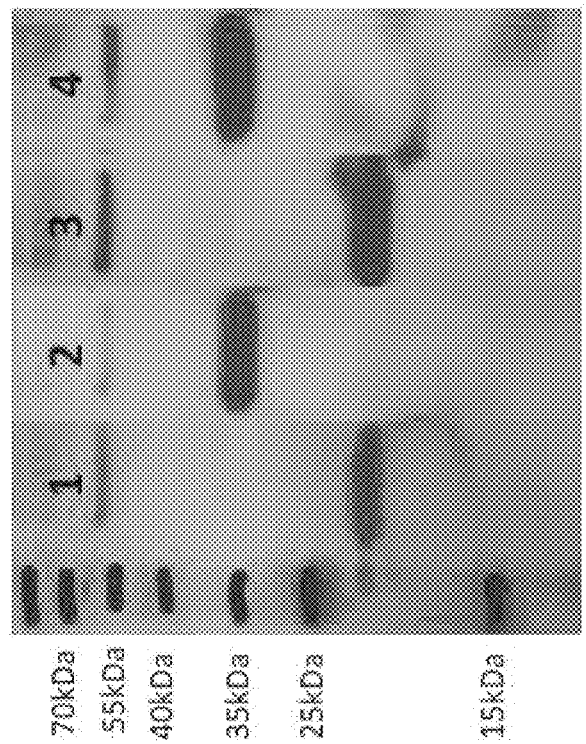
Figure 19C:
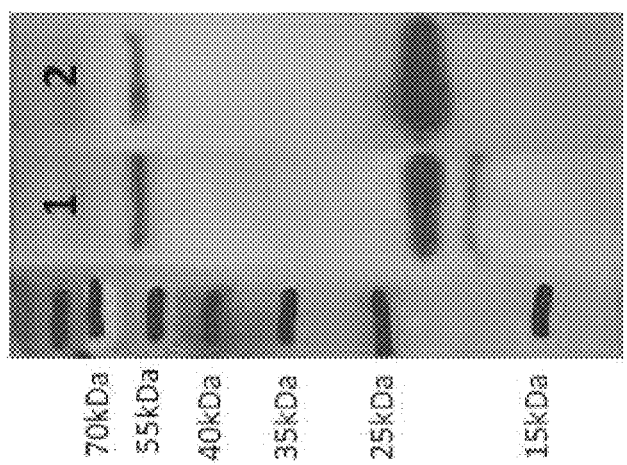

Protein samples concentrated and prepared from cell supernatants show specific protein band at the expected molecular weight on Western blots corresponding to Quads 3 (46.1 kDa), 4 (46.4 kDa), 12 (47.8 kDa) and 13 (48.1 kDa) (FIGS. 18A and 18B). The Western blot expression data unequivocally shows soluble expression of TCR-NHR2 TD fusion proteins in HEK293T. These data are the first report demonstrating soluble expression of TCR-NHR2 TD fusion proteins expressed in eukaryotic cells such as HEK293T cells.

Detection of soluble protein expression from both tetrameric (Quads 3 & 4) and octameric (Quads 12 & 13) TCR-NHR2 TD formats highlights the potential applicability of NHR2 TD in a broad setting. Use of NHR2 TD fusion molecules could be used for the preparation of therapeutic molecules and protein molecules for use in diagnostics and imaging.

Example 6: Intracellular Protein Expression of Antibody Fragments Fused to NHR2 TD To further exemplify the versatility of NHR2 TD, several different antibody fragment formats fused to NHR2 TD were constructed for testing their expression in HEK293T cells.

Figure 11B:
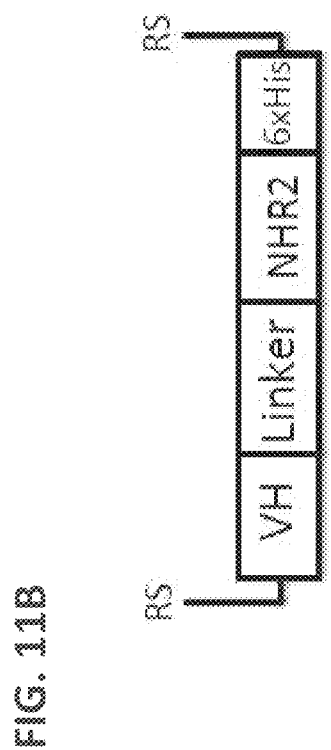
FIG. 11B: A schematic drawing of the domain arrangements for assembly of tetravalent dAbs, including linker and NHR2 domains.

Quads 14 and 15 contain an antibody VH domain fused to NHR2 TD either with or without a peptide linker located between the VH and NHR2 TD as schematically depicted in FIGS. 11B and 21. The VH domain in Quads 14 and 15 are specific for GFP (green fluorescent protein). Several other versions of this format were also constructed and tested with VH specific for therapeutically useful drug targets. Sequences of the binding domains are listed in Table 4. Some of these include Quad 34 (specific for TNFα), Quad 38 (specific for VEGF), Quad 40 (specific for EGFR) and Quad 44 (specific for CD38).

Quads 38 and 44 were further developed to include an additional binding arm with the inclusion of a second VH domain specific for EGFR and CD138 respectively yielding Quads 42 and 46. Quads 42 and 46 represent bispecific molecules with the capability to multimerise via the NHR2 TD domain to form bispecific tetramers.

In another example, an effector molecule (human IL2) was linked to the C-terminus of Quads 14 & 15 resulting in Quads 18 and 19, whereby the VH-NHR2-IL2 molecule is tetravalent and bifunctional.

Figure 12B:
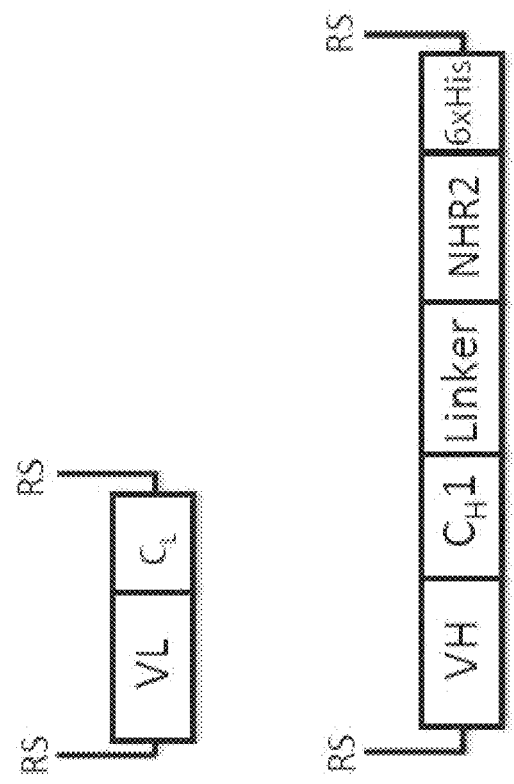
FIG. 12B: A schematic drawing of the domain arrangements for assembly of tetravalent Fabs, including linker and NHR2 domains in the heavy chain, and light chain variable and constant domains.

In another example, antibody Fab fragment (VH-CH1) was linked to NHR2 TD (Quads 23 and 24) and as schematically depicted in FIGS. 12A-12B. Quads 23 and 24 represent tetravalent Fab molecules when co-expressed or mixed and assembled in-vitro with a second chain containing immunoglobulin light chain (e.g. Quad 25).

Figure 13B:
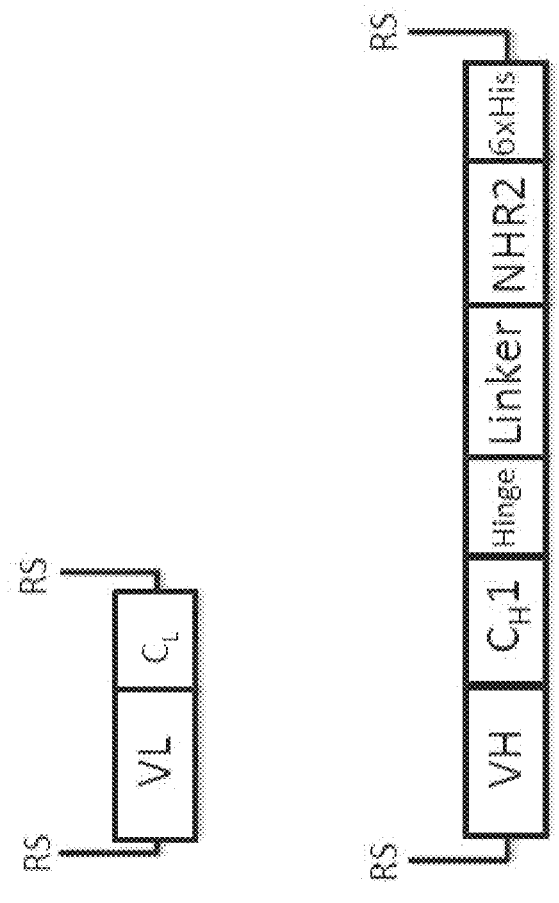
FIG. 13B: A schematic drawing of the domain arrangements for assembly of octavalent Fabs, including hinge, linker and NHR2 domains in the heavy chain, and light chain variable and constant domains.

In yet another example, a human IgG1 hinge domain was included to Quads 23 and 24, which is referred to as Quads 26 and 27 and as schematically depicted in FIGS. 13A-13B. Quads 26 and 27 represent octavalent Fab molecules when co-expressed or mixed and assembled in-vitro with a second chain containing immunoglobulin light chain domains (e.g. Quad 25).

The following Quad vectors, Quads 14, 15, 18, 19, 23, 24, 26, 27, 34, 38, 40, 42, 44 and 46 all of which are His-tagged were transfected in HEK293T cells. Protein samples were prepared from whole-cell extracts as described above, separated out on SDS-PAGE and transferred onto Amersham Hybond 0.45 µM PVDF membrane. Specific protein expression were probed using anti-His HRP (Sigma, A7058) diluted 1/2500 in TBST, 1% milk powder.

Specific protein expression in whole cell extracts could be detected for all the different antibody-NHR2 TD fusion proteins tested using Quads 14, 15, 18, 19, 23, 24, 26, 27, 34, 38, 40, 42, 44 and 46 (FIGS. 19A-19D). Interestingly, Quads 18 and 19 containing an effector domain (IL2) fused to the C-terminus of NHR2 TD domain, in addition to the VH binding domain fused to the N-terminus of NHR2 TD showed good protein expression.

Expression of Quads 23 and 24 polypeptides highlights the potential to use NHR2 TD to form tetravalent antibody Fab molecules when co-expressed or mixed in-vitro with a partner soluble Quad molecule (e.g. Quad 25). Similarly expression of Quads 26 and 27, which include human IgG1 hinge domain highlight the potential to use NHR2 TD to form octavalent antibody Fab molecules when co-expressed or mixed in-vitro with a partner soluble second partner chain (e.g. Quad 25).

Quads 42 and 46 bispecific molecules containing an additional VH domain fused to the C-terminus of NHR2 TD domain also showed good protein expression. These data highlights the versatility of the NHR2 TD domain and its ability to be fused to different binding and effector molecules for developing a vast array of protein formats. The data also suggest it is possible to fuse protein molecules to both the N-terminus and C-terminus of NHR2 TD, which allows for the development of bispecific multivalent protein molecules.

Example 7: Multivalent Assembly of Antibody Fragments Fused to NHR2 TD

NHR2 TD is responsible for the oligomerisation of ETO into a tetrameric complex. Using the NHR2 TD domain, it is possible to fuse binding domains and effector molecules to the N-terminus or C-terminus or both N- and C-terminus without effecting expression as shown in examples 4-6. Binding domains could be TCR variable and constant domains, antibody and antibody fragments or effector molecules such as IL2. It is also possible to express proteins in a soluble format when fused to NHR2 TD (FIGS. 18A-18B) despite NHR2 TD being a part of an intracellularly expressed protein where in nature it is only expressed inside the cell.

To demonstrate whether NHR2 TD retains its potential to oligomerise once it is fused to a binding domain, Quads 14 and 15 were expressed in HEK293T cells and protein samples were prepared from whole cell extracts as described above. Protein samples were separated out on PAGE gel under denaturing and non-denaturing (native) conditions. Native gels were prepared using the protocol described above, but without SDS. Proteins from PAGE gels were transferred onto Amersham Hybond 0.45 µM PVDF membrane. Specific protein expression was probed with anti-human IgG HRP detection antibody.

As expected under denaturing conditions, expression of VH-NHR2 TD from Quads 14 and 15 can be seen as a monomer where a specific protein band can be detected at the expected molecular weight (22 and 22.3 kDa) (FIG. 20A). Under non-denaturing and thus native conditions, interestingly no monomer or dimer of VH-NHR2 TD from Quads 14 and 15 can be detected (FIG. 20B). Only a high molecular weight protein band believed to be tetramers of VH-NHR2 TD from Quads 14 and 15 can be detected. The assembly of tetramers appears to be highly efficient and pure judging by the protein intensity and the absence of any detectable monomers and dimers of Quads 14 and 15.

Together with the data in examples 4-7, there is conclusive evidence NHR2 TD is highly versatile allowing fusion of various protein binding domains and effector molecules. NHR2 TD allows soluble expression of proteins from eukaryotic cells such as HEK293T cells and they form highly stable and pure tetrameric molecules.

REFERENCES

Ali, S. A. et al., 1999. Transferrin Trojan Horses as a Rational Approach for the Biological Delivery of Therapeutic Peptide Domains. *Journal of Biological Chemistry*, 274(34), pp. 24066-24073.

Barbas et al. (1992) supra

Bentley, G. A. & Mariuzza, R. A., 1996. THE STRUCTURE OF THE T CELL ANTIGEN RECEPTOR. *Annual Review of Immunology*, 14(1), pp. 563-590.

Binz, H. K. et al., 2003. Designing repeat proteins: well-expressed, soluble and stable proteins from combinatorial libraries of consensus ankyrin repeat proteins. *Journal of molecular biology*, 332(2), pp. 489-503.

Bixby, K. A. et al., 1999. Zn2+-binding and molecular determinants of tetramerization in voltage-gated K+ channels. *Nature structural biology*, 6(1), pp. 38-43.

Borghouts, C., Kunz, C. & Groner, B., 2005. Peptide aptamers: recent developments for cancer therapy. *Expert Opinion on Biological Therapy*, 5(6), pp. 783-797.

Breitling, F. et al., 1991. A surface expression vector for antibody screening. *Gene*, 104(2), pp. 147-53.

Burton, D. R. et al., 1991. A large array of human monoclonal antibodies to type 1 human immunodeficiency virus from combinatorial libraries of asymptomatic seropositive individuals. Proceedings of the National Academy of Sciences of the United States of America, 88(22), pp. 10134-7.

Chang, C. N., Landolfi, N. F. & Queen, C., 1991. Expression of antibody Fab domains on bacteriophage surfaces. Potential use for antibody selection. *Journal of immunology* (Baltimore, Md.: 1950), 147(10), pp. 3610-4.

Chaudhary, V. K. et al., 1990. A rapid method of cloning functional variable-region antibody genes in *Escherichia coli* as single-chain immunotoxins. Proceedings of the National Academy of Sciences, 87(3), pp. 1066-1070.

Chiswell, D. J. & McCafferty, J., 1992. Phage antibodies: will new "coliclonal" antibodies replace monoclonal antibodies? *Trends in biotechnology*, 10(3), pp. 80-4.

Clackson, T. et al., 1991. Making antibody fragments using phage display libraries. *Nature*, 352(6336), pp. 624-8.

Davis, M. M. & Bjorkman, P. J., 1988. T-cell antigen receptor genes and T-cell recognition. *Nature*, 334(6181), pp. 395-402.

Ding, X.-F. et al., 2008. Characterization and Expression of a Human KCTD1 Gene Containing the BTB Domain, Which Mediates Transcriptional Repression and Homomeric Interactions. *DNA and Cell Biology*, 27(5), pp. 257-265.

Fujiwara, Y. & Minor, D. L., 2008. X-ray Crystal Structure of a TRPM Assembly Domain Reveals an Antiparallel Four-stranded Coiled-coil. *Journal of Molecular Biology*, 383(4), pp. 854-870.

Hawkins, R. E. & Winter, G., 1992. Cell selection strategies for making antibodies from variable gene libraries: trapping the memory pool. *European journal of immunology*, 22(3), pp. 867-70.

Herrin, B. R. & Cooper, M. D., 2010. Alternative adaptive immunity in jawless vertebrates. *Journal of immunology* (Baltimore, Md.: 1950), 185(3), pp. 1367-74.

Hoogenboom, H. R. et al., 1991. Multi-subunit proteins on the surface of filamentous phage: methodologies for displaying antibody (Fab) heavy and light chains. *Nucleic acids research*, 19(15), pp. 4133-7.

Hosse, R. J., Rothe, A. & Power, B. E., 2006. *A new generation of protein display scaffolds for molecular recognition. Protein science: a publication of the Protein Society*, 15(1), pp. 14-27.

Irving, R. A. et al., 2001. Ribosome display and affinity maturation: from antibodies to single V-domains and steps towards cancer therapeutics. *Journal of immunological methods*, 248(1-2), pp. 31-45.

Jeffrey, P. D., Gorina, S. & Pavletich, N. P., 1995. *Crystal structure of the tetramerization domain of the p53 tumor suppressor at* 1.7 angstroms. Science (New York, N.Y.), 267(5203), pp. 1498-502.

Kang, A. S. et al., 1991. *Linkage of recognition and replication functions by assembling combinatorial antibody Fab libraries along phage surfaces.* Proceedings of the National Academy of Sciences, 88(10), pp. 4363-4366.

Kohl, A. et al., 2003. *Designed to be stable: Crystal structure of a consensus ankyrin repeat protein.* Proceedings of the National Academy of Sciences, 100(4), pp. 1700-1705.

Lerner, R. A. et al., 1992. Antibodies without immunization. Science (New York, N.Y.), 258(5086), pp. 1313-4.

Liu, Y. et al., 2006. The tetramer structure of the Nervy homology two domain, NHR2, is critical for AML1/ETO's activity. *Cancer Cell,* 9(4), pp. 249-260.

Lowman, H. B. et al., 1991. Selecting high-affinity binding proteins by monovalent phage display. *Biochemistry,* 30(45), pp. 10832-8.

Marks et al. (1991) supra

Marks, J. D. et al., 1991. By-passing immunization. Human antibodies from V-gene libraries displayed on phage. *Journal of molecular biology,* 222(3), pp. 581-97.

Marks, J. D. et al., 1992. Molecular evolution of proteins on filamentous phage. Mimicking the strategy of the immune system. *The Journal of biological chemistry,* 267(23), pp. 16007-10.

McCafferty et al. (1990) supra

McCafferty, J. et al., 1990. Phage antibodies: filamentous phage displaying antibody variable domains. *Nature,* 348 (6301), pp. 552-4.

Moysey, R., Vuidepot, A.-L. & Boulter, J. M., 2004. Amplification and one-step expression cloning of human T cell receptor genes. *Analytical biochemistry,* 326(2), pp. 284-6.

Panowski, S. et al., 2014. Site-specific antibody drug conjugates for cancer therapy. *mAbs,* 6(1), pp. 34-45.

Parker, M. H. et al., 2005. Antibody mimics based on human fibronectin type three domain engineered for thermostability and high-affinity binding to vascular endothelial growth factor receptor two. *Protein engineering, design & selection: PEDS,* 18(9), pp. 435-44.

Perez, H. L. et al., 2014. Antibody-drug conjugates: Current status and future directions. *Drug Discovery Today,* 19(7), pp. 869-881.

Reddy Chichili, V. P., Kumar, V. & Sivaraman, J., 2013. Linkers in the structural biology of protein-protein interactions. *Protein science: a publication of the Protein Society,* 22(2), pp. 153-67.

Shao, C.-Y., Secombes, C. J. & Porter, A. J., 2007. Rapid isolation of IgNAR variable single-domain antibody fragments from a shark synthetic library. *Molecular immunology,* 44(4), pp. 656-65.

Silverman, J. et al., 2005. Multivalent avimer proteins evolved by exon shuffling of a family of human receptor domains. *Nature* Biotechnology, 23(12), pp. 1556-1561.

Skerra, A., 2000. Lipocalins as a scaffold. *Biochimica et Biophysica Acta (BBA)—Protein Structure and Molecular Enzymology,* 1482(1-2), pp. 337-350.

Thie, H. et al., 2009. Multimerization domains for antibody phage display and antibody production. *New biotechnology,* 26(6), pp. 314-21.

Tonegawa, S., 1988. Somatic generation of immune diversity. *Bioscience reports,* 8(1), pp. 3-26.

Wälchli, S. et al., 2011. A Practical Approach to T-Cell Receptor Cloning and Expression M. M. Rodrigues, ed. *PLoS ONE,* 6(11), p.e27930.

Wikman, M. et al., 2004. Selection and characterization of HER2/neu-binding affibody ligands. *Protein Engineering Design and Selection,* 17(5), pp. 455-462.

Young, P. A., Morrison, S. L. & Timmerman, J. M., 2014. Antibody-cytokine fusion proteins for treatment of cancer: Engineering cytokines for improved efficacy and safety. *Seminars in Oncology,* 41(5), pp. 623-636.

Zahnd, C. et al., 2007. A designed ankyrin repeat protein evolved to picomolar affinity to Her2. *Journal of molecular biology,* 369(4), pp. 1015-28.

Zhang, J. et al., 2009. Transient expression and purification of chimeric heavy chain antibodies. *Protein Expression and Purification,* 65(1), pp. 77-82.

Expert Opinion on Investigational Drugs 16(6) 909-917 (June 2007)

Chapter 7—Non-Antibody Scaffolds from *Handbook of Therapeutic Antibodies* (2007, edited by Stefan Dubel)

TABLE 1

SEQUENCE LISTING

| SEQ ID NO: | | AMINO ACID SEQUENCE | NOTES |
|---|---|---|---|
| 1 | Human p53 isoform 1 | MEEPQSDPSVEPPLSQETFSDLWKLLPENN VLSPLPSQAMDDLMLSPDDIEQWFTEDPGP DEAPRMPEAAPPVAPAPAAPTPAAPAPAPS WPLSSSVPSQKTYQGSYGFRLGFLHSGTAK SVTCTYSPALNKMFCQLAKTCPVQLWVDST PPPGTRVRAMAIYKQSQHMTEVVRRCPHHE RCSDSDGLAPPQHLIRVEGNLRVEYLDDRN TFRHSVVVPYEPPEVGSDCTTIHYNYMCNS SCMGGMNRRPILTIITLEDSSGNLLGRNSF EVRVCACPGRDRRTEEENLRKKGEPHHELP PGSTKRALPNNTSSSPQPKKKPLDGEYFTL QIRGRERFEMFRELNEALELKDAQAGKEPG GSRAHSSHLKSKKGQSTSRHKKLMFKTEGP DSD | Also known as: p53, p53alpha This isoform is denoted as the 'canonical' sequence. Tetramerization sequence in underline bold (amino acid position numbers 325 to 356) |
| 2 | Human p53 isoform 2 | MEEPQSDPSVEPPLSQETFSDLWKLLPENN VLSPLPSQAMDDLMLSPDDIEQWFTEDPGP DEAPRMPEAAPPVAPAPAAPTPAAPAPAPS WPLSSSVPSQKTYQGSYGFRLGFLHSGTAK SVTCTYSPALNKMFCQLAKTCPVQLWVDST PPPGTRVRAMAIYKQSQHMTEVVRRCPHHE RCSDSDGLAPPQHLIRVEGNLRVEYLDDRN | Also known as: I9RET, p53beta The sequence of this isoform differs from the canonical sequence (isoform 1) as follows: 332-341: IRGRERFEMF → |

TABLE 1-continued

SEQUENCE LISTING

| SEQ ID NO: | | AMINO ACID SEQUENCE | NOTES |
|---|---|---|---|
| | | TFRHSVVVPYEPPEVGSDCTTIHYNYMCNS SCMGGMNRRPILTIITLEDSSGNLLGRNSF EVRVCACPGRDRRTEEENLRKKGEPHHELP PGSTKRALPNNTSSSPQPKKKPLDGEYFTL QDQTSFQKENC | DQTSFQKENC 342-393: Missing. |
| 3 | Human p53 isoform 3 | MEEPQSDPSVEPPLSQETFSDLWKLLPENN VLSPLPSQAMDDLMLSPDDIEQWFTEDPGP DEAPRMPEAAPPVAPAPAAPTPAAPAPAPS WPLSSSVPSQKTYQGSYGFRLGFLHSGTAK SVTCTYSPALNKMFCQLAKTCPVQLWVDST PPPGTRVRAMAIYKQSQHMTEVVRRCPHHE RCSDSDGLAPPQHLIRVEGNLRVEYLDDRN TFRHSVVVPYEPPEVGSDCTTIHYNYMCNS SCMGGMNRRPILTIITLEDSSGNLLGRNSF EVRVCACPGRDRRTEEENLRKKGEPHHELP PGSTKRALPNNTSSSPQPKKKPLDGEYFTL QMLLDLRWCYFLINSS | Also known as: p53gamma The sequence of this isoform differs from the canonical sequence as follows: 332-346: IRGRERFEMFRELNE → MLLDLRWCYFLINSS 347-393: Missing |
| 4 | Human p53 isoform 4 | MDDLMLSPDDIEQWFTEDPGPDEAPRMPEA APPVAPAPAAPTPAAPAPAPSWPLSSSVPS QKTYQGSYGFRLGFLHSGTAKSVTCTYSPA LNKMFCQLAKTCPVQLWVDSTPPPGTRVRA MAIYKQSQHMTEVVRRCPHHERCSDSDGLA PPQHLIRVEGNLRVEYLDDRNTFRHSVVVP YEPPEVGSDCTTIHYNYMCNSSCMGGMNRR PILTIITLEDSSGNLLGRNSFEVRVCACPG RDRRTEEENLRKKGEPHHELPPGSTKRALP NNTSSSPQPKKKPLDGEYFTLQIRGRERFE MFRELNEALELKDAQAGKEPGGSRAHSSHL KSKKGQSTSRHKKLMFKTEGPDSD | Also known as: Del40-p53, Del40-p53alpha, p47 The sequence of this isoform differs from the canonical sequence as follows: 1-39: Missing. |
| 5 | Human p53 isoform 5 | MDDLMLSPDDIEQWFTEDPGPDEAPRMPEA APPVAPAPAAPTPAAPAPAPSWPLSSSVPS QKTYQGSYGFRLGFLHSGTAKSVTCTYSPA LNKMFCQLAKTCPVQLWVDSTPPPGTRVRA MAIYKQSQHMTEVVRRCPHHERCSDSDGLA PPQHLIRVEGNLRVEYLDDRNTFRHSVVVP YEPPEVGSDCTTIHYNYMCNSSCMGGMNRR PILTIITLEDSSGNLLGRNSFEVRVCACPG RDRRTEEENLRKKGEPHHELPPGSTKRALP NNTSSSPQPKKKPLDGEYFTLQDQTSFQKE NC | Also known as: Del40-p53beta. The sequence of this isoform differs from the canonical sequence as follows: 1-39: Missing. 332-341: IRGRERFEMF → DQTSFQKENC 342-393: Missing. |
| 6 | Human p53 isoform 6 | MDDLMLSPDDIEQWFTEDPGPDEAPRMPEA APPVAPAPAAPTPAAPAPAPSWPLSSSVPS QKTYQGSYGFRLGFLHSGTAKSVTCTYSPA LNKMFCQLAKTCPVQLWVDSTPPPGTRVRA MAIYKQSQHMTEVVRRCPHHERCSDSDGLA PPQHLIRVEGNLRVEYLDDRNTFRHSVVVP YEPPEVGSDCTTIHYNYMCNSSCMGGMNRR PILTIITLEDSSGNLLGRNSFEVRVCACPG RDRRTEEENLRKKGEPHHELPPGSTKRALP NNTSSSPQPKKKPLDGEYFTLQMLLDLRWC YFLINSS | Also known as: Del40-p53gamma. The sequence of this isoform differs from the canonical sequence as follows: 1-39: Missing. 332-346: IRGRERFEMFRELNE → MLLDLRWCYFLINSS 347-393: Missing. |
| 7 | Human p53 isoform 7 | MFCQLAKTCPVQLWVDSTPPPGTRVRAMAI YKQSQHMTEVVRRCPHHERCSDSDGLAPPQ HLIRVEGNLRVEYLDDRNTFRHSVVVPYEP PEVGSDCTTIHYNYMCNSSCMGGMNRRPIL TIITLEDSSGNLLGRNSFEVRVCACPGRDR RTEEENLRKKGEPHHELPPGSTKRALPNNT SSSPQPKKKPLDGEYFTLQIRGRERFEMFR ELNEALELKDAQAGKEPGGSRAHSSHLKSK KGQSTSRHKKLMFKTEGPDSD | Also known as: Del133-p53, Del133-p53alpha. The sequence of this isoform differs from the canonical sequence as follows: 1-132: Missing. |
| 8 | Human p53 isoform 8 | MFCQLAKTCPVQLWVDSTPPPGTRVRAMAI YKQSQHMTEVVRRCPHHERCSDSDGLAPPQ HLIRVEGNLRVEYLDDRNTFRHSVVVPYEP PEVGSDCTTIHYNYMCNSSCMGGMNRRPIL TIITLEDSSGNLLGRNSFEVRVCACPGRDR RTEEENLRKKGEPHHELPPGSTKRALPNNT SSSPQPKKKPLDGEYFTLQDQTSFQKENC | Also known as: Del133-p53beta. The sequence of this isoform differs from the canonical sequence as follows: 1-132: Missing. 332-341: IRGRERFEMF → DQTSFQKENC 342-393: Missing. |

TABLE 1-continued

SEQUENCE LISTING

| SEQ ID NO: | | AMINO ACID SEQUENCE | NOTES |
|---|---|---|---|
| 9 | Human p53 isoform 9 | MFCQLAKTCPVQLWVDSTPPPGTRVRAMAI YKQSQHMTEVVRRCPHHERCSDSDGLAPPQ HLIRVEGNLRVEYLDDRNTFRHSVVVPYEP PEVGSDCTTIHYNYMCNSSCMGGMNRRPIL TIITLEDSSGNLLGRNSFEVRVCACPGRDR RTEEENLRKKGEPHHELPPGSTKRALPNNT SSSPQPKKKPLDGEYFTLQMLLDLRWCYFL INSS | Also known as: Del133-p53gamma. The sequence of this isoform differs from the canonical sequence as follows: 1-132: Missing. 332-346: IRGRERFEMFRELNE → MLLDLRWCYFLINSS 347-393: Missing. |
| 10 | A human p53-TD | GEYFTLQIRGRERFEMFRELNEALELKDAQ AG | |
| 11 | A human p63-TD | RSPDDELLYLPVRGRETYEMLLKIKESLEL MQYLPQHTIETYRQQQQQH | |
| 12 | A human p73-TD | KKRRHGDEDTYYLQVRGRENFEILMKLKES LELMELVPQPLV | |

TABLE 2

Example Human Proteins Comprising a Tetramerization Domain

| Protein Number | Uniprot Entry | Entry name | Protein names | Gene names |
|---|---|---|---|---|
| 1 | P04637 | P53_HUMAN | Cellular tumor antigen p53 (Antigen NY-CO-13) (Phosphoprotein p53) (Tumor suppressor p53) | TP53 P53 |
| 2 | Q719H9 | KCTD1_HUMAN | BTB/POZ domain-containing protein KCTD1 (Potassium channel tetramerization domain-containing protein 1) | KCTD1 C18orf5 |
| 3 | P51787 | KCNQ1_HUMAN | Potassium voltage-gated channel subfamily KQT member 1 (IKs producing slow voltage-gated potassium channel subunit alpha KvLQT1) (KQT-like 1) (Voltage-gated potassium channel subunit Kv7.1) | KCNQ1 KCNA8 KCNA9 KVLQT1 |
| 4 | Q06455 | MTG8_HUMAN | Protein CBFA2T1 (Cyclin-D-related protein) (Eight twenty one protein) (Protein ETO) (Protein MTG8) (Zinc finger MYND domain-containing protein 2) | RUNX1T1 AML1T1 CBFA2T1 CDR ETO MTG8 ZMYND2 |
| 5 | Q9H3F6 | BACD3_HUMAN | BTB/POZ domain-containing adapter for CUL3-mediated RhoA degradation protein 3 (hBACURD3) (BTB/POZ domain-containing protein KCTD10) (Potassium channel tetramerization domain-containing protein 10) | KCTD10 ULR061 MSTP028 |
| 6 | Q12809 | KCNH_HUMAN | Potassium voltage-gated channel subfamily H member 2 (Eag homolog) (Ether-a-go-go-related gene potassium channel 1) (ERG-1) (Eag-related protein 1) (Ether-a-go-go-related protein 1) (H-ERG) (hERG-1) (hERG1) (Voltage-gated potassium channel subunit Kv11.1) | KCNH2 ERG ERG1 HERG |
| 7 | Q96SI1 | KCD15_HUMAN | BTB/POZ domain-containing protein KCTD15 (Potassium channel tetramerization domain-containing protein 15) | KCTD15 |
| 8 | P02766 | TTHY_HUMAN | Transthyretin (ATTR) (Prealbumin) (TBPA) | TTR PALB |
| 9 | Q14681 | KCD2_HUMAN | BTB/POZ domain-containing protein KCTD2 (Potassium channel tetramerization domain-containing protein 2) | KCTD2 KIAA0176 |
| 10 | Q7Z5Y7 | KCD20_HUMAN | BTB/POZ domain-containing protein KCTD20 (Potassium channel tetramerization domain containing 20) | KCTD20 C6orf69 |
| 11 | P50552 | VASP_HUMAN | Vasodilator-stimulated phosphoprotein (VASP) | VASP |
| 12 | Q68DU8 | KCD16_HUMAN | BTB/POZ domain-containing protein KCTD16 (Potassium channel tetramerization domain-containing protein 16) | KCTD16 KIAA1317 |

TABLE 2-continued

Example Human Proteins Comprising a Tetramerization Domain

| Protein Number | Uniprot Entry | Entry name | Protein names | Gene names |
|---|---|---|---|---|
| 13 | Q09470 | KCNA1_HUMAN | Potassium voltage-gated channel subfamily A member 1 (Voltage-gated K(+) channel HuKI) (Voltage-gated potassium channel HBK1) (Voltage-gated potassium channel subunit Kv1.1) | KCNA1 |
| 14 | P13501 | CCL5_HUMAN | C-C motif chemokine 5 (EoCP) (Eosinophil chemotactic cytokine) (SIS-delta) (Small-inducible cytokine A5) (T cell-specific protein P228) (TCP228) (T-cell-specific protein RANTES) [Cleaved into: RANTES(3-68); RANTES(4-68)] | CCL5 D17S136E SCYA5 |
| 15 | P08069 | IGF1R_HUMAN | Insulin-like growth factor 1 receptor (EC 2.7.10.1) (Insulin-like growth factor I receptor) (IGF-I receptor) (CD antigen CD221) [Cleaved into: Insulin-like growth factor 1 receptor alpha chain; Insulin-like growth factor 1 receptor beta chain] | IGF1R |
| 16 | Q14003 | KCNC3_HUMAN | Potassium voltage-gated channel subfamily C member 3 (KSHIIID) (Voltage-gated potassium channel subunit Kv3.3) | KCNC3 |
| 17 | O15350 | P73_HUMAN | Tumor protein p73 (p53-like transcription factor) (p53-related protein) | TP73 P73 |
| 18 | Q12791 | KCMA1_HUMAN | Calcium-activated potassium channel subunit alpha-1 (BK channel) (BKCA alpha) (Calcium-activated potassium channel, subfamily M subunit alpha-1) (K(VCA)alpha) (KCa1.1) (Maxi K channel) (MaxiK) (Slo-alpha) (Slo1) (Slowpoke homolog) (Slo homolog) (hSlo) | KCNMA1 KCNMA SLO |
| 19 | P42261 | GRIA_HUMAN | Glutamate receptor 1 (GluR-1) (AMPA-selective glutamate receptor 1) (GluR-A) (GluR-K1) (Glutamate receptor ionotropic, AMPA 1) (GluA1) | GRIA1 GLUH1 GLUR1 |
| 20 | P22303 | ACES_HUMAN | Acetylcholinesterase (AChE) (EC 3.1.1.7) | ACHE |
| 21 | P04040 | CATA_HUMAN | Catalase (EC 1.11.1.6) | CAT |
| 22 | Q9H8Y8 | GORS2_HUMAN | Golgi reassembly-stacking protein 2 (GRS2) (Golgi phosphoprotein 6) (GOLPH6) (Golgi reassembly-stacking protein of 55 kDa) (GRASP55) (p59) | GORASP2 GOLPH6 |
| 23 | P34897 | GLYM_HUMAN | Serine hydroxymethyltransferase, mitochondrial (SHMT) (EC 2.1.2.1) (Glycine hydroxymethyltransferase) (Serine methylase) | SHMT2 |
| 24 | P13760 | 2B14_HUMAN | HLA class II histocompatibility antigen, DRB1-4 beta chain (MHC class II antigen DRB1*4) (DR-4) (DR4) | HLA-DRB1 |
| 25 | P04229 | 2B11_HUMAN | HLA class II histocompatibility antigen, DRB1-1 beta chain (MHC class II antigen DRB1*1) (DR-1) (DR1) | HLA-DRB1 |
| 26 | P35914 | HMGCL_HUMAN | Hydroxymethylglutaryl-CoA lyase, mitochondrial (HL) (HMG-CoA lyase) (EC 4.1.3.4) (3-hydroxy-3-methylglutarate-CoA lyase) | HMGCL |
| 27 | Q29974 | 2B1G_HUMAN | HLA class II histocompatibility antigen, DRB1-16 beta chain (MHC class II antigen DRB1*16) (DR-16) (DR16) | HLA-DRB1 |
| 28 | Q9TQE0 | 2B19_HUMAN | HLA class II histocompatibility antigen, DRB1-9 beta chain (MHC class II antigen DRB1*9) (DR-9) (DR9) | HLA-DRB1 |
| 29 | Q9UDR5 | AASS_HUMAN | Alpha-aminoadipic semialdehyde synthase, mitochondrial (LKR/SDH) [Includes: Lysine ketoglutarate reductase (LKR) (LOR) (EC 1.5.1.8); Saccharopine dehydrogenase (SDH) (EC 1.5.1.9)] | AASS |
| 30 | P13761 | 2B17_HUMAN | HLA class II histocompatibility antigen, DRB1-7 beta chain (MHC class II antigen DRB1*7) (DR-7) (DR7) | HLA-DRB1 |
| 31 | P49450 | CENPA_HUMAN | Histone H3-like centromeric protein A (Centromere autoantigen A) (Centromere protein A) (CENP-A) | CENPA |

TABLE 2-continued

Example Human Proteins Comprising a Tetramerization Domain

| Protein Number | Uniprot Entry | Entry name | Protein names | Gene names |
|---|---|---|---|---|
| 32 | Q9Y2W7 | CSEN_HUMAN | Calsenilin (A-type potassium channel modulatory protein 3) (DRE-antagonist modulator) (DREAM) (Kv channel-interacting protein 3) (KChIP3) | KCNIP3 CSEN DREAM KCHIP3 |
| 33 | Q16630 | CPSF6_HUMAN | Cleavage and polyadenylation specificity factor subunit 6 (Cleavage and polyadenylation specificity factor 68 kDa subunit) (CFIm68) (CPSF 68 kDa subunit) (Pre-mRNA cleavage factor Im 68 kDa subunit) (Protein HPBRII-4/7) | CPSF6 CFIM68 |
| 34 | O43809 | CPSF5_HUMAN | Cleavage and polyadenylation specificity factor subunit 5 (Cleavage and polyadenylation specificity factor 25 kDa subunit) (CFIm25) (CPSF 25 kDa subunit) (Nucleoside diphosphate-linked moiety X motif 21) (Nudix motif 21) (Pre-mRNA cleavage factor Im 25 kDa subunit) | NUDT21 CFIM25 CPSF25 CPSF5 |
| 35 | Q8N684 | CPSF7_HUMAN | Cleavage and polyadenylation specificity factor subunit 7 (Cleavage and polyadenylation specificity factor 59 kDa subunit) (CFIm59) (CPSF 59 kDa subunit) (Pre-mRNA cleavage factor Im 59 kDa subunit) | CPSF7 |
| 36 | Q14999 | CUL7_HUMAN | Cullin-7 (CUL-7) | CUL7 KIAA0076 |
| 37 | Q9UI08 | EVL_HUMAN | Ena/VASP-like protein (Ena/vasodilator-stimulated phosphoprotein-like) | EVL RNB6 |
| 38 | Q05193 | DYN1_HUMAN | Dynamin-1 (EC 3.6.5.5) | DNM1 DNM |
| 39 | Q8N8S7 | ENAH_HUMAN | Protein enabled homolog | ENAH MENA |
| 40 | Q96PP8 | GBP5_HUMAN | Guanylate-binding protein 5 (EC 3.6.5.-) (GBP-TA antigen) (GTP-binding protein 5) (GBP-5) (Guanine nucleotide-binding protein 5) | GBP5 UNQ2427/ PRO4987 |
| 41 | Q92947 | GCDH_HUMAN | Glutaryl-CoA dehydrogenase, mitochondrial (GCD) (EC 1.3.8.6) | GCDH |
| 42 | Q13614 | MTMR2_HUMAN | Myotubularin-related protein 2 (Phosphatidylinositol-3,5-bisphosphate 3-phosphatase) (EC 3.1.3.95) (Phosphatidylinositol-3-phosphate phosphatase) (EC 3.1.3.64) | MTMR2 KIAA1073 |
| 43 | Q99784 | NOE1_HUMAN | Noelin (Neuronal olfactomedin-related ER localized protein) (Olfactomedin-1) | OLFM1 NOE1 NOEL1 |
| 44 | P50542 | PEX5_HUMAN | Peroxisomal targeting signal 1 receptor (PTS1 receptor) (PTS1R) (PTS1-BP) (Peroxin-5) (Peroxisomal C-terminal targeting signal import receptor) (Peroxisome receptor 1) | PEX5 PXR1 |
| 45 | P42262 | GRIA2_HUMAN | Glutamate receptor 2 (GluR-2) (AMPA-selective glutamate receptor 2) (GluR-B) (GluR-K2) (Glutamate receptor ionotropic, AMPA 2) (GluA2) | GRIA2 GLUR2 |
| 46 | P48058 | GRIA4_HUMAN | Glutamate receptor 4 (GluR-4) (GluR4) (AMPA-selective glutamate receptor 4) (GluR-D) (Glutamate receptor ionotropic, AMPA 4) (GluA4) | GRIA4 GLUR4 |
| 47 | P42263 | GRIA3_HUMAN | Glutamate receptor 3 (GluR-3) (AMPA-selective glutamate receptor 3) (GluR-C) (GluR-K3) (Glutamate receptor ionotropic, AMPA 3) (GluA3) | GRIA3 GLUR3 GLURC |
| 48 | O60741 | HCN1_HUMAN | Potassium/sodium hyperpolarization-activated cyclic nucleotide-gated channel 1 (Brain cyclic nucleotide-gated channel 1) (BCNG-1) | HCN1 BCNG1 |
| 49 | Q9UL51 | HCN2_HUMAN | Potassium/sodium hyperpolarization-activated cyclic nucleotide-gated channel 2 (Brain cyclic nucleotide-gated channel 2) (BCNG-2) | HCN2 BCNG2 |
| 50 | Q9Y3Q4 | HCN4_HUMAN | Potassium/sodium hyperpolarization-activated cyclic nucleotide-gated channel 4 | HCN4 |

TABLE 2-continued

Example Human Proteins Comprising a Tetramerization Domain

| Protein Number | Uniprot Entry | Entry name | Protein names | Gene names |
|---|---|---|---|---|
| 51 | P04035 | HMDH_HUMAN | 3-hydroxy-3-methylglutaryl-coenzyme A reductase (HMG-CoA reductase) (EC 1.1.1.34) | HMGCR |
| 52 | Q8NCD3 | HJURP_HUMAN | Holliday junction recognition protein (14-3-3-associated AKT substrate) (Fetal liver-expressing gene 1 protein) (Up-regulated in lung cancer 9) | HJURP FAKTS FLEG1 URLC9 |
| 53 | Q9NZV8 | KCND2_HUMAN | Potassium voltage-gated channel subfamily D member 2 (Voltage-gated potassium channel subunit Kv4.2) | KCND2 KIAA1044 |
| 54 | P48547 | KCNC1_HUMAN | Potassium voltage-gated channel subfamily C member 1 (NGK2) (Voltage-gated potassium channel subunit Kv3.1) (Voltage-gated potassium channel subunit Kv4) | KCNC1 |
| 55 | Q96CX2 | KCD12_HUMAN | BTB/POZ domain-containing protein KCTD12 (Pfetin) (Predominantly fetal expressed T1 domain) | KCTD12 C13orf2 KIAA1778 PFET1 |
| 56 | P16389 | KCNA_HUMAN | Potassium voltage-gated channel subfamily A member 2 (NGK1) (Voltage-gated K(+) channel HuKIV) (Voltage-gated potassium channel HBK5) (Voltage-gated potassium channel subunit Kv1.2) | KCNA2 |
| 57 | P56696 | KCNQ4_HUMAN | Potassium voltage-gated channel subfamily KQT member 4 (KQT-like 4) (Potassium channel subunit alpha KvLQT4) (Voltage-gated potassium channel subunit Kv7.4) | KCNQ4 |
| 58 | Q9NXV2 | KCTD5_HUMAN | BTB/POZ domain-containing protein KCTD5 | KCTD5 |
| 59 | Q14721 | KCNB1_HUMAN | Potassium voltage-gated channel subfamily B member 1 (Delayed rectifier potassium channel 1) (DRK1) (h-DRK1) (Voltage-gated potassium channel subunit Kv2.1) | KCNB1 |
| 60 | Q86WG5 | MTMRD_HUMAN | Myotubularin-related protein 13 (SET-binding factor 2) | SBF2 CMT4B2 KIAA1766 MTMR13 |
| 61 | Q15070 | OXA1L_HUMAN | Mitochondrial inner membrane protein OXA1L (Hsa) (OXA1Hs) (Oxidase assembly 1-like protein) (OXA1-like protein) | OXA1L |
| 62 | P11498 | PYC_HUMAN | Pyruvate carboxylase, mitochondrial (EC 6.4.1.1) (Pyruvic carboxylase) (PCB) | PC |
| 63 | P33764 | S10A3_HUMAN | Protein S100-A3 (Protein S-100E) (S100 calcium-binding protein A3) | S100A3 S100E |
| 64 | P58743 | S26A5_HUMAN | Prestin (Solute carrier family 26 member 5) | SLC26A5 PRES |
| 65 | Q9UIL1 | SCOC_HUMAN | Short coiled-coil protein | SCOC SCOCO HRIHFB2072 |
| 66 | P02549 | SPTA1_HUMAN | Spectrin alpha chain, erythrocytic 1 (Erythroid alpha-spectrin) | SPTA1 SPTA |
| 67 | Q96QT4 | TRPM7_HUMAN | Transient receptor potential cation channel subfamily M member 7 (EC 2.7.11.1) (Channel-kinase 1) (Long transient receptor potential channel 7) (LTrpC-7) (LTrpC7) | TRPM7 CHAK1 LTRPC7 |
| 68 | Q9HCF6 | TRPM3_HUMAN | Transient receptor potential cation channel subfamily M member 3 (Long transient receptor potential channel 3) (LTrpC-3) (LTrpC3) (Melastatin-2) (MLSN2) | TRPM3 KIAA1616 LTRPC3 |
| 69 | Q7Z4N2 | TRPM1_HUMAN | Transient receptor potential cation channel subfamily M member 1 (Long transient receptor potential channel 1) (LTrpC1) (Melastatin-1) | TRPM1 LTRPC1 MLSN MLSN1 |
| 70 | Q9NQA5 | TRPV5_HUMAN | Transient receptor potential cation channel subfamily V member 5 (TrpV5) (Calcium transport protein 2) (CaT2) (Epithelial calcium channel 1) (ECaC) (ECaC1) (Osm-9-like TRP channel 3) (OTRPC3) | TRPV5 ECAC1 |

TABLE 2-continued

Example Human Proteins Comprising a Tetramerization Domain

| Protein Number | Uniprot Entry | Entry name | Protein names | Gene names |
|---|---|---|---|---|
| 71 | Q9BX84 | TRPM6_HUMAN | Transient receptor potential cation channel subfamily M member 6 (EC 2.7.11.1) (Channel kinase 2) (Melastatin-related TRP cation channel 6) | TRPM6 CHAK2 |
| 72 | P49638 | TTPA_HUMAN | Alpha-tocopherol transfer protein (Alpha-TTP) | TTPA TPP1 |
| 73 | Q8NBZ7 | UXS1_HUMAN | UDP-glucuronic acid decarboxylase 1 (EC 4.1.1.35) (UDP-glucuronate decarboxylase 1) (UGD) (UXS-1) | UXS1 UNQ2538/ PRO6079 |
| 74 | Q13426 | XRCC4_HUMAN | DNA repair protein XRCC4 (X-ray repair cross-complementing protein 4) | XRCC4 |
| 75 | A0A0A6YY98 | A0A0A6YY98_HUMAN | Transient receptor potential cation channel subfamily V member 5 | TRPV5 |
| 76 | H0YLN8 | H0YLN8_HUMAN | Transient receptor potential cation channel subfamily M member 7 (Transient receptor potential cation channel, subfamily M, member 7, isoform CRA_c) | TRPM7 hCG_39859 |
| 77 | A0A0C4DFW9 | A0A0C4DFW9_HUMAN | Cellular tumor antigen p53 | TP73 hCG_19088 |
| 78 | G5E9G1 | G5E9G1_HUMAN | Transient receptor potential cation channel subfamily M member 3 (Transient receptor potential cation channel, subfamily M, member 3, isoform CRA_a) | TRPM3 hCG_2042991 |
| 79 | H7BYP1 | H7BYP1_HUMAN | Transient receptor potential cation channel subfamily M member 3 (Transient receptor potential cation channel, subfamily M, member 3, isoform CRA_c) | TRPM3 hCG_2042991 |
| 80 | A0A024R4C3 | A0A024R4C3_HUMAN | Tumor protein p73, isoform CRA_a | TP73 hCG_19088 |
| 81 | A0A0S2Z4N5 | A0A0S2Z4N5_HUMAN | Tumor protein p63 isoform 1 (Tumor protein p73-like, isoform CRA_a) (Fragment) | TP63 TP73L hCG_16028 |
| 82 | A0A024R5V1 | A0A024R5V1_HUMAN | Transient receptor potential cation channel, subfamily M, member 7, isoform CRA_a | TRPM7 hCG_39859 |
| 83 | X5D8S6 | X5D8S6_HUMAN | Adenylosuccinate lyase (ASL) (EC 4.3.2.2) (Adenylosuccinase) (Fragment) | ADSL hCG_40060 |
| 84 | C9D7D0 | C9D7D0_HUMAN | Cellular tumor antigen p53 | TP63 |
| 85 | K7PPA8 | K7PPA8_HUMAN | Cellular tumor antigen p53 | TP53 |
| 86 | A2A3F4 | A2A3F4_HUMAN | Transient receptor potential cation channel subfamily M member 3 | TRPM3 |
| 87 | Q2XSC7 | Q2XSC7_HUMAN | Cellular tumor antigen p53 | TP53 |
| 88 | A0A024R209 | A0A024R209_HUMAN | Transient receptor potential cation channel, subfamily M, member 1, isoform CRA_a | TRPM1 hCG_37570 |
| 89 | Q1MSX0 | Q1MSX0_HUMAN | Cellular tumor antigen p53 (Fragment) | TP53 |
| 90 | A0A0G2JN34 | A0A0G2JN34_HUMAN | Transient receptor potential cation channel subfamily M member 1 | TRPM1 |
| 91 | H6U5S3 | H6U5S3_HUMAN | Cellular tumor antigen p53 (Fragment) | |
| 92 | H2EHT1 | H2EHT1_HUMAN | Cellular tumor antigen p53 | TP53 |
| 93 | H6U5S2 | H6U5S2_HUMAN | Cellular tumor antigen p53 (Fragment) | |
| 94 | B4DNI2 | B4DNI2_HUMAN | Cellular tumor antigen p53 | |
| 95 | C9D7C9 | C9D7C9_HUMAN | Cellular tumor antigen p53 | TP63 |
| 96 | B6E4X6 | B6E4X6_HUMAN | Cellular tumor antigen p53 | |
| 97 | A0A087WZU8 | A0A087WZU8_HUMAN | Cellular tumor antigen p53 | TP53 |

TABLE 2-continued

Example Human Proteins Comprising a Tetramerization Domain

| Protein Number | Uniprot Entry | Entry name | Protein names | Gene names |
|---|---|---|---|---|
| 98 | K7PPU4 | K7PPU4_HUMAN | Cellular tumor antigen p53 | TP53 |
| 99 | A0A0U1RQC9 | A0A0U1RQC9_HUMAN | Cellular tumor antigen p53 | TP53 |
| 100 | Q5U0E4 | Q5U0E4_HUMAN | Cellular tumor antigen p53 | |
| 101 | Q53GA5 | Q53GA5_HUMAN | Cellular tumor antigen p53 (Fragment) | |
| 102 | A2A3F7 | A2A3F7_HUMAN | Transient receptor potential cation channel subfamily M member 3 | TRPM3 |
| 103 | B4DMH2 | B4DMH2_HUMAN | Cellular tumor antigen p53 | |
| 104 | B7Z8X6 | B7Z8X6_HUMAN | Cellular tumor antigen p53 | |
| 105 | A0A141PNN3 | A0A141PNN3_HUMAN | Cellular tumor antigen p53 | TP63 |
| 106 | A0A141PNN4 | A0A141PNN4_HUMAN | Cellular tumor antigen p53 | TP63 |
| 107 | A0A087X1Q1 | A0A087X1Q1_HUMAN | Cellular tumor antigen p53 | TP53 |
| 108 | E5RMA8 | E5RMA8_HUMAN | Cellular tumor antigen p53 | TP53 |
| 109 | A0A0S2Z4N6 | A0A0S2Z4N6_HUMAN | Tumor protein p63 isoform 2 (Fragment) | TP63 |
| 110 | E9PBI7 | E9PBI7_HUMAN | Transient receptor potential cation channel subfamily M member 3 | TRPM3 |
| 111 | A0A0G2JMR4 | A0A0G2JMR4_HUMAN | Transient receptor potential cation channel subfamily M member 1 | TRPM1 |
| 112 | Q9H637 | Q9H637_HUMAN | cDNA: FLJ22628 fis, clone HSI06177 | |
| 113 | A0A0G2JPN6 | A0A0G2JPN6_HUMAN | Transient receptor potential cation channel subfamily M member 1 | TRPM1 |
| 114 | A0A024R212 | A0A024R212_HUMAN | Transient receptor potential cation channel, subfamily M, member 1, isoform CRA_b | TRPM1 hCG_37570 |
| 115 | A0A0G2JMJ5 | A0A0G2JMJ5_HUMAN | Transient receptor potential cation channel subfamily M member 1 | TRPM1 |
| 116 | H0YM61 | H0YM61_HUMAN | Transient receptor potential cation channel subfamily M member 1 (Fragment) | TRPM1 |
| 117 | H0YKU7 | H0YKU7_HUMAN | Transient receptor potential cation channel subfamily M member 1 (Fragment) | TRPM1 |
| 118 | A0A0A0MTQ9 | A0A0A0MTQ9_HUMAN | Transient receptor potential cation channel subfamily M member 1 (Fragment) | TRPM1 |
| 119 | A2A3F3 | A2A3F3_HUMAN | Transient receptor potential cation channel subfamily M member 3 | TRPM3 |

The amino acid and nucleotide sequences of each of these proteins and the TD thereof is incorporated herein by reference for use in the present invention and for potential inclusion in one or more claims herein.

TABLE 3

DNA sequences encoding Quad polypeptides

| SEQ ID NO: | POLYPEPTIDE | NUCLEOTIDE SEQUENCE |
|---|---|---|
| 13 | Quad 1 | ATGAGCCTCGGGCTCCTGTGCTGTGGGGCCTTTTCTCTCCTGTGGGCAGGTCCA GTGAATGCCGGTGTCACTCAGACCCCAAAATTCCAGGTCCTGAAGACAGGACAGAGCATG ACACTGCAGTGTGCCCAGGATATGAACCATGAATACATGTCCTGGTATCGACAAGACCCA GGCATGGGGCTGAGGCTGATTCATTACTCAGTTGCCATCCAGACAACTGACCAAGGAGAA GTCCCCAATGGCTACAATGTCTCCAGATCAACCATCGAGGATTTCCCGCTCAGGCTGCTG TCGGCTGCTCCCTCCCAGACATCTGTGTACTTCTGTGCCAGCAGTTACCTGGGGAACACC GGGGAGCTGTTTTTTGGAGAAGGCTCTAGGCTGACCGTACTGGAGGACCTGAAAAACGTG TTCCCACCCGAGGTCGCTGTGTTTGAGCCATCAGAAGCAGAGATCTCCCACACCCAAAAG GCCACACTGGTGTGCCTGGCCACAGGCTTCTACCCCGACCATGTGGAGCTGAGCTGGTGG GTGAATGGGAAGGAGGTGCACAGTGGGGTCAGCACAGACCCGCAGCCCCTCAAGGAGCAG CCCGCCCTCAATGACTCCAGATACGCTCTGAGCAGCCGCCTGAGGGTCTCGGCCACCTTC TGGCAGGACCCCCGCAACCACTTCCGCTGTCAAGTCCAGTTCTACGGGCTCTCGGAGAAT GACGAGTGGACCCAGGATAGGGCCAAACCCGTCACCCAGATCGTCAGCGCCGAGGCCTGG GGTAGAGCAGACGCCAGCACCAAGGGCCCCTCTGTGTTCCCTCTGGCCCCTTCCAGCAAG TCCACCTCTGGCGGAACAGCCGCTCTGGGCTGCCTCGTGAAGGACTACTTCCCCGAGCCT GTGACCGTGTCCTGGAACTCTGGCGCTCTGACCAGCGGAGTGCACACCTTCCCTGCTGTG CTGCAGTCCTCCGGCCTGTACTCCCTGTCCTCCGTCGTGACCGTGCCTTCCAGCTCTCTG GGCACCCAGACCTACATCTGCAACGTGAACCACAAGCCCTCCAACACCAAGGTGGACAAG AAGGTGCTAACAGACAGAGAATGGGCAGAAGAGTGGAAACATCTTGACCATCTGTTAAAC TGCATAATGGACATGGTAGAAAAAACAAGGCGATCTCTCACCGTACTAAGGCGGTGTCAA GAAGCAGACCGGGAAGAATTGAATTACTGGATCCGGCGGTACAGTGACGCCGAGGACTAC AAGGACGACGACGACAAGCACCACCACCATCACCAC |
| 14 | Quad 2 | ATGAGCCTCGGGCTCCTGTGCTGTGGGGCCTTTTCTCTCCTGTGGGCAGGTCCA GTGAATGCCGGTGTCACTCAGACCCCAAAATTCCAGGTCCTGAAGACAGGACAGAGCATG ACACTGCAGTGTGCCCAGGATATGAACCATGAATACATGTCCTGGTATCGACAAGACCCA GGCATGGGGCTGAGGCTGATTCATTACTCAGTTGCCATCCAGACAACTGACCAAGGAGAA GTCCCCAATGGCTACAATGTCTCCAGATCAACCATCGAGGATTTCCCGCTCAGGCTGCTG TCGGCTGCTCCCTCCCAGACATCTGTGTACTTCTGTGCCAGCAGTTACCTGGGGAACACC GGGGAGCTGTTTTTTGGAGAAGGCTCTAGGCTGACCGTACTGGAGGACCTGAAAAACGTG TTCCCACCCGAGGTCGCTGTGTTTGAGCCATCAGAAGCAGAGATCTCCCACACCCAAAAG GCCACACTGGTGTGCCTGGCCACAGGCTTCTACCCCGACCATGTGGAGCTGAGCTGGTGG GTGAATGGGAAGGAGGTGCACAGTGGGGTCAGCACAGACCCGCAGCCCCTCAAGGAGCAG CCCGCCCTCAATGACTCCAGATACGCTCTGAGCAGCCGCCTGAGGGTCTCGGCCACCTTC TGGCAGGACCCCCGCAACCACTTCCGCTGTCAAGTCCAGTTCTACGGGCTCTCGGAGAAT GACGAGTGGACCCAGGATAGGGCCAAACCCGTCACCCAGATCGTCAGCGCCGAGGCCTGG GGTAGAGCAGACGCCAGCACCAAGGGCCCCTCTGTGTTCCCTCTGGCCCCTTCCAGCAAG TCCACCTCTGGCGGAACAGCCGCTCTGGGCTGCCTCGTGAAGGACTACTTCCCCGAGCCT GTGACCGTGTCCTGGAACTCTGGCGCTCTGACCAGCGGAGTGCACACCTTCCCTGCTGTG CTGCAGTCCTCCGGCCTGTACTCCCTGTCCTCCGTCGTGACCGTGCCTTCCAGCTCTCTG GGCACCCAGACCTACATCTGCAACGTGAACCACAAGCCCTCCAACACCAAGGTGGACAAG AAGGTGGGAGGAGGTGGGAGCCTAACAGACAGAGAATGGGCAGAAGAGTGGAAACATCTT GACCATCTGTTAAACTGCATAATGGACATGGTAGAAAAAACAAGGCGATCTCTCACCGTA CTAAGGCGGTGTCAAGAAGCAGACCGGGAAGAATTGAATTACTGGATCCGGCGGTACAGT GACGCCGAGGACTACAAGGACGACGACGACAAGCACCACCACCATCACCAC |
| 15 | Quad 3 | ATGAGCCTCGGGCTCCTGTGCTGTGGGGCCTTTTCTCTCCTGTGGGCAGGTCCA GTGAATGCCGGTGTCACTCAGACCCCAAAATTCCAGGTCCTGAAGACAGGACAGAGCATG ACACTGCAGTGTGCCCAGGATATGAACCATGAATACATGTCCTGGTATCGACAAGACCCA GGCATGGGGCTGAGGCTGATTCATTACTCAGTTGCCATCCAGACAACTGACCAAGGAGAA GTCCCCAATGGCTACAATGTCTCCAGATCAACCATCGAGGATTTCCCGCTCAGGCTGCTG TCGGCTGCTCCCTCCCAGACATCTGTGTACTTCTGTGCCAGCAGTTACCTGGGGAACACC GGGGAGCTGTTTTTTGGAGAAGGCTCTAGGCTGACCGTACTGGAGGACCTGAAAAACGTG TTCCCACCCGAGGTCGCTGTGTTTGAGCCATCAGAAGCAGAGATCTCCCACACCCAAAAG GCCACACTGGTGTGCCTGGCCACAGGCTTCTACCCCGACCATGTGGAGCTGAGCTGGTGG GTGAATGGGAAGGAGGTGCACAGTGGGGTCTGCACAGACCCGCAGCCCCTCAAGGAGCAG CCCGCCCTCAATGACTCCAGATACGCTCTGAGCAGCCGCCTGAGGGTCTCGGCCACCTTC TGGCAGGACCCCCGCAACCACTTCCGCTGTCAAGTCCAGTTCTACGGGCTCTCGGAGAAT GACGAGTGGACCCAGGATAGGGCCAAACCCGTCACCCAGATCGTCAGCGCCGAGGCCTGG GGTAGAGCAGACGCCAGCACCAAGGGCCCCTCTGTGTTCCCTCTGGCCCCTTCCAGCAAG TCCACCTCTGGCGGAACAGCCGCTCTGGGCTGCCTCGTGAAGGACTACTTCCCCGAGCCT GTGACCGTGTCCTGGAACTCTGGCGCTCTGACCAGCGGAGTGCACACCTTCCCTGCTGTG CTGCAGTCCTCCGGCCTGTACTCCCTGTCCTCCGTCGTGACCGTGCCTTCCAGCTCTCTG GGCACCCAGACCTACATCTGCAACGTGAACCACAAGCCCTCCAACACCAAGGTGGACAAG AAGGTGCTAACAGACAGAGAATGGGCAGAAGAGTGGAAACATCTTGACCATCTGTTAAAC TGCATAATGGACATGGTAGAAAAAACAAGGCGATCTCTCACCGTACTAAGGCGGTGTCAA GAAGCAGACCGGGAAGAATTGAATTACTGGATCCGGCGGTACAGTGACGCCGAGGACTAC AAGGACGACGACGACAAGCACCACCACCATCACCAC |

TABLE 3-continued

DNA sequences encoding Quad polypeptides

| SEQ ID NO: | POLYPEPTIDE | NUCLEOTIDE SEQUENCE |
|---|---|---|
| 16 | Quad 4 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCTGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGCCAGCACCAAGGGCCCCTCTGTGTTCCCTCTGGCCCCTTCCAGCAAG<br>TCCACCTCTGGCGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGGAGGAGGTGGGAGCCTAACAGACAGAGAATGGGCAGAAGAGTGGAAACATCTT<br>GACCATCTGTTAAACTGCATAATGGACATGGTAGAAAAAACAAGGCGATCTCTCACCGTA<br>CTAAGGCGGTGTCAAGAAGCAGACCGGGAAGAATTGAATTACTGGATCCGGCGGTACAGT<br>GACGCCGAGGACTACAAGGACGACGACGACAAGCACCACCACCATCACCAC |
| 17 | Quad 5 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCTGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACCTAACAGACAGAGAATGGGCAGAAGAGTGGAAACATCTTGACCATCTG<br>TTAAACTGCATAATGGACATGGTAGAAAAAACAAGGCGATCTCTCACCGTACTAAGGCGG<br>TGTCAAGAAGCAGACCGGGAAGAATTGAATTACTGGATCCGGCGGTACAGTGACGCCGAG<br>GACTACAAGGACGACGACGACAAGCACCACCACCATCACCAC |
| 18 | Quad 6 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCTGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGAGGAGGTGGGAGCCTAACAGACAGAGAATGGGCAGAAGAGTGGAAA<br>CATCTTGACCATCTGTTAAACTGCATAATGGACATGGTAGAAAAAACAAGGCGATCTCTC<br>ACCGTACTAAGGCGGTGTCAAGAAGCAGACCGGGAAGAATTGAATTACTGGATCCGGCGG<br>TACAGTGACGCCGAGGACTACAAGGACGACGACGACAAGCACCACCACCATCACCAC |
| 19 | Quad 7 | ATGGAGACCCTCTTGGGCCTGCTTATCCTTTGGCTGCAGCTGCAATGGGTGAGC<br>AGCAAACAGGAGGTGACACAGATTCCTGCAGCTCTGAGTGTCCCAGAAGGAGAAACTTG<br>GTTCTCAACTGCAGTTTCACTGATAGCGCTATTTACAACCTCCAGTGGTTTAGGCAGGAC<br>CCTGGGAAAGGTCTCACATCTCTGTTGCTTATTACACCTTGGCAGAGAGCAAACAAGT<br>GGAAGACTTAATGCCTCGCTGGATAAATCATCAGGACGTAGTACTTTATACATTGCAGCT<br>TCTCAGCCTGGTGACTCAGCCACCTACCTCTGTGCTGTGAGGCCCCTGCTTGACGGAACA<br>TACATACCTACATTTGGAAGAGGAACCAGCCTTATTGTTCATCCGTATATCCAGAACCCT<br>GACCCTGCCGTGTACCAGCTGAGAGACTCTAAATCCAGTGACAAGTCTGTCTGCCTATTC<br>ACCGATTTTGATTCTCAAACAAATGTGTCACAAAGTAAGGATTCTGATGTGTATATCACA<br>GACAAAACTGTGCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGAC<br>ACCTTCTTCCCAGCCCAGAAAGTTCACGGTGGCCGCTCCCTCCGTGTTCATCTTCCCA<br>CCTTCCGACGAGCAGCTGAAGTCCGGCACCGCTTCTGTCGTGTGCCTGCTGAACAACTTC<br>TACCCCCGCGAGGCCAAGGTGCAGTGGAAGGTGGACAACGCCCTGCAGTCCGGCAACTCC |

TABLE 3-continued

DNA sequences encoding Quad polypeptides

| SEQ ID NO: | POLYPEPTIDE | NUCLEOTIDE SEQUENCE |
|---|---|---|
|  |  | CAGGAATCCGTGACCGAGCAGGACTCCAAGGACAGCACCTACTCCCTGTCCTCCACCCTG<br>ACCCTGTCCAAGGCCGACTACGAGAAGCACAAGGTGTACGCCTGCGAAGTGACCCACCAG<br>GGCCTGTCTAGCCCCGTGACCAAGTCTTTCAACCGGGGCGAGTGT |
| 20 | Quad 8 | ATGGAGACCCTCTTGGGCCTGCTTATCCTTTGGCTGCAGCTGCAATGGGTGAGC<br>AGCAAACAGGAGGTGACACAGATTCCTGCAGCTCTGAGTGTCCCAGAAGGAGAAAACTTG<br>GTTCTCAACTGCAGTTTCACTGATAGCGCTATTTACAACCTCCAGTGGTTTAGGCAGGAC<br>CCTGGGAAAGGTCTCACATCTCTGTTGCTTATTACACCTTGGCAGAGAGAGCAAACAAGT<br>GGAAGACTTAATGCCTCGCTGGATAAATCATCAGGACGTAGTACTTTATACATTGCAGCT<br>TCTCAGCCTGGTGACTCAGCCACCTACCTCTGTGCTGTGAGGCCCTGCTTGACGGAACA<br>TACATACCTACATTTGGAAGAGGAACCAGCCTTATTGTTCATCCGTATATCCAGAACCCT<br>GACCCTGCCGTGTACCAGCTGAGAGACTCTAAATCCAGTGACAAGTCTGTCTGCCTATTC<br>ACCGATTTTGATTCTCAAACAAATGTGTCACAAAGTAAGGATTCTGATGTGTATATCACA<br>GACAAATGTGTCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGAC<br>ACCTTCTTCCCCAGCCCAGAAAGTTCCACGGTGGCCGCTCCCTCCGTGTTCATCTTCCCA<br>CCTTCCGACGAGCAGCTGAAGTCCGGCACCGCTTCTGTCGTGTGCCTGCTGAACAACTTC<br>TACCCCCGCGAGGCCAAGGTGCAGTGGAAGGTGGACAACGCCCTGCAGTCCGGCAACTCC<br>CAGGAATCCGTGACCGAGCAGGACTCCAAGGACAGCACCTACTCCCTGTCCTCCACCCTG<br>ACCCTGTCCAAGGCCGACTACGAGAAGCACAAGGTGTACGCCTGCGAAGTGACCCACCAG<br>GGCCTGTCTAGCCCCGTGACCAAGTCTTTCAACCGGGGCGAGTGT |
| 21 | Quad 9 | ATGGAGACCCTCTTGGGCCTGCTTATCCTTTGGCTGCAGCTGCAATGGGTGAGC<br>AGCAAACAGGAGGTGACACAGATTCCTGCAGCTCTGAGTGTCCCAGAAGGAGAAAACTTG<br>GTTCTCAACTGCAGTTTCACTGATAGCGCTATTTACAACCTCCAGTGGTTTAGGCAGGAC<br>CCTGGGAAAGGTCTCACATCTCTGTTGCTTATTACACCTTGGCAGAGAGAGCAAACAAGT<br>GGAAGACTTAATGCCTCGCTGGATAAATCATCAGGACGTAGTACTTTATACATTGCAGCT<br>TCTCAGCCTGGTGACTCAGCCACCTACCTCTGTGCTGTGAGGCCCTGCTTGACGGAACA<br>TACATACCTACATTTGGAAGAGGAACCAGCCTTATTGTTCATCCGTATATCCAGAACCCT<br>GACCCTGCCGTGTACCAGCTGAGAGACTCTAAATCCAGTGACAAGTCTGTCTGCCTATTC<br>ACCGATTTTGATTCTCAAACAAATGTGTCACAAAGTAAGGATTCTGATGTGTATATCACA<br>GACAAATGTGTCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGAC<br>ACCTTCTTCCCCAGCCCAGAAAGTTCC |
| 22 | Quad 10 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCAGCACAGACCCGCAGCCCCTCAAGGACAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGCTAACAGACAGAGAATGGGCAGAAGAGTGGAAACATCTTGACCATCTGTTAAAC<br>TGCATAATGGACATGGTAGAAAAAACAAGGCGATCTCTCACCGTACTAAGGCGGTGTCAA<br>GAAGCAGACCGGGAAGAATTGAATTACTGGATCCGGCGGTACAGTGACGCCGAGGCACCT<br>ACTTCAAGTTCTACAAAGAAAACACAGCTACAACTGGAGCATTTACTGCTGGATTTACAG<br>ATGATTTTGAATGGAATTAATAATTACAAGAATCCCAAACTCACCAGGATGCTCACATTT<br>AAGTTTTACATGCCCAAGAAGGCCACAGAACTGAAACATCTTCAGTGTCTAGAAGAAGAA<br>CTCAAACCTCTGGAGGAAGTGCTAAATTTAGCTCAAAGCAAAAACTTTCACTTAAGACCC<br>AGGGACTTAATCAGCAATATCAACGTAATAGTTCTGGAACTAAAGGGATCTGAAACAACA<br>TTCATGTGTGAATATGCTGATGAGACAGCAACCATTGTAGAATTTCTGAACAGATGGATT<br>ACCTTTTGTCAAAGCATCATCTCAACACTGACTGACTACAAGGACGACGACGACAAGCAC<br>CACCACCATCACCAC |
| 23 | Quad 11 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCAGCACAGACCCGCAGCCCCTCAAGGAGCAG |

TABLE 3-continued

DNA sequences encoding Quad polypeptides

| SEQ ID NO: | POLYPEPTIDE | NUCLEOTIDE SEQUENCE |
|---|---|---|
| | | CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGGGAGGAGGTGGGAGCCTAACAGACAGAGAATGGGCAGAAGAGTGGAAACATCTT<br>GACCATCTGTTAAACTGCATAATGGACATGGTAGAAAAAACAAGGCGATCTCTCACCGTA<br>CTAAGGCGGTGTCAAGAAGCAGACCGGGAAGAATTGAATTACTGGATCCGGCGGTACAGT<br>GACGCCGAGGCACCTACTTCAAGTTCTACAAAGAAAACACAGCTACAACTGGAGCATTTA<br>CTGCTGGATTTACAGATGATTTTGAATGGAATTAATAATTACAAGAATCCCAAACTCACC<br>AGGATGCTCACATTTAAGTTTTACATGCCCAAGAAGGCCACAGAACTGAAACATCTTCAG<br>TGTCTAGAAGAAGAACTCAAACCTCTGGAGGAAGTGCTAAATTTAGCTCAAAGCAAAAAC<br>TTTCACTTAAGACCCAGGGACTTAATCAGCAATATCAACGTAATAGTTCTGGAACTAAAG<br>GGATCTGAAACAACATTCATGTGTGAATATGCTGATGAGACAGCAACCATTGTAGAATTT<br>CTGAACAGATGGATTACCTTTTGTCAAAGCATCATCTCAACACTGACTGACTACAAGGAC<br>GACGACGACAAGCACCACCACCATCACCAC |
| 24 | Quad 12 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCAGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGGAACCCAAGTCCTGCGACAAGACCCACACCTGTCCCCCTTGTCCTCTAACAGAC<br>AGAGAATGGGCAGAAGAGTGGAAACATCTTGACCATCTGTTAAACTGCATAATGGACATG<br>GTAGAAAAAACAAGGCGATCTCTCACCGTACTAAGGCGGTGTCAAGAAGCAGACCGGGAA<br>GAATTGAATTACTGGATCCGGCGGTACAGTGACGCCGAGGACTACAAGGACGACGACGAC<br>AAGCACCACCACCATCACCAC |
| 25 | Quad 13 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGCTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGCCTGGCCACAGGCTTCTACCCCGACCATGTGGAGCTGAGCTGGTGG<br>GTGAATGGGAAGGAGGTGCACAGTGGGGTCAGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGGAACCCAAGTCCTGCGACAAGACCCACACCTGTCCCCCTTGTCCTGGAGGAGGT<br>GGGAGCCTAACAGACAGAGAATGGGCAGAAGAGTGGAAACATCTTGACCATCTGTTAAAC<br>TGCATAATGGACATGGTAGAAAAAACAAGGCGATCTCTCACCGTACTAAGGCGGTGTCAA<br>GAAGCAGACCGGGAAGAATTGAATTACTGGATCCGGCGGTACAGTGACGCCGAGGACTAC<br>AAGGACGACGACGACAAGCACCACCACCATCACCAC |
| 26 | Quad 14 | ATGGAGCTGGGGCTGAGCTGGGTGGTCCTGGCTGCTCTACTACAAGGTGTCCAG<br>GCTCAGGTTCAGCTGGTTGAAAGCGGTGGTGCACTGGTTCAGCCTGGTGGTAGCCTGCGT<br>CTGAGCTGTGCAGCAAGCGGTTTTCCGGTTAATCGTTATAGCATGCGTTGGGTATCGTCAG<br>GCACCGGGTAAGAACGTGAATGGGTTGCAGGTATGAGCAGTGCCGGTGATCGTAGCAGC<br>TATGAAGATAGCGTTAAAGGTCGTTTTACCATCAGCCGTGATGATGCACGTAATACCGTT<br>TATCTGCAAATGAATAGCCTGAAACCGGAAGATACCGCAGTGTATTATTGCAATGTTAAC<br>GTGGGCTTTGAATATTGGGGTCAGGGCACCCAGGTTACCGTTAGCAGCAAACTAACAGAC |

TABLE 3-continued

DNA sequences encoding Quad polypeptides

| SEQ ID NO: | POLYPEPTIDE | NUCLEOTIDE SEQUENCE |
|---|---|---|
| | | AGAGAATGGGCAGAAGAGTGGAAACATCTTGACCATCTGTTAAACTGCATAATGGACATG<br>GTAGAAAAAACAAGGCGATCTCTCACCGTACTAAGGCGGTGTCAAGAAGCAGACCGGGAA<br>GAATTGAATTACTGGATCCGGCGGTACAGTGACGCCGAGGACTACAAGGACGACGACGAC<br>AAGCACCACCACCATCACCAC |
| 27 | Quad 15 | ATGGAGCTGGGGCTGAGCTGGGTGGTCCTGGCTGCTCTACTACAAGGTGTCCAG<br>GCTCAGGTTCAGCTGGTTGAAAGCGGTGGTGCACTGGTTCAGCCTGGTGGTAGCCTGCGT<br>CTGAGCTGTGCAGCAAGCGGTTTTCCGGTTAATCGTTATAGCATGCGTTGGTATCGTCAG<br>GCACCGGGTAAAGAACGTGAATGGGTTGCAGGTATGAGCAGTGCCGGTGATCGTAGCAGC<br>TATGAAGATAGCGTTAAAGGTCGTTTTACCATCAGCCGTGATGATGCACGTAATACCGTT<br>TATCTGCAAATGAATAGCCTGAAACCGGAAGATACCGCAGTGTATTATTGCAATGTTAAC<br>GTGGGCTTTGAATATTGGGGTCAGGGCACCCAGGTTACCGTTAGCAGCAAAGGAGGAGGT<br>GGGAGCCTAACAGACAGAGAATGGGCAGAAGAGTGGAAACATCTTGACCATCTGTTAAAC<br>TGCATAATGGACATGGTAGAAAAAACAAGGCGATCTCTCACCGTACTAAGGCGGTGTCAA<br>GAAGCAGACCGGGAAGAATTGAATTACTGGATCCGGCGGTACAGTGACGCCGAGGACTAC<br>AAGGACGACGACGACAAGCACCACCACCATCACCAC |
| 28 | Quad 18 | ATGGAGCTGGGGCTGAGCTGGGTGGTCCTGGCTGCTCTACTACAAGGTGTCCAG<br>GCTCAGGTTCAGCTGGTTGAAAGCGGTGGTGCACTGGTTCAGCCTGGTGGTAGCCTGCGT<br>CTGAGCTGTGCAGCAAGCGGTTTTCCGGTTAATCGTTATAGCATGCGTTGGTATCGTCAG<br>GCACCGGGTAAAGAACGTGAATGGGTTGCAGGTATGAGCAGTGCCGGTGATCGTAGCAGC<br>TATGAAGATAGCGTTAAAGGTCGTTTTACCATCAGCCGTGATGATGCACGTAATACCGTT<br>TATCTGCAAATGAATAGCCTGAAACCGGAAGATACCGCAGTGTATTATTGCAATGTTAAC<br>GTGGGCTTTGAATATTGGGGTCAGGGCACCCAGGTTACCGTTAGCAGCAAACTAACAGAC<br>AGAGAATGGGCAGAAGAGTGGAAACATCTTGACCATCTGTTAAACTGCATAATGGACATG<br>GTAGAAAAAACAAGGCGATCTCTCACCGTACTAAGGCGGTGTCAAGAAGCAGACCGGGAA<br>GAATTGAATTACTGGATCCGGCGGTACAGTGACGCCGAGGCACCTACTTCAAGTTCTACA<br>AAGAAAACACAGCTACAACTGGAGCATTTACTGCTGGATTTACAGATGATTTTGAATGGA<br>ATTAATAATTACAAGAATCCCAAACTCACCAGGATGCTCACATTTAAGTTTTACATGCCC<br>AAGAAGGCCACAGAACTGAAACATCTTCAGTGTCTAGAAGAAGAACTCAAACCTCTGGAG<br>GAAGTGCTAAATTTAGCTCAAAGCAAAAACTTTCACTTAAGACCCAGGGACTTAATCAGC<br>AATATCAACGTAATAGTTCTGGAACTAAAGGGATCTGAAACAACATTCATGTGTGAATAT<br>GCTGATGAGACAGCAACCATTGTAGAATTTCTGAACAGATGGATTACCTTTTGTCAAAGC<br>ATCATCTCAACACTGACTGACTACAAGGACGACGACGACAAGCACCACCACCATCACCAC |
| 29 | Quad 19 | ATGGAGCTGGGGCTGAGCTGGGTGGTCCTGGCTGCTCTACTACAAGGTGTCCAG<br>GCTCAGGTTCAGCTGGTTGAAAGCGGTGGTGCACTGGTTCAGCCTGGTGGTAGCCTGCGT<br>CTGAGCTGTGCAGCAAGCGGTTTTCCGGTTAATCGTTATAGCATGCGTTGGTATCGTCAG<br>GCACCGGGTAAAGAACGTGAATGGGTTGCAGGTATGAGCAGTGCCGGTGATCGTAGCAGC<br>TATGAAGATAGCGTTAAAGGTCGTTTTACCATCAGCCGTGATGATGCACGTAATACCGTT<br>TATCTGCAAATGAATAGCCTGAAACCGGAAGATACCGCAGTGTATTATTGCAATGTTAAC<br>GTGGGCTTTGAATATTGGGGTCAGGGCACCCAGGTTACCGTTAGCAGCAAAGGAGGAGGT<br>GGGAGCCTAACAGACAGAGAATGGGCAGAAGAGTGGAAACATCTTGACCATCTGTTAAAC<br>TGCATAATGGACATGGTAGAAAAAACAAGGCGATCTCTCACCGTACTAAGGCGGTGTCAA<br>GAAGCAGACCGGGAAGAATTGAATTACTGGATCCGGCGGTACAGTGACGCCGAGGCACCT<br>ACTTCAAGTTCTACAAAGAAAACACAGCTACAACTGGAGCATTTACTGCTGGATTTACAG<br>ATGATTTTGAATGGAATTAATAATTACAAGAATCCCAAACTCACCAGGATGCTCACATTT<br>AAGTTTTACATGCCCAAGAAGGCCACAGAACTGAAACATCTTCAGTGTCTAGAAGAAGAA<br>CTCAAACCTCTGGAGGAAGTGCTAAATTTAGCTCAAAGCAAAAACTTTCACTTAAGACCC<br>AGGGACTTAATCAGCAATATCAACGTAATAGTTCTGGAACTAAAGGGATCTGAAACAACA<br>TTCATGTGTGAATATGCTGATGAGACAGCAACCATTGTAGAATTTCTGAACAGATGGATT<br>ACCTTTTGTCAAAGCATCATCTCAACACTGACTGACTACAAGGACGACGACGACAAGCAC<br>CACCACCATCACCAC |
| 30 | Quad 20 | ATGGAGACCCTCTTGGGCCTGCTTATCCTTTGGCTGCAGCTGCAATGGGTGAGC<br>AGCAAACAGGAGGTGACACAGATTCCTGCAGCTCTGAGTGTCCCAGAAGGAGAAAACTTG<br>GTTCTCAACTGCAGTTTCACTGATAGCGCTATTTACAACCTCCAGTGGTTTAGGCAGGAC<br>CCTGGGAAAGGTCTCACATCTCTGTTGCTTATTACACCTTGGCAGAGAGAGCAAACAAGT<br>GGAAGACTTAATGCCTCGCTGGATAAATCATCAGGACGTAGTACTTTATACATTGCAGCT<br>TCTCAGCCTGGTGACTCAGCCACCTACCTCTGTGCTGTGAGGCCCCTGCTTGACGGAACA<br>TACATACCTACATTTGGAAGAGGAACCAGCCTTATTGTTCATCCGTATATCCAGAACCCT<br>GACCCTGCCGTGTACCAGCTGAGAGACTCTAAATCCAGTGACAAGTCTGTCTGCCTATTC<br>ACCGATTTTGATTCTCAAACAAATGTGTCACAAAGTAAGGATTCTGATGTGTATATCACA<br>GACAAAACTGTGCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGAC<br>ACCTTCTTCCCCAGCCCAGAAAGTTCCGCCAGCACCAAGGGCCCTCTGTGTTCCCTCTG<br>GCCCCTTCCAGCAAGTCCACCTCTGGCGGAACAGCCGCTCTGGGCTGCCTCGTGAAGGAC<br>TACTTCCCCGAGCCTGTGACCGTGTCCTGGAACTCTGGCGCTCTGACCAGCGGAGTGCAC<br>ACCTTCCCTGCTGTGCTGCAGTCCTCCGGCCTGTACTCCCTGTCCTCCGTCGTGACCGTG<br>CCTTCCAGCTCTCTGGGCACCCAGACCTACATCTGCAACGTGAACCACAAGCCCTCCAAC<br>ACCAAGGTGGACAAGAAGGTGTTGCATGGCACACGTCAAGAAGAAATGATTGATCACAGA<br>CTAACAGACAGAGAATGGGCAGAAGAGTGGAAACATCTTGACCATCTGTTAAACTGCATA<br>ATGGACATGGTAGAAAAAACAAGGCGATCTCTCACCGTACTAAGGCGGTGTCAAGAAGCA<br>GACCGGGAAGAATTGAATTACTGGATCCGGCGGTACAGTGACGCCGAGGACTTAAAAGAC<br>TACAAGGACGACGACGACAAGCACCACCACCATCACCAC |

TABLE 3-continued

DNA sequences encoding Quad polypeptides

| SEQ ID NO: | POLYPEPTIDE | NUCLEOTIDE SEQUENCE |
|---|---|---|
| 31 | Quad 21 | ATGGAGACCCTCTTGGGCCTGCTTATCCTTTGGCTGCAGCTGCAATGGGTGAGC<br>AGCAAACAGGAGGTGACACAGATTCCTGCAGCTCTGAGTGTCCCAGAAGGAGAAAACTTG<br>GTTCTCAACTGCAGTTTCACTGATAGCGCTATTTACAACCTCCAGTGGTTTAGGCAGGAC<br>CCTGGGAAAGGTCTCACATCTCTGTTGCTTATTACACCTTGGCAGAGAGAGCAAACAAGT<br>GGAAGACTTAATGCCTCGCTGGATAAATCATCAGGACGTAGTACTTTATACATTGCAGCT<br>TCTCAGCCTGGTGACTCAGCCACCTACCTCTGTGCTGTGAGGCCCCTGCTTGACGGAACA<br>TACATACCTACATTTGGAAGAGGAACCAGCCTTATTGTTCATCCGTATATCCAGAACCCT<br>GACCCTGCCGTGTACCAGCTGAGAGACTCTAAATCCAGTGACAAGTCTGTCTGCCTATTC<br>ACCGATTTTGATTCTCAAACAAATGTGTCACAAAGTAAGGATTCTGATGTGTATATCACA<br>GACAAAACTGTGCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGAC<br>ACCTTCTTCCCCAGCCCAGAAAGTTCCGCCAGCACCAAGGGCCCCTCTGTGTTCCCTCTG<br>GCCCCTTCCAGCAAGTCCACCTCTGGCGGAACAGCCGCTCTGGGCTGCCTCGTGAAGGAC<br>TACTTCCCCGAGCCTGTGACCGTGTCCTGGAACTCTGGCGCTCTGACCAGCGGAGTGCAC<br>ACCTTCCCTGCTGTGCTGCAGTCCTCCGGCCTGTACTCCCTGTCCTCCGTCGTGACCGTG<br>CCTTCCAGCTCTCTGGGCACCCAGACCTACATCTGCAACGTGAACCACAAGCCCTCCAAC<br>ACCAAGGTGGACAAGAAGGTGGGAGGAGGTGGGAGCTTGCATGGCACACGTCAAGAAGAA<br>ATGATTGATCACAGACTAACAGACAGAGAATGGGCAGAAGAGTGGAAACATCTTGACCAT<br>CTGTTAAACTGCATAATGGACATGGTAGAAAAAAACAAGGCGATCTCTCACCGTACTAAGG<br>CGGTGTCAAGAAGCAGACCGGGAAGAATTGAATTACTGGATCCGGCGGTACAGTGACGCC<br>GAGGACTTAAAAGACTACAAGGACGACGACGACAAGCACCACCACCATCACCAC |
| 32 | Quad 22 | ATGAGCCTCGGGCTCCTGTGCTGTGGGGCCTTTTCTCTCCTGTGGGCAGGTCCA<br>GTGAATGCCGGTGTCACTCAGACCCCAAAATTCCAGGTCCTGAAGACAGGACAGAGCATG<br>ACACTGCAGTGTGCCCAGGATATGAACCATGAATACATGTCCTGGTATCGACAAGACCCA<br>GGCATGGGGCTGAGGCTGATTCATTACTCAGTTGCCATCCAGACAACTGACCAAGGAGAA<br>GTCCCCAATGGCTACAATGTCTCCAGATCAACCATCGAGGATTTCCCGCTCAGGCTGTG<br>TCGGCTGCTCCCTCCCAGACATCTGTGTACTTCTGTGCCAGCAGTTACCTGGGGAACACC<br>GGGGAGCTGTTTTTTGGAGAAGGCTCTAGGCTGACCGTACTGGAGGACCTGAAAAACGTG<br>TTCCCACCCGAGGTCGCTGTGTTTGAGCCATCAGAAGCAGAGATCTCCCACACCCAAAAG<br>GCCACACTGGTGTGTGCCTGGCCACAGGCTTCTACCCCGACCATGTGGAGCTGAGCTGGTGG<br>GTGAATGGGAAGGAGGTGCACAGTGGGGTCAGCACAGACCCGCAGCCCCTCAAGGAGCAG<br>CCCGCCCTCAATGACTCCAGATACGCTCTGAGCAGCCGCCTGAGGGTCTCGGCCACCTTC<br>TGGCAGGACCCCCGCAACCACTTCCGCTGTCAAGTCCAGTTCTACGGGCTCTCGGAGAAT<br>GACGAGTGGACCCAGGATAGGGCCAAACCCGTCACCCAGATCGTCAGCGCCGAGGCCTGG<br>GGTAGAGCAGACACGGTGGCCGCTCCCTCCGTGTTCATCTTCCCACCTTCCGACGAGCAG<br>CTGAAGTCCGGCACCGCTTCTGTCGTGTGCCTGCTGAACAACTTCTACCCCCGCGAGGCC<br>AAGGTGCAGTGGAAGGTGGACAACGCCCTGCAGTCCGGCAACTCCCAGGAATCCGTGACC<br>GAGCAGGACTCCAAGGACAGCACCTACTCCCTGTCCTCCACCCTGACCCTGTCCAAGGCC<br>GACTACGAGAAGCACAAGGTGTACGCCTGCGAAGTGACCCACCAGGGCCTGTCTAGCCCC<br>GTGACCAAGTCTTTCAACCGGGGCGAGTGT |
| 33 | Quad 23 | ATGAACTTCGGGCTCAGCTTGATTTTCCTTGCCCTTATTTTAAAAGGTGTCCAG<br>TGTGAGGTGCAACTGGTGGAGTCTGGGGGAGGCTTAGTGAAGCCTGGGGGGTCCCTGAAA<br>CTCTCCTGTGCAGCCTCTGGACTCACTTTCAGTAGCTATGCCATGTCTTGGGTTCGCCAG<br>ACTCCAGAGAAGAGGCTGGAGTGGGTCGCATCCATTAGTAGTGGTGGTTTCACCTACTAT<br>CCAGACAGTGTGAAGGGCCGATTCACCATCTCCAGAGATAATGCCAGGAACATCCTGTAT<br>CTGCAAATGAGCAGTCTGAGGTCTGAGGACACGGCCATGTATTACTGTGCAAGAGACGAG<br>GTACGGGGTACCTCGATGTCTGGGGCGCAGGGACCACGGTCACCGTTTCCTCGGCCAGC<br>ACCAAGGGCCCCTCTGTGTTCCCTCTGGCCCCTTCCAGCAAGTCCACCTCTGGCGGAACA<br>GCCGCTCTGGGCTGCCTCGTGAAGGACTACTTCCCCGAGCCTGTGACCGTGTCCTGGAAC<br>TCTGGCGCTCTGACCAGCGGAGTGCACACCTTCCCTGCTGTGCTGCAGTCCTCCGGCCTG<br>TACTCCCTGTCCTCCGTCGTGACCGTGCCTTCCAGCTCTCTGGGCACCCAGACCTACATC<br>TGCAACGTGAACCACAAGCCCTCCAACACCAAGGTGGACAAGAAGGTGCTAACAGACAGA<br>GAATGGGCAGAAGAGTGGAAACATCTTGACCATCTGTTAAACTGCATAATGGACATGGTA<br>GAAAAAACAAGGCGATCTCTCACCGTACTAAGGCGGTGTCAAGAAGCAGACCGGGAAGAA<br>TTGAATTACTGGATCCGGCGGTACAGTGACGCCGAGGACTACAAGGACGACGACGACAAG<br>CACCACCACCATCACCAC |
| 34 | Quad 24 | ATGAACTTCGGGCTCAGCTTGATTTTCCTTGCCCTTATTTTAAAAGGTGTCCAG<br>TGTGAGGTGCAACTGGTGGAGTCTGGGGGAGGCTTAGTGAAGCCTGGGGGGTCCCTGAAA<br>CTCTCCTGTGCAGCCTCTGGACTCACTTTCAGTAGCTATGCCATGTCTTGGGTTCGCCAG<br>ACTCCAGAGAAGAGGCTGGAGTGGGTCGCATCCATTAGTAGTGGTGGTTTCACCTACTAT<br>CCAGACAGTGTGAAGGGCCGATTCACCATCTCCAGAGATAATGCCAGGAACATCCTGTAT<br>CTGCAAATGAGCAGTCTGAGGTCTGAGGACACGGCCATGTATTACTGTGCAAGAGACGAG<br>GTACGGGGTACCTCGATGTCTGGGGCGCAGGGACCACGGTCACCGTTTCCTCGGCCAGC<br>ACCAAGGGCCCCTCTGTGTTCCCTCTGGCCCCTTCCAGCAAGTCCACCTCTGGCGGAACA<br>GCCGCTCTGGGCTGCCTCGTGAAGGACTACTTCCCCGAGCCTGTGACCGTGTCCTGGAAC<br>TCTGGCGCTCTGACCAGCGGAGTGCACACCTTCCCTGCTGTGCTGCAGTCCTCCGGCCTG<br>TACTCCCTGTCCTCCGTCGTGACCGTGCCTTCCAGCTCTCTGGGCACCCAGACCTACATC<br>TGCAACGTGAACCACAAGCCCTCCAACACCAAGGTGGACAAGAAGGTGGGAGGAGGTGGG<br>AGCCTAACAGACAGAGAATGGGCAGAAGAGTGGAAACATCTTGACCATCTGTTAAACTGC |

TABLE 3-continued

DNA sequences encoding Quad polypeptides

| SEQ ID NO: | POLYPEPTIDE | NUCLEOTIDE SEQUENCE |
|---|---|---|
| | | ATAATGGACATGGTAGAAAAAACAAGGCGATCTCTCACCGTACTAAGGCGGTGTCAAGAA<br>GCAGACCGGGAAGAATTGAATTACTGGATCCGGCGGTACAGTGACGCCGAGGACTACAAG<br>GACGACGACGACAAGCACCACCACCATCACCAC |
| 35 | Quad 25 | ATGAAATACCTATTGCCTACGGCAGCCGCTGGATTGTTATTACTCGCGGCCCAG<br>CCGGCCATGGCGGCCTACAAAGATATCCAGATGACACAGACTACATCCTCCCTGTCTGCC<br>TCTCTGGGAGACAGAGTCACCATCAGTTGCAGTGCAAGTCAGGGCATTAGCAATTATTTA<br>AACTGGTATCAGCAGAAACCAGATGGAACTGTTAAACTCCTGATCTATTACACATCAAGT<br>TTACACTCAGGAGTCCCATCAAGGTTCAGTGGCAGTGGGTCTGGGACAGATTATTCTCTC<br>ACCATCAGCAACCTGGAACCTGAAGATATTGCCACTTATTATTGTCAGCAGTATAGCAAG<br>CTTCCGTACACGTTCGGAGGGGGGACCAAGCTGGAAATAAAACGTACGGTGGCCGCTCCC<br>TCCGTGTTCATCTTCCCACCTTCCGACGAGCAGCTGAAGTCCGGCACCGCTTCTGTCGTG<br>TGCCTGCTGAACAACTTCTACCCCCGCGAGGCCAAGGTGCAGTGGAAGGTGGACAACGCC<br>CTGCAGTCCGGCAACTCCCAGGAATCCGTGACCGAGCAGGACTCCAAGGACAGCACCTAC<br>TCCCTGTCCTCCACCCTGACCCTGTCCAAGGCCGACTACGAGAAGCACAAGGTGTACGCC<br>TGCGAAGTGACCCACCAGGGCCTGTCTAGCCCCGTGACCAAGTCTTTCAACCGGGGCGAG<br>TGT |
| 36 | Quad 26 | ATGAACTTCGGGCTCAGCTTGATTTTCCTTGCCCTTATTTTAAAAGGTGTCCAG<br>TGTGAGGTGCAACTGGTGGAGTCTGGGGGAGGCTTAGTGAAGCCTGGGGGGTCCCTGAAA<br>CTCTCCTGTGCAGCCTCTGGACTCACTTTCAGTAGCTATGCCATGTCTTGGGTTCGCCAG<br>ACTCCAGAGAAGAGGCTGGAGTGGGTCGCATCCATTAGTAGTGGTGGTTTCACCTACTAT<br>CCAGACAGTGTGAAGGGCCGATTCACCATCTCCAGAGATAATGCCAGGAACATCCTGTAT<br>CTGCAAATGAGCAGTCTGAGGTCTGAGGACACGGCCATGTATTACTGTGCAAGAGACGAG<br>GTACGGGGGTACCTCGATGTCTGGGGCGCAGGGACCACGGTCACCGTTTCCTCGGCCAGC<br>ACCAAGGGCCCCTCTGTGTTCCCTCTGGCCCCTTCCAGCAAGTCCACCTCTGGCGGAACA<br>GCCGCTCTGGGCTGCCTCGTGAAGGACTACTTCCCCGAGCCTGTGACCGTGTCCTGGAAC<br>TCTGGCGCTCTGACCAGCGGAGTGCACACCTTCCCTGCTGTGCTGCAGTCCTCCGGCCTG<br>TACTCCCTGTCCTCCGTCGTGACCGTGCCTTCCAGCTCTCTGGGCACCCAGACCTACATC<br>TGCAACGTGAACCACAAGCCCTCCAACACCAAGGTGGACAAGAAGGTGGAACCCAAGTCC<br>TGCGACAAGACCCACACCTGTCCCCCTTGTCCTCTAACAGACAGAGAATGGGCAGAAGAG<br>TGGAAACATCTTGACCATCTGTTAAACTGCATAATGGACATGGTAGAAAAAACAAGGCGA<br>TCTCTCACCGTACTAAGGCGGTGTCAAGAAGCAGACCGGGAAGAATTGAATTACTGGATC<br>CGGCGGTACAGTGACGCCGAGGACTACAAGGACGACGACGACAAGCACCACCACCATCAC<br>CAC |
| 37 | Quad 27 | ATGAACTTCGGGCTCAGCTTGATTTTCCTTGCCCTTATTTTAAAAGGTGTCCAG<br>TGTGAGGTGCAACTGGTGGAGTCTGGGGGAGGCTTAGTGAAGCCTGGGGGGTCCCTGAAA<br>CTCTCCTGTGCAGCCTCTGGACTCACTTTCAGTAGCTATGCCATGTCTTGGGTTCGCCAG<br>ACTCCAGAGAAGAGGCTGGAGTGGGTCGCATCCATTAGTAGTGGTGGTTTCACCTACTAT<br>CCAGACAGTGTGAAGGGCCGATTCACCATCTCCAGAGATAATGCCAGGAACATCCTGTAT<br>CTGCAAATGAGCAGTCTGAGGTCTGAGGACACGGCCATGTATTACTGTGCAAGAGACGAG<br>GTACGGGGGTACCTCGATGTCTGGGGCGCAGGGACCACGGTCACCGTTTCCTCGGCCAGC<br>ACCAAGGGCCCCTCTGTGTTCCCTCTGGCCCCTTCCAGCAAGTCCACCTCTGGCGGAACA<br>GCCGCTCTGGGCTGCCTCGTGAAGGACTACTTCCCCGAGCCTGTGACCGTGTCCTGGAAC<br>TCTGGCGCTCTGACCAGCGGAGTGCACACCTTCCCTGCTGTGCTGCAGTCCTCCGGCCTG<br>TACTCCCTGTCCTCCGTCGTGACCGTGCCTTCCAGCTCTCTGGGCACCCAGACCTACATC<br>TGCAACGTGAACCACAAGCCCTCCAACACCAAGGTGGACAAGAAGGTGGAACCCAAGTCC<br>TGCGACAAGACCCACACCTGTCCCCCTTGTCCTGGAGGAGGTGGGAGCCTAACAGACAGA<br>GAATGGGCAGAAGAGTGGAAACATCTTGACCATCTGTTAAACTGCATAATGGACATGGTA<br>GAAAAAACAAGGCGATCTCTCACCGTACTAAGGCGGTGTCAAGAAGCAGACCGGGAAGAA<br>TTGAATTACTGGATCCGGCGGTACAGTGACGCCGAGGACTACAAGGACGACGACGACAAG<br>CACCACCACCATCACCAC |
| 38 | Quad 28 | ATGGGATGGTCTTGTATAATTCTGTTCCTGGTGGCAACAGCAACAGGAGTGCAT<br>AGCGAGGTGCAGCTGGTGGAGTCTGGGGGAGGCTTGGTACAGCCCGGCAGGTCCCTGAGA<br>CTCTCCTGTGCGGCCTCTGGATTCACCTTTGATGATTATGCCATGCACTGGGTCCGGCAA<br>GCTCCAGGGAAGGGCCTGGAATGGGTCTCAGCTATCACTTGGAATAGTGGTCACATAGAC<br>TATGCGGACTCTGTGGAGGGCCGATTCACCATCTCCAGAGACAACGCCAAGAACTCCCTG<br>TATCTGCAAATGAACAGTCTGAGAGCTGAGGATACGGCCGTATATTACTGTGCAAAGTC<br>TCGTACCTTAGCACCGCGTCCTCCCTTGACTATTGGGGCCAAGGTACCCTGGTCACCGTC<br>TCGAGTGCCAGCACCAAGGGCCCCTCTGTGTTCCCTCTGGCCCCTTCCAGCAAGTCCACC<br>TCTGGCGGAACAGCCGCTCTGGGCTGCCTCGTGAAGGACTACTTCCCCGAGCCTGTGACC<br>GTGTCCTGGAACTCTGGCGCTCTGACCAGCGGAGTGCACACCTTCCCTGCTGTGCTGCAG<br>TCCTCCGGCCTGTACTCCCTGTCCTCCGTCGTGACCGTGCCTTCCAGCTCTCTGGGCACC<br>CAGACCTACATCTGCAACGTGAACCACAAGCCCTCCAACACCAAGGTGGACAAGAAGGTG<br>TTGCATGGCACACGTCAAGAAGAAATGATTGATCACAGACTAACAGACAGAGAATGGGCA<br>GAAGAGTGGAAACATCTTGACCATCTGTTAAACTGCATAATGGACATGGTAGAAAAAACA<br>AGGCGATCTCTCACCGTACTAAGGCGGTGTCAAGAAGCAGACCGGGAAGAATTGAATTAC<br>TGGATCCGGCGGTACAGTGACGCCGAGGACTAAAAGACTACAAGGACGACGACGACAAG<br>CACCACCACCATCACCAC |
| 39 | Quad 29 | ATGGGATGGTCTTGTATAATTCTGTTCCTGGTGGCAACAGCAACAGGAGTGCAT<br>AGCGAGGTGCAGCTGGTGGAGTCTGGGGGAGGCTTGGTACAGCCCGGCAGGTCCCTGAGA<br>CTCTCCTGTGCGGCCTCTGGATTCACCTTTGATGATTATGCCATGCACTGGGTCCGGCAA |

TABLE 3-continued

DNA sequences encoding Quad polypeptides

| SEQ ID NO: | POLYPEPTIDE | NUCLEOTIDE SEQUENCE |
|---|---|---|
| | | GCTCCAGGGAAGGGCCTGGAATGGGTCTCAGCTATCACTTGGAATAGTGGTCACATAGAC<br>TATGCGGACTCTGTGGAGGGCCGATTCACCATCTCCAGAGACAACGCCAAGAACTCCCTG<br>TATCTGCAAATGAACAGTCTGAGAGCTGAGGATACGGCCGTATATTACTGTGCGAAAGTC<br>TCGTACCTTAGCACCGCGTCCTCCCTTGACTATTGGGGCCAAGGTACCCTGGTCACCGTC<br>TCGAGTGCCAGCACCAAGGGCCCCTCTGTGTTCCCTCTGGCCCCTTCCAGCAAGTCCACC<br>TCTGGCGGAACAGCCGCTCTGGGCTGCCTCGTGAAGGACTACTTCCCCGAGCCTGTGACC<br>GTGTCCTGGAACTCTGGCGCTCTGACCAGCGGAGTGCACACCTTCCCTGCTGTGCTGCAG<br>TCCTCCGGCCTGTACTCCCTGTCCTCCGTCGTGACCGTGCCTTCCAGCTCTCTGGGCACC<br>CAGACCTACATCTGCAACGTGAACCACAAGCCCTCCAACACCAAGGTGGACAAGAAGGTG<br>GAGGAGGTGGGAGCTTGCATGGCACACGTCAAGAAGAAATGATTGATCACAGACTAACA<br>GACAGAGAATGGGCAGAAGAGTGGAAACATCTTGACCATCTGTTAAACTGCATAATGGAC<br>ATGGTAGAAAAAACAAGGCGATCTCTCACCGTACTAAGGCGGTGTCAAGAAGCAGACCGG<br>GAAGAATTGAATTACTGGATCCGGCGGTACAGTGACGCCGAGGACTTAAAAGACTACAAG<br>GACGACGACGACAAGCACCACCACCATCACCAC |
| 40 | Quad 30 | ATGGACATGAGGGTCCCTGCTCAGCTCCTGGGACTCCTGCTGCTCTGGCTCCCA<br>GATACCAGATGTGACATCCAGATGACCCAGTCTCCATCCTCCTGTCTGCATCTGTAGGG<br>GACAGAGTCACCATCACTTGTCGGGCAAGTCAGGGCATCAGAAATTACTTAGCCTGGTAT<br>CAGCAAAAACCAGGGAAAGCCCCTAAGCTCCTGATCTATGCTGCATCCACTTTGCAATCA<br>GGGGTCCCATCTCGGTTCAGTGGCAGTGGATCTGGGACAGATTTCACTCTCACCATCAGC<br>AGCCTACAGCCTGAAGATGTTGCAACTTATTACTGTCAAAGGTATAACCGTGCACCGTAT<br>ACTTTTGGCCAGGGGACCAAGGTGGAAATCAAACGTACGGTGGCCGCTCCCTCCGTGTTC<br>ATCTTCCCACCTTCCGACGAGCAGCTGAAGTCCGGCACCGCTTCTGTCGTGTGCCTGCTG<br>AACAACTTCTACCCCCGCGAGGCCAAGGTGCAGTGGAAGGTGGACAACGCCCTGCAGTCC<br>GGCAACTCCCAGGAATCCGTGACCGAGCAGGACTCCAAGGACAGCACCTACTCCCTGTCC<br>TCCACCCTGACCCTGTCCAAGGCCGACTACGAGAAGCACAAGGTGTACGCCTGCGAAGTG<br>ACCCACCAGGGCCTGTCTAGCCCCGTGACCAAGTCTTTCAACCGGGGCGAGTGT |
| 41 | Quad 31 | ATGGGATGGTCTTGTATAATTCTGTTCCTGGTGGCAACAGCAACAGGAGTGCAT<br>AGCGAGGTCCAACTTGTCGAAAGTGGCGGCGGTTTGGTTCAACCTGGAGGTTCACTTGA<br>CTGTCATGTGCAGCGAGCGGTTATACATTTACGAATTATGGCATGAATTGGGTTAGACAG<br>GCACCAGGAAAGGGACTGGAGTGGGTAGGCTGGATCAATACCTACACAGGAGAACCAACG<br>TATGCCGCAGACTTCAAACGACGGTTTACATTTTCCTTGGATACCTCTAAGTCTACAGCG<br>TATCTCCAAATGAATTCACTTCGAGCGGAAGATACCGCGGTCTACTATTGCGCCAAATAC<br>CCTCATTATTATGGGTCATCTCACTGGTATTTCGATGTCTGGGGTCAGGGAACACTGGTA<br>ACCGTGTCATCCGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGTTGCATGGCACACGTCAAGAAGAAATGATTGATCACAGACTAACAGACAGAGAA<br>TGGGCAGAAGAGTGGAAACATCTTGACCATCTGTTAAACTGCATAATGGACATGGTAGAA<br>AAAACAAGGCGATCTCTCACCGTACTAAGGCGGTGTCAAGAAGCAGACCGGGAAGAATTG<br>AATTACTGGATCCGGCGGTACAGTGACGCCGAGGACTTAAAAGACTACAAGGACGACGAC<br>GACAAGCACCACCACCATCACCAC |
| 42 | Quad 32 | ATGGGATGGTCTTGTATAATTCTGTTCCTGGTGGCAACAGCAACAGGAGTGCAT<br>AGCGAGGTCCAACTTGTCGAAAGTGGCGGCGGTTTGGTTCAACCTGGAGGTTCACTTGA<br>CTGTCATGTGCAGCGAGCGGTTATACATTTACGAATTATGGCATGAATTGGGTTAGACAG<br>GCACCAGGAAAGGGACTGGAGTGGGTAGGCTGGATCAATACCTACACAGGAGAACCAACG<br>TATGCCGCAGACTTCAAACGACGGTTTACATTTTCCTTGGATACCTCTAAGTCTACAGCG<br>TATCTCCAAATGAATTCACTTCGAGCGGAAGATACCGCGGTCTACTATTGCGCCAAATAC<br>CCTCATTATTATGGGTCATCTCACTGGTATTTCGATGTCTGGGGTCAGGGAACACTGGTA<br>ACCGTGTCATCCGCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTG<br>CTGCAGTCCTCCGGCCTGTACTCCCTGTCCTCCGTCGTGACCGTGCCTTCCAGCTCTCTG<br>GGCACCCAGACCTACATCTGCAACGTGAACCACAAGCCCTCCAACACCAAGGTGGACAAG<br>AAGGTGGAGGAGGTGGGAGCTTGCATGGCACACGTCAAGAAGAAATGATTGATCACAGA<br>CTAACAGACAGAGAATGGGCAGAAGAGTGGAAACATCTTGACCATCTGTTAAACTGCATA<br>ATGGACATGGTAGAAAAAACAAGGCGATCTCTCACCGTACTAAGGCGGTGTCAAGAAGCA<br>GACCGGGAAGAATTGAATTACTGGATCCGGCGGTACAGTGACGCCGAGGACTTAAAAGAC<br>TACAAGGACGACGACGACAAGCACCACCACCATCACCAC |
| 43 | Quad 33 | ATGGACATGAGGGTCCCTGCTCAGCTCCTGGGGCTCCTGCAGCTCTGGCTCTCA<br>GGTGCCAGATGTGACATCCAAATGACCCAGAGTCCTTCCAGCCTCAGTGCGTCAGTGGGA<br>GATCGAGTGACGATAACGTGTTCTGCCAGCCAAGACATTTCCAACTATCTTAATTGGTAC<br>CAGCAGAAACCGGGAAAGGCCCCGAAAGTGCTCATATACTTTACCAGCAGTCTTCACTCT<br>GGAGTTCCTAGCCGGTTTAGCGGCTCAGGTAGTGGCACCGATTTCACTCTGACCATTAGT<br>TCTCTTCAACCGGAAGATTTTGCAACCTACTATTGTCAGCAGTATTCAACGGTACCTTGG<br>ACCTTCGGCCAAGGCACCAAAGTCGAGATTAAGCGTACGGTGGCCGCTCCCTCCGTGTTC<br>ATCTTCCCACCTTCCGACGAGCAGCTGAAGTCCGGCACCGCTTCTGTCGTGTGCCTGCTG<br>AACAACTTCTACCCCCGCGAGGCCAAGGTGCAGTGGAAGGTGGACAACGCCCTGCAGTCC |

TABLE 3-continued

DNA sequences encoding Quad polypeptides

| SEQ ID NO: | POLYPEPTIDE | NUCLEOTIDE SEQUENCE |
|---|---|---|
| | | GGCAACTCCCAGGAATCCGTGACCGAGCAGGACTCCAAGGACAGCACCTACTCCCTGTCC<br>TCCACCCTGACCCTGTCCAAGGCCGACTACGAGAAGCACAAGGTGTACGCCTGCGAAGTG<br>ACCCACCAGGGCCTGTCTAGCCCCGTGACCAAGTCTTTCAACCGGGGCGAGTGT |
| 44 | Quad 34 | ATGGATATGCGCGTCCCGGCACAGCTGCTCGGCTTGTTGTTGCTGTGGTTGAGA<br>GCTAGGTGCGATATACAGATGACTCAGTCCCCTTCCAGTCTTTCAGCCAGTGTCGGCGAC<br>CGGGTTACCATTACTTGTCGGGCAAGTCAATCTATAGATAGTTATTTGCATTGGTATCAA<br>CAAAAACCAGGCAAAGCGCCTAAGTTGTTGATATATTCCGCATCTGAACTGCAATCAGGC<br>GTTCCTTCACGCTTTTCTGGAAGCGGCAGCGGAACCGATTTCACTCTTACCATAAGTAGT<br>CTCCAGCCGGAGGATTTTGCTACATACTATTGTCAACAAGTAGTGTGGCGACCGTTCACC<br>TTCGGACAGGGGACAAAAGTAGAAATCAAGCGGGGAGGAGGTGGGAGCTTGCATGGCACA<br>CGTCAAGAAGAAATGATTGATCACAGACTAACAGACAGAGAATGGGCAGAAGAGTGGAAA<br>CATCTTGACCATCTGTTAAACTGCATAATGGACATGGTAGAAAAAACAAGGCGATCTCTC<br>ACCGTACTAAGGCGGTGTCAAGAAGCAGACCGGGAAGAATTGAATTACTGGATCCGGCGG<br>TACAGTGACGCCGAGGACTTAAAAGACTACAAGGACGACGACGACAAGCACCACCACCAT<br>CACCAC |
| 45 | Quad 36 | ATGGAGTTTGGCCTCAGTTGGTTGTTTTTGGTAGCGAAAATTAAAGTACAGTGT<br>GAAGTCCAACTCCTGGAGAGCGGGGGGGGTCGGTACAACCAGGCGGCTCACTGCGGCTT<br>AGCTGCGCAGCCTCCGGGTTCACGTTCGCACATGAAACGATGGTGTGGGTGCGCCAGGCA<br>CCGGGGAAGGGACTCGAATGGGTCTCACATATACCTCCTGACGGTCAGGATCCTTTTTAC<br>GCGGACTCTGTGAAGGGACGATTCACAATAAGTAGAGACAATAGTAAGAACACCCTTTAT<br>TTGCAGATGAACAGTCTGCGGGCGGAAGATACAGCAGTATATCATTGTGCCCTGCTGCCC<br>AAACGAGGTCCGTGGTTTGACTATTGGGGACAGGGGACTCTCGTTACTGTAAGCTCCGGA<br>GGAGGTGGGAGCTTGCATGGCACACGTCAAGAAGAAATGATTGATCACAGACTAACAGAC<br>AGAGAATGGGCAGAAGAGTGGAAACATCTTGACCATCTGTTAAACTGCATAATGGACATG<br>GTAGAAAAAACAAGGCGATCTCTCACCGTACTAAGGCGGTGTCAAGAAGCAGACCGGGAA<br>GAATTGAATTACTGGATCCGGCGGTACAGTGACGCCGAGGACTTAAAAGACTACAAGGAC<br>GACGACGACAAGCACCACCACCATCACCAC |
| 46 | Quad 38 | ATGGACATGAGGGTCCCCGCTCAGCTCCTGGGGCTCCTGCTACTCTGGCTCCGA<br>GCCAGATGTGATATACAGATGACCCAATCACCAAGCAGCTTGTCCGCTTCAGTGGGCGAC<br>AGGGTAACTATAACATGCCGCGCAAGCCAATGGATAGGTCCAGAACTCTCATGGTACCAA<br>CAAAAACCAGGGAAAGCGCCGAAACTGCTTATCTATCACACAAGCATTTTGCAATCTGGG<br>GTACCTAGTCGATTCAGTGGCTCTGGCAGTGGGACTGACTTTACACTCACCATAAGTTCT<br>CTCCAACCAGAGGACTTTGCAACATACTATTGTCAGCAATATATGTTTCAACCACGCACC<br>TTTGGACAAGGCACAAAAGTTGAAATCCGCGGAGGAGGTGGGAGCTTGCATGGCACACGT<br>CAAGAAGAAATGATTGATCACAGACTAACAGACAGAGAATGGGCAGAAGAGTGGAAACAT<br>CTTGACCATCTGTTAAACTGCATAATGGACATGGTAGAAAAAACAAGGCGATCTCTCACC<br>GTACTAAGGCGGTGTCAAGAAGCAGACCGGGAAGAATTGAATTACTGGATCCGGCGGTAC<br>AGTGACGCCGAGGACTTAAAAGACTACAAGGACGACGACGACAAGCACCACCACCATCAC<br>CAC |
| 47 | Quad 40 | ATGGACATGAGGGTCCCCGCTCAGCTCCTGGGGCTCCTGCTACTCTGGCTCCGA<br>GCCAGATGTGATATTCAAATGACACAGTCACCAACGAGTCTTTCCGCGAGCGTTGGGGAC<br>CGAGTGACAATAACTTGTCGAGCCTCTCAGTGGATTGGCAACTTGCTGGACTGGTATCAG<br>CAAAAGCCGGGAGAAGCCCCGAAGCTGCTCATATACTATGCTTCCTTCCTCCAGAGTGGA<br>GTACCTAGCAGATTCAGCGGGGGGGATTCGGGACTGATTTCACTCTTACAATCAGCTCT<br>CTTCAACCCGAGGACTTCGCAACGTACTACTGTCAACAAGCTAACCCTGCGCCGCTTACT<br>TTCGGACAAGGCACTAAGGTCGAAATTAAGCGAGGAGGAGGTGGGAGCTTGCATGGCACA<br>CGTCAAGAAGAAATGATTGATCACAGACTAACAGACAGAGAATGGGCAGAAGAGTGGAAA<br>CATCTTGACCATCTGTTAAACTGCATAATGGACATGGTAGAAAAAACAAGGCGATCTCTC<br>ACCGTACTAAGGCGGTGTCAAGAAGCAGACCGGGAAGAATTGAATTACTGGATCCGGCGG<br>TACAGTGACGCCGAGGACTTAAAAGACTACAAGGACGACGACGACAAGCACCACCACCAT<br>CACCAC |
| 48 | Quad 42 | ATGGACATGAGGGTCCCCGCTCAGCTCCTGGGGCTCCTGCTACTCTGGCTCCGA<br>GCCAGATGTGATATACAGATGACCCAATCACCAAGCAGCTTGTCCGCTTCAGTGGGCGAC<br>AGGGTAACTATAACATGCCGCGCAAGCCAATGGATAGGTCCAGAACTCTCATGGTACCAA<br>CAAAAACCAGGGAAAGCGCCGAAACTGCTTATCTATCACACAAGCATTTTGCAATCTGGG<br>GTACCTAGTCGATTCAGTGGCTCTGGCAGTGGGACTGACTTTACACTCACCATAAGTTCT<br>CTCCAACCAGAGGACTTTGCAACATACTATTGTCAGCAATATATGTTTCAACCACGCACC<br>TTTGGACAAGGCACAAAAGTTGAAATCCGCGGAGGAGGTGGGAGCTTGCATGGCACACGT<br>CAAGAAGAAATGATTGATCACAGACTAACAGACAGAGAATGGGCAGAAGAGTGGAAACAT<br>CTTGACCATCTGTTAAACTGCATAATGGACATGGTAGAAAAAACAAGGCGATCTCTCACC<br>GTACTAAGGCGGTGTCAAGAAGCAGACCGGGAAGAATTGAATTACTGGATCCGGCGGTAC<br>AGTGACGCCGAGGACTTAAAAGGTGGAGGAGGTAGCGATATTCAAATGACACAGTCACCA<br>ACGAGTCTTTCCGCGAGCGTTGGGGACCGAGTGACAATAACTTGTCGAGCCTCTCAGTGG<br>ATTGGCAACTTGCTGGACTGGTATCAGCAAAAGCCGGGAGAAGCCCCGAAGCTGCTCATA<br>TACTATGCTTCCTTCCTCCAGAGTGGAGTACCTAGCAGATTCAGCGGGGGGGATTCGGG<br>ACTGATTTCACTCTTACAATCAGCTCTCTTCAACCCGAGGACTTCGCAACGTACTACTGT<br>CAACAAGCTAACCCTGCGCCGCTTACTTTCGGACAAGGCACTAAGGTCGAAATTAAGCGA<br>GACTACAAGGACGACGACGACAAGCACCACCACCATCACCAC |

TABLE 3-continued

DNA sequences encoding Quad polypeptides

| SEQ ID NO: | POLYPEPTIDE | NUCLEOTIDE SEQUENCE |
|---|---|---|
| 49 | Quad 44 | ATGGACATGAGGGTCCCCGCTCAGCTCCTGGGGCTCCTGCTACTCTGGCTCCGA<br>GCCAGATGTGACATTCAGATGACTCAGTCACCATCCTCATTGTCTGCATCAGTTGGTGAC<br>CGAGTTACGATCACATGTCGAGCAAGCCAAAATATAGATTCCAGACTTTCATGGTACCAG<br>CAGAAGCCTGGTAAAGCGCCGAAACTCCTCATATATCGCACGAGCGTATTGCAATCTGGT<br>GTGCCTTCTCGATTTTCAGGATCTGGGTCTGGCACTGACTTCACCTTGACAATATCTTCT<br>CTTCAGCCCGAAGATTTCGCTACCTACTACTGCCAACAATGGGACATGTTTCCTCTGACC<br>TTCGGACAGGGTACAAAGGTCGAGATTAAACGGGGAGGAGGTGGGAGCTTGCATGGCACA<br>CGTCAAGAAGAAATGATTGATCACAGACTAACAGACAGAGAATGGGCAGAAGAGTGGAAA<br>CATCTTGACCATCTGTTAAACTGCATAATGGACATGGTAGAAAAAACAAGGCGATCTCTC<br>ACCGTACTAAGGCGGTGTCAAGAAGCAGACCGGGAAGAATTGAATTACTGGATCCGGCGG<br>TACAGTGACGCCGAGGACTTAAAAGACTACAAGGACGACGACGACAAGCACCACCACCAT<br>CACCAC |
| 50 | Quad 46 | ATGGACATGAGGGTCCCCGCTCAGCTCCTGGGGCTCCTGCTACTCTGGCTCCGA<br>GCCAGATGTGACATTCAGATGACTCAGTCACCATCCTCATTGTCTGCATCAGTTGGTGAC<br>CGAGTTACGATCACATGTCGAGCAAGCCAAAATATAGATTCCAGACTTTCATGGTACCAG<br>CAGAAGCCTGGTAAAGCGCCGAAACTCCTCATATATCGCACGAGCGTATTGCAATCTGGT<br>GTGCCTTCTCGATTTTCAGGATCTGGGTCTGGCACTGACTTCACCTTGACAATATCTTCT<br>CTTCAGCCCGAAGATTTCGCTACCTACTACTGCCAACAATGGGACATGTTTCCTCTGACC<br>TTCGGACAGGGTACAAAGGTCGAGATTAAACGGGGAGGAGGTGGGAGCTTGCATGGCACA<br>CGTCAAGAAGAAATGATTGATCACAGACTAACAGACAGAGAATGGGCAGAAGAGTGGAAA<br>CATCTTGACCATCTGTTAAACTGCATAATGGACATGGTAGAAAAAACAAGGCGATCTCTC<br>ACCGTACTAAGGCGGTGTCAAGAAGCAGACCGGGAAGAATTGAATTACTGGATCCGGCGG<br>TACAGTGACGCCGAGGACTTAAAAGGTGGAGGAGGTAGCGATATACAGATGACTCAATCC<br>CCTTCATCCCTCTCAGCTTCCGTAGGGGACAGAGTTACTATAACGTGTCGAGCTAGTCAA<br>GACATAGGTGATCGCTGAGGTGGTATCAGCAAAAACCGGGTAAAGCACCTAAACTCCTC<br>ATATATCATGGTTCCAGGTTGGAGTCAGGCGTGCCGTCACGATTCTCTGGGTCACGCTCT<br>GGCACTGACTTCACATTGACGATTAGTTCTCTCCAGCCCGAAGACTTCGCCACCTACTAC<br>TGTCAACAGCAATGGTTTCGCCCGTATACTTTTGGGCAGGGTACAAAGGTTGAGATTAAA<br>CGGGACTACAAGGACGACGACGACAAGCACCACCACCATCACCAC |

TABLE 4

Amino acid seuuences of binding moieties, domains and peptides

| SEQ ID NO: | Domain/petptide | Product* | Domain/peptide Amino Acid Sequence |
|---|---|---|---|
| 51 | Anti-TNF alpha H | HUMIRA ® | EVQLVESGGGLVQPGRSLRLSCAASGFTFDDYAMHWVRQAPGKGLEWVSAITWNSGHIDY<br>ADSVEGRFTISRDNAKNSLYLQMNSLRAEDTAVYYCAKVSYLSTASSLDYWGQGTLVTVS<br>S |
| 52 | Anti TNF alpha VL | HUMIRA ® | DIQMTQSPSSLSASVGDRVTITCRASQGIRNYLAWYQQKPGKAPKLLIYAASTLQSGVPS<br>RFSGSGSGTDFTLTISSLQPEDVATYYCQRYNRAPYTFGQGTKVEIKR |
| 53 | Anti-CD20 VH | Rituximab | QVQLQQPGAELVKPGASVKMSCKASGYTFTSYNMHWVKQTPGRGLEWIGAIYPGNGDTSY<br>NQKFKGKATLTADKSSSTAYMQLSSLTSEDSAVYYCARSTYYGGDWYFNVWGAGTTVTVS<br>A |
| 54 | Anti-CD20 VL | Rituximab | QIVLSQSPAILSASPGEKVTMTCRASSSVSYIHWFQQKPGSSPKPWIYATSNLASGVPVR<br>FSGSGSGTSYSLTISRVEAEDAATYYCQQWTSNPPTFGGGTKLEIKR |
| 55 | Anti-VEGF VH | AVASTIN ® | EVQLVESGGGLVQPGGSLRLSCAASGYTFTNYGMNWVRQAPGKGLEWVGWINTYTGEPT<br>Y<br>AADFKRRFTFSLDTSKSTAYLQMNSLRAEDTAVYYCAKYPHYYGSSHWYFDVWGQGTLVT<br>VSS |
| 56 | Anti-VEGF VL | AVASTIN ® | DIQMTQSPSSLSASVGDRVTITCSASQDISNYLNWYQQKPGKAPKVLIYFTSSLHSGVPS<br>RFSGSGSGTDFTLTISSLQPEDFATYYCQQYSTVPWTFGQGTKVEIKR |
| 57 | Anti-HER2 VH | HERCEPTIN ® | EVQLVESGGGLVQPGGSLRLSCAASGFTFTDYTMDWVRQAPGKGLEWVADVNPNSGGSI<br>Y<br>NQRFKGRFTLSVDRSKNTLYLQMNSLRAEDTAVYYCARNLGPSFYFDYWGQGTLVTVSS |
| 58 | Anti-HER2 VL | HERCEPTIN ® | DIQMTQSPSSLSASVGDRVTITCKASQDVSIGVAWYQQKPGKAPKLLIYSASYRYTGVPS<br>RFSGSGSGTDFTLTISSLQPEDFATYYCQQYYIYPYTFGQGTKVEIKR |
| 59 | Anti-IL6R VH | ACTEMRA ® | EVQLQESGPGLVRPSQTLSLTCTVSGYSITSDHAWSWVRQPPGRGLEWIGYISYSGITTY<br>NPSLKSRVIMLRDTSKNQFSLRLSSVTAADTAVYYCARSLARTTAMDYWGQGSLVTVSS |

TABLE 4-continued

Amino acid sequences of binding moieties, domains and peptides

| SEQ ID NO: | Domain/peptide | Product* | Domain/peptide Amino Acid Sequence |
|---|---|---|---|
| 60 | Anti-IL6R VL | ACTEMRA ® | DIQMTQSPSSLSASVGDRVTITCRASQDISSYLNWYQQKPGKAPKLLIYYTSRLHSGVPSRF SGSGSGTDFTFTISSLQPEDIATYYCQQGNTLPYTFGQGTKVEIKR |
| 61 | Anti-PD-1 VH | Nivolumab | QVQLVESGGGVVQPGRSLRLDCKASGITFSNSGMHWVRQAPGKGLEWVAVIWYDGSKRY YADSVKGRFTISRDNSKNTLFLQMNSLRAEDTAVYYCATNDDYWGQGTLVTVSS |
| 62 | Anti-PD-1 VL | Nivolumab | EIVLTQSPATLSLSPGERATLSCRASQSVSSYLAWYQQKPGQAPRLLIYDASNRATGIPARF SGSGSGTDFTLTISSLEPEDFAVYYCQQSSNWPRTFGQGTKVEIKR |
| 63 | Anti-CTLA4 VH | Ipilimumab | QVQLVESGGGVVQPGRSLRLSCAASGFTFSSYTMHWVRQAPGKGLEWVTFISYDGNNKY YADSVKGRFTISRDNSKNTLYLQMNSLRAEDTAIYYCARTGWLGPFDYWGQGTLVTVSS |
| 64 | Anti-CTLA4 VL | Ipilimumab | EIVLTQSPGTLSLSPGERATLSCRASQSVGSSYLAWYQQKPGQAPRLLIYGAFSRATGIP DRFSGSGSGTDFTLTISRLEPEDFAVYYCQQYGSSPWTFGQGTKVEIKR |
| 65 | Anti-TNFR1 dAb VH | DOM1h-131-206 | EVQLLESGGGLVQPGGSLRLSCAASGFTFAHETMVWVRQAPGKGLEWVSHIPPDGQDPFY ADSVKGRFTISRDNSKNTLYLQMNSLRAEDTAVYHCALLPKRGPWFDYWGQGTLVTVSS |
| 66 | Anti-TNFα dAb | TAR 1-5-19 Vk | DIQMTQSPSSLSASVGDRVTITCRASQSIDSYLHWYQQKPGKAPKLLIYSASELQSGVPSRF SGSGSGTDFTLTISSLQPEDFATYYCQQVVWRPFTFGQGTKVEIKR |
| 67 | Anti-VEGF dAb | TAR15-10 Vk | DIQMTQSPSSLSASVGDRVTITCRASQWIGPELSWYQQKPGKAPKLLIYHTSILQSGVPSRF SGSGSGTDFTLTISSLQPEDFATYYCQQYMFQPRTFGQGTKVEIR |
| 68 | Anti-EGFR dAb | DOM16-39-109 Vk | DIQMTQSPTSLSASVGDRVTITCRASQWIGNLLDWYQQKPGEAPKLLIYYASFLQSGVPSRF SGGGFGTDFTLTISSLQPEDFATYYCQQANPAPLTFGQGTKVEIKR |
| 69 | Anti-CD38 dAb | DOM 11-3 Vk | DIQMTQSPSSLSASVGDRVTITCRASQNIDSRLSWYQQKPGKAPKLLIYRTSVLQSGVPSRF SGSGSGTDFTLTISSLQPEDFATYYCQQWDMFPLTFGQGTKVEIKR |
| 70 | Anti-CD138 dAb | DOM 12-45 Vk | DIQMTQSPSSLSASVGDRVTITCRASQDIGDRLRWYQQKPGKAPKLLIYHGSRLESGVPSRF SGSRSGTDFTLTISSLQPEDFATYYCQQQWFRPYTFGQGTKVEIKR |
| 71 | Anti-NY•ESO-1 Vα | | KQEVTQIPAALSVPEGENLVLNCSFTDSAIYNLQWFRQDPGKGLTSLLLITPWQREQTSGRL NASLDKSSGRSTLYIAASQPGDSATYLCAVRPLLDGTYIPTFGRGTSLIVHPY |
| 72 | Anti-NY•ESO-1 Vβ | | NAGVTQTPKFQVLKTGQSMTLQCAQDMNHEYMSWYRQDPGMGLRLIHYSVAIQTDQGEV PNGYNVSRSTIEDFPLRLLSAAPSQTSVYFCASSYLGNTGELFFGEGSRLTVL |
| 73 | IL2 | Human IL2 | APTSSSTKKTQLQLEHLLLDLQMILNGINNYKNPKLTRMLTFKFYMPKKATELKHLQCLEEEL KPLEEVLNLAQSKNFHLRPRDLISNINVIVLELKGSETTFMCEYADETATIVEFLNRWITFCQSI ISTLT |
| 74 | Anti-GFP VH | NANOBODY ™ | QVQLVESGGALVQPGGSLRLSCAASGFPVNRYSMRWYRQAPGKEREWVAGMSSAGDRS S YEDSVKGRFTISRDDARNTVYLQMNSLKPEDTAVYYCNVNVGFEYWGQGTQVTVSS |
| 75 | Anti-IL1R1 | DOM4-122-23 Vk | DIQMTQSPSSLSASVGDRVTITCRASQSIIKHLKWYQQKPGKAPKLLIYGASRLQSGVPSRFS GSGSGTDFTLTISSLQPEDFATYYCQQGARWPQTFGQGTKVEIKR |
| 76 | FLT1 | EYLEA ™ | SDTGRPFVEMYSEIPEIIHMTEGRELVIPCRVTSPNITVTLKKFPLDTLIPDGKRIIWDS RKGFIISNATYKEIGLLTCEATVNGHLYKTNYLTHRQTNTIIDV |
| 77 | KDR | EYLEA ™ | VLSPSHGIELSVGEKLVLNCTARTELNVGIDFNWEYPSSKHQHKKLVNRDLKTQSGSEMKKF LSTLTIDGVTRSDQGLYTCAASSGLMTKKNSTFVRVHEK |
| 78 | | Aflibercept | SDTGRPFVEMYSEIPEIIHMTEGRELVIPCRVTSPNITVTLKKFPLDTLIPDGKRIIWDS RKGFIISNATYKEIGLLTCEATVNGHLYKTNYLTHRQTNTIIDVVLSPSHGIELSVGEKL VLNCTARTELNVGIDFNWEYPSSKHQHKKLVNRDLKTQSGSEMKKFLSTLTIDGVTRSDQ GLYTCAASSGLMTKKNSTFVRVHEKDKTHTCPPCPAPELLGGPSVFLFPPKPKDTLMISR TPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVMHEALHNH YTQKSLSLSPG |
| 79 | GLP-1(7-37)-Pro9 | | HARGTFTSDVSSYLEGIDAAKEFIAWLVKGRG |
| 80 | Peptide YY | | IKPEAPGEDASPEELNRYYASLRHYLNLVTRQRY |
| 81 | EXENDIN-4 | | HGEGTFTSDLSKQMEEEAVRLFIEWLKNGGRSSGARRS |

TABLE 4-continued

Amino acid sequences of binding moieties, domains and peptides

| SEQ ID NO: | Domain/peptide | Product* | Domain/peptide Amino Acid Sequence |
|---|---|---|---|
| 82 | | DURAGLUTIDE ™ | HGEGTFTSDVSSYLEEQAAKEFIAWLVKGGGGGGGSGGGGSGGGGSAESKYGPPCPPCP APEAAGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDCSFFLYSRLTVDK SRWQEGNVFSCSVMHEALHNHYTQKSLSLSLG |

*indicates product comprising the domain.

TABLE 5

Amino acid sequences of Quad polypeptides

| SEQ ID NO: | POLY-PEPTIDE | AMINO ACID SEQUENCE |
|---|---|---|
| 83 | Quad 1 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LEFGEGSRLTVLEDLKNVEPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV LTDREWAEEWKHLDHLLNCIMDMVEKTRRSLTVLRRCQEADREELNYWIRRYSDAE |
| 84 | Quad 2 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LEFGEGSRLTVLEDLKNVEPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV GGGGSLTDREWAEEWKHLDHLLNCIMDMVEKTRRSLTVLRRCQEADREELNYWIRRYSDA E |
| 85 | Quad 3 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LEFGEGSRLTVLEDLKNVEPPEVAVFEPSEAEISHTQKATLVCLATGFYPDHVELSWWVN GKEVHSGVCTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV LTDREWAEEWKHLDHLLNCIMDMVEKTRRSLTVLRRCQEADREELNYWIRRYSDAE |
| 86 | Quad 4 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LEFGEGSRLTVLEDLKNVEPPEVAVFEPSEAEISHTQKATLVCLATGFYPDHVELSWWVN GKEVHSGVCTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV GGGGSLTDREWAEEWKHLDHLLNCIMDMVEKTRRSLTVLRRCQEADREELNYWIRRYSDA E |
| 87 | Quad 5 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVFPPEVAVFEPSEAEISHTQKATLVCLATGFYPDHVELSWWVN GKEVHSGVCTDPQPLKEQPALNDSRYALSSRLRVSATFWQDPRNHFRCQVQFYGLSENDE WTQDRAKPVTQIVSAEAWGRADLTDREWAEEWKHLDHLLNCIMDMVEKTRRSLTVLRRCQ EADREELNYWIRRYSDAE |
| 88 | Quad 6 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVEPPEVAVFEPSEAEISHTQKATLVCLATGFYPDHVELSWWVN GKEVHSGVCTDPQPLKEQPALNDSRYALSSRLRVSATFWQDPRNHFRCQVQFYGLSENDE WTQDRAKPVTQIVSAEAWGRADGGGGSLTDREWAEEWKHLDHLLNCIMDMVEKTRRSLTV LRRCQEADREELNYWIRRYSDAE |
| 89 | Quad 7 | KQEVTQIPAALSVPEGENLVLNCSFTDSAIYNLQWFRQDPG KGLTSLLLITPWQREQTSGRLNASLDKSSGRSTLYIAASQPGDSATYLCAVRPLLDGTYI PTFGRGTSLIVHPYIQNPDDPAVYQLRDSKSSDKSVCLFTDFDSQTNVSQSKDSDVYITDK TVLDMRSMDEKSNSAVAWSNKSDFACANAENNSIIPEDTFFPSPESSTVAAPSVFIFPPS DEQLKSGTASVVCLLNNFYPREAKVQWKVDNALQSGNSQESVTEQDSKDSTYSLSSTLTL SKADYEKHKVYACEVTHQGLSSPVTKSFNRGEC |

TABLE 5-continued

Amino acid sequences of Quad polypeptides

| SEQ ID NO: | POLY-PEPTIDE | AMINO ACID SEQUENCE |
|---|---|---|
| 90 | Quad 8 | KQEVTQIPAALSVPEGENLVLNCSFTDSAIYNLQWFRQDPG KGLTSLLLITPWQREQTSGRLNASLDKSSGRSTLYIAASQPGDSATYLCAVRPLLDGTYI PTFGRGTSLIVHPYIQNPDPAVYQLRDSKSSDKSVCLFTDFDSQTNVSQSKDSDVYITDK CVLDMRSMDEKSNSAVAWSNKSDFACANAENNSIIPEDTFFPSPESSTVAAPSVFIFPPS DEQLKSGTASVVCLLNNFYPREAKVQWKVDNALQSGNSQESVTEQDSKDSTYSLSSTLTL SKADYEKHKVYACEVTHQGLSSPVTKSFNRGEC |
| 91 | Quad 9 | KQEVTQIPAALSVPEGENLVLNCSFTDSAIYNLQWFRQDPG KGLTSLLLITPWQREQTSGRLNASLDKSSGRSTLYIAASQPGDSATYLCAVRPLLDGTYI PTFGRGTSLIVHPYIQNPDPAVYQLRDSKSSDKSVCLFTDFDSQTNVSQSKDSDVYITDK CVLDMRSMDEKSNSAVAWSNKSDFACANAENNSIIPEDTFFPSPESS |
| 92 | Quad 10 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVFPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV LTDREWAEEWKHLDHLLNCIMDMVEKTRRSLTVLRRCQEADREELNYWIRRYSDAEAPTS SSTKKTQLQLEHLLLDLQMILNGINNYKNPKLTRMLTFKFYMPKKATELKHLQCLEEELK PLEEVLNLAQSKNFHLRPRDLISNINVIVLELKGSETTFMCEYADETATIVEFLNRWITF CQSIISTLT |
| 93 | Quad 11 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVFPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV GGGGSLTDREWAEEWKHLDHLLNCIMDMVEKTRRSLTVLRRCQEADREELNYWIRRYSDA EAPTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLN RWITFCQSIISTLT |
| 94 | Quad 12 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVFPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV EPKSCDKTHTCPPCPLTDREWAEEWKHLDHLLNCIMDMVEKTRRSLTVLRRCQEADREEL NYWIRRYSDAE |
| 95 | Quad 13 | NAGVTQTPKFQVLKTGQSMTLQCAQDMNHEYMSWYRQDPGM GLRLIHYSVAIQTTDQGEVPNGYNVSRSTIEDFPLRLLSAAPSQTSVYFCASSYLGNTGE LFFGEGSRLTVLEDLKNVFPPEVAVFEPSEAEISHTQKATLVCLATGFYPDHVELSWWVN GKEVHSGVSTDPQPLKEQPALNDSRYALSSRLRVSATFWQDPRNHFRCQVQFYGLSENDE WTQDRAKPVTQIVSAEAWGRADASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVDKKV EPKSCDKTHTCPPCPGGGGSLTDREWAEEWKHLDHLLNCIMDMVEKTRRSLTVLRRCQEA DREELNYWIRRYSDAE |
| 96 | Quad 14 | QVQLVESGGALVQPGGSLRLSCAASGFPVNRYSMRWYRQAP GKEREWVAGMSSAGDRSSYEDSVKGRFTISRDDARNTVYLQMNSLKPEDTAVYYCNVNVG FEYWGQGTQVTVSSKLTDREWAEEWKHLDHLLNCIMDMVEKTRRSLTVLRRCQEADREEL NYWIRRYSDAE |
| 97 | Quad15 | QVQLVESGGALVQPGGSLRLSCAASGFPVNRYSMRWYRQAP GKEREWVAGMSSAGDRSSYEDSVKGRFTISRDDARNTVYLQMNSLKPEDTAVYYCNVNVG FEYWGQGTQVTVSSKGGGGSLTDREWAEEWKHLDHLLNCIMDMVEKTRRSLTVLRRCQEA DREELNYWIRRYSDAE |
| 98 | Quad 18 | QVQLVESGGALVQPGGSLRLSCAASGFPVNRYSMRWYRQAP GKEREWVAGMSSAGDRSSYEDSVKGRFTISRDDARNTVYLQMNSLKPEDTAVYYCNVNVG FEYWGQGTQVTVSSKLTDREWAEEWKHLDHLLNCIMDMVEKTRRSLTVLRRCQEADREEL NYWIRRYSDAEAPTSSSTKKTQLQLEHLLLDLQMILNGINNYKNPKLTRMLTEKEYMPKK ATELKHLQCLEEELKPLEEVLNLAQSKNFHLRPRDLISNINVIVLELKGSETTFMCEYAD ETATIVEFLNRWITFCQSIISTLT |
| 99 | Quad 19 | QVQLVESGGALVQPGGSLRLSCAASGFPVNRYSMRWYRQAP GKEREWVAGMSSAGDRSSYEDSVKGRFTISRDDARNTVYLQMNSLKPEDTAVYYCNVNVG FEYWGQGTQVTVSSKGGGGSLTDREWAEEWKHLDHLLNCIMDMVEKTRRSLTVLRRCQEA |

TABLE 5-continued

Amino acid sequences of Quad polypeptides

| SEQ ID NO: | POLY-PEPTIDE | AMINO ACID SEQUENCE |
|---|---|---|
| | | DREELNYWIRRYSDAEAPTSSSTKKTQLQLEHLLLDLQMILNGINNYKNPKLTRMLTEKE<br>YMPKKATELKHLQCLEEELKPLEEVLNLAQSKNFHLRPRDLISNINVIVLELKGSETTFM<br>CEYADETATIVEFLNRWITFCQSIISTLT |
| 100 | Quad 20 | KQEVTQIPAALSVPEGENLVLNCSFTDSAIYNLQWFRQDPG<br>KGLTSLLLITPWQREQTSGRLNASLDKSSGRSTLYIAASQPGDSATYLCAVRPLLDGTYI<br>PTFGRGTSLIVHPYIQNPDPAVYQLRDSKSSDKSVCLFTDFDSQTNVSQSKDSDVYITDK<br>TVLDMRSMDEKSNSAVAWSNKSDFACANAENNSIIPEDTFFPSPESSASTKGPSVFPLAP<br>SSKSTSGGTAALGCLVKDYFPEPVTVSWNSGALTSGVHTFPAVLQSSGLYSLSSVVTVPS<br>SSLGTQTYICNVNHKPSNTKVDKKVLHGTRQEEMIDHRLTDREWAEEWKHLDHLLNCIMD<br>MVEKTRRSLTVLRRCQEADREELNYWIRRYSDAEDLK |
| 101 | Quad 21 | KQEVTQIPAALSVPEGENLVLNCSFTDSAIYNLQWFRQDPG<br>KGLTSLLLITPWQREQTSGRLNASLDKSSGRSTLYIAASQPGDSATYLCAVRPLLDGTYI<br>PTFGRGTSLIVHPYIQNPDPAVYQLRDSKSSDKSVCLFTDFDSQTNVSQSKDSDVYITDK<br>TVLDMRSMDEKSNSAVAWSNKSDFACANAENNSIIPEDTFFPSPESSASTKGPSVFPLAP<br>SSKSTSGGTAALGCLVKDYFPEPVTVSWNSGALTSGVHTFPAVLQSSGLYSLSSVVTVPS<br>SSLGTQTYICNVNHKPSNTKVDKKVGGGGSLHGTRQEEMIDHRLTDREWAEEWKHLDHLL<br>NCIMDMVEKTRRSLTVLRRCQEADREELNYWIRRYSDAEDLK |
| 102 | Quad 22 | NAGVTQTPKFQVLKTGQSMTLQCAQDMNHEYMSWYRQDPGM<br>GLRLIHYSVAIQTTDQGEVPNGYNVSRSTIEDFPLRLLSAAPSQTSVYFCASSYLGNTGE<br>LFFGEGSRLTVLEDLKNVFPPEVAVFEPSEAEISHTQKATLVCLATGFYPDHVELSWWVN<br>GKEVHSGVSTDPQPLKEQPALNDSRYALSSRLRVSATFWQDPRNHFRCQVQFYGLSENDE<br>WTQDRAKPVTQIVSAEAWGRADTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVT<br>KSFNRGEC |
| 103 | Quad 28 | EVQLVESGGGLVQPGRSLRLSCAASGFTFDDYAMHWVRQAP<br>GKGLEWVSAITWNSGHIDYADSVEGRFTISRDNAKNSLYLQMNSLRAEDTAVYYCAKVSY<br>LSTASSLDYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKVDKKVLH<br>GTRQEEMIDHRLTDREWAEEWKHLDHLLNCIMDMVEKTRRSLTVLRRCQEADREELNYWI<br>RRYSDAEDLK |
| 104 | Quad 29 | EVQLVESGGGLVQPGRSLRLSCAASGFTFDDYAMHWVRQAP<br>GKGLEWVSAITWNSGHIDYADSVEGRFTISRDNAKNSLYLQMNSLRAEDTAVYYCAKVSY<br>LSTASSLDYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKVDKKVGG<br>GGSLHGTRQEEMIDHRLTDREWAEEWKHLDHLLNCIMDMVEKTRRSLTVLRRCQEADREE<br>LNYWIRRYSDAEDLK |
| 105 | Quad 30 | DIQMTQSPSSLSASVGDRVTITCRASQGIRNYLAWYQQ<br>KPGKAPKLLIYAASTLQSGVPSRFSGSGSGTDFTLTISSLQPEDVATYYCQRYNRAPYTF<br>GQGTKVEIKRTVAAPSVFIFPPSDEQLKSGTASVVCLLNNFYPREAKVQWKVDNALQSGN<br>SQESVTEQDSKDSTYSLSSTLTLSKADYEKHKVYACEVTHQGLSSPVTKSFNRGEC |
| 106 | Quad 31 | EVQLVESGGGLVQPGGSLRLSCAASGYTFTNYGMNWVRQAP<br>GKGLEWVGWINTYTGEPTYAADFKRRFTFSLDTSKSTAYLQMNSLRAEDTAVYYCAKYPH<br>YYGSSHWYFDVWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKKV<br>LHGTRQEEMIDHRLTDREWAEEWKHLDHLLNCIMDMVEKTRRSLTVLRRCQEADREELNY<br>WIRRYSDAEDLK |
| 107 | Quad 32 | EVQLVESGGGLVQPGGSLRLSCAASGYTFTNYGMNWVRQAP<br>GKGLEWVGWINTYTGEPTYAADFKRRFTFSLDTSKSTAYLQMNSLRAEDTAVYYCAKYPH<br>YYGSSHWYFDVWGQGTLVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSNTKVDKKV<br>GGGGSLHGTRQEEMIDHRLTDREWAEEWKHLDHLLNCIMDMVEKTRRSLTVLRRCQEADR<br>EELNYWIRRYSDAEDLK |
| 108 | Quad 33 | DIQMTQSPSSLSASVGDRVTITCSASQDISNYLNWYQQ<br>KPGKAPKVLIYFTSSLHSGVPSRFSGSGSGTDFTLTISSLQPEDFATYYCQQYSTVPWTF<br>GQGTKVEIKRTVAAPSVFIFPPSDEQLKSGTASVVCLLNNFYPREAKVQWKVDNALQSGN<br>SQESVTEQDSKDSTYSLSSTLTLSKADYEKHKVYACEVTHQGLSSPVTKSFNRGEC |
| 109 | Quad 34 | DIQMTQSPSSLSASVGDRVTITCRASQSIDSYLHWYQQK<br>PGKAPKLLIYSASELQSGVPSRFSGSGSGTDFTLTISSLQPEDFATYYCQQVVWRPFTFG<br>QGTKVEIKRGGGGSLHGTRQEEMIDHRLTDREWAEEWKHLDHLLNCIMDMVEKTRRSLTV<br>LRRCQEADREELNYWIRRYSDAEDLK |
| 110 | Quad 36 | EVQLLESGGGLVQPGGSLRLSCAASGFTFAHETMVWVRQAPG<br>KGLEWVSHIPPDGQDPFYADSVKGRFTISRDNSKNTLYLQMNSLRAEDTAVYHCALLPKR<br>GPWFDYWGQGTLVTVSSGGGGSLHGTRQEEMIDHRLTDREWAEEWKHLDHLLNCIMDMVE<br>KTRRSLTVLRRCQEADREELNYWIRRYSDAEDLK |

TABLE 5-continued

Amino acid sequences of Quad polypeptides

| SEQ ID NO: | POLY-PEPTIDE | AMINO ACID SEQUENCE |
|---|---|---|
| 111 | Quad 38 | DIQMTQSPSSLSASVGDRVTITCRASQWIGPELSWYQQK PGKAPKLLIYHTSILQSGVPSRFSGSGSGTDFTLTISSLQPEDFATYYCQQYMFQPRTFG QGTKVEIRGGGGSLHGTRQEEMIDHRLTDREWAEEWKHLDHLLNCIMDMVEKTRRSLTVL RRCQEADREELNYWIRRYSDAEDLK |
| 112 | Quad 40 | DIQMTQSPTSLSASVGDRVTITCRASQWIGNLLDWYQQK PGEAPKLLIYYASFLQSGVPSRFSGGGFGTDFTLTISSLQPEDFATYYCQQANPAPLTFG QGTKVEIKRGGGGSLHGTRQEEMIDHRLTDREWAEEWKHLDHLLNCIMDMVEKTRRSLTV LRRCQEADREELNYWIRRYSDAEDLK |
| 113 | Quad 42 | DIQMTQSPSSLSASVGDRVTITCRASQWIGPELSWYQQK PGKAPKLLIYHTSILQSGVPSRFSGSGSGTDFTLTISSLQPEDFATYYCQQYMFQPRTFG QGTKVEIRGGGGSLHGTRQEEMIDHRLTDREWAEEWKHLDHLLNCIMDMVEKTRRSLTVL RRCQEADREELNYWIRRYSDAEDLKGGGGSDIQMTQSPTSLSASVGDRVTITCRASQWIG NLLDWYQQKPGEAPKLLIYYASFLQSGVPSRFSGGGFGTDFTLTISSLQPEDFATYYCQQ ANPAPLTFGQGTKVEIKR |
| 114 | Quad 44 | DIQMTQSPSSLSASVGDRVTITCRASQNIDSRLSWYQQK PGKAPKLLIYRTSVLQSGVPSRFSGSGSGTDFTLTISSLQPEDFATYYCQQWDMFPLTEG QGTKVEIKRGGGGSLHGTRQEEMIDHRLTDREWAEEWKHLDHLLNCIMDMVEKTRRSLTV LRRCQEADREELNYWIRRYSDAEDLK |
| 115 | Quad 46 | DIQMTQSPSSLSASVGDRVTITCRASQNIDSRLSWYQQK PGKAPKLLIYRTSVLQSGVPSRFSGSGSGTDFTLTISSLQPEDFATYYCQQWDMFPLTEG QGTKVEIKRGGGGSLHGTRQEEMIDHRLTDREWAEEWKHLDHLLNCIMDMVEKTRRSLTV LRRCQEADREELNYWIRRYSDAEDLKGGGGSDIQMTQSPSSLSASVGDRVTITCRASQDI GDRLRWYQQKPGKAPKLLIYHGSRLESGVPSRFSGSRSGTDFTLTISSLQPEDFATYYCQ QQWERPYTEGQGTKVEIKR |

TABLE 6

DNA and amino acid sequences of NHR2 TDs

| SEQ ID NO: | NHR2 TD | DNA SEQUENCE |
|---|---|---|
| 116 | NHR2 TD | CTAACAGACAGAGAATGGGCAGAAGAGTGGAAACATCTTGACCATCTGTTAAACTGCATA ATGGACATGGTAGAAAAAACAAGGCGATCTCTCACCGTACTAAGGCGGTGTCAAGAAGCA GACCGGGAAGAATTGAATTACTGGATCCGGCGGTACAGTGACGCCGAG |
| 117 | NHR2* TD | TTGCATGGCACACGTCAAGAAGAAATGATTGATCACAGACTAACAGACAGAGAATGGGCA GAAGAGTGGAAACATCTTGACCATCTGTTAAACTGCATAATGGACATGGTAGAAAAAACA AGGCGATCTCTCACCGTACTAAGGCGGTGTCAAGAAGCAGACCGGGAAGAATTGAATTAC TGGATCCGGCGGTACAGTGACGCCGAGGACTTAAAA |
| 118 | NHR2** TD | GGCACACGTCAAGAAGAAATGATTGATCACAGACTAACAGACAGAGAATGGGCAGAAGAG TGGAAACATCTTGACCATCTGTTAAACTGCATAATGGACATGGTAGAAAAAACAAGGCGA TCTCTCACCGTACTAAGGCGGTGTCAAGAAGCAGACCGGGAAGAATTGAATTACTGGATC CGGCGGTACAGTGACGCCGAG |
| 119 | NHR2*** TD | CAAGAAGAAATGATTGATCACAGACTAACAGACAGAGAATGGGCAGAAGAGTGGAAACAT CTTGACCATCTGTTAAACTGCATAATGGACATGGTAGAAAAAACAAGGCGATCTCTCACC GTACTAAGGCGGTGTCAAGAA |
| | NHR2 TD | AMINO ACID SEQUENCE |
| 120 | NHR2 TD | LTDREWAEEWKHLDHLLNCIMDMVEKTRRSLTVLRRCQEADREELNYWIRRYSDAE |
| 121 | NHR2* TD | LHGTRQEEMIDHRLTDREWAEEWKHLDHLLNCIMDMVEKTRRSLTVLRRCQEADREELNY WIRRYSDAEDLK |
| 122 | NHR2** TD | GTRQEEMIDHRLTDREWAEEWKHLDHLLNCIMDMVEKTRRSLTVLRRCQEADREELNYWI RRYSDAE |
| 123 | NHR2*** TD | QEEMIDHRLTDREWAEEWKHLDHLLNCIMDMVEKTRRSLTVLRRCQE |

NHR2* TD and NHR2** TD include additional amino acid residues at the N- and/or C-terminus.
NHR2*** only includes amino acid residues of the annotated NHR2 domain according to Pubmed (Reference: UniProtKB-Q06455 (MTG8_HUMAN)).

TABLE 7

Human p53 TD sequences

| SEQ ID NO: | p53 TD | DNA SEQUENCE |
|---|---|---|
| 124 | p53 TD | AAGAAGAAACCACTGGATGGAGAATATTTCACCCTTCAGATCCGTGGGCGTGAGCGCTTCGAGATGTTCCGAGAGCTGAATGAGGCCTTGGAACTCAAGGATGCCCAGGCTGGGAAGGAGCCAGGG |
| 125 | p53* TD | GGAGAATATTTCACCCTTCAGATCCGTGGGCGTGAGCGCTTCGAGATGTTCCGAGAGCTGAATGAGGCCTTGGAACTCAAGGATGCCCAGGCTGGG |

| SEQ ID NO: | p53 TD | AMINO ACID SEQUENCE |
|---|---|---|
| 126 | p53 TD | KKKPLDGEYFTLQIRGRERFEMFRELNEALELKDAQAGKEPG |
| 10 | p53* TD | GEYFTLQIRGRERFEMFRELNEALELKDAQAG | p53* TD is a truncated version of p53 TD

---

The invention claimed is:

1. A protein multimer of at least first, second, third and fourth copies of an effector domain or a peptide, wherein the multimer is multimerized by first, second, third and fourth self-associating tetramerization domains (TDs) which are associated together, wherein each tetramerization domain is comprised by a respective engineered polypeptide comprising one or more copies of said effector domain or peptide, wherein
   (i) each TD is a p53 TD or a homologue or orthologue thereof;
   (ii) the multimer is soluble in an aqueous medium and is obtainable by extracellular secretion from a eukaryotic cell; and
   (iii) wherein the multimer comprises eukaryotic cell glycosylation.

2. The multimer of claim 1, wherein:
   (i) the multimer comprises a tetramer or an octamer of said domain or peptide;
   (ii) the multimer comprises a tetramer or octamer of an immunoglobulin superfamily binding site;
   (iii) the effector domain is an immunoglobulin superfamily domain; or
   (iv) the effector domain or peptide is an antibody variable or constant domain, a TCR variable or constant domain, an incretin, an insulin peptide, or a hormone peptide.

3. The multimer of claim 1, wherein each engineered polypeptide comprises first and second copies of said effector domain or peptide, wherein each engineered polypeptide comprises in N- to C-terminal direction (i) a first of said copies—TD— the second of said copies; (ii) TD—the first and second copies; or (iii) said first and second copies—TD.

4. The multimer of claim 1, wherein the engineered polypeptide comprises one or more copies of a second type of effector domain or peptide, wherein the second type of effector domain or peptide is different from the first effector domain or peptide.

5. The multimer of claim 1, wherein the multimer:
   (i) comprises 4 TDs and 4, 8, 12 or 16 copies of the effector domain or peptide;
   (ii) comprises first, second, third and fourth identical copies of an engineered polypeptide, the polypeptide comprising a TD and one, two or more copies of the effector domain or peptide;
   (iii) comprises a single type of engineered polypeptide, wherein the multimer is obtainable at >90% purity;
   (iv) consists of copies of the engineered polypeptide; or
   (v) is bispecific for antigen or pMHC binding.

6. The multimer of claim 1, wherein each TD comprises (i) an amino acid sequence identical to SEQ ID NO: 10 or 126 or at least 80% identical thereto.

7. The multimer of claim 1, wherein the multimer comprises a tetramer or octamer of an antigen binding site of an antibody selected from the group consisting of REOPRO®; Abciximab; RITUXAN®; Rituximab; ZENAPAX®; Daclizumab; SIMULECT®; Basiliximab; SYNAGIS®; Palivizumab; REMICADE®; Infliximab; HERCEPTIN®; MYLOTARG®; Gemtuzumab; CAMPATH®; Alemtuzumab; ZEVALIN®; Ibritumomab; HUMIRA®; Adalimumab; XOLAIR®; Omalizumab; BEXXAR®; Tositumomab; RAPTIVA™; Efalizumab; ERBITUX®; Cetuximab; AVASTIN®; Bevacizumab; TYSABRI®; Natalizumab;-ACTEMRA®; Tocilizumab; VECTIBIX®; Panitumumab; LUCENTIS®; Ranibizumab; SOLIRIS®; Eculizumab; CIMZIA®; Certolizumab; SIMPONI®; Golimumab, ILARIS®; Canakinumab; STELARA®; Ustekinumab; ARZERRA®; Ofatumumab; PROLIA®; Denosumab;-NUMAX™; Motavizumab; ABTHRAX™; Raxibacumab; BENLYSTA®; Belimumab; YERVOY®; Ipilimumab; ADCETRIS®; Brentuximab Vedotin; PERJETA®; Pertuzumab; KADCYLA®; Ado-trastuzumab; KEYTRUDA®, OPDIVO®, GAZYVA® and Obinutuzumab.

8. A tetramer or octamer of
   (a) TCR V domains or TCR binding sites, wherein the tetramer or octamer is soluble in aqueous solution;
   (b) antibody single variable domains, wherein the tetramer or octamer is soluble in aqueous solution;
   (c) TCR V domains or TCR binding sites, wherein the tetramer or octamer is capable of being extracellularly expressed by HEK293 cells; or
   (d) antibody variable domains, wherein the tetramer or octamer is capable of being extracellularly expressed by HEK293 cells,
wherein the tetramer or octamer comprises eukaryotic cell glycosylation.

9. A pharmaceutical composition comprising the multimer claim 1 and a pharmaceutically acceptable carrier, diluent or excipient.

10. An engineered polypeptide or a monomer of the multimer of claim 1.

11. The engineered polypeptide of claim 10, comprising in N- to C-terminal direction:
   (a) TCR V1—TCR C1—antibody CH1—optional linker—TD, wherein
      (i) V1 is a Vα and C1 is a Cα;
      (ii) V1 is a Vβ and C1 is a Cβ;
      (iii) V1 is a Vγ and C1 is a Cγ; or
      (iv) V1 is a Vδ and C1 is a Cδ;
      or
   (b) TCR V1—antibody CH1—optional linker—TD, wherein
      (i) V1 is a Vα;
      (ii) V1 is a Vβ;
      (iii) V1 is a Vγ; or
      (iv) V1 is a Vδ;
      or
   (c) antibody V1—antibody CH1—optional linker—TD, wherein
      (i) V1 is a VH; or
      (ii) V1 is a VL; or (d) antibody V1—optional antibody CH1—antibody Fc—optional linker—TD, wherein
  (i) V1 is a VH; or
  (ii) V1 is a VL; or
(e) antibody V1—antibody CL—optional linker—TD, wherein
  (i) V1 is a VH; or
  (ii) V1 is a VL; or
(f) TCR V1—TCR C1—optional linker—TD, wherein
  (i) V1 is a Vα and C1 is a Cα;
  (ii) V1 is a Vβ and C1 is a Cβ;
  (iii) V1 is a Vγ and C1 is a Cγ; or
  (iv) V1 is a Vδ and C1 is a Cδ.

12. A nucleic acid encoding the engineered polypeptide or monomer of claim 10.

13. A eukaryotic host cell comprising the nucleic acid of claim 12 for secreted expression of the engineered polypeptide or monomer.

14. A method for producing secreted multimers, wherein the method comprises secreting the multimers from eukaryotic cells comprising the nucleic acid of claim 12.

15. A mixture comprising (i) a eukaryotic cell line encoding an engineered polypeptide of claim 10; and (ii) multimers, wherein the cell line is in a medium comprising secretion products of the cells, wherein the secretion products comprise the multimers.

16. The multimer of claim 1, wherein the eukaryotic cell is a mammalian cell.

17. The multimer of claim 16, wherein the eukaryotic cell is a Chinese Hamster Ovary (CHO) cell, HEK293 cell, or Cos cell.

18. A protein multimer of at least first, second, third and fourth copies of an effector domain or a peptide, wherein the multimer is multimerized by first, second, third and fourth self-associating tetramerization domains (TDs) which are associated together, wherein each tetramerization domain is comprised by a respective engineered polypeptide comprising one or more copies of said effector domain or peptide, wherein
  (i) each TD is a p53 TD or a homologue or orthologue thereof;
  (ii) the multimer is soluble in an aqueous medium and is obtainable by extracellular secretion from a eukaryotic cell; and
  (iii) wherein each engineered polypeptide comprises first and second copies of said effector domain or peptide, wherein each engineered polypeptide comprises in N- to C-terminal direction (i) a first of said copies—TD—the second of said copies; (ii) TD—the first and second copies; or (iii) said first and second copies—TD.

19. An engineered polypeptide, wherein the engineered polypeptide comprises one or more copies of an effector domain or peptide and a self-associating tetramerization domain (TD),
  wherein the TD is capable of multimerizing to form a protein multimer of at least first, second, third and fourth copies of the effector domain or peptide,
  wherein the TD is a p53 TD or a homologue or orthologue thereof, and
  (i) each TD of the multimer is a p53 TD or a homologue or orthologue thereof; and
  (ii) the multimer is soluble in an aqueous medium and is obtainable by extracellular secretion of the engineered polypeptide from a eukaryotic cell, and the engineered polypeptide comprises in N- to C-terminal direction:
    (a) antibody V1—antibody CH1—optional linker—TD, wherein
      (i) V1 is a VH; or
      (ii) V1 is a VL; or
    (b) antibody V1—optional antibody CH1—antibody Fc—optional linker—TD, wherein
      (i) V1 is a VH; or
      (ii) V1 is a VL; or
    (c) antibody V1—antibody CL—optional linker—TD, wherein
      (i) V1 is a VH; or
      (i) V1 is a VL.

20. The multimer of claim 18, wherein each TD comprises (i) an amino acid sequence identical to SEQ ID NO: 10 or 126 or at least 95% identical thereto.

21. The engineered polypeptide of claim 19, wherein the engineered polypeptide comprises in N- to C-terminal direction: antibody V1—antibody CH1—optional linker—TD, wherein V1 is a VH; or V1 is a VL.

22. The engineered polypeptide of claim 19, wherein each TD comprises (i) an amino acid sequence identical to SEQ ID NO: 10 or 126 or at least 95% identical thereto.

23. The multimer of claim 18, wherein the engineered polypeptide comprises one or more copies of a second type of effector domain or peptide, wherein the second type of effector domain or peptide is different from the first effector domain or peptide.

24. The engineered polypeptide of claim 19, wherein the engineered polypeptide comprises one or more copies of a second type of effector domain or peptide, wherein the second type of effector domain or peptide is different from the first effector domain or peptide.

25. An engineered polypeptide or a monomer of the multimer of claim 18.

* * * * *